(12) United States Patent
Jasti et al.

(10) Patent No.: US 11,505,644 B2
(45) Date of Patent: Nov. 22, 2022

(54) POLYMER EMBODIMENTS COMPRISING NANOHOOP-CONTAINING POLYMER BACKBONES AND METHODS OF MAKING AND USING THE SAME

(71) Applicants: University of Oregon, Eugene, OR (US); The Johns Hopkins University, Baltimore, MD (US); Georgetown University, Washington, DC (US)

(72) Inventors: Ramesh Jasti, Eugene, OR (US); Ruth Maust, Eugene, OR (US); Curtis Colwell, Eugene, OR (US); John Dayton Tovar, Baltimore, MD (US); Garvin Peters, Philadelphia, PA (US); Haley Bates, Orange, CA (US); Miklos Kertesz, Bethesda, MD (US); Girishma Grover, Washington, DC (US)

(73) Assignees: University of Oregon, Eugene, OR (US); Georgetown University, Washington, DC (US); The Johns Hopkins University, Baltimore, MD (US)

(*) Notice: Subject to any disclaimer, the term of this patent is extended or adjusted under 35 U.S.C. 154(b) by 0 days.

(21) Appl. No.: 17/033,458

(22) Filed: Sep. 25, 2020

(65) Prior Publication Data
US 2021/0095070 A1    Apr. 1, 2021

Related U.S. Application Data

(60) Provisional application No. 62/907,145, filed on Sep. 27, 2019.

(51) Int. Cl.
*C08G 61/12* (2006.01)
*C08G 61/10* (2006.01)
*C07C 15/14* (2006.01)

(52) U.S. Cl.
CPC ........... *C08G 61/126* (2013.01); *C07C 15/14* (2013.01); *C08G 61/10* (2013.01);
(Continued)

(58) Field of Classification Search
CPC ............... C08G 61/126; C08G 61/10; C08G 2261/124; C08G 2261/1412; C08G 2261/148; C08G 2261/312; C08G 2261/3229; C08G 2261/3328; C08G 2261/42; C07C 15/14
See application file for complete search history.

(56) References Cited

U.S. PATENT DOCUMENTS 8,461,403 B2   6/2013  Jasti et al.
8,895,768 B2   11/2014 Yamago
(Continued)

OTHER PUBLICATIONS

Kwan et al., J. Am. Chem. Soc. 2004, 126, 8638-8639.*
(Continued)

*Primary Examiner* — Shane Fang
(74) *Attorney, Agent, or Firm* — Klarquist Sparkman, LLP

(57) ABSTRACT

Polymer embodiments comprising nanohoop-containing polymer backbones are described, along with methods of making and using the same. The polymer embodiments exhibit unique radial and linear conjugation and can be used in a variety of devices, such as electronic and/or optoelectronic devices.

21 Claims, 60 Drawing Sheets

(52) U.S. Cl.
 CPC .. *C08G 2261/124* (2013.01); *C08G 2261/148* (2013.01); *C08G 2261/1412* (2013.01); *C08G 2261/312* (2013.01); *C08G 2261/3229* (2013.01); *C08G 2261/3328* (2013.01); *C08G 2261/42* (2013.01)

(56) References Cited

U.S. PATENT DOCUMENTS

| | | | |
|---|---|---|---|
| 9,090,473 | B2 | 7/2015 | Jasti et al. |
| 9,481,618 | B2 | 11/2016 | Itami et al. |
| 9,527,737 | B2 | 12/2016 | Itami et al. |
| 2004/0202603 | A1 | 10/2004 | Fischer |
| 2011/0166390 | A1 | 7/2011 | Jasti et al. |
| 2012/0220790 | A1 | 8/2012 | Yamago |
| 2016/0372684 | A1 | 12/2016 | Jasti et al. |
| 2018/0290952 | A1 | 10/2018 | Jasti et al. |
| 2019/0025315 | A1 | 1/2019 | Jasti et al. |

OTHER PUBLICATIONS

Ogi et al., ACS Macro Lett. Jan. 2012, 1199-1203.*
Ball et al., "Stepping into the Light: Conjugated Macrocycles with Donor-Acceptor Motifs," ACS Cent. Sci., 1, 416-417, Oct. 27, 2015.
Darzi et al., "Selective syntheses of [7]-[12]Cycloparaphenylenes using orthogonal Suzuki-Miyaura cross-coupling reactions," *Journal of Organic Chemistry*, vol. 77, pp. 6624-6628, Jul. 17, 2012.
Darzi et al., "Synthesis, Properties, and Design Principles of Donor-Acceptor Nanohoops," *ACS Central Science*, vol. 1, pp. 335-342, Sep. 3, 2015.
Darzi et al., "The dynamic, size-dependent properties of [5]-[12]cycloparaphenylenes," *Chem. Soc. Rev.*, vol. 44, pp. 6401-6410, Apr. 27, 2015.
Darzi, Research Presentation/Slides, Sep. 24, 2014.
Final Office Action issued for U.S. Appl. No. 16/041,676 dated Aug. 27, 2020.
Final Office Action issued for U.S. Appl. No. 15/187,644 dated Aug. 19, 2020.
Havinga et al., "A new class of small band gap organic polymer conductors," *Polymer Bulletin*, 29(119): 119-126, Aug. 1992.
Hirst "Synthesis of Nitrogen-Substituted Cycloparaphenylenes," Dissertation, May 2014.
Hirst "Synthesis of Nitrogen-Substituted Cycloparaphenylenes," Thesis Defense Presentation, May 13, 2014.
Ishii et al., "Synthesis and dimerization of chloro[10]cyclopharaphenylene: A directly connected cycloparaphenylene dimer," *Organic Letters*, 16(8): 2174-2176, Apr. 1, 2014.
Iwamoto et al., "Selective and Random Syntheses of [n]Cycloparaphenylenes (n=8-13) and Size Dependence of Their Electronic Properties," *Journal of the American Chemical Society*, 133(21): 8354-8361, May 4, 2011.
Iwamoto et al., "Size-Selective Encapsulation of $C_{60}$ by [10]Cycloparaphenylene: Formation of the Shortest Fullerene-Peapod," *Agnew. Chem. Int. Ed.*, vol. 50, pp. 8342-8344, Jul. 18, 2011.
Jasti et al., "Synthesis, Characterization, and Theory of [9]-, [12]-, and [18]Cycloparaphenylene: Carbon Nanohoop Structures," *J. Am. Chem. Soc.*, vol. 130, pp. 17646-17647, Dec. 4, 2008.
Kikuchi et al., "Definitive evidence for the contribution of biradical character in a closed-shell molecule, derivative of 1,4-Bis-(4,5-diphenylimidazol-2-ylidene)cyclohexa-2,5,-diene," *JACS Communications*, 126(21): 6526-6527, May 11, 2004.
Kubota et al., "η6-cycloparaphenylene transition metal complexes: synthesis, structure, photophysical properties, and application to the selective monofunctionalization of cycloparaphenylenes," *JACS*,vol. 137, pp. 1356-1361, Jan. 12, 2015.

Kuwabara et al., "Curved oligophenylenes as donors in shape-persistent donor-acceptor macrocycles with solvatofluorochromic properties," *Angew. Chem. Int. Ed.*, 54(33): 9646-9649, Aug. 10, 2015.
Matsui et al., "Synthesis and properties of cycloparaphenylene-2,5-pyridylidene: a nitrogen-containing carbon nanoring," *Organic Letters*, 14(7): 1888-1891, Mar. 23, 2012.
Mutoh et al., "Entropy-controlled biradical-quinoid isomerization of a π-conjugated delocalized biradical," *Phys. Chem. Chem. Phys.*, 17(2): 1151-1155, Nov. 17, 2014.
Nishihara et al., "Excited states in cycloparaphenylenes: dependence of optical properties on ring length," *Journal of Physical Chemistry Letters*, vol. 3, pp. 3125-3128, Oct. 12, 2012.
Non-Final Office Action issued for U.S. Appl. No. 16/041,676 dated Feb. 6, 2020.
Oki et al., "One-pot synthesis of a rice-ball-shaped cyclophane with syn-diethanoanthracene-fused dipyrrole and hexafluorobenzene," *Chem. Lett.*, vol. 46, pp. 243-244, Nov. 26, 2016.
Ozasa et al., "Studies of polyphenyls and polyphenylenes. II. The synthesis and physical properties of polyphenyls containing para linkage," *Bull. Chem. Soc. Jpn.*, 53(9): 2610-2617, 1980.
Rio et al., "Cyclotetrahalo-p-phenylenes: simulations of halogen substituted cycloparaphenylenes and their interaction with $C_{60}$," *Phys. Chem. Chem. Phys.*, 18(33): 23257-23263, Jul. 22, 2016.
Salvatella, "The alkyl group is a –I+R substituent," *Educacion Quimica*, vol. 28, pp. 232, 237, Jul. 17, 2017.
Takase et al., "Donor-acceptor segregated paracyclophanes composed of naphthobipyrrole and stacked fluoroarenes," *Organic Letters*, 15(13): 3202-3205, Jun. 21, 2013.
Xia et al., "Gram-scale synthesis and crystal structures of [8]- and [10]CPP, and the solid-state structure of $C_{60}$@[10]CPP," *Chemical Science*, vol. 3, pp. 3018-3021, Jul. 11, 2012.
Xia et al., "Synthesis, Characterization and Computational Studies of Cycloparaphenylene Dimers," *J. Am. Chem. Soc.*, 134(48): 19709-19715, Nov. 6, 2012.
Xue et al., "Cyclo-meta-phenylene revisited: nickel-mediated synthesis, molecular structures, and device applications," *Journal of Organic Chemistry*, vol. 79, pp. 9735-9739, pp. 9735-9739, Sep. 29, 2014.
Zhang et al., "Giant Cyclo[n]thiophenes with Extended π Conjugation," *Angewandte Chemie Int. Ed.*, 48(36): 6632-6635, Jun. 27, 2009.
Friederich et al., "Auf dem Weg zu makrocyclischen para-Phenylenen. ", *Chemische Berichte*, (1993), pp. 1723-1732, vol. 126(7).
Fujitsuka et al.,"Radical Ions of Cycloparaphenylenes: Size Dependence Contrary to the Neutral Molecules.", *The Journal of Physical Chemistry Letters*, (2014), pp. 2302-2305, vol. 5(13).
Jasti et al., "Synthesis, Characterization, and Theory of [9]-, [12]-, and [18]Cycloparaphenylene: Carbon Nanohoop Structures.", *Journal of the American Chemical Society*, (2008), pp. 17646-17647, vol. 130(52).
Kammermeier et al., "Ring-Expanding Metathesis of Tetradehydroanthracene—Synthesis and Structure of a Tubelike, Fully Conjugated Hydrocarbon.", *Angewandte Chemie International Edition*,(1996), pp. 2669-2671, vol. 35(22).
Kawase et al., "Cyclic [6]- and [8]Paraphenylacetylenes.",*Angewandte Chemie International Edition*, (1996), pp. 2664-2666, vol. 35(22).
Kayahara et al., "Synthesis and Characterization of [n]CPP (n=5, 6, 8, 10, and 12) Radical Cation and Dications: Size-Dependent Absorption, Spin, and Charge Delocalization.", *Journal of the American Chemical Society*, (2016), pp. 338-344, vol. 138(1).
Schaub et al., "Strain-Promoted Reactivity of Alkyne-Containing Cycloparaphenylenes.", *Angewandte Chemie International Edition*, (2018), pp. 16348-16353, vol. 57(50).
Segawa et al., "Theoretical Studies on the Structures and Strain Energies of Cycloparaphenylenes.", *Organic Letters*, (2010), pp. 2262-2265, vol. 12(10).
Takaba et al., "Selective Synthesis of [12]Cycloparaphenylene.", *Angewandte Chemie International Edition*, (2009), pp. 6112-6116, vol. 48(33).
Talipov et al., "A Circle Has No End: Role of Cyclic Topology and Accompanying Structural Reorganization on the Hole Distribution

(56) References Cited

OTHER PUBLICATIONS in Cyclic and Linear Poly-p-phenylene Molecular Wires.", *Journal of the American Chemical Society*, (2015), pp. 14999-15006, vol. 137(47).

Toriumi et al., "In-Plane Aromaticity in Cycloparaphenylene Dications: A Magnetic Circular Dichroism and Theoretical Study.", *Journal of the American Chemical Society*, (2015), pp. 82-85, vol. 137(1).

Xu et al., "A Supramolecular [10]CPP Junction Enables Efficient Electron Transfer in Modular Porphyrin-[10]CPP ⊃ Fullerene Complexes.", *Angewandte Chemie International Edition*, (2018), pp. 11549-11553, vol. 57(36).

Yamago et al., "Synthesis of [8]Cycloparaphenylene from a Square-Shaped Tetranuclear Platinum Complex.", *Angewandte Chemie International Edition*, (2010), pp. 757-759, vol. 49(4).

* cited by examiner

POLYMER EMBODIMENTS COMPRISING NANOHOOP-CONTAINING POLYMER BACKBONES AND METHODS OF MAKING AND USING THE SAME

CROSS REFERENCE TO RELATED APPLICATION

This application claims the benefit of the earlier filing date of U.S. Provisional Patent Application No. 62/907,145, filed on Sep. 27, 2019; the entirety of this prior application is incorporated by reference herein.

ACKNOWLEDGMENT OF GOVERNMENT SUPPORT

This invention was made with government support under Contract No. DE-SC0019017 awarded by the Department of Energy. The government has certain rights in the invention.

FIELD

Disclosed herein are embodiments of a polymer comprising a nanohoop-containing polymeric backbone and methods of making and using the same.

SUMMARY

Disclosed herein are embodiments of a polymer having a structure according to Formula I

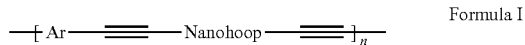

Formula I wherein the nanohoop comprises six or more aromatic ring systems and wherein each aromatic ring system is bound to at least two other aromatic ring systems of the nanohoop by two separate single covalent bonds positioned para, ortho, or meta relative to one another; Ar is an aromatic ring system; and n is an integer selected from 2 or greater.

Also disclosed herein are embodiments of a compound having a structure according to Formula V or Formula VI,

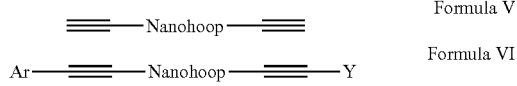

Formula V

Formula VI wherein the nanohoop comprises six or more aromatic ring systems and wherein each aromatic ring system is bound to at least two other aromatic ring systems of the nanohoop by two separate single covalent bonds positioned para, ortho, or meta relative to one another; Ar is an aromatic ring system; and Y is hydrogen, copper, a palladium complex, or an aromatic ring system.

Also disclosed herein are embodiments of a method, comprising exposing a polymerizable nanohoop monomer to a transition metal catalyst, a copper-containing reagent, a base, and an aromatic coupling partner functionalized with a halogen atom to provide a polymer as described herein; wherein the polymerizable nanohoop monomer has a structure according to Formula V

Formula V wherein the nanohoop of Formula V comprises six or more aromatic ring systems and wherein each aromatic ring system is bound to at least two other aromatic ring systems of the nanohoop by two separate single covalent bonds positioned para, ortho, or meta relative to one another.

Also disclosed herein are embodiments of a method, comprising: coupling a nanohoop intermediate with an aromatic monomer functionalized with an alkyne moiety to provide a non-aromatized nanohoop intermediate; and exposing the non-aromatized nanohoop intermediate to a reductive aromatization to provide a polymerizable nanohoop monomer having a structure according to Formula V.

The foregoing and other objects and features of the present disclosure will become more apparent from the following detailed description, which proceeds with reference to the accompanying figures.

BRIEF DESCRIPTION OF THE DRAWINGS

FIGS. 13A and 13B show HOMO and LUMO orbitals for monomer 1[8]-Th, respectively; (ii) FIGS. 13C and 13D show HOMO and LUMO orbitals for monomer 2[8]-Th-Me, respectively; (iii) FIGS. 13E and 13F show HOMO and LUMO orbitals for monomer 3[8]-Th-Me, respectively; and (iv) FIGS. 13G and 13H show HOMO and LUMO orbitals for [6]CPP, respectively.

DETAILED DESCRIPTION

I. Overview of Terms

Figure 1:
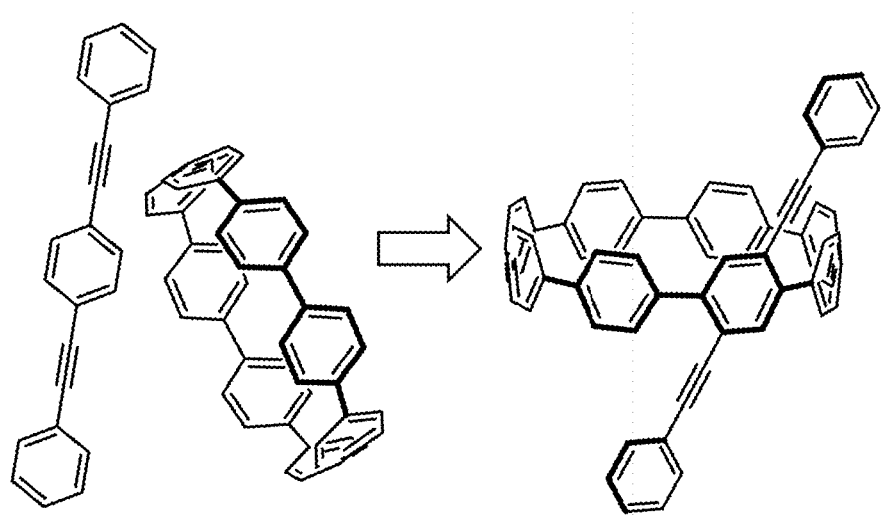
FIG. 1 illustrates a representation of combined linear and curved delocalization pathways.

The following explanations of terms are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting, unless otherwise indicated. Other features of the disclosure are apparent from the following detailed description and the claims.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that can depend on the desired properties sought and/or limits of detection under standard test conditions/methods. When directly and explicitly distinguishing embodiments from discussed prior art, the embodiment numbers are not approximates unless the word "about" is recited. Furthermore, not all alternatives recited herein are equivalents.

To facilitate review of the various embodiments of the disclosure, the following explanations of specific terms are provided. Certain functional group terms include a symbol "-" which is used to show how the defined functional group attaches to, or within, the polymerizable nanohoop monomers, polymerizable nanohoop intermediates, and/or polymers to which it is bound. Also, a dashed bond (i.e., "---") as used in certain formulas described herein indicates an optional bond (that is, a bond that may or may not be present). A person of ordinary skill in the art would recognize that the definitions provided below and the polymerizable nanohoop monomers, polymerizable nanohoop intermediates, and/or polymers and formulas included herein are not intended to include impermissible substitution patterns (e.g., methyl substituted with 5 different groups, and the like). Such impermissible substitution patterns are easily recognized by a person of ordinary skill in the art. In formulas and polymerizable nanohoop monomers, polymerizable nanohoop intermediates, and/or polymers disclosed herein, a hydrogen atom is present and completes any formal valency requirements (but may not necessarily be illustrated wherever a functional group or other atom is not illustrated. For example, a phenyl ring that is drawn as

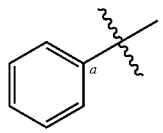 [SMILES: *c1ccccc1]

comprises a hydrogen atom attached to each carbon atom of the phenyl ring other than the "a" carbon, even though such hydrogen atoms are not illustrated. Any functional group disclosed herein and/or defined above can be substituted or unsubstituted, unless otherwise indicated herein.

Acyl Halide: —C(O)X, wherein X is a halogen, such as Br, F, I, or Cl.

Aldehyde: —C(O)H.

Aliphatic: A hydrocarbon group having at least one carbon atom to 50 carbon atoms ($C_{1-50}$), such as one to 25 carbon atoms (1-25), or one to ten carbon atoms ($C_{1-10}$), and which includes alkanes (or alkyl), alkenes (or alkenyl), alkynes (or alkynyl), including cyclic versions thereof, and further including straight- and branched-chain arrangements, and all stereo and position isomers as well. An aliphatic group is distinct from an aromatic group.

Aliphatic-aromatic: An aromatic group that is or can be coupled to a polymerizable nanohoop monomer, polymerizable nanohoop intermediate, and/or polymer disclosed herein, wherein the aromatic group is or becomes coupled through an aliphatic group.

Aliphatic-aryl: An aryl group that is or can be coupled to a polymerizable nanohoop monomer, polymerizable nanohoop intermediate, and/or polymer disclosed herein, wherein the aryl group is or becomes coupled through an aliphatic group.

Aliphatic-heteroaryl: A heteroaryl group that is or can be coupled to a polymerizable nanohoop monomer, polymerizable nanohoop intermediate, and/or polymer disclosed herein, wherein the heteroaryl group is or becomes coupled through an aliphatic group.

Alkenyl: An unsaturated monovalent hydrocarbon having at least two carbon atom to 50 carbon atoms ($C_{2-50}$), such as two to 25 carbon atoms ($C_{2-25}$), or two to ten carbon atoms ($C_{2-10}$), and at least one carbon-carbon double bond, wherein the unsaturated monovalent hydrocarbon can be derived from removing one hydrogen atom from one carbon atom of a parent alkene. An alkenyl group can be branched, straight-chain, cyclic (e.g., cycloalkenyl), cis, or trans (e.g., E or Z).

Alkoxy: —O-aliphatic, such as —O-alkyl, —O-alkenyl, —O-alkynyl; with exemplary embodiments including, but not limited to, methoxy, ethoxy, n-propoxy, isopropoxy, n-butoxy, t-butoxy, sec-butoxy, n-pentoxy (wherein any of the aliphatic components of such groups can comprise no double or triple bonds, or can comprise one or more double and/or triple bonds).

Alkyl: A saturated monovalent hydrocarbon having at least one carbon atom to 50 carbon atoms ($C_{1-50}$), such as one to 25 carbon atoms ($C_{1-25}$), or one to ten carbon atoms ($C_{1-10}$), wherein the saturated monovalent hydrocarbon can be derived from removing one hydrogen atom from one carbon atom of a parent compound (e.g., alkane). An alkyl group can be branched, straight-chain, or cyclic (e.g., cycloalkyl).

Alkynyl: An unsaturated monovalent hydrocarbon having at least two carbon atom to 50 carbon atoms ($C_{2-50}$), such as two to 25 carbon atoms ($C_{2-25}$), or two to ten carbon atoms ($C_{2-10}$), and at least one carbon-carbon triple bond, wherein the unsaturated monovalent hydrocarbon can be derived from removing one hydrogen atom from one carbon atom of a parent alkyne. An alkynyl group can be branched, straight-chain, or cyclic (e.g., cycloalkynyl).

Amide: —C(O)NR$^a$R$^b$ or —NR$^a$C(O)R$^b$ wherein each of R$^a$ and R$^b$ independently is selected from hydrogen, aliphatic, heteroaliphatic, haloaliphatic, haloheteroaliphatic, aromatic, or an organic functional group.

Amino: —NR$^a$R$^b$, wherein each of R$^a$ and R$^b$ independently is selected from hydrogen, aliphatic, heteroaliphatic, haloaliphatic, haloheteroaliphatic, aromatic, or an organic functional group.

Aromatic: A cyclic, conjugated group or moiety of, unless specified otherwise, from 5 to 15 ring atoms having a single ring (e.g., phenyl) or multiple condensed rings in which at least one ring is aromatic (e.g., naphthyl, indolyl, or pyrazolopyridinyl); that is, at least one ring, and optionally multiple condensed rings, have a continuous, delocalized π-electron system.

Typically, the number of out of plane π-electrons corresponds to the Huckel rule (4n+2). The point of attachment to the parent structure typically is through an aromatic portion of the condensed ring system. For example,

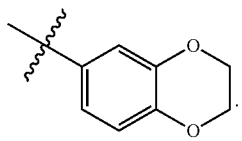 [SMILES: *c1ccc2c(c1)OCCO2]

However, in certain examples, context or express disclosure may indicate that the point of attachment is through a non-aromatic portion of the condensed ring system. For example,

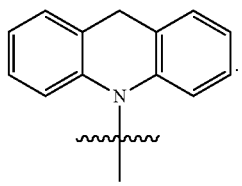 [SMILES: *N1c2ccccc2Cc2ccccc21]

An aromatic group or moiety may comprise only carbon atoms in the ring, such as in an aryl group or moiety, or it may comprise one or more ring carbon atoms and one or more ring heteroatoms comprising a lone pair of electrons (e.g. S, O, N, P, or Si), such as in a heteroaryl group or moiety. Aromatic groups may be substituted with one or more groups other than hydrogen, such as aliphatic, heteroaliphatic, haloaliphatic, haloheteroaliphatic, aromatic, or an organic functional group.

Aryl: An aromatic carbocyclic group comprising at least five carbon atoms to 15 carbon atoms ($C_5$-$C_{15}$), such as five to ten carbon atoms ($C_5$-$C_{10}$), having a single ring or multiple condensed rings, which condensed rings can or may not be aromatic provided that the point of attachment to a remaining position of the polymerizable nanohoop monomers, polymerizable nanohoop intermediates, and/or polymers disclosed herein is through an atom of the aromatic carbocyclic group. Aryl groups may be substituted with one or more groups other than hydrogen, such as aliphatic, heteroaliphatic, haloaliphatic, haloheteroaliphatic, aromatic, or an organic functional group.

Aroxy: —O-aromatic.

Azo: —N=NR$^a$ wherein R$^a$ is hydrogen, aliphatic, heteroaliphatic, haloaliphatic, haloheteroaliphatic, aromatic, or an organic functional group.

Carbamate: —OC(O)NR$^a$R$^b$, wherein each of R$^a$ and R$^b$ independently is selected from hydrogen, aliphatic, heteroaliphatic, haloaliphatic, haloheteroaliphatic, aromatic, or an organic functional group.

Carboxyl: —C(O)OH.

Carboxylate: —C(O)O— or salts thereof, wherein the negative charge of the carboxylate group may be balanced with an M$^+$ counterion, wherein M$^+$ may be an alkali ion, such as K$^+$, Na$^+$, Li$^+$; an ammonium ion, such as $^+$N(R$^b$)$_4$ where R$^b$ is hydrogen, aliphatic, heteroaliphatic, haloaliphatic, haloheteroaliphatic, aromatic, or an organic functional group; or an alkaline earth ion, such as [Ca$^{2+}$]$_{0.5}$, [Mg$^{2+}$]$_{0.5}$, or [Ba$^{2+}$]$_{0.5}$.

Cyano: —CN.

Disulfide: —SSR$^a$, wherein R$^a$ is selected from hydrogen, aliphatic, heteroaliphatic, haloaliphatic, haloheteroaliphatic, aromatic, or an organic functional group.

Dithiocarboxylic: —C(S)SR$^a$ wherein R$^a$ is selected from hydrogen, aliphatic, heteroaliphatic, haloaliphatic, haloheteroaliphatic, aromatic, or an organic functional group.

Ester: —C(O)OR$^a$ or —OC(O)R$^a$, wherein R$^a$ is selected from aliphatic, heteroaliphatic, haloaliphatic, haloheteroaliphatic, aromatic, or an organic functional group.

Ether: -aliphatic-O-aliphatic, -aliphatic-O-aromatic, -aromatic-O-aliphatic, or -aromatic-O-aromatic.

Halo (or halide or halogen): Fluoro, chloro, bromo, or iodo. In some embodiments, this can include astatine.

Haloaliphatic: An aliphatic group wherein one or more hydrogen atoms, such as one to 10 hydrogen atoms, independently is replaced with a halogen atom, such as fluoro, bromo, chloro, or iodo.

Haloaliphatic-aryl: An aryl group that is or can be coupled to a polymerizable nanohoop monomer, polymerizable nanohoop intermediate, and/or polymer disclosed herein, wherein the aryl group is or becomes coupled through a haloaliphatic group.

Haloaliphatic-heteroaryl: A heteroaryl group that is or can be coupled to a polymerizable nanohoop monomer, polymerizable nanohoop intermediate, and/or polymer disclosed herein, wherein the heteroaryl group is or becomes coupled through a haloaliphatic group.

Haloalkyl: An alkyl group wherein one or more hydrogen atoms, such as one to 10 hydrogen atoms, independently is replaced with a halogen atom, such as fluoro, bromo, chloro, or iodo. In an independent embodiment, haloalkyl can be a CX$_3$ group, wherein each X independently can be selected from fluoro, bromo, chloro, iodo (or in some embodiments, astatine).

Heteroaliphatic: An aliphatic group comprising at least one heteroatom to 20 heteroatoms, such as one to 15 heteroatoms, or one to 5 heteroatoms, which can be selected from, but not limited to oxygen, nitrogen, sulfur, silicon, boron, selenium, phosphorous, and oxidized forms thereof within the group. Alkoxy, ether, amino, disulfide, peroxy, and thioether groups are exemplary (but non-limiting) examples of heteroaliphatic. In some embodiments, a fluorophore can also be described herein as a heteroaliphatic group, such as when the heteroaliphatic group is a heterocyclic group.

Heteroaliphatic-aryl: An aryl group that is or can be coupled to a polymerizable nanohoop monomer, polymerizable nanohoop intermediate, and/or polymer disclosed herein, wherein the aryl group is or becomes coupled through a heteroaliphatic group.

Heteroaryl: An aryl group comprising at least one heteroatom to six heteroatoms, such as one to four heteroatoms, which can be selected from, but not limited to oxygen, nitrogen, sulfur, silicon, boron, selenium, phosphorous, and oxidized forms thereof within the ring. Such heteroaryl groups can have a single ring or multiple condensed rings, wherein the condensed rings may or may not be aromatic and/or contain a heteroatom, provided that the point of attachment is through an atom of the aromatic heteroaryl group. However, in certain examples, context or express disclosure may indicate that the point of attachment is through a non-aromatic portion of the condensed ring system. Heteroaryl groups may be substituted with one or more groups other than hydrogen, such as aliphatic, heteroaliphatic, haloaliphatic, haloheteroaliphatic, aromatic, or an organic functional group. In some embodiments, a fluorophore can also be described herein as a heteroaryl group.

Heteroatom: An atom other than carbon or hydrogen, such as (but not limited to) oxygen, nitrogen, sulfur, silicon, boron, selenium, or phosphorous. In particular disclosed embodiments, such as when valency constraints do not permit, a heteroatom does not include a halogen atom.

Ketone: —C(O)R$^a$, wherein R$^a$ is selected from aliphatic, heteroaliphatic, haloaliphatic, haloheteroaliphatic, aromatic, or an organic functional group.

Nanohoop: A compound comprising linked rings, such as linked aromatic rings (or groups), that are organized to form a hoop-like structure. In some embodiments, the rings can be linked in a para-, ortho-, or meta-substituted manner, or other positional manner. In some embodiments, the rings of the nanohoop skeleton are all linked in a para-substituted manner such that the bonds connecting each ring to two other rings of the nanohoop compound are para-substituted relative to each other. In some additional embodiments, at least one ring of the nanohoop skeleton is linked in a meta-substituted manner such that the bonds connecting this ring to two other rings of the nanohoop compound are meta-substituted relative to each other.

Organic Functional Group: A functional group that may be provided by any combination of aliphatic, heteroaliphatic, aromatic, haloaliphatic, and/or haloheteroaliphatic groups, or that may be selected from, but not limited to, aldehyde; aroxy; acyl halide; halogen; nitro; cyano; azide; carboxyl (or carboxylate); amide; ketone; carbonate; imine; azo; carbamate; hydroxyl; thiol; sulfonyl (or sulfonate); oxime; ester; thiocyanate; thioketone; thiocarboxylic acid; thioester; dithiocarboxylic acid or ester; phosphonate; phosphate; silyl ether; sulfinyl; thial; or combinations thereof.

Oxime: —CR$^a$=NOH, wherein R$^a$ is hydrogen, aliphatic, heteroaliphatic, haloaliphatic, haloheteroaliphatic, aromatic, or an organic functional group.

Peroxy: —O—OR$^a$ wherein R$^a$ is hydrogen, aliphatic, heteroaliphatic, haloaliphatic, haloheteroaliphatic, aromatic, or an organic functional group.

Phosphate: —O—P(O)(OR$^a$)$_2$, wherein each R$^a$ independently is hydrogen, aliphatic, heteroaliphatic, haloaliphatic, haloheteroaliphatic, aromatic, or an organic functional group; or wherein one or more R$^a$ groups are not present and the phosphate group therefore has at least one negative charge, which can be balanced by a counterion, M⁺, wherein each M⁺ independently can be an alkali ion, such as K⁺, Na⁺, Li⁺; an ammonium ion, such as ⁺N(R$^b$)$_4$ where R$^b$ is H, hydrogen, aliphatic, heteroaliphatic, haloaliphatic, haloheteroaliphatic, aromatic, or an organic functional group; or an alkaline earth ion, such as [Ca$^{2+}$]$_{0.5}$, [Mg$^{2+}$]$_{0.5}$, or [Ba$^{2+}$]$_{0.5}$.

Phosphonate: —P(O)(OR$^a$)$_2$, wherein each R$^a$ independently is hydrogen, aliphatic, heteroaliphatic, haloaliphatic, haloheteroaliphatic, aromatic, or an organic functional group; or wherein one or more R$^a$ groups are not present and the phosphate group therefore has at least one negative charge, which can be balanced by a counterion, M⁺, wherein each M⁺ independently can be an alkali ion, such as K⁺, Na⁺, Li⁺; an ammonium ion, such as ⁺N(R$^b$)$_4$ where R$^b$ is hydrogen, aliphatic, heteroaliphatic, haloaliphatic, haloheteroaliphatic, aromatic, or an organic functional group; or an alkaline earth ion, such as [Ca$^{2+}$]$_{0.5}$, [Mg$^{2+}$]$_{0.5}$, or [Ba$^{2+}$]$_{0.5}$.

Silyl Ether: —OSiR$^a$R$^b$, wherein each of R$^a$ and R$^b$ independently is selected from hydrogen, aliphatic, heteroaliphatic, haloaliphatic, haloheteroaliphatic, aromatic, or an organic functional group.

Sulfinyl: —S(O)R$^a$, wherein R$^a$ is selected from hydrogen, aliphatic, heteroaliphatic, haloaliphatic, haloheteroaliphatic, aromatic, or an organic functional group.

Sulfonyl: —SO$_2$R$^a$, wherein R$^a$ is selected from hydrogen, aliphatic, heteroaliphatic, haloaliphatic, haloheteroaliphatic, aromatic, or an organic functional group.

Sulfonamide: —SO$_2$NR$^a$R$^b$ or —N(R$^a$)SO$_2$R$^b$, wherein each of R$^a$ and R$^b$ independently is selected from hydrogen, aliphatic, heteroaliphatic, haloaliphatic, haloheteroaliphatic, aromatic, or an organic functional group.

Sulfonate: —SO$_3^-$, wherein the negative charge of the sulfonate group may be balanced with an M⁺ counter ion, wherein M⁺ may be an alkali ion, such as K⁺, Na⁺, Li⁺; an ammonium ion, such as ⁺N(R$^b$)$_4$ where R$^b$ is hydrogen, aliphatic, heteroaliphatic, haloaliphatic, haloheteroaliphatic, aromatic, or an organic functional group; or an alkaline earth ion, such as [Ca$^{2+}$]$_{0.5}$, [Mg$^{2+}$]$_{0.5}$, or [Ba$^{2+}$]$_{0.5}$.

Thial: —C(S)H.

Thiocarboxylic acid: —C(O)SH, or —C(S)OH.

Thiocyanate: —S—CN or —N=C=S.

Thioester: —C(O)SR$^a$ or —C(S)OR$^a$ wherein R$^a$ is selected from hydrogen, aliphatic, heteroaliphatic, haloaliphatic, haloheteroaliphatic, aromatic, or an organic functional group.

Thioether: —S-aliphatic or —S-aromatic, such as —S-alkyl, —S-alkenyl, —S-alkynyl, —S-aryl, or —S-heteroaryl; or -aliphatic-S-aliphatic, -aliphatic-S-aromatic, -aromatic-S-aliphatic, or -aromatic-S-aromatic.

Thioketone: —C(S)R$^a$ wherein R$^a$ is selected from hydrogen, aliphatic, heteroaliphatic, haloaliphatic, haloheteroaliphatic, aromatic, or an organic functional group.

Thiophenyl: A five-membered aromatic ring comprising a sulfur atom and having a structure

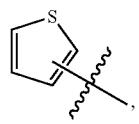

wherein the five-membered aromatic ring can be substituted with one or more substituents.

II. Introduction

Molecules with radial pi-conjugation as opposed to the more standard manifestations of linear pi-conjugation have fascinated chemists for decades. Despite certain advances in developing molecules containing radial pi-conjugation, the use of nanohoop radial conjugation has not been utilized in the design of pi-conjugated polymeric materials, where the nature of the pi-electron circuits play a role in defining the resulting electronic properties. Given that radical ions created within nanohoops can delocalize partially or entirely around the cyclic frameworks depending on the molecular size, the present disclosure is directed to new motifs containing extended delocalization in conjugated polymer systems whereby excitons or charge carriers would freely migrate along the linear pi-conjugated backbone as well as radially through the nanohoop structure. This combination of radial and linear conjugation opens new possibilities for inter-polymer energy migration or even supramolecular sensing schemes that blend the molecular selectivity of nanohoops with the sensitivity enhancements known for pi-conjugated electronic polymers.

Figure 3:
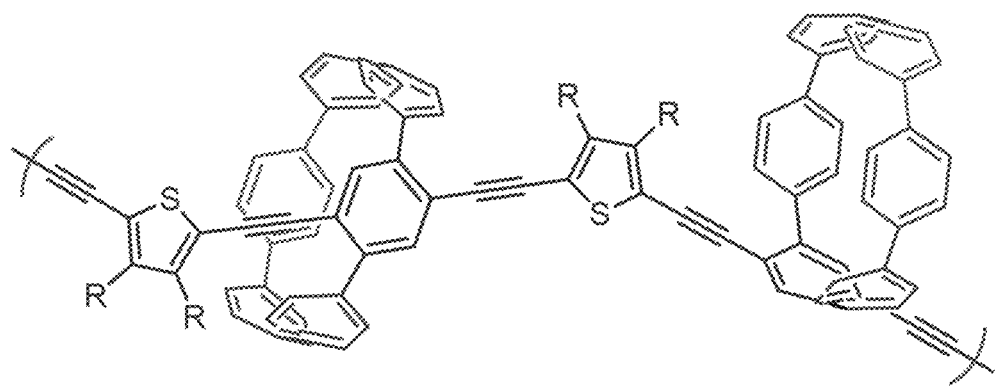
FIG. 3 illustrates a representation of combined linear and curved delocalization pathways with examples shown in a polymer embodiment.

Disclosed herein are embodiments of polymerizable nanohoop monomers and their subsequent polymerization into conjugated polymers comprising nanohoop-containing polymeric backbones. In particular embodiments, the nanohoop monomer becomes part of the polymer backbone by the fact that two carbon atoms of at least one aromatic ring system of the nanohoop become directly and covalently attached to at least one functional group of the polymer backbone (as opposed to extending from the polymer backbone as a side chain). Solely by way of example, see FIG. 3. Because the nanohoop becomes part of the polymeric backbone, conjugation is achieved linearly (through at least one nanohoop ring system to alkyne arms of a diyne-aromatic linker component) and radially (through the nanohoop itself). Also disclosed herein are computational methods that can be used to understand electronic processes and that can be used in making polymer nanohoops. The electronic properties of the polymer nanohoop embodiments disclosed herein reveal unique modes of delocalization not afforded by either the curved or linear pi-conjugation pathways in isolation and can serve as new compounds for conjugated polymer electronics.

III. Polymer and Polymerizable Nanohoop Monomer/Intermediate Embodiments

Disclosed herein are embodiments of a polymer comprising a nanohoop-containing polymeric backbone. In such polymer embodiments, the nanohoops used to make the polymer become part of the polymeric backbone rather than extending from the polymeric backbone. In particular embodiments, at least one ring system of the nanohoop becomes part of the polymeric backbone of the polymer. The polymeric backbone also comprises a diyne-aromatic linker component comprising an aromatic group functionalized with two alkyne "arms." In particular embodiments, the polymer can have a structure satisfying Formula I.

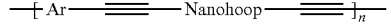

Formula I

With reference to Formula I, the nanohoop can be a nanohoop comprising any suitable number of aromatic ring systems wherein each aromatic ring system is bound to at least two other ring systems of the nanohoop through two separate single covalent bonds tare positioned para, ortho, or meta relative to one another (e.g., 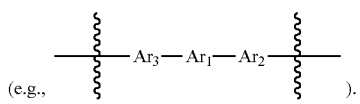 ).

In some embodiments, the nanohoop comprises 6 or more aromatic ring systems (e.g., 6 to 100 aromatic ring systems, or 6 to 50, or 6 to 25, or 6 to 15, or 6 to 10 aromatic ring systems). In particular embodiments, at least one ring system of the nanohoop is covalently attached to the remainder of the polymeric backbone, such as the diyne-aromatic linker component. In particular embodiments, one diyne-aromatic linker component is bound to a carbon atom of a single ring system of the nanohoop and a second diyne-aromatic linker component is bound to a second carbon atom of the single ring system of the nanohoop wherein the two diyne-aromatic linker components are positioned para relative to one another. As such, in some embodiments, the nanohoop is bound to the two alkyne groups of Formula I by two different carbon atoms of a single aromatic ring system of the nanohoop. This positioning repeats throughout the polymer backbone. In yet other embodiments, one diyne-aromatic linker component is bound to a carbon atom of a single ring system of the nanohoop and a second diyne-aromatic linker component is bound to a carbon atom of a different single ring system of the nanohoop so as to provide a dis-jointed polymer chain. As such, in some embodiments, the nanohoop is bound to the two alkyne groups of Formula I by two different carbon atoms of two different aromatic ring systems of the nanohoop.

The aromatic component of the diyne-aromatic linker (e.g., "Ar" as illustrated in Formula I) can be an aromatic ring system and can, in some embodiments, include one or more substituents attached to the aromatic ring system. Any number of substituents can be attached to the aromatic ring system. Exemplary substituents are disclosed below. With reference to Formula I, n can be an integer ranging from 2 or greater, such as 2 to 10,000 or greater, or 2 to 1000 or greater, or 2 to 100 or greater, or the like.

In some embodiments, the polymer has a structure satisfying Formulas IIA or IIB.

Formula IIA

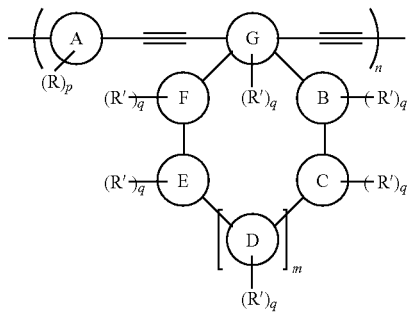

Formula IIB

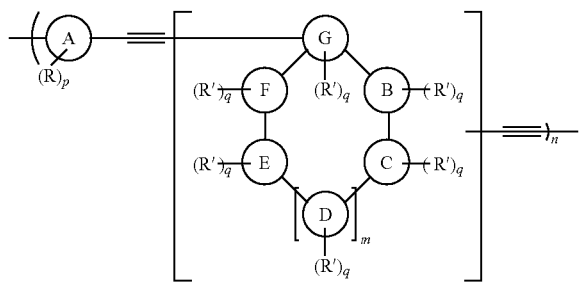

As illustrated by Formula IIA, the polymer has a skeleton wherein the nanohoop is bound to the two alkyne groups of Formula IIA by two different carbon atoms of a single aromatic ring system of the nanohoop. As illustrated by Formula IIB, the nanohoop is bound to the two alkyne groups of Formula IIB by two different carbon atoms of two different aromatic ring systems of the nanohoop (with reference to Formula IIB, one alkyne group is attached to ring G, whereas the floating alkyne group is intended to indicate that the floating alkyne group is attached to any one of rings, B, C, D, E, or F through a bond formed between the alkyne and a carbon atom of the ring system, and typically not an R' group).

With reference to Formulas IIA and IIB, each A ring independently can be an aromatic ring system. In some embodiments, each A ring is an aryl or heteroaryl ring. In particular disclosed embodiments, each A ring independently is phenyl, naphthyl, pyridinyl, thiophenyl, furanyl, imidazoyl, or other six-membered or 5-membered aryl or heteroaryl rings). In representative embodiments, each A ring independently is a phenyl or thiophenyl group (e.g., benzene or thiophene). Each R independently can be selected from aliphatic, heteroaliphatic, haloaliphatic, halo-heteroaliphatic, aromatic, or an organic functional group. In some embodiments, each R independently is selected from aliphatic. In some embodiments, each R independently is 2-ethylhexyl or octyl. Each of rings B, C, D, E, F, and G independently can be an aromatic ring system, such as an aryl or heteroaryl group. In particular embodiments, each of rings B, C, D, E, F, and G independently can be phenyl. Each R' independently can be aliphatic, heteroaliphatic, haloaliphatic, aromatic, or an organic functional group. With reference to Formulas IIA and IIB, n is as recited above for Formula I; each m independently is an integer selected from 1 to 95, such 1 to 50, or 1 to 25, or 1 to 15, or 1 to 10; each p independently is an integer selected from 0 to 10, such as 1 to 5, or 1 to 4, or 1 to 3; and each q independently is an integer selected from 0 to 10, such as 1 to 5, or 1 to 4, or 1 to 3. In particular embodiments, each m independently is an integer selected from 1 to 10, such as 1, 2, 3, 4, 5, 6, 7, 8, 9, or 10, each p independently is 0, 1, or 2, and each q independently is 0, 1, 2, 3, or 4.

In some embodiments, the polymer can have a structure satisfying any one of Formulas IIIA, IIIB, IVA, IVA', IVB, or IVB'.

Formula IIIA

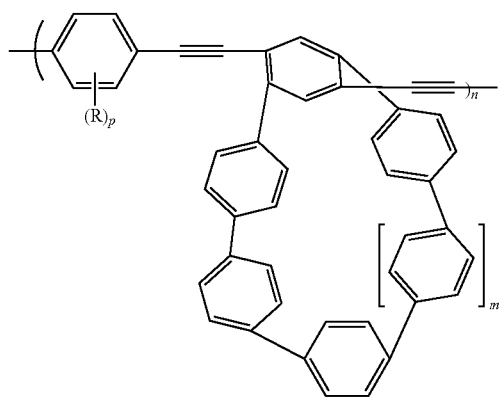

Formula IIIB

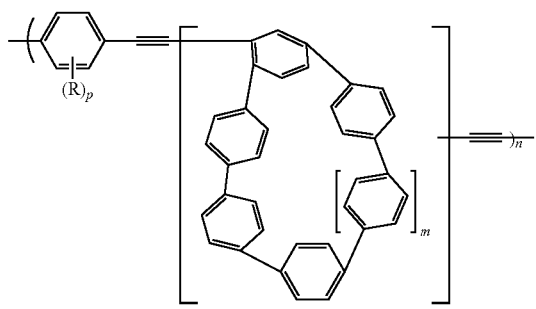

Formula IVA

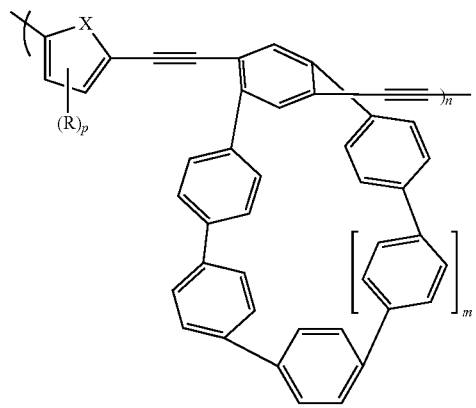

Formula IVA'

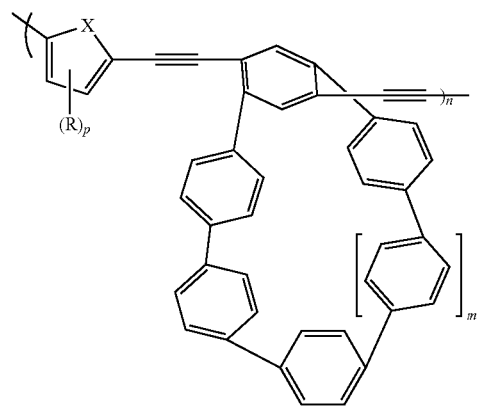

Formula IVB

Formula IVB'

With reference to Formulas IIIA, IIIB, IVA, IVA', IVB, and IVB', each X independently can be selected from O, NH, or S; each R independently can be as recited above for Formulas IIA or IIB; each p independently can be as recited above for Formulas IIA or IIB, and n and m independently can be as recited above for Formulas IIA or IIB. In particular embodiments, each R independently can be aliphatic. In particular embodiments for Formulas IVA and IVB, X is O, NH, or S. In particular embodiments, each m is 1 or 3 and p is 2.

Representative polymer embodiments are illustrated below.

m = 1 or 3

-continued
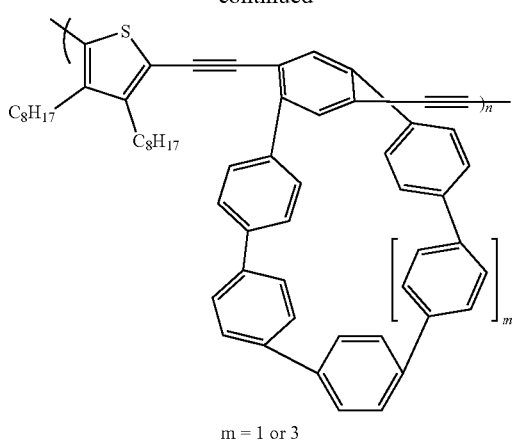
m = 1 or 3
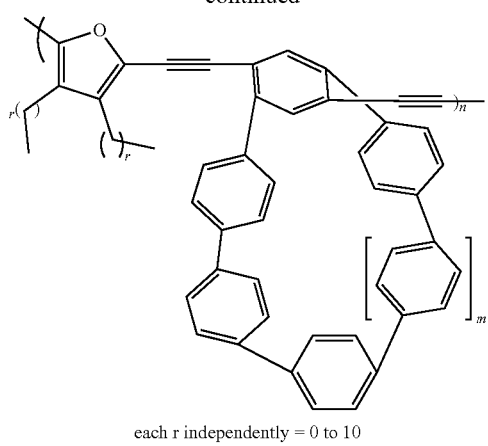
each r independently = 0 to 10
m = 1 or 3
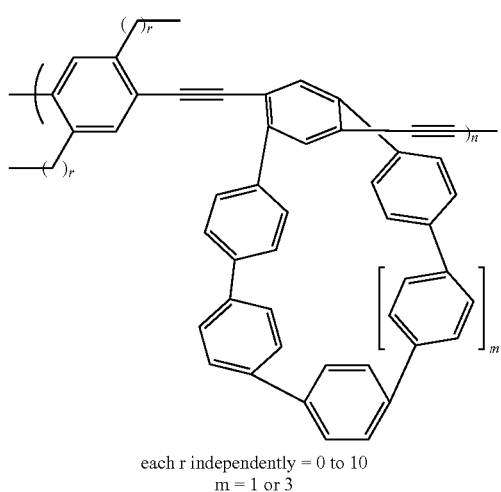
each r independently = 0 to 10
m = 1 or 3
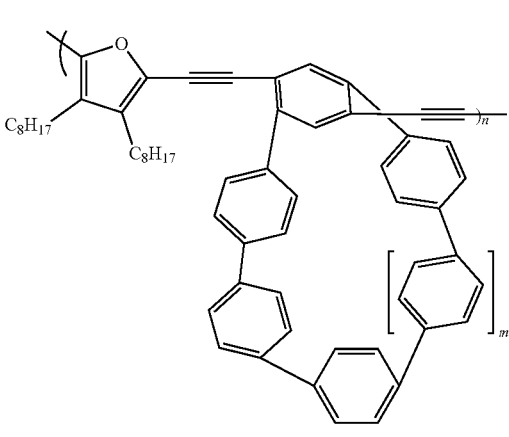
m = 1 or 3
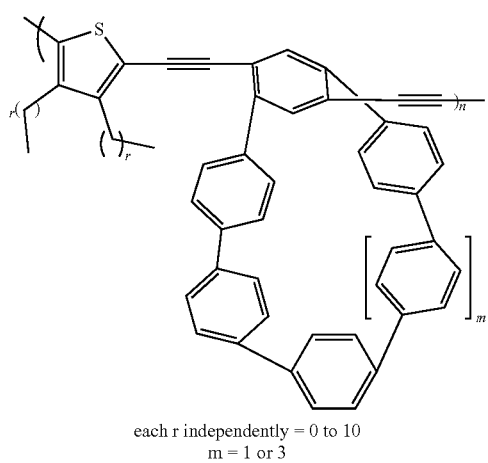
each r independently = 0 to 10
m = 1 or 3
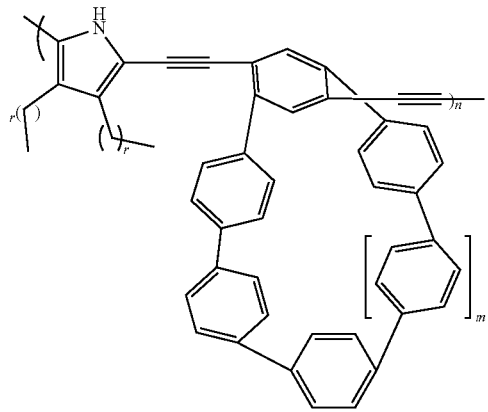
each r independently = 0 to 10
m = 1 or 3

-continued
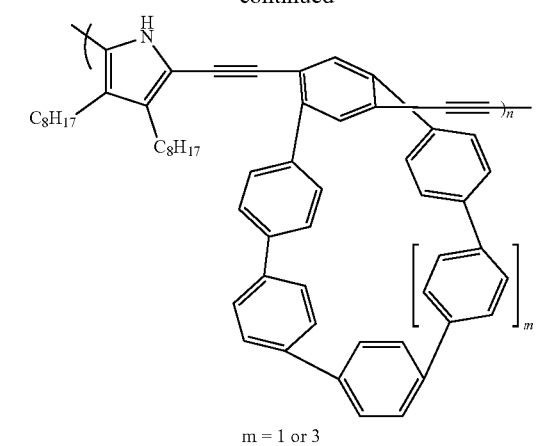
m = 1 or 3
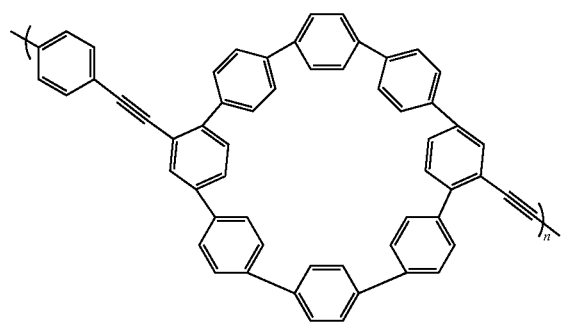
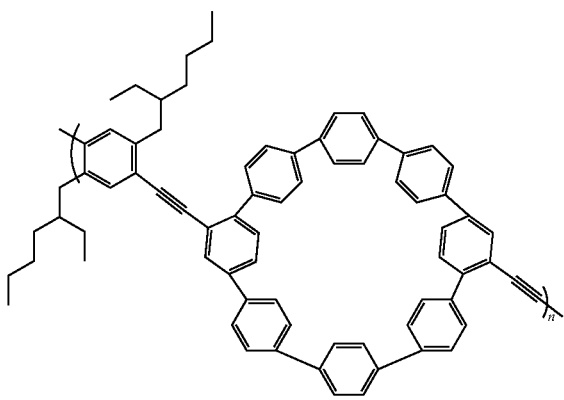
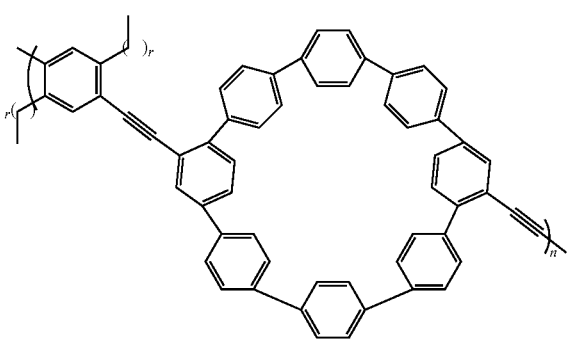
each r independently = 0 to 10
-continued
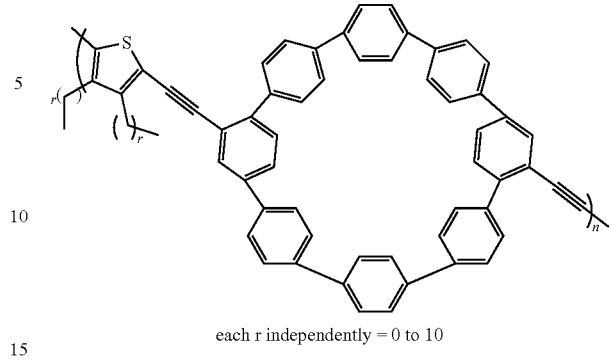
each r independently = 0 to 10
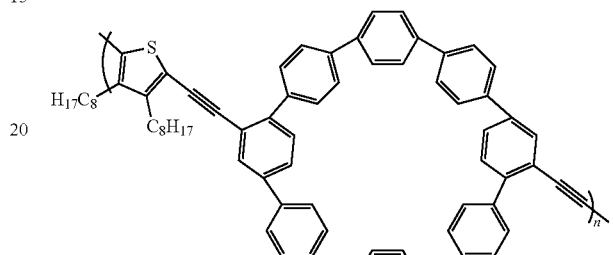
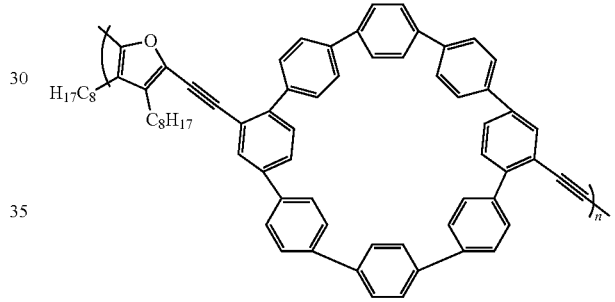
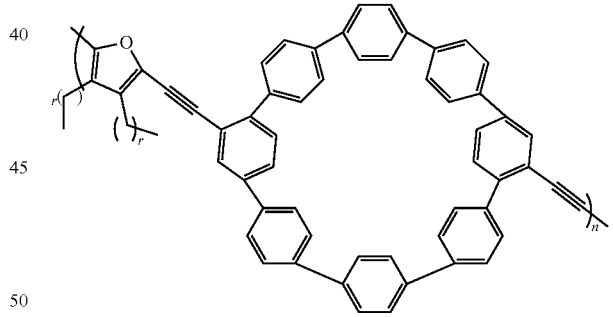
each r independently = 0 to 10
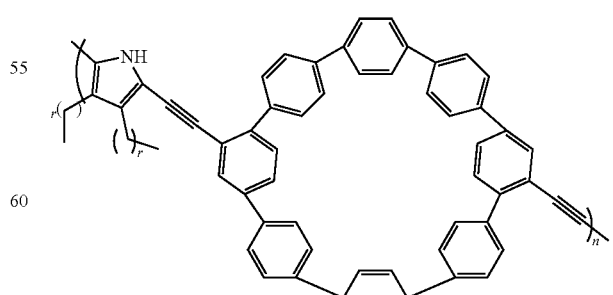
each r independently = 0 to 10

-continued

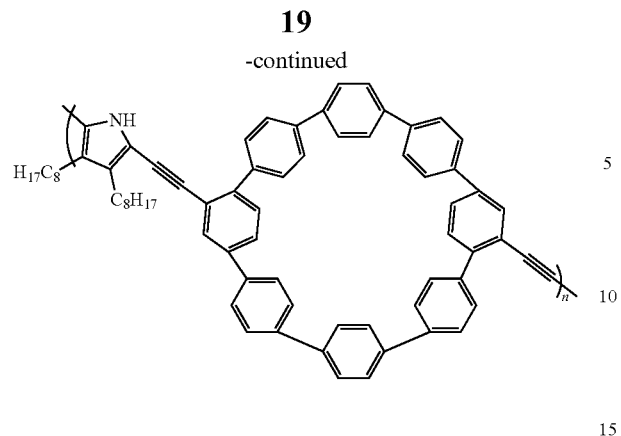

Also disclosed herein are embodiments of polymerizable nanohoop monomer compounds and/or polymerizable nanohoop intermediates that can be used to make polymer embodiments described above. In some embodiments, the polymerizable nanohoop monomer compound and/or polymerizable nanohoop intermediate can have a structure satisfying Formula V or VI below. With reference to these formulas, the nanohoop can be as disclosed for any of the formulas discussed above, Ar can be an aromatic ring system as disclosed above for any of the formulas discussed above, and Y can be hydrogen, Cu, a palladium complex, or an Ar group.

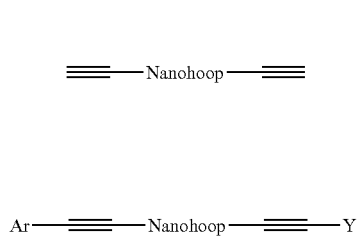

Formula V

Formula VI

In some embodiments, the polymerizable nanohoop monomer compound and/or polymerizable nanohoop intermediate can have a structure satisfying Formulas VIIA, VIIB, VIIIA, or VIIIB below. With reference to these formulas, the indicated variables can be as recited above for the polymer Formulas IIA, IIB, IIIA, IIIB, IVA, IVA', IVB, or IVB'. In particular embodiments, the Ar group is a phenyl or a five-membered heteroaryl group (e.g., a thiophenyl group, a furanyl group, a pyrrolyl group, or the like) and Y is hydrogen or copper.

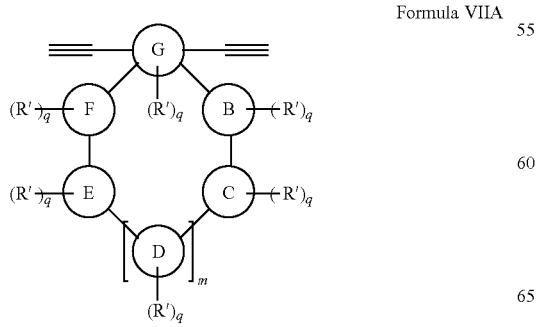

Formula VIIA

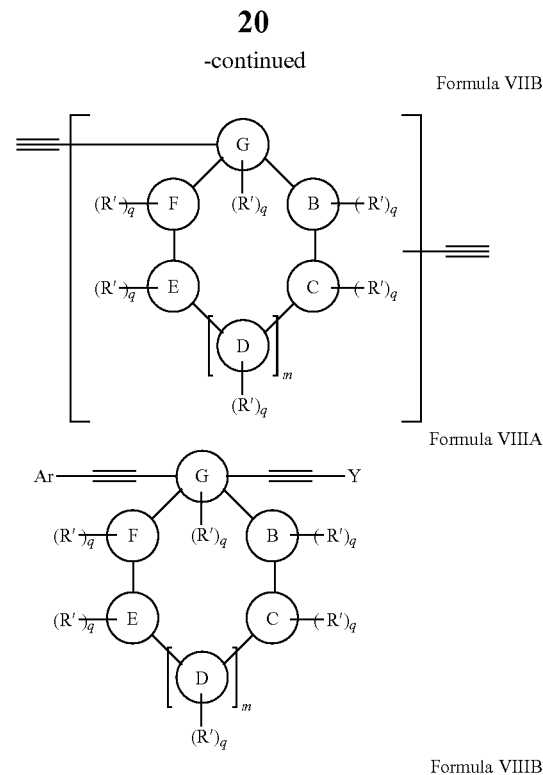

Formula VIIB

Formula VIIIA

Formula VIIIB

In some embodiments, the polymerizable nanohoop monomer compound and/or polymerizable nanohoop intermediate can have a structure satisfying Formulas IXA, IXB, XA, or XB below. With reference to these formulas, m and Y can be as recited herein. In some embodiments, the Ar group is a phenyl or a five-membered heteroaryl group (e.g., a thiophenyl group, a furanyl group, a pyrrolyl group, or the like) comprising a halogen substituent.

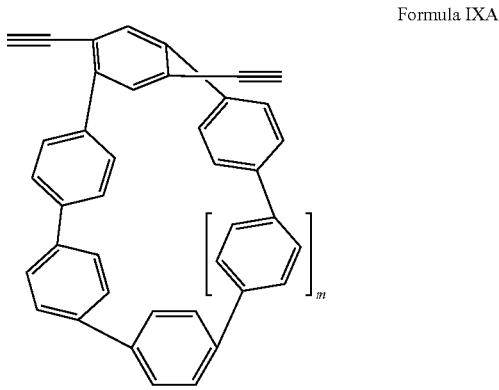

Formula IXA

Formula IXB
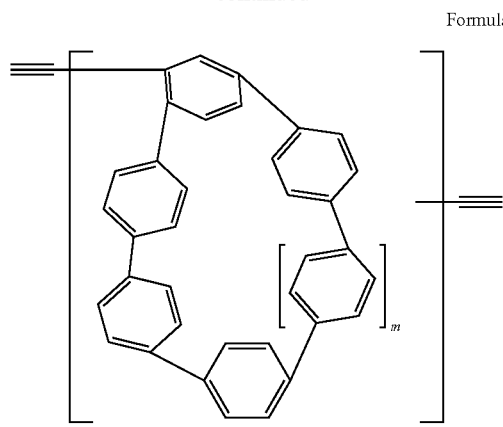
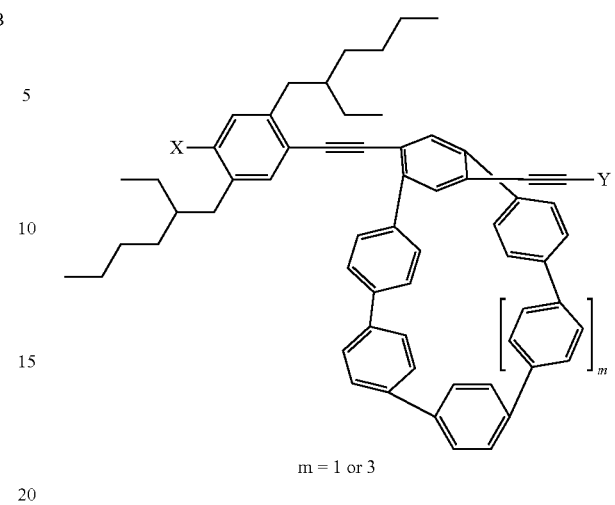
m = 1 or 3
Formula XA
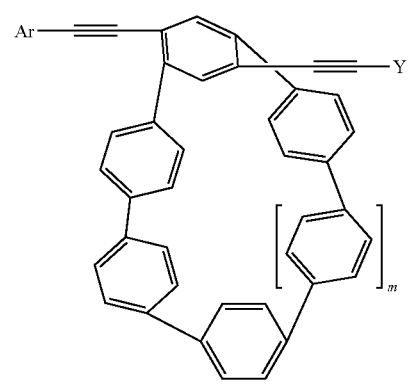
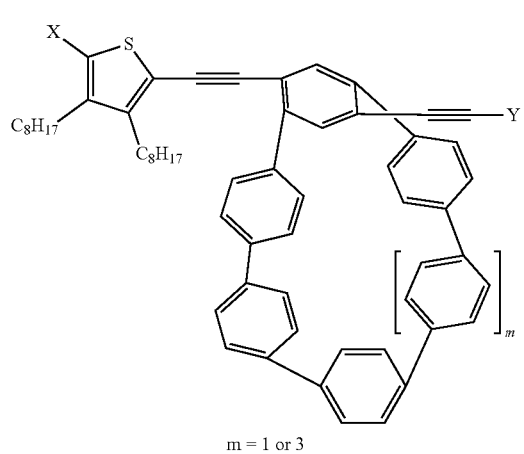
m = 1 or 3
Formula XB
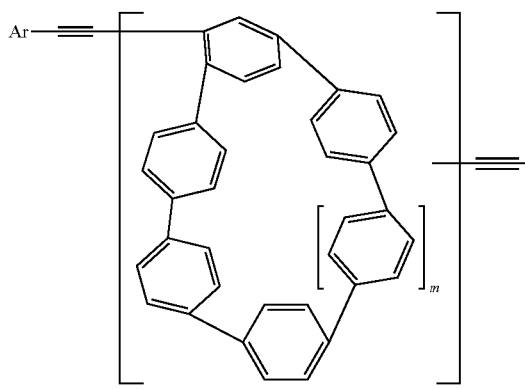
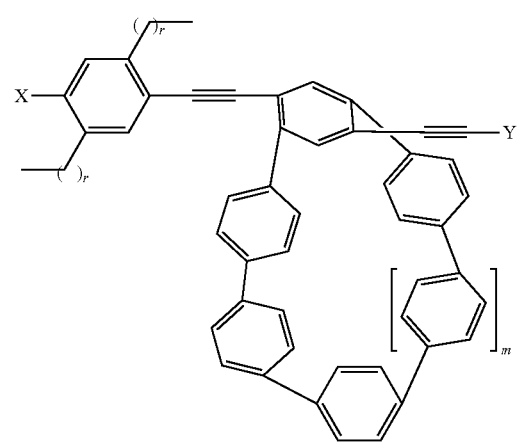
each r independently = 0 to 10
m = 1 or 3
Representative polymerizable nanohoop monomer compounds and/or polymerizable nanohoop intermediates are illustrated below, wherein X is a halogen, m is 1 or 3, and Y is hydrogen, copper, a palladium complex, or an Ar group.

-continued
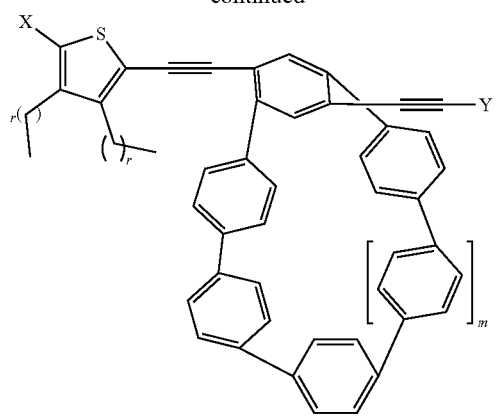
each r independently = 0 to 10
m = 1 or 3
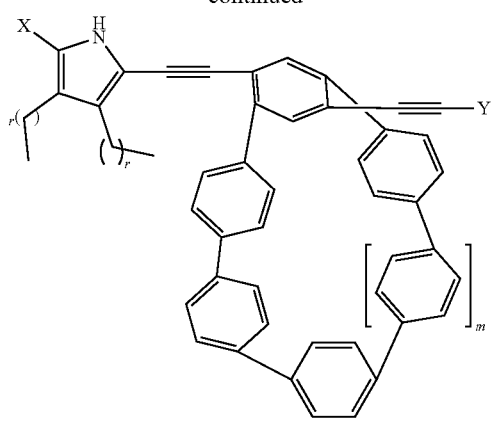
each r independently = 0 to 10
m = 1 or 3
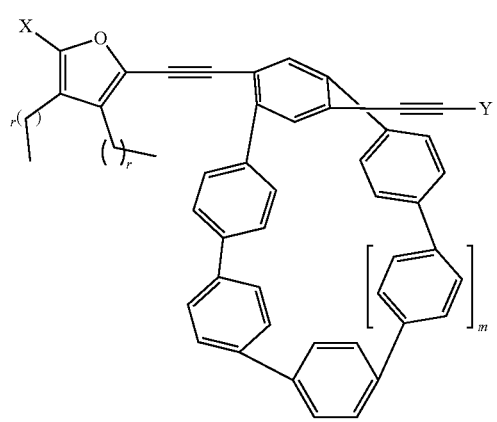
each r independently = 0 to 10
m = 1 or 3
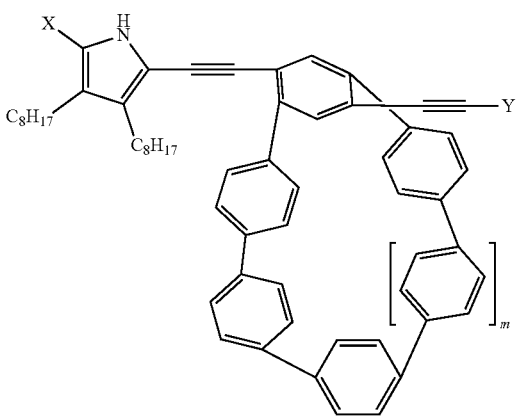
m = 1 or 3
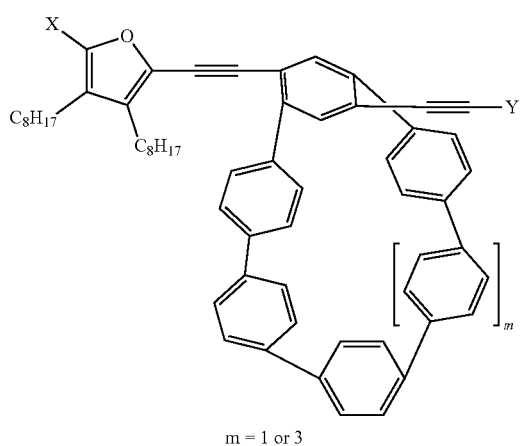
m = 1 or 3
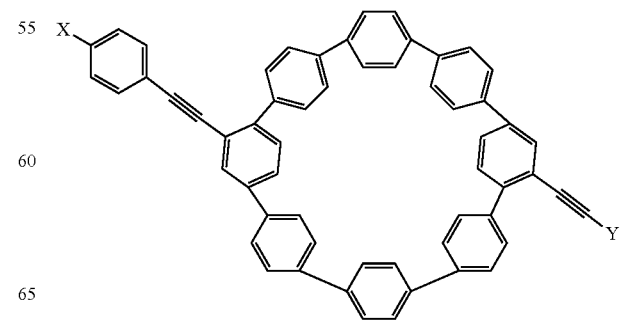

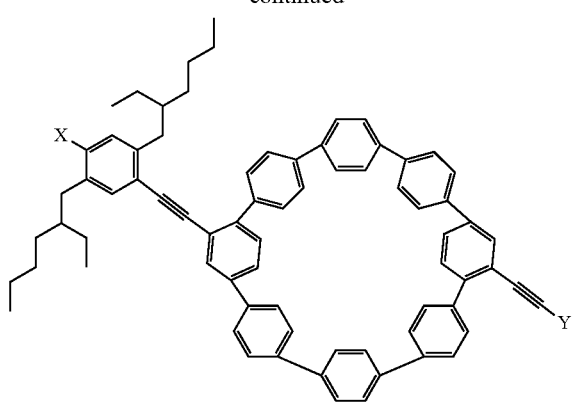
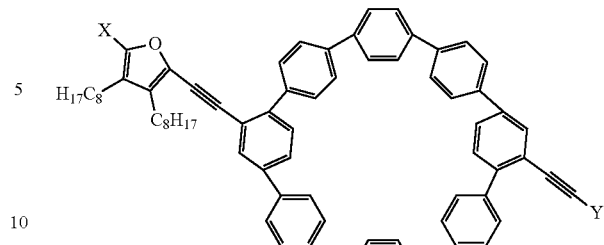
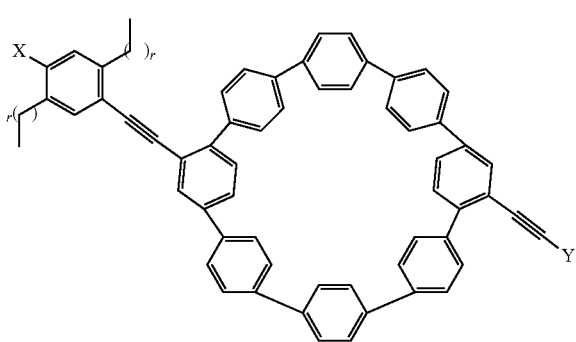
each r independently = 0 to 10
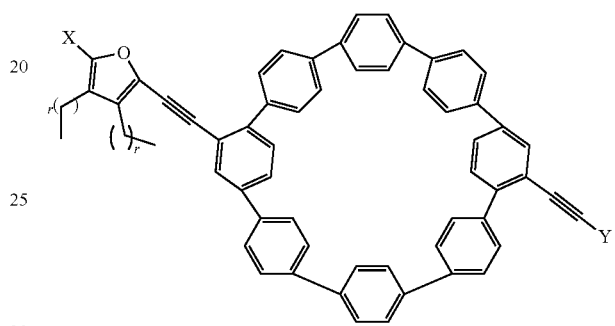
each r independently = 0 to 10
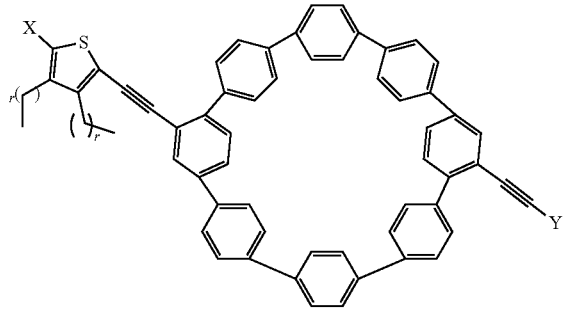
each r independently = 0 to 10
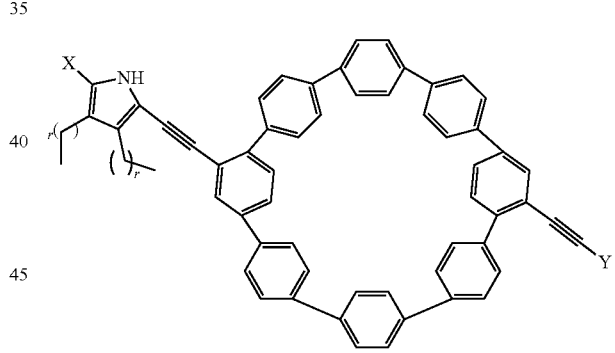
each r independently = 0 to 10
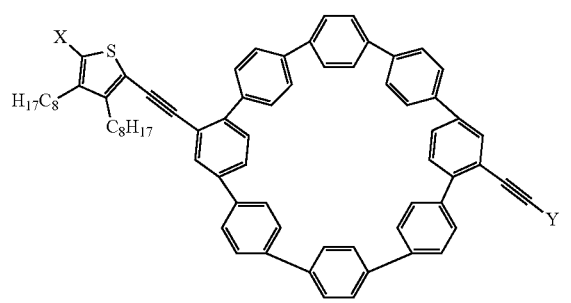
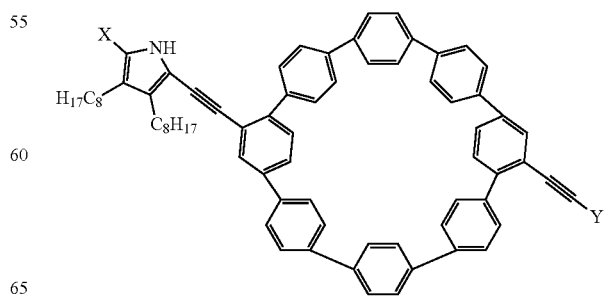

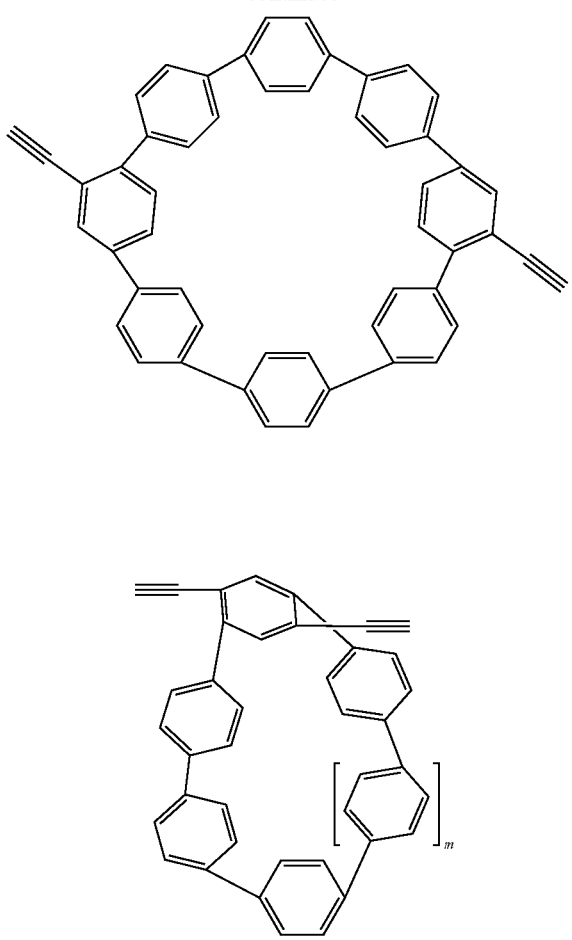

IV. Method Embodiments

Methods of making polymer embodiments are disclosed herein, as well as methods for making polymerizable nanohoop monomer embodiments. In particular embodiments, the method can comprise exposing a polymerizable nanohoop monomer (or a combination of two or more different polymerizable nanohoop monomer embodiments) to a transition metal catalyst, a copper-containing reagent, and a base, as well as an aromatic coupling partner functionalized with at least one halogen atom (and in some embodiments with two halogen atoms). In particular embodiments, the polymerizable nanohoop monomer comprises at least one ring of the nanohoop that is functionalized with two alkyne "arms" and at least one of these alkyne groups becomes bound to the aromatic coupling partner thereby forming a polymerizable intermediate that can bind with one or more such polymerizable intermediates to provide the polymer comprising polymeric backbone comprising a diyne-aromatic linker component and the nanohoops. In yet additional embodiments, the polymerizable nanohoop monomer comprises one ring of the nanohoop that is functionalized with one alkyne "arm" and another ring of the nanohoop that is functionalized with a second alkyne "arm" and at least one of these alkyne groups becomes bound to the aromatic coupling partner thereby forming a polymerizable intermediate that can bind with one or more such polymerizable intermediates to provide the polymer comprising polymeric backbone comprising a diyne-aromatic linker component and the nanohoops. In particular embodiments, the transition metal catalyst is a palladium catalyst (e.g., Pd(PPh$_3$)$_4$, (Ph$_3$P)$_2$PdCl$_2$, Pd(acac)$_2$, Pd(OAc)$_2$, or the like), the copper-containing reagent is CuI, and the base is an amine base (e.g., NEt$_3$ or the like), Cs$_2$CO$_3$, K$_2$CO$_3$, K$_3$PO$_4$, or the like. In some embodiments, the aromatic coupling partner is a dihalide-functionalized phenyl group (e.g., a dihalide-functionalized benzene) or a dihalide-functionalized five-membered heteroaryl group (e.g., a dihalide-functionalized thiophene, a dihalide-functionalized furan, a dihalide-functionalized pyrrole, or the like). In some embodiments, each halide group on such groups independently can be bromo, fluoro, chloro, or iodo. In particular embodiments, the aromatic coupling partner is a dibromo benzene or dibromo thiophene; a dichloro benzene or dichloro thiophene; or a diiodo phenyl or diiodo thiophene. The dihalide-functionalized aromatic coupling partner can further comprise one or more additional substituents (e.g., R in Formulas IIA and IIB).

In particular embodiments, polymerizable nanohoop monomer embodiments used in the method to make polymer embodiments disclosed herein can be made according to the method embodiments similar to the representative embodiments illustrated in Schemes 1, 2, and/or 3. A person of ordinary skill in the art will recognize, with the benefit of the present disclosure, that embodiments wherein the polymerizable nanohoop monomer comprises two different ring systems, each bearing one of the two alkyne groups, can be made by coupling a nanohoop precursor functionalized with one TMS-alkyne group (e.g., wherein nanohoop precursor 3 in Scheme 1 comprises a TMS-alkyne group) with a TMS-alkyne aromatic ring system (e.g., wherein starting material 1 in Scheme 1 comprises only one TMS-alkyne group).

Scheme 1

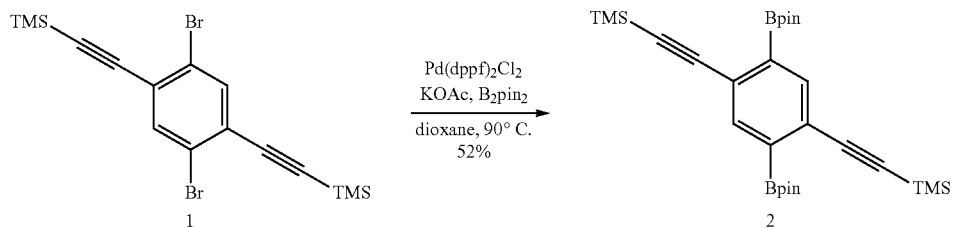

-continued
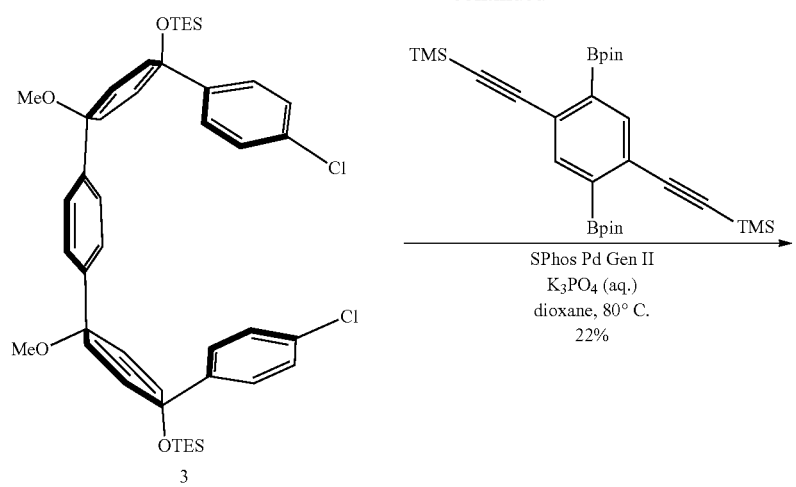
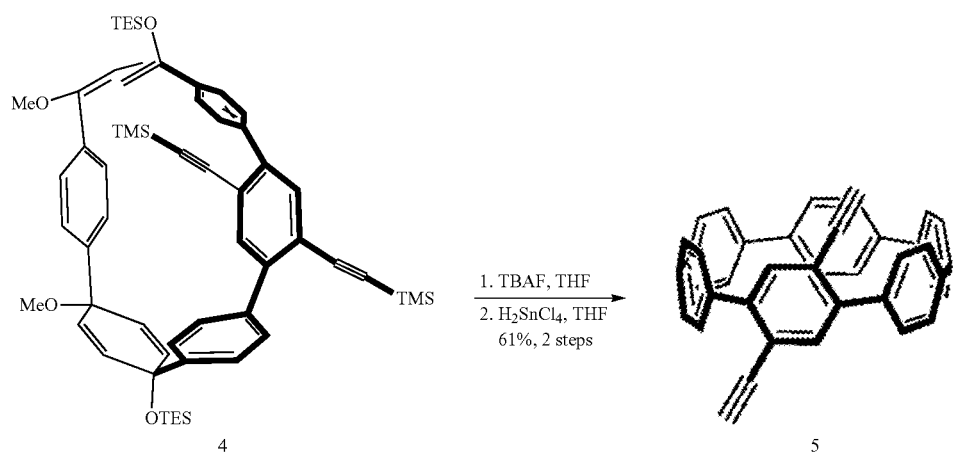
Scheme 2
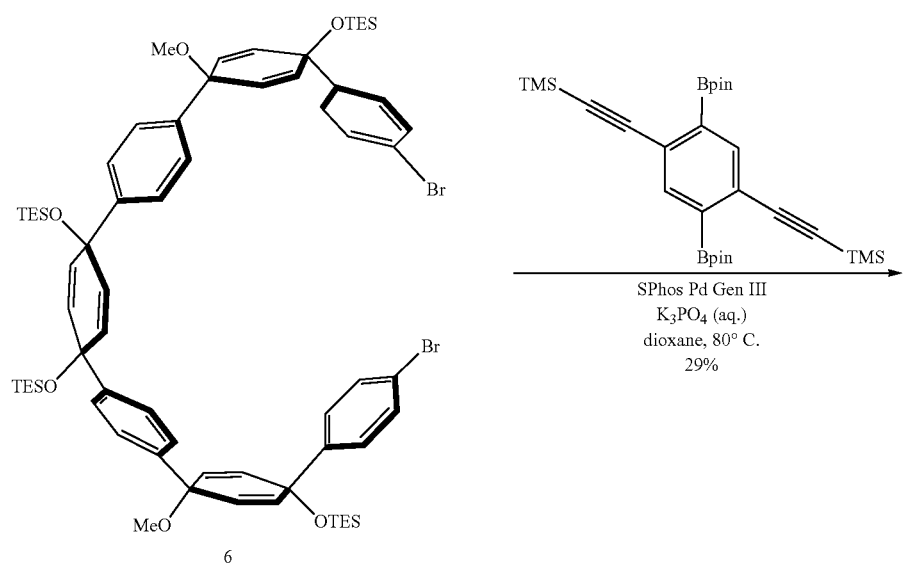

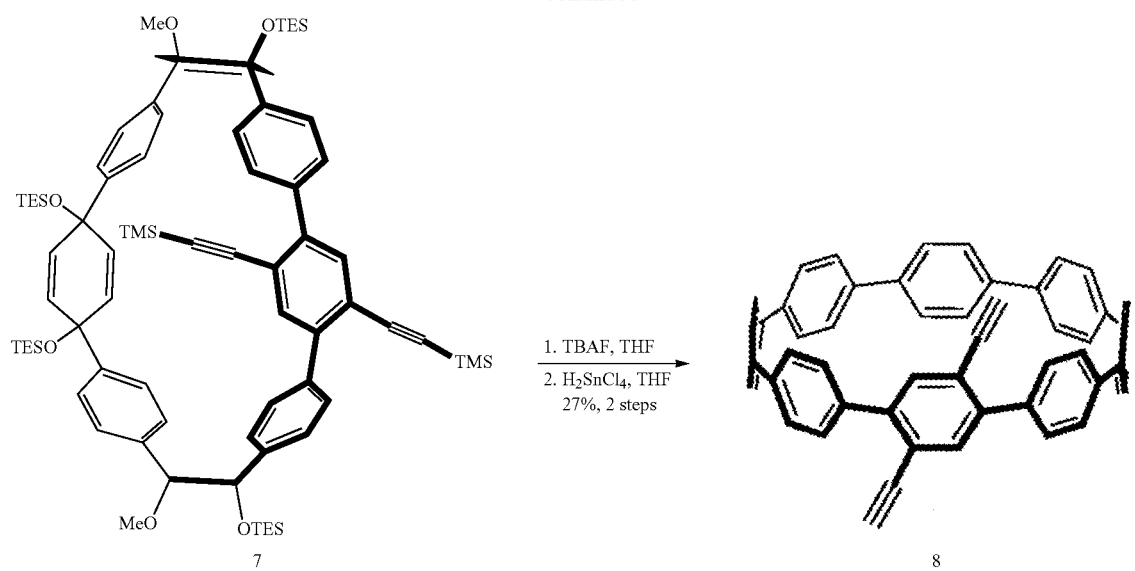
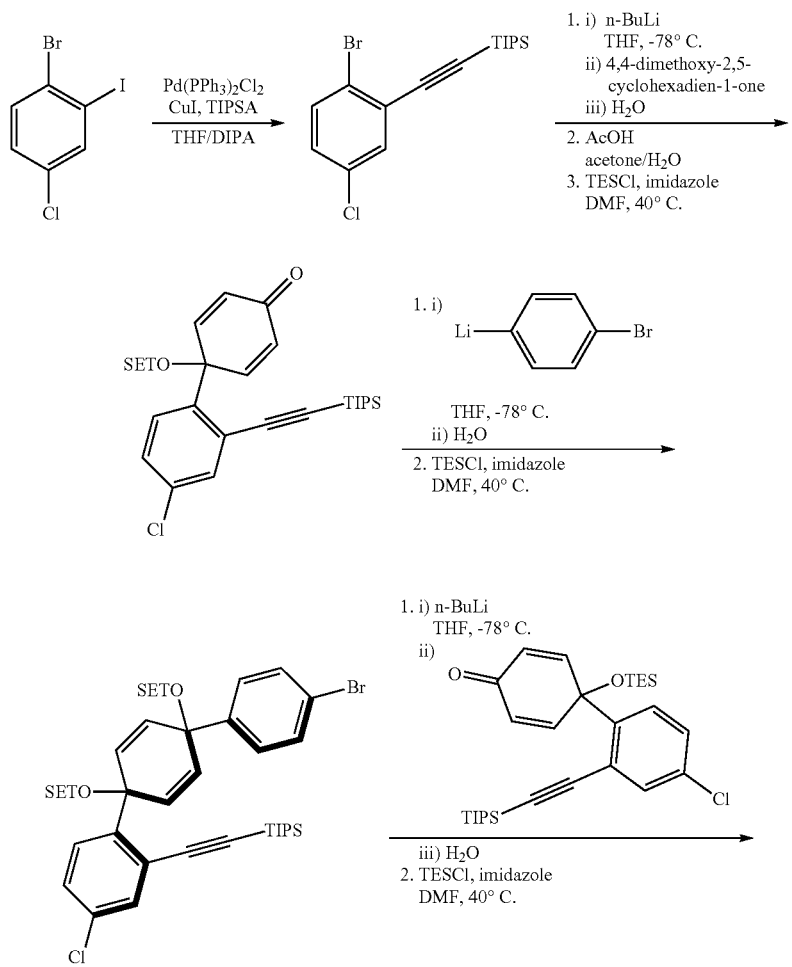

-continued
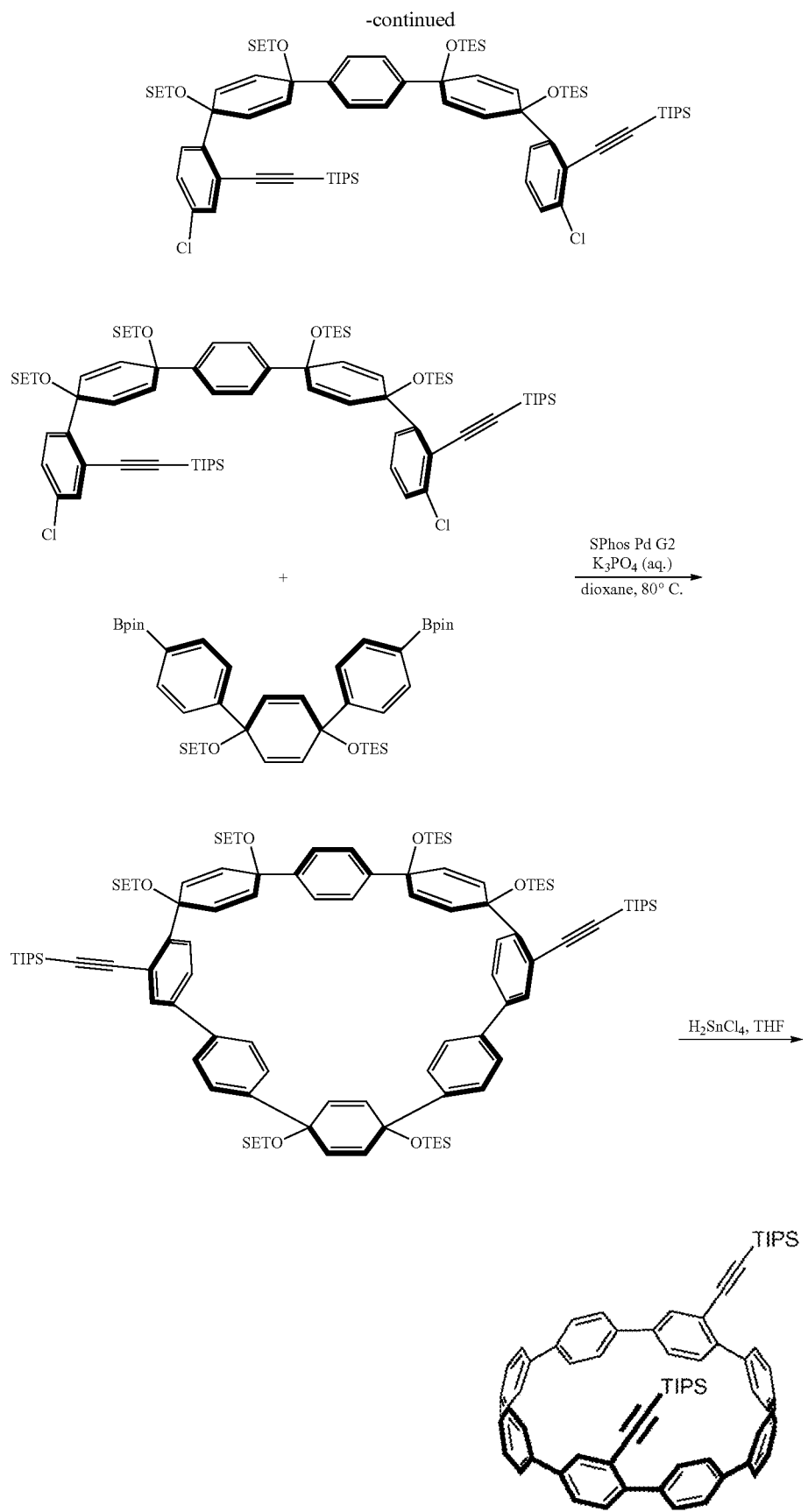

In some embodiments, the polymer embodiments disclosed herein can be used electronic devices, optoelectric devices, and other types of devices employing conjugated polymers. In some embodiments, polymer embodiments can be used as a graphene surrogate and thus can be used in applications that typically employ graphene and/or graphene derivatives. In yet additional embodiments, polymer embodiments can be used as a component for sensor devices (e.g., devices that employ supramolecular sensing).

V. Overview of Several Embodiments

Disclosed herein are embodiments of a polymer having a structure according to Formula I

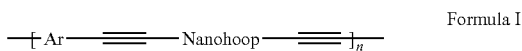

Formula I wherein the nanohoop comprises six or more aromatic ring systems and wherein each aromatic ring system is bound to at least two other aromatic ring systems of the nanohoop by two separate single covalent bonds positioned para, ortho, or meta relative to one another; Ar is an aromatic ring system; and n is an integer selected from 2 or greater.

In some embodiments, the nanohoop is bound to the two alkyne groups of Formula I by two different carbon atoms of a single aromatic ring system of the nanohoop. In some such embodiments, the two different carbon atoms of the single aromatic ring system of the nanohoop are positioned para relative to one another.

In yet some additional embodiments, the nanohoop is bound to the two alkyne groups of Formula I by two different carbon atoms of two different aromatic ring systems of the nanohoop.

In any or all of the above embodiments, the Ar group is an aryl ring or a heteroaryl ring.

In any or all of the above embodiments, the Ar group is selected from phenyl, naphthyl, pyridinyl, thiophenyl, furanyl, or imidazoyl.

In any or all of the above embodiments, n is an integer ranging from 2 to 10,000.

In any or all of the above embodiments, the polymer has a structure according to Formulas IIA or IIB as disclosed herein wherein each A ring independently is an aromatic ring system; each R independently is selected from aliphatic, heteroaliphatic, haloaliphatic, haloheteroaliphatic, aromatic, or an organic functional group; each of rings B, C, D, E, F, and G independently is an aromatic ring system; each R' independently is aliphatic, heteroaliphatic, haloaliphatic, aromatic, or an organic functional group; each m independently is an integer selected from 1 to 95; each p independently is an integer selected from 0 to 10; n is an integer selected from 2 or greater; and each q independently is an integer selected from 0 to 10.

In any or all of the above embodiments, each of rings A, B, C, D, E, F, and G independently is aryl or heteroaryl.

In any or all of the above embodiments, each A ring is a phenyl ring, furan, thiophene, or pyrrole, and wherein each of rings B, C, D, E, F, and G independently is phenyl.

In any or all of the above embodiments, p is 2 and each R independently is selected from aliphatic.

In any or all of the above embodiments, the polymer has a structure according to Formulas IIIA, IIIB, IVA', or IVB' as disclosed herein wherein each R is selected from aliphatic, heteroaliphatic, haloaliphatic, haloheteroaliphatic, aromatic, or an organic functional group; each m independently is an integer selected from 1 to 95; and each p independently is an integer selected from 0 to 10.

In any or all of the above embodiments, the polymer is selected from any of the polymer species disclosed herein.

In any or all of the above embodiments, wherein the polymer is

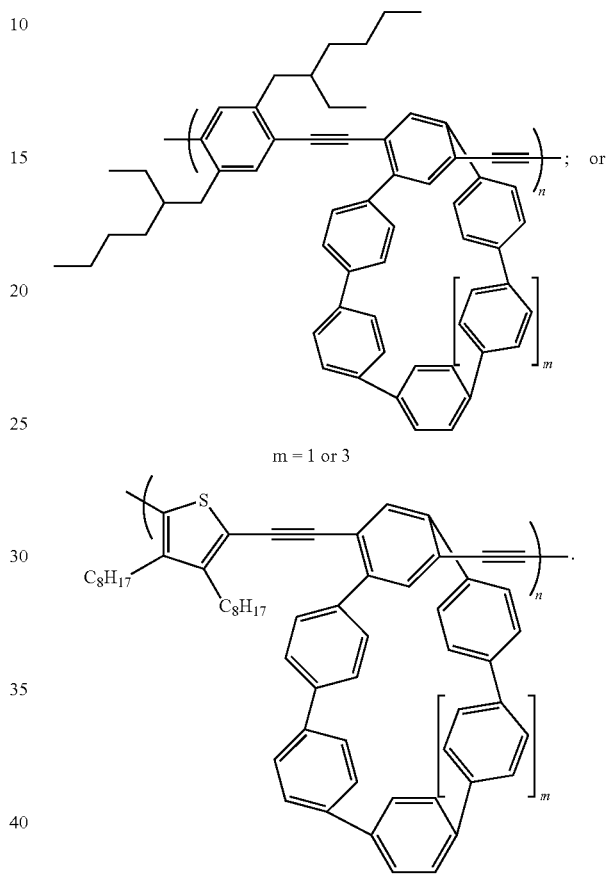

Also disclosed herein are embodiments of a compound having a structure according to Formula V or Formula VI,

Formula V

Formula VI wherein the nanohoop comprises six or more aromatic ring systems and wherein each aromatic ring system is bound to at least two other aromatic ring systems of the nanohoop by two separate single covalent bonds positioned para, ortho, or meta relative to one another; Ar is an aromatic ring system; and Y is hydrogen, copper, a palladium complex, or an aromatic ring system.

In some embodiments, the compound has a structure according to Formula VIIA, VIIB, VIIIA, or VIIIB as disclosed herein, wherein each of rings B, C, D, E, F, and G independently is an aromatic ring system; each R' independently is aliphatic, heteroaliphatic, haloaliphatic, aromatic, or an organic functional group; each m independently is an integer selected from 1 to 95; and each q independently is an integer selected from 0 to 10.

In some embodiments, the compound has a structure according to Formula IXA, IXB, XA, or XB as disclosed herein and wherein m is 1 or 3.

Also disclosed herein are embodiments of a method, comprising exposing a polymerizable nanohoop monomer to a transition metal catalyst, a copper-containing reagent, a base, and an aromatic coupling partner functionalized with a halogen atom to provide the polymer according to any or all of the polymer embodiments described above; wherein the polymerizable nanohoop monomer has a structure according to Formula V

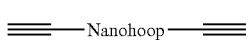

Formula V wherein the nanohoop of Formula V comprises six or more aromatic ring systems and wherein each aromatic ring system is bound to at least two other aromatic ring systems of the nanohoop by two separate single covalent bonds positioned para, ortho, or meta relative to one another.

In some embodiments, the transition metal catalyst is a palladium catalyst, the copper-containing reagent is CuI, the base is an amine base, $Cs_2CO_3$, $K_2CO_3$, or $K_3PO_4$, and the aromatic coupling partner comprises an aryl or heteroaryl ring functionalized with the halogen atom.

Also disclosed herein are embodiments of a method, comprising: coupling a nanohoop intermediate with an aromatic monomer functionalized with an alkyne moiety to provide a non-aromatized nanohoop intermediate; and exposing the non-aromatized nanohoop intermediate to a reductive aromatization to provide the polymerizable nanohoop monomer according to any or all polymerizable nanohoop monomer embodiments disclosed herein, wherein the polymerizable nanohoop monomer has a structure according to Formula V.

In some embodiments, the aromatic monomer is functionalized with two alkyne moieties.

VI. Examples

Commercially available materials were used without purification. Moisture- and oxygen-sensitive reactions were carried out in flame-dried glassware and under an inert atmosphere of purified nitrogen using syringe/septa technique. Toluene was purified using an Innovative Technologies SPS-400-6 Solvent Purification System and further dried over Acros Organic 4 Å molecular sieves prior to use. Tetrahydrofuran (THF), 1,4-dioxane, and dimethylformamide (DMF) were dried by filtration through alumina according to the methods described by Grubbs.

All other solvents and reagents were purchased from Sigma-Aldrich, Fisher Scientific, Alfa Aesar, or Oakwood chemicals and used without further purification.

$^1$H NMR spectra were obtained on either a Bruker Avance 400 MHz Spectrometer, a Bruker Avance III 400 MHz Spectrometer or a Bruker Avance III HD 500 MHz Spectrometer, with residual protio-solvent resonances used as the internal standard ($CHCl_3$: 7.26 ppm, $CHDCl_2$: 5.32 ppm, $C_3HD_5O$: 2.05 ppm). Data are reported as: Chemical shift (multiplicity, integration, coupling constant). $^{13}$C NMR spectra were obtained on either a Bruker Avance 400 MHz Spectrometer (100 MHz), a Bruker Avance III 400 MHz Spectrometer (100 MHz), or a Bruker Avance III HD 500 MHz (126 MHz) Spectrometer, with solvent resonances used as the internal standard ($CDCl_3$: 77.2 ppm, $CD_2Cl_2$: 53.8 ppm, acetone-$d_6$: 29.8 ppm). Data are reported as chemical shifts (ppm). High resolution mass spectrometry (HRMS) was performed on a VG-70SE Magnetic Sector Mass Spectrometer. Matrix-assisted laser desorption/ionization spectrometry (MALDI) was performed on a Bruker AutoFlex III MALDI-ToF/ToF Mass Spectrometer using α-cyano-4-hydroxycinnamic acid (CHCA) as the matrix. UV/vis absorption data for [6]- and [8]CPP were recorded on an Agilent Cary 100 spectrophotometer. All other UV-Vis data were collected on a Cary 50 Bio UV-Vis Spectrophotometer. Photoluminescence spectra for [6]- and [8]CPP were recorded on a Horiba Jobin Yvon Fluoromax-4 Fluorometer. All other photoluminescence data were collected on a Photon Technology International (PTI) Fluorometer (QuantaMaster 40) with a 75-W Ushio Xenon short arc lamp, using Felix32 version 4.9 software. Gel permeation chromatography was performed on an Agilent 1260 Infinity Series (degasser, iso pump, TCC, DAD) using unstabilized THF at 40° C. vs. Agilent EasiVial PS-M polystyrene standards. Flash Chromatography was performed under manual air pressure on silica ($SiO_2$, 40-63 μm, 230-400 mesh). Automated flash chromatography was performed using a Biotage Isolera One. Thin Layer Chromatography (TLC) was performed using Sorbent Technologies Silica Gel XHT TLC plates. Developed plates were visualized using UV light at wavelengths of 254 and 365 nm.

Calculations were performed using Gaussian 16 Revision C.01. All optimizations on small molecules and oligomers were performed using ground state DFT calculations with PBE1PBE/6-31G(d). All excited state calculations were performed using TD-DFT for singlet excited stated with 6 or 12 states using PBE1PBE/6-31G(d). All the UV-Vis absorption spectra were obtained with broadening of Half Width at Half Height of 0.2 eV or 1613 cm$^{-1}$. The energies at different torsional angles for 3[6]-Th were calculated using single point excited state TD-DFT calculation with PBE1PBE/6-31G(d) with 12 states. Molecular orbitals were obtained using Chemcraft software with contour value of 0.03. All the ground state and excited state calculations were performed in the gas phase unless stated otherwise. The calculations for small molecules and oligomers refer to the closed shell configuration.

Example 1

1,4-diBpin-2,5-diTMSA Benzene 2

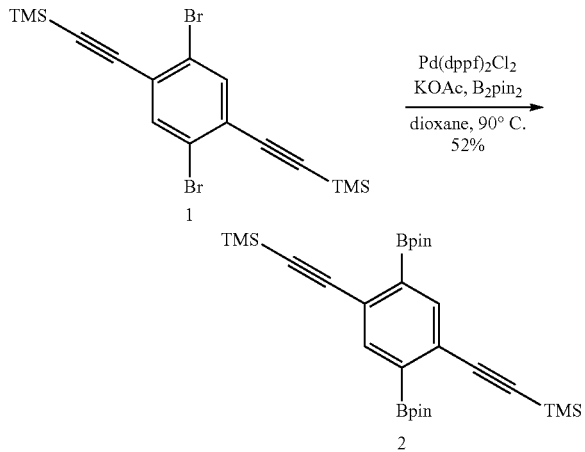

KOAc (6.05 g, 61.6 mmol, 6.6 eq) was added to a round bottom flask under vacuum and flame dried. Upon cooling, dibromide (4.00 g, 9.34 mmol, 1 eq), Pd(dppf)$_2$Cl$_2$ (229 mg, 280 μmol, 0.03 eq) and bis(pinacolato)diboron (5.69 g, 22.4 mmol, 2.4 eq) were added. The vessel was fitted with a rubber septum and evacuated/backfilled with nitrogen. Dioxane (30 mL) was added, the reaction was warmed to 90° C. and stirred at this temperature for 18 hours. The mixture was filtered through celite, washed with EtOAc, and concentrated under reduced pressure. The resulting residue was recrystallized in EtOH to yield brown crystals (2.54 g, 52%). $^1$H NMR (500 MHz, CDCl$_3$) δ 7.82 (s, 2H), 1.36 (s, 24H), 0.25 (s, 18H). $^{13}$C NMR (126 MHz, CDCl$_3$) δ 139.54, 126.81, 105.47, 97.81, 84.27, 25.08, 0.09, $^{13}$C—B signal not observed. IR (neat): 2981, 2154, 1372, 1324, 1249 cm$^{-1}$. HRMS (ASAP) (m/z): [M+H]$^+$ calculated for C$_{28}$H$_{45}$B$_2$O$_4$Si$_2$, 523.3042; found, 523.3091.

Example 2

DiTMSA[6]Macrocycle diOTES diOMe 4

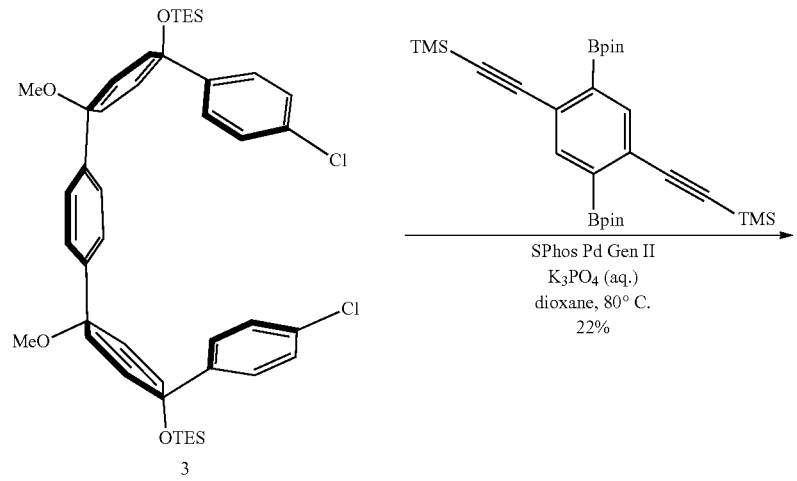

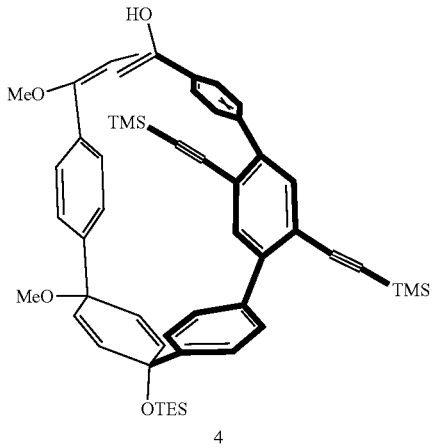

A flame-dried flask was charged with bisboronate 2 (318 mg, 0.609 mmol, 1.05 equiv.), dichloride 3 (450 mg, 0.58 mmol, 1.00 equiv.), and SPhos Pd Gen 11 (63 mg, 0.087 mmol, 0.15 equiv.). The flask was evacuated for 5 minutes and backfilled with nitrogen for 5 cycles. The flask was then purged with nitrogen for 1 hr. Dry dioxane (290 mL) was sparged for 1 hr, added to the reaction flask, and heated to 80° C. A 2 M. aqueous solution of K$_3$PO$_4$ was sparged with nitrogen for 1 hr., then 29 mL of K$_3$PO$_4$ solution was added to the reaction. The reaction was stirred for 2 hr at 80° C. After the reaction was cooled to room temperature, the dioxane was removed under reduced pressure, then the resulting material was filtered through a celite pad with ethyl acetate and water. The filtrate was extracted with ethyl acetate (2×). The combined organic layers were washed with water (2×) and brine (1×), then dried over sodium sulfate and concentrated under reduced pressure. The material was purified by automated column chromatography in 0% to 15% EtOAc in hexanes and by gel permeation chromatography to yield the product as a tan solid (245 mg, 22%). $^1$H NMR (500 MHz, CDCl$_3$) δ 7.40 (d, J=8.3 Hz, 4H), 7.33 (s, 2H), 7.30 (d, J=8.4 Hz, 4H), 6.85 (s, 4H), 6.31 (dd, J=10.2, 2.5 Hz, 2H), 6.12 (dd, J=10.3, 2.5 Hz, 2H), 5.79 (dd, J=10.3, 2.5 Hz, 2H), 5.44 (dd, J=10.0, 2.5 Hz, 2H), 3.28 (s, 6H), 0.98 (t, J=7.9 Hz, 18H), 0.67 (q, J=7.9 Hz, 12H), 0.19 (s, 18H).

$^{13}$C NMR (126 MHz, CDCl$_3$) δ 144.52, 142.84, 142.59, 140.25, 137.99, 137.30, 133.53, 131.64, 128.98, 126.62, 125.97, 125.95, 119.54, 104.63, 99.50, 74.26, 71.43, 51.59, 7.18, 6.68, 0.15. IR (neat): 2935, 2875, 2821, 2151, 1491, 1459, 1402, 1248, 1176, 1073, 1005, 948, 820, 721 cm$^{-1}$.

Figure 15A:
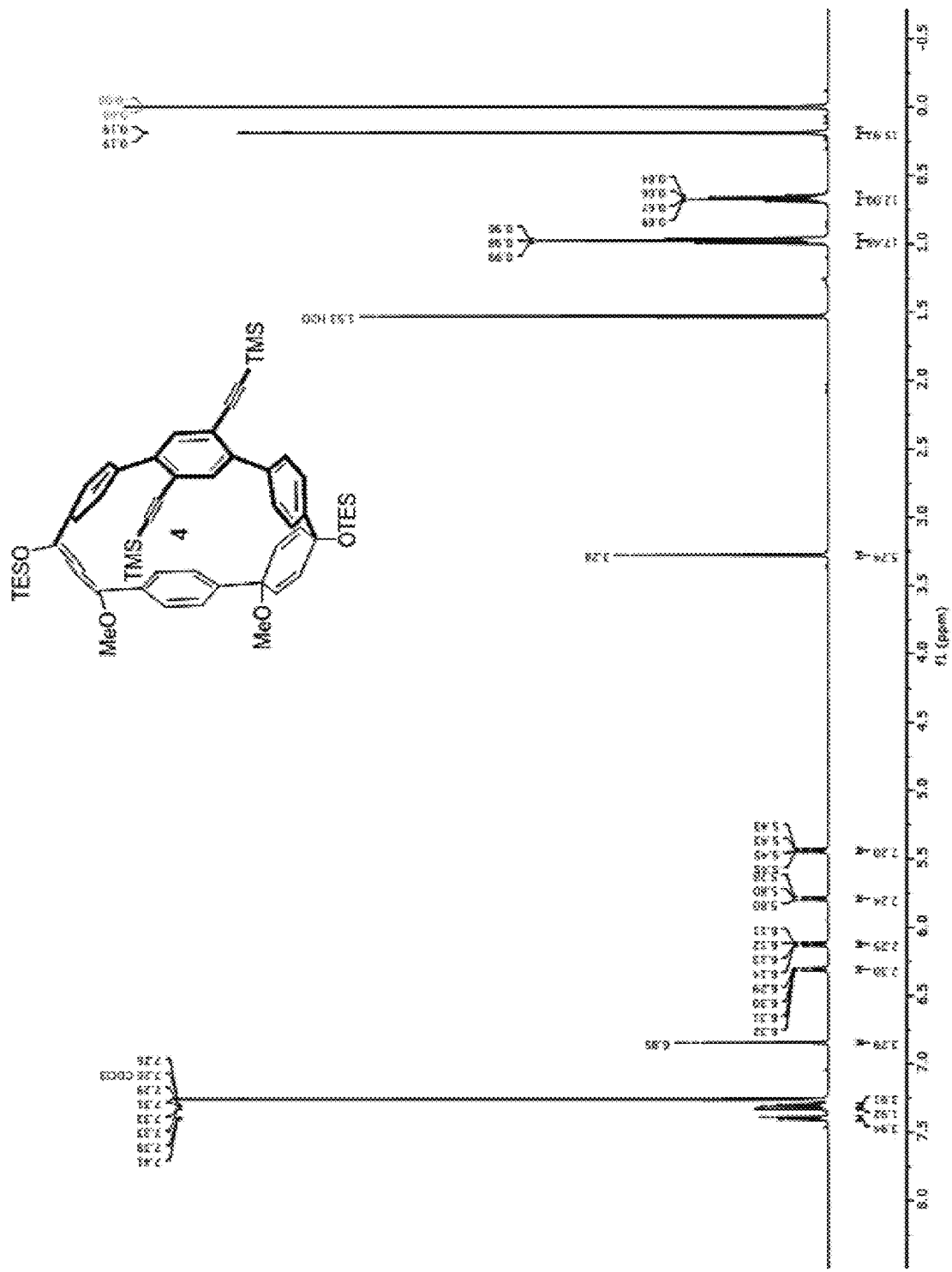
FIGS. 15A-15L show $^1$H-NMR and $^{13}$C-NMR spectra for various polymerizable nanohoop monomers and/or polymerizable nanohoop intermediates.
Figure 15B:
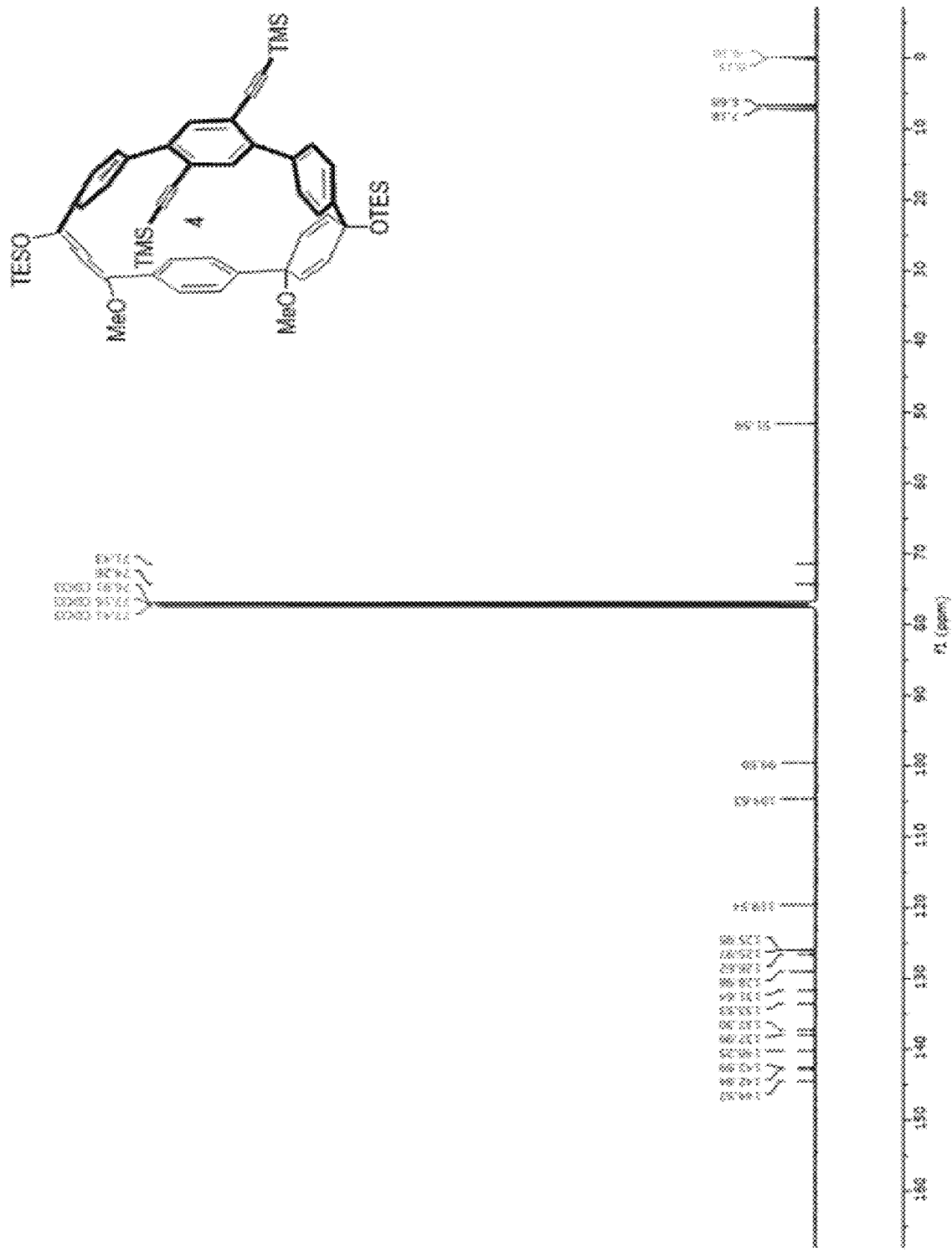

HRMS (FTMS+c ESI) (m/z): [M]+ calculated for $C_{60}H_{76}O_4Si_4$, 972.4815; found, 972.4827. See FIG. 15A and FIG. 15B for proton and carbon NMR spectra.

Example 3

Diethynyl[6]Macrocycle diOMe diol 9

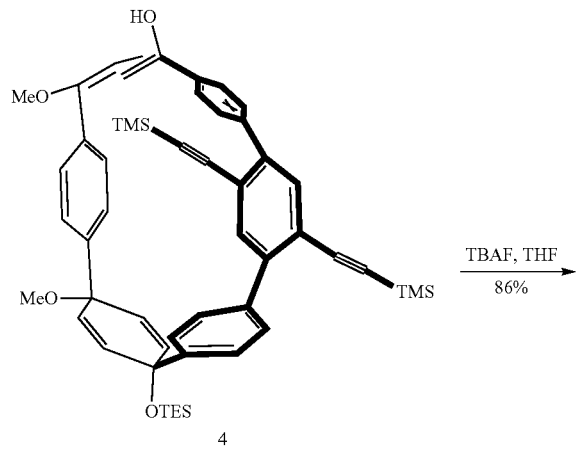

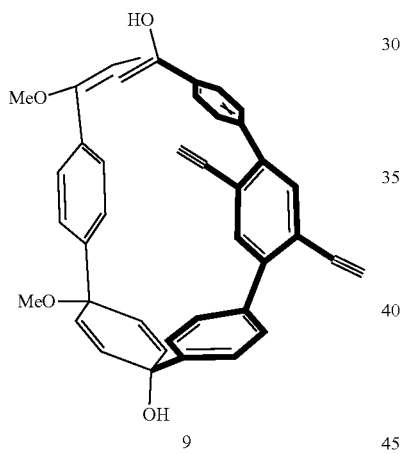

Figure 15C:
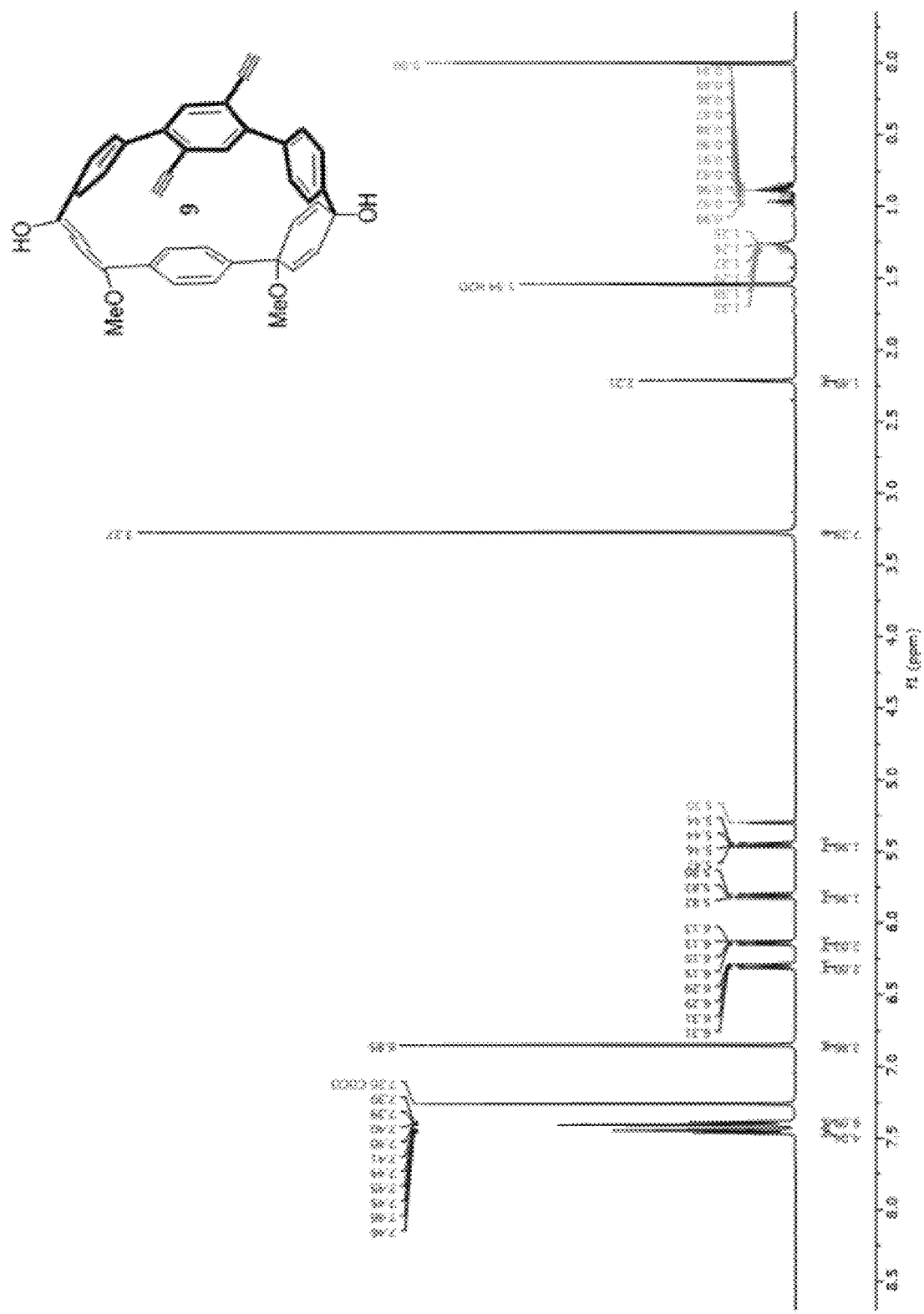
Figure 15D:
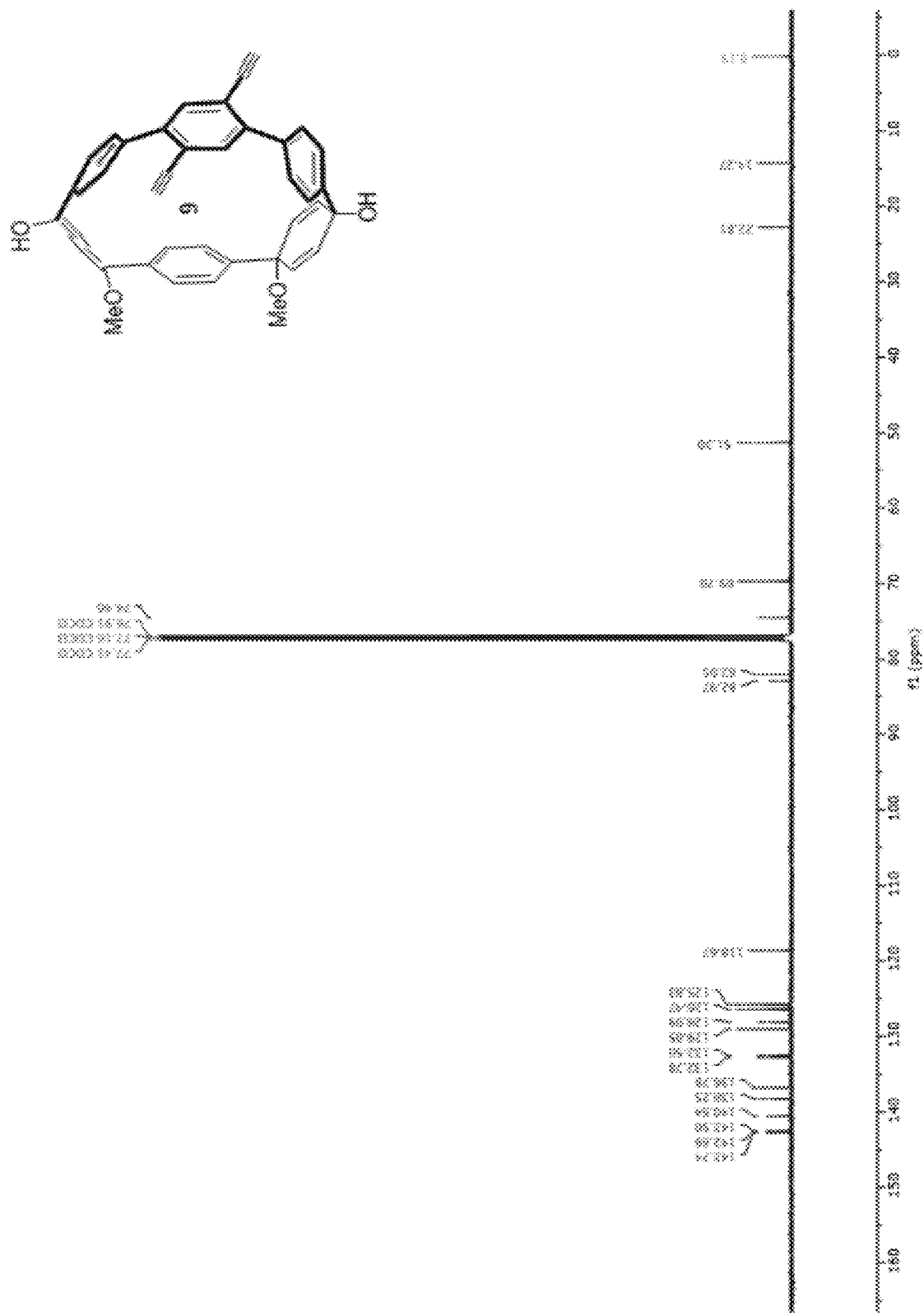

Macrocycle 4 (225 mg, 0.231 mmol, 1.00 equiv.) was added to a flame-dried flask and dissolved in THF (1.5 mL, 150 mM). A 1 M. solution of TBAF (1.0 mL, 0.971 mmol, 4.20 equiv.) was added slowly to the solution, and the reaction was stirred for 1 hr. The reaction was quenched with water and extracted with DCM (3×). The combined organic layers were washed with water (2×) and brine (1×) before being dried over sodium sulfate. Solvent was removed under reduced pressure. The product was purified by column chromatography in 0% to 100% ethyl acetate in dichloromethane (120 mg, 86%). $^1$H NMR (500 MHz, CDCl$_3$) δ 7.45 (d, J=8.6 Hz, 4H), 7.41 (s, 2H), 7.40 (d, J=8.7 Hz, 4H), 6.85 (s, 4H), 6.30 (dd, J=10.2, 2.5 Hz, 2H), 6.14 (dd, J=10.1, 2.6 Hz, 2H), 5.81 (dd, J=10.2, 2.5 Hz, 2H), 5.45 (dd, J=10.1, 2.4 Hz, 2H), 3.27 (s, 6H), 2.21 (s, 2H). $^{13}$C NMR (126 MHz, CDCl$_3$) δ 142.74, 142.69, 142.50, 140.54, 138.25, 136.78, 132.78, 132.50, 129.05, 128.09, 126.47, 125.83, 118.67, 82.97, 82.05, 74.46, 69.70, 51.30, 22.81, 14.27. IR (neat): 3275, 2931, 2870, 1483, 1461, 1403, 1352, 1173, 1052, 1021, 945, 831, 764 cm$^{-1}$. HRMS (TOF MS EI+) (m/z): [M]+ calculated for $C_{42}H_{32}O_4$, 600.2301; found, 600.2302. See FIG. 15C and FIG. 15D for proton and carbon NMR spectra.

Example 4

Diethynyl[6]CPP 5

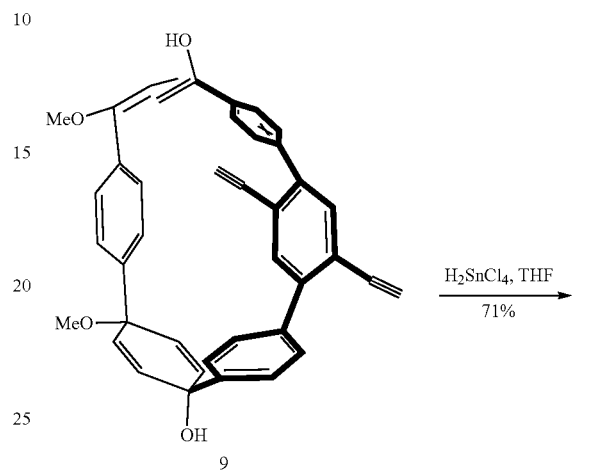

Figure 15E:
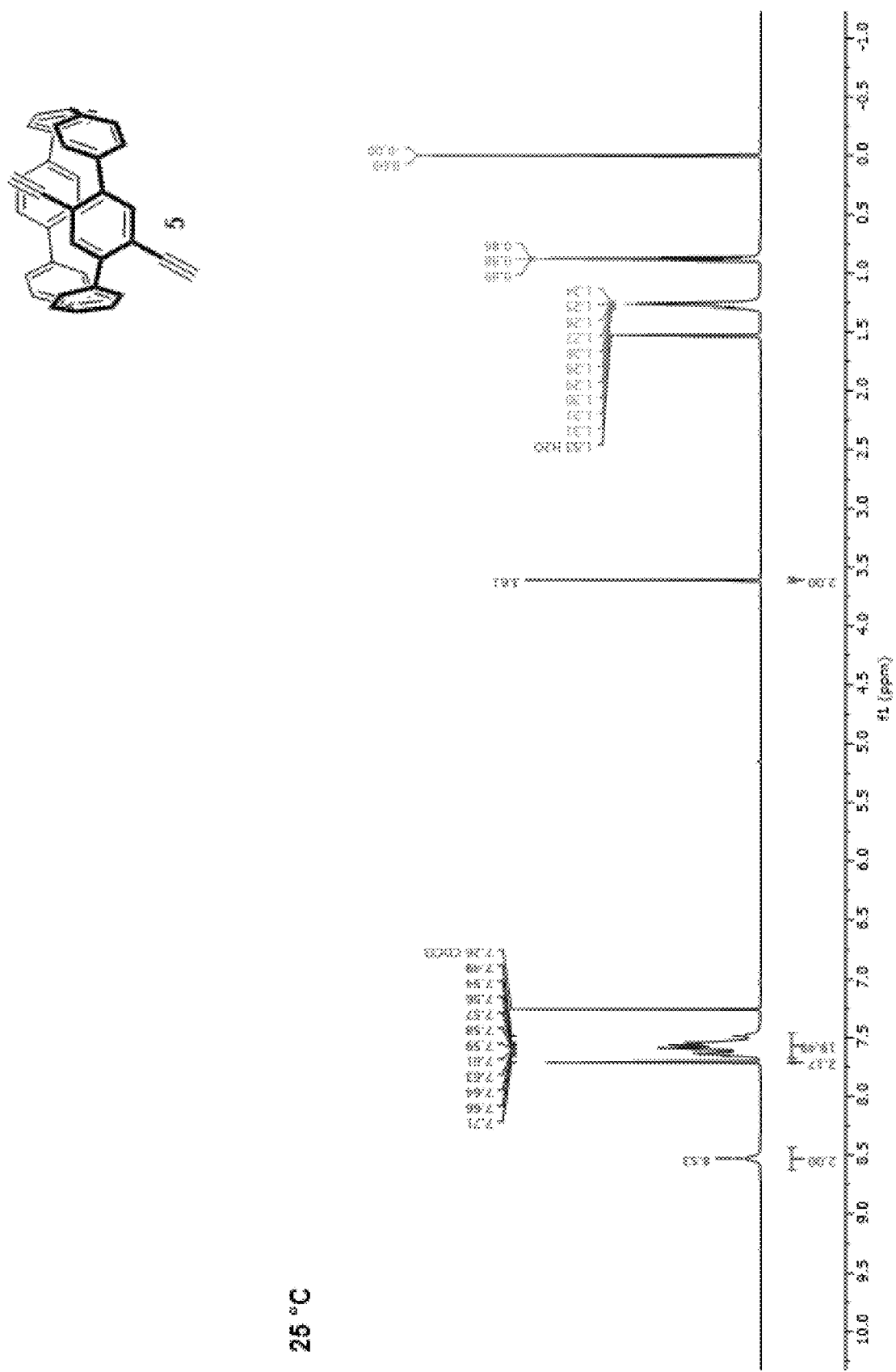
Figure 15F:
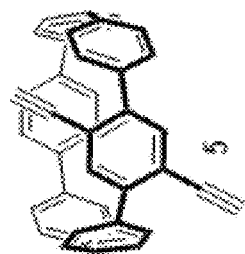
Figure 15F:
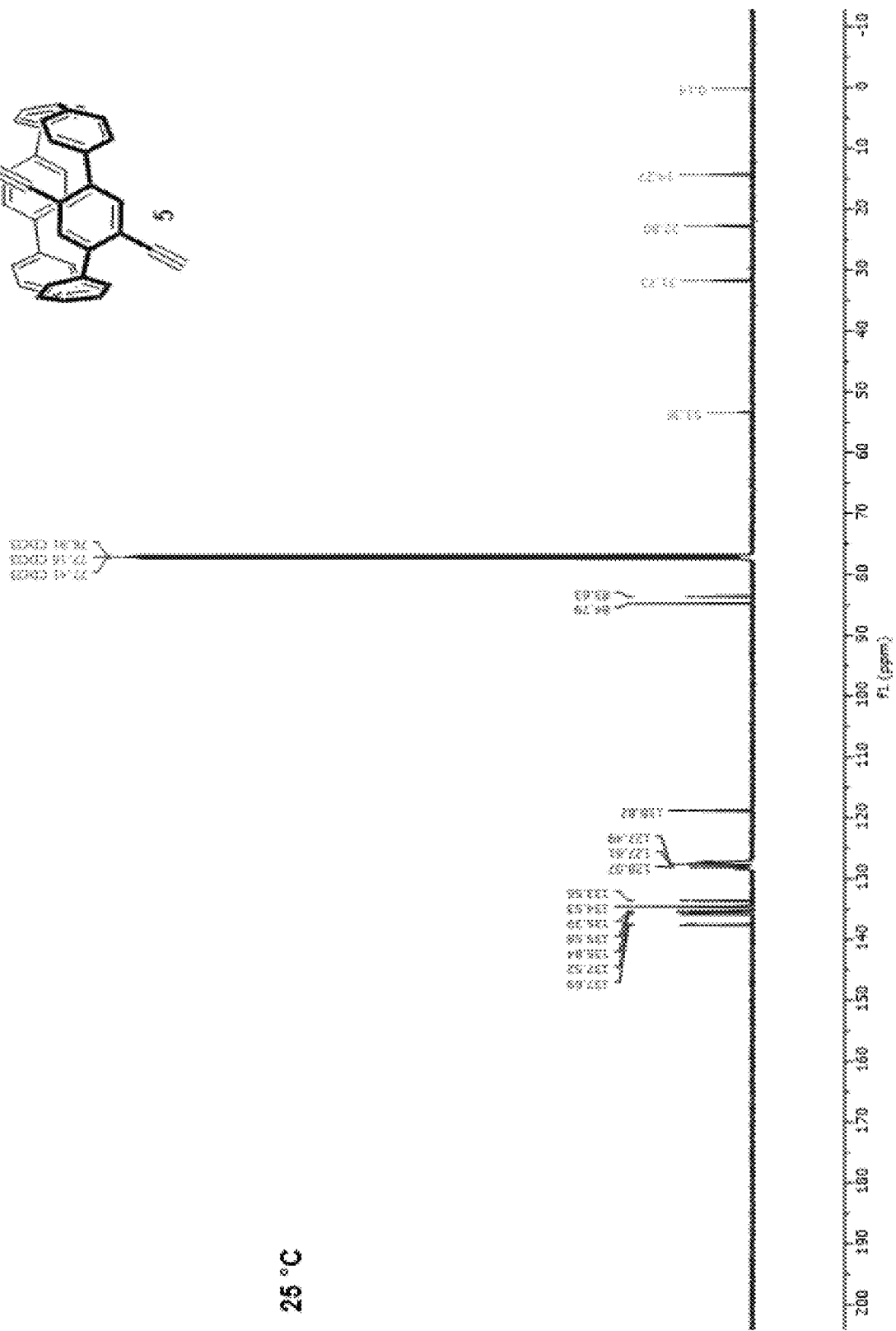
Figure 16A:
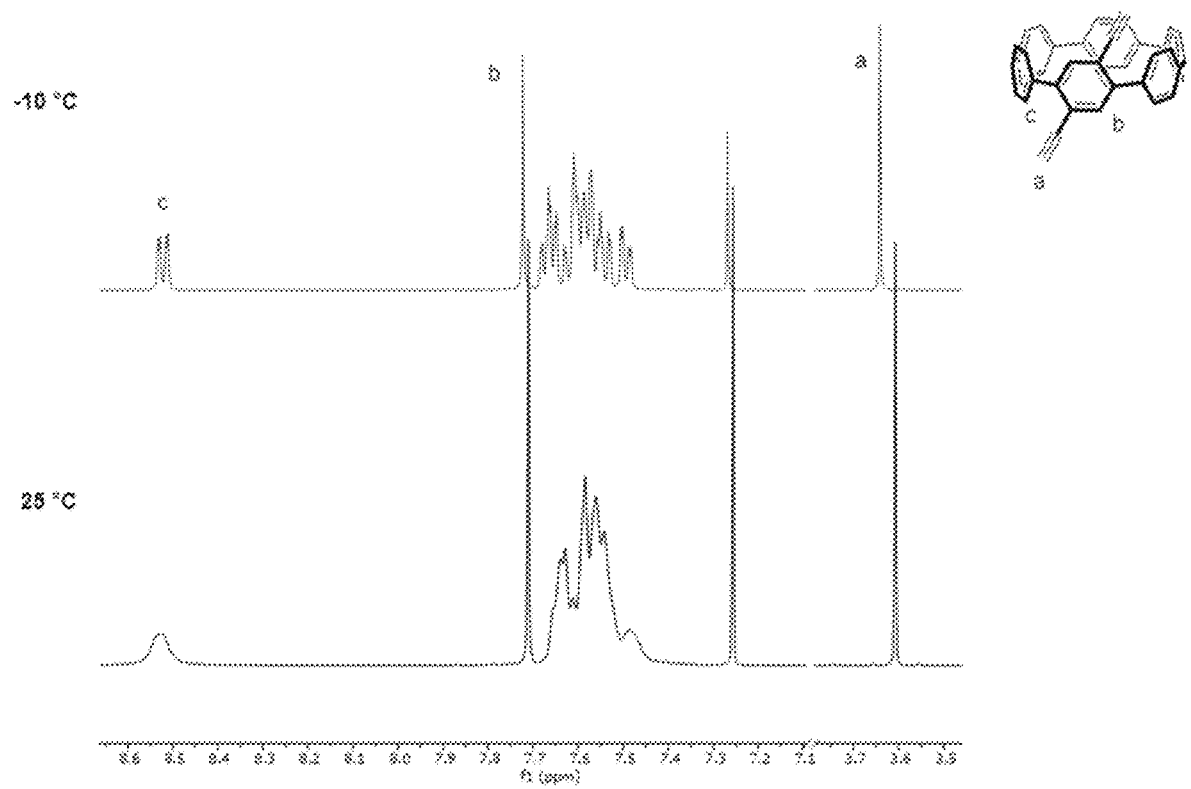
FIGS. 16A and 16B show $^1$H-NMR (FIG. 16A) and $^{13}$C-NMR (FIG. 16B) spectra for polymerizable nanohoop monomer 5 at −10° C. (top spectrum) and 25° C. (bottom spectrum).
Figure 16B:
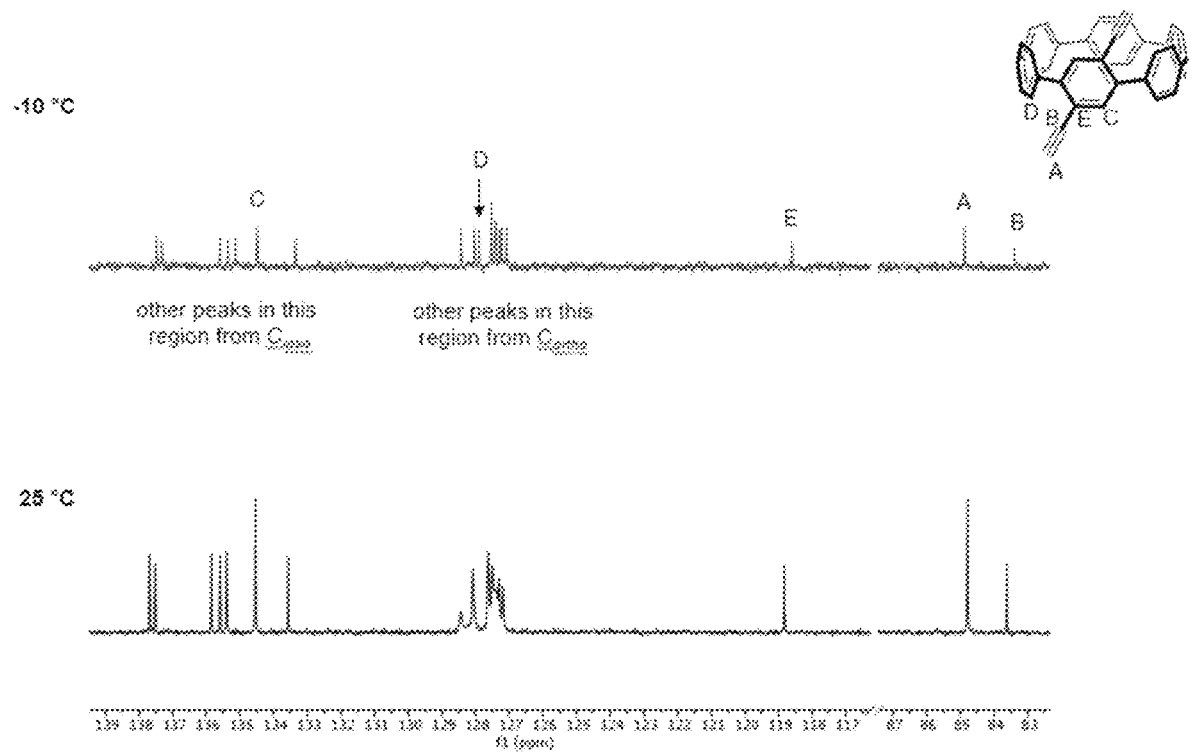
Figure 17A:
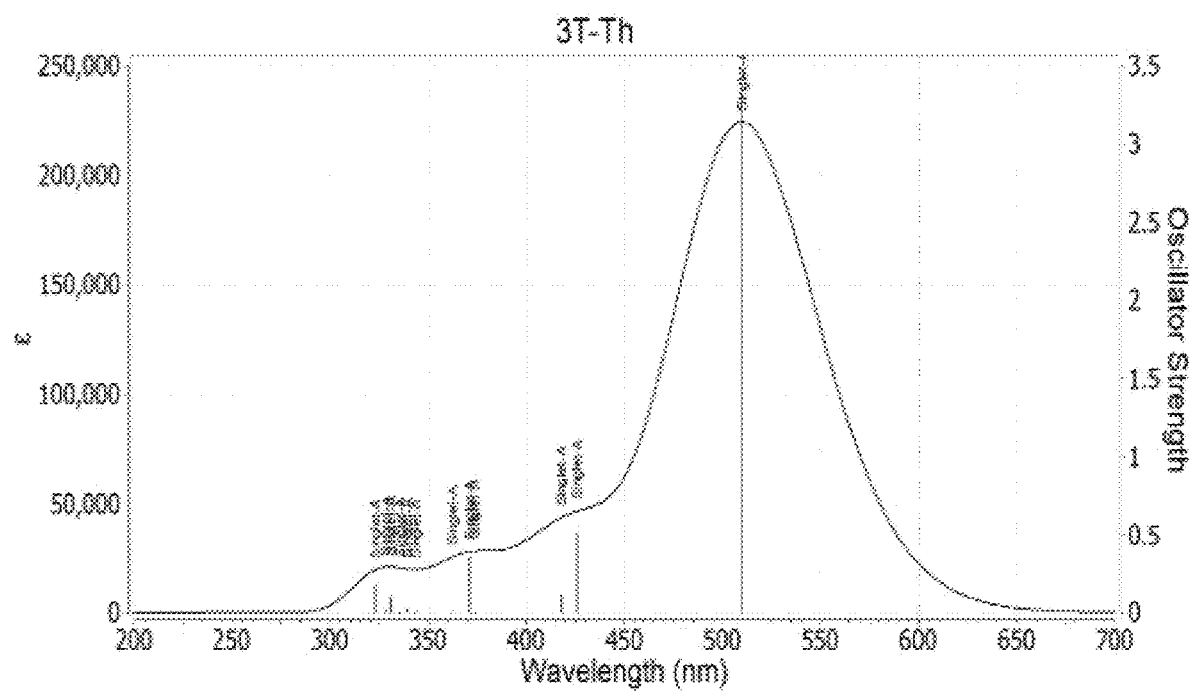
FIGS. 17A-17D show predicted spectra and geometries of 3T-Th with long alkyl chains and with methyl groups.
Figure 17B:
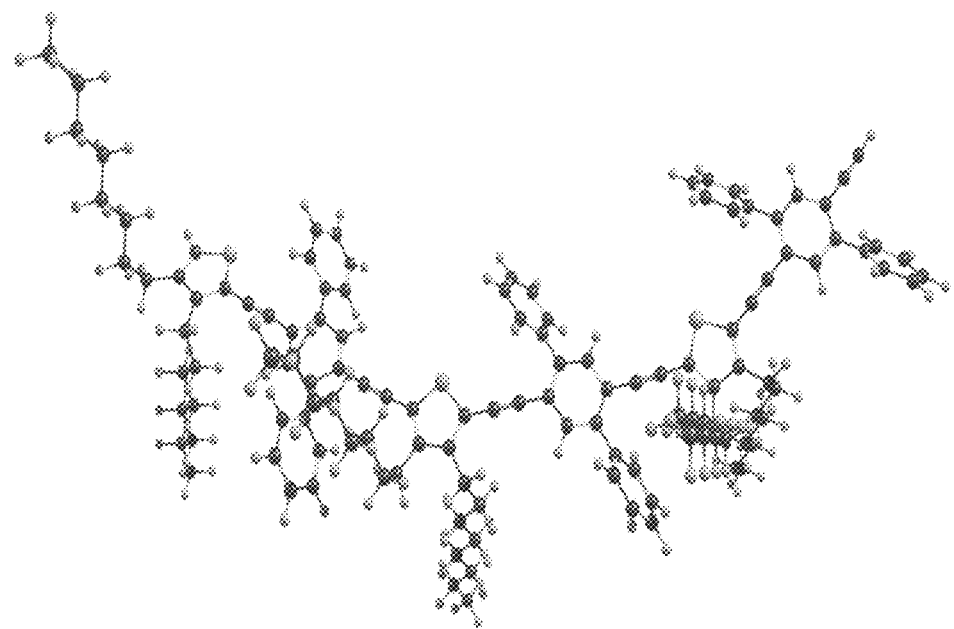
Figure 17C:
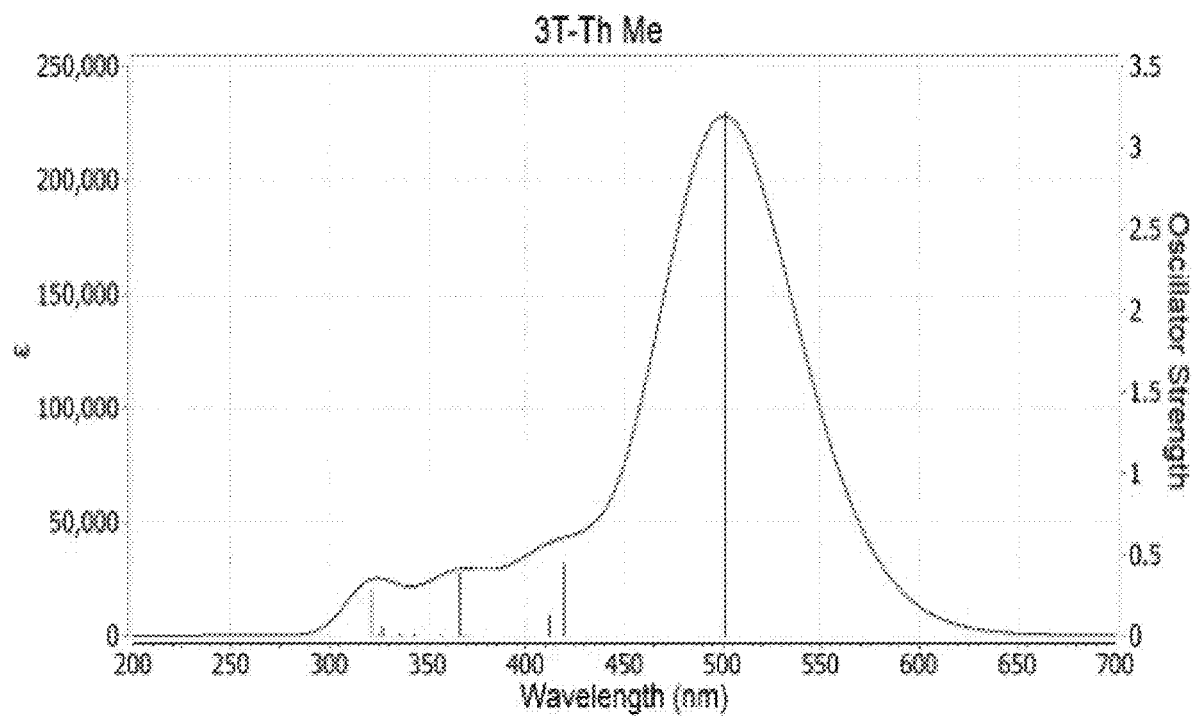
Figure 17D:
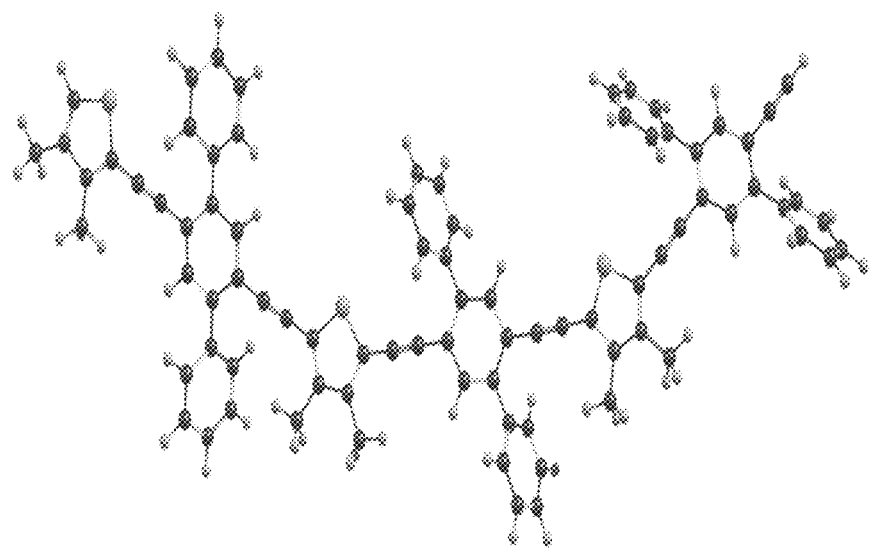
Figure 18A:
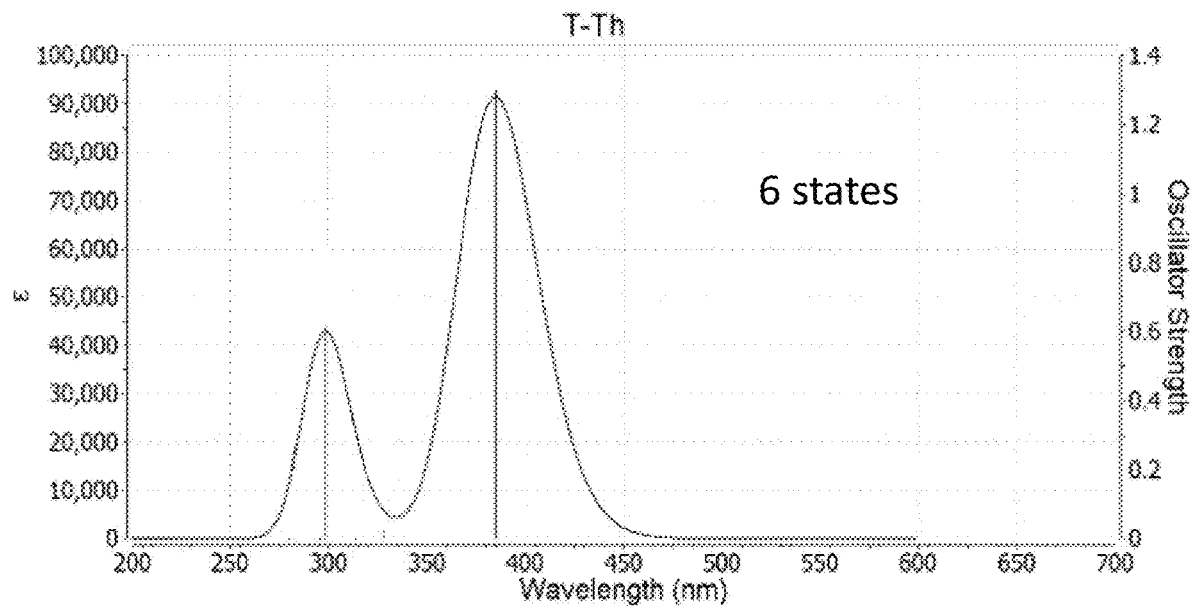
FIGS. 18A-18D are computed spectra obtained by excited state calculations performed using TD-DFT for singlet excited stated with 6 states (FIG. 18A) and 12 states (FIG. 18B) for T-Th and with 6 states (FIG. 18C) and 12 states (FIG. 18D) for [8]-Th substituted with methyl group.
Figure 18B:
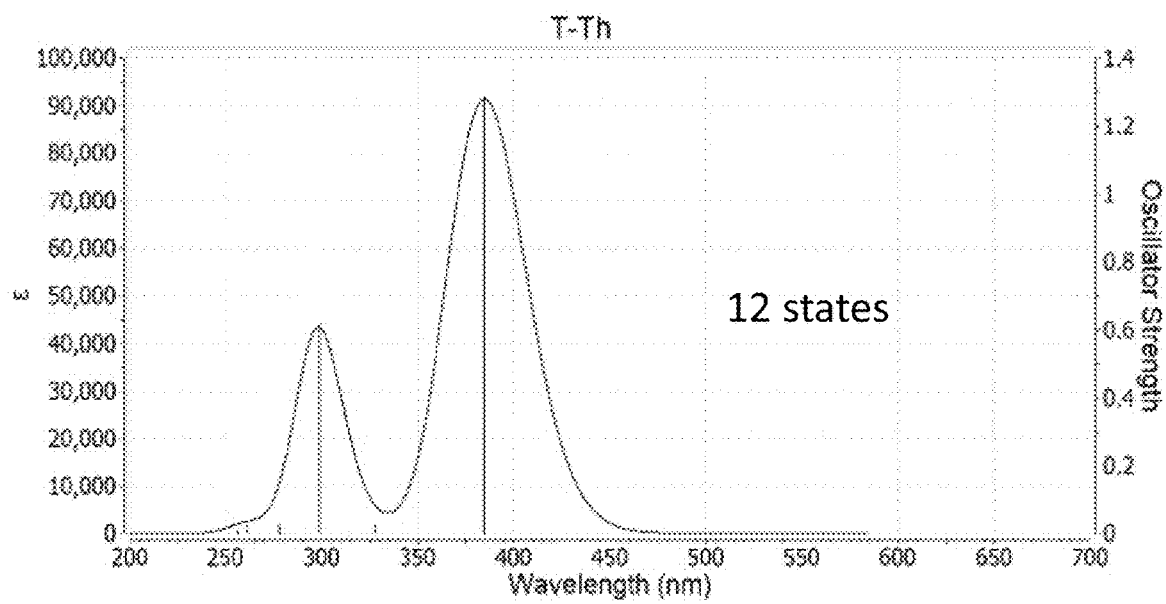
Figure 18C:
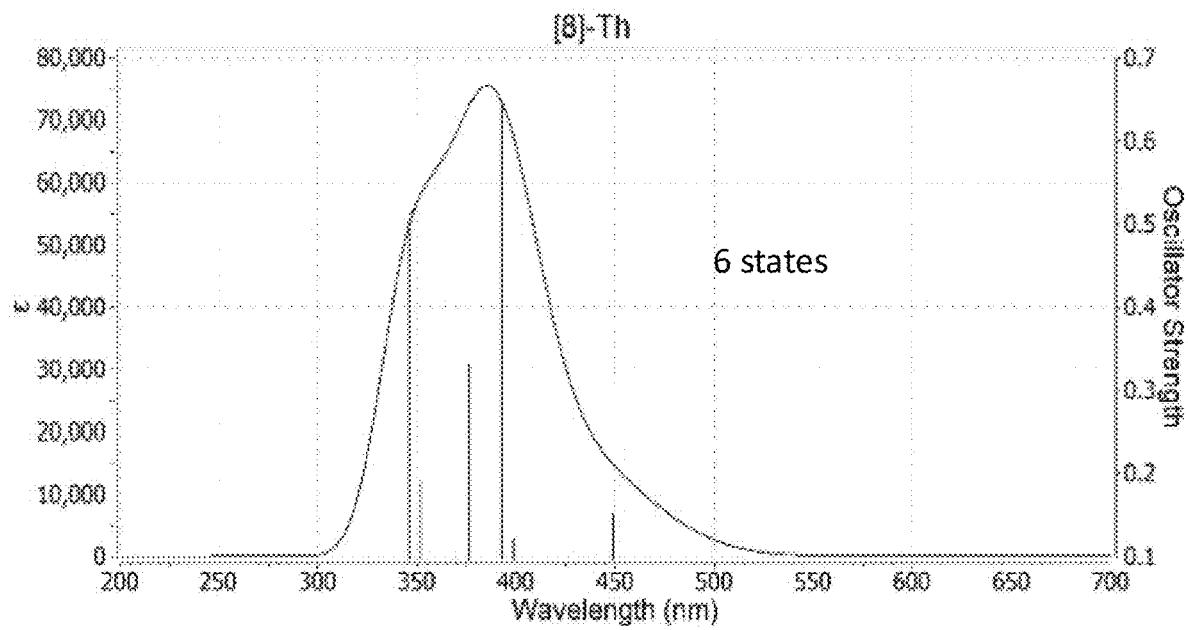
Figure 18D:
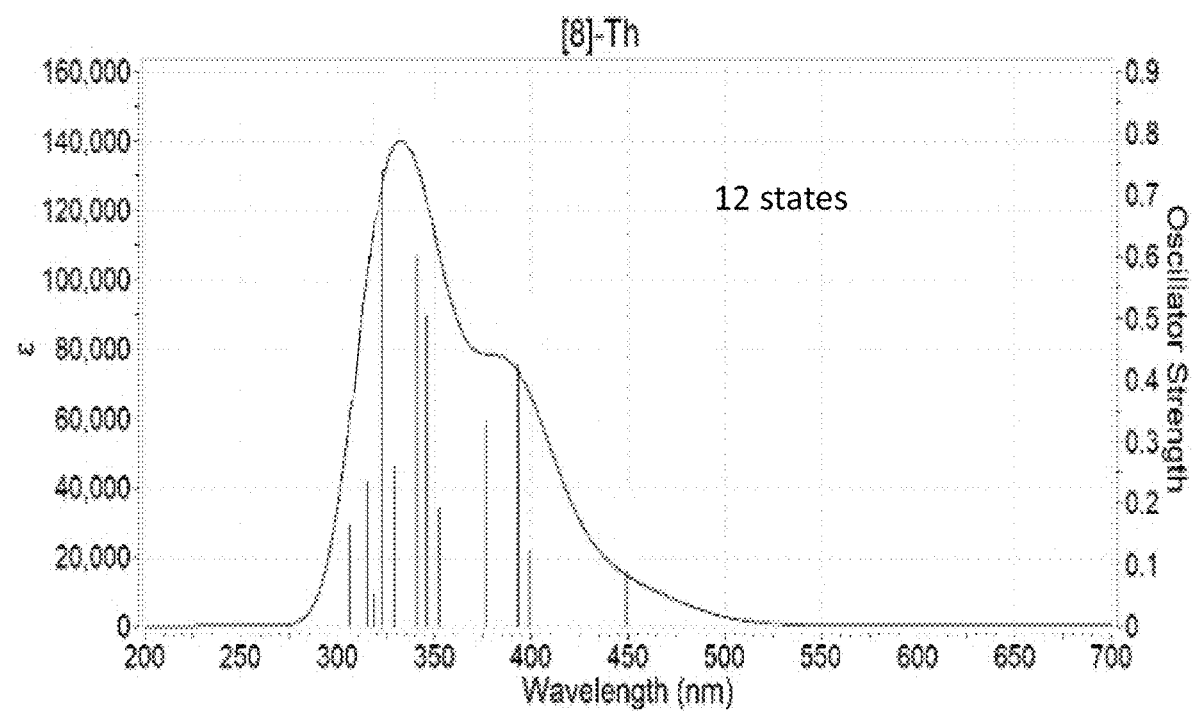
Figure 19A:
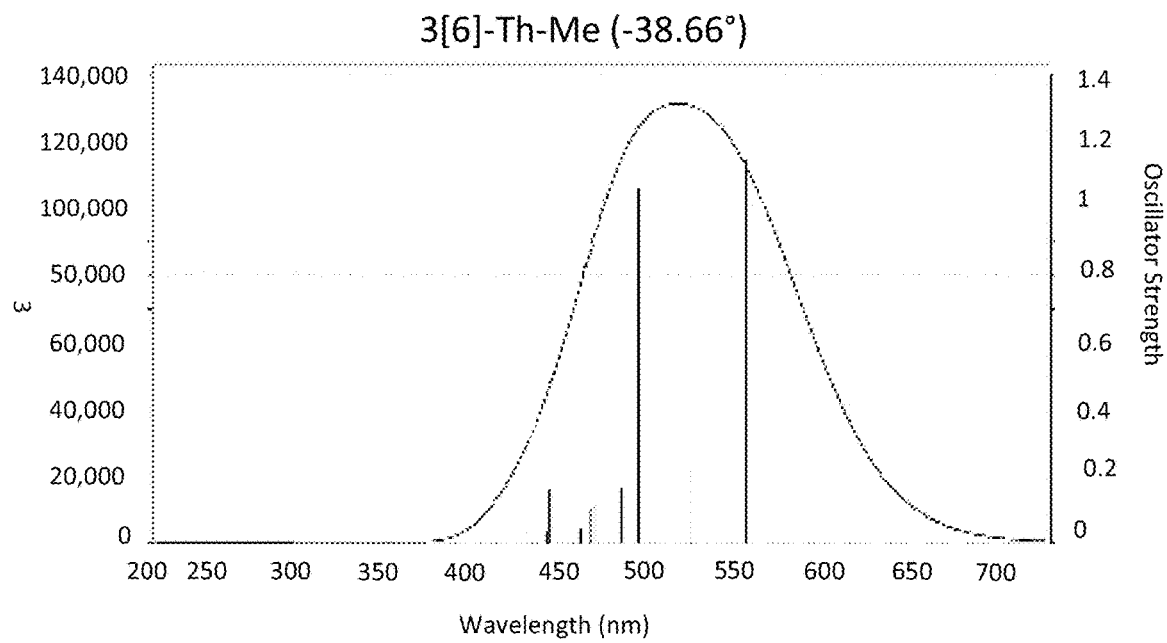
FIGS. 19A-19L are UV-vis spectra as a function of a torsion as defined in FIG. 11.
Figure 19B:
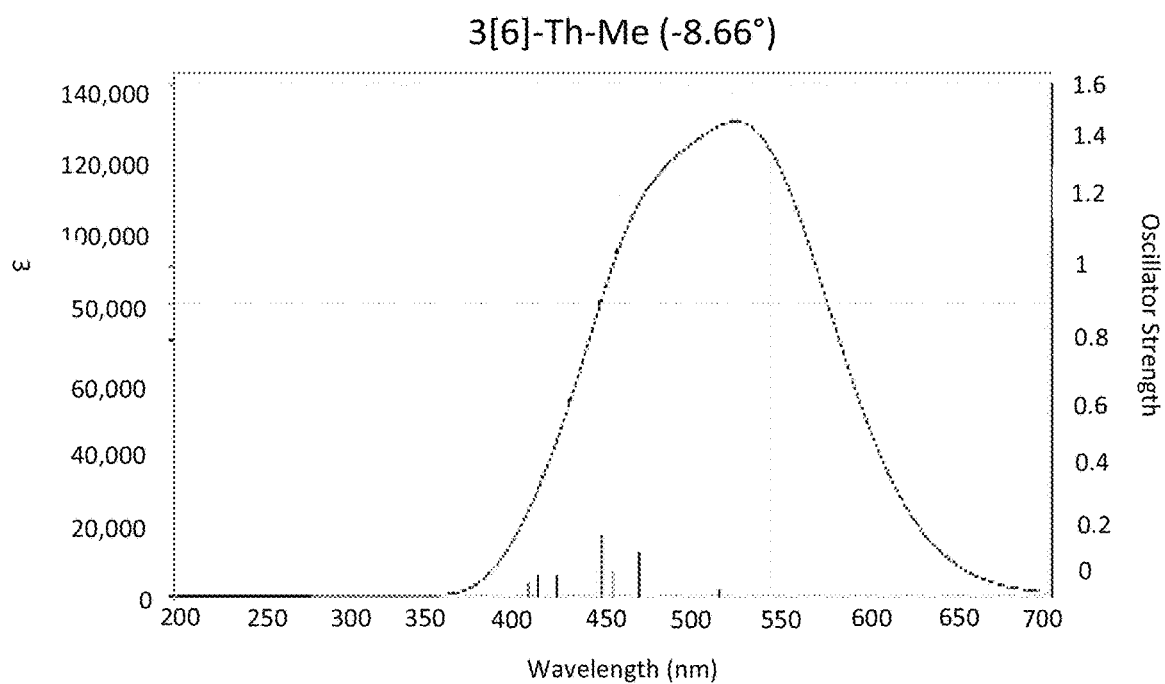
Figure 19C:
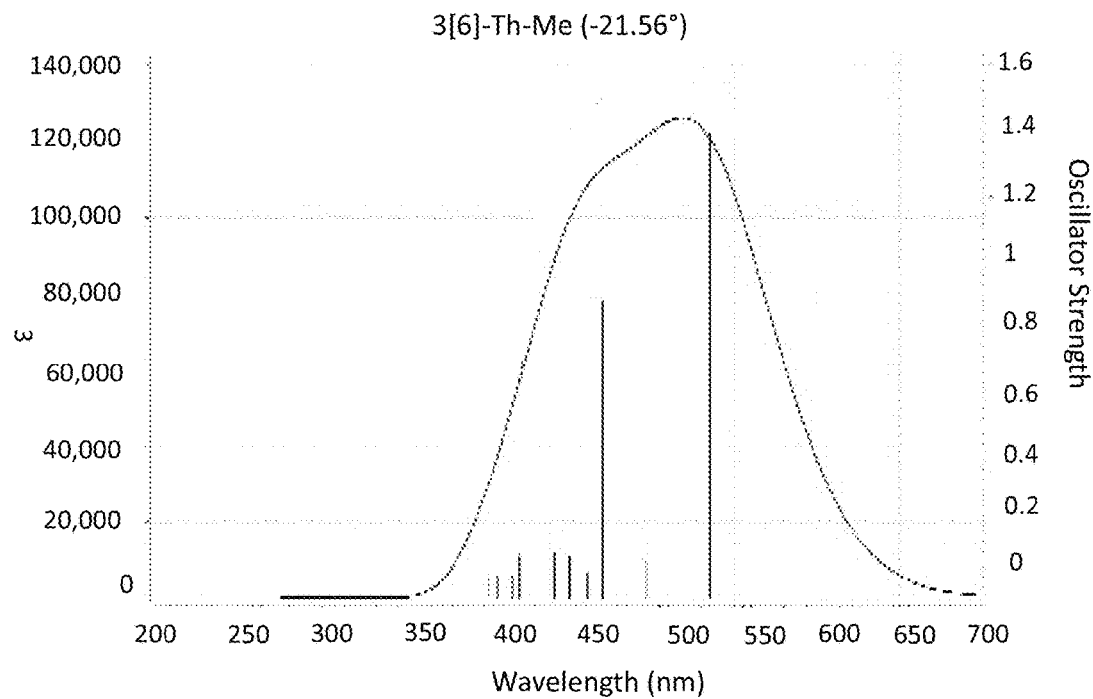
Figure 19D:
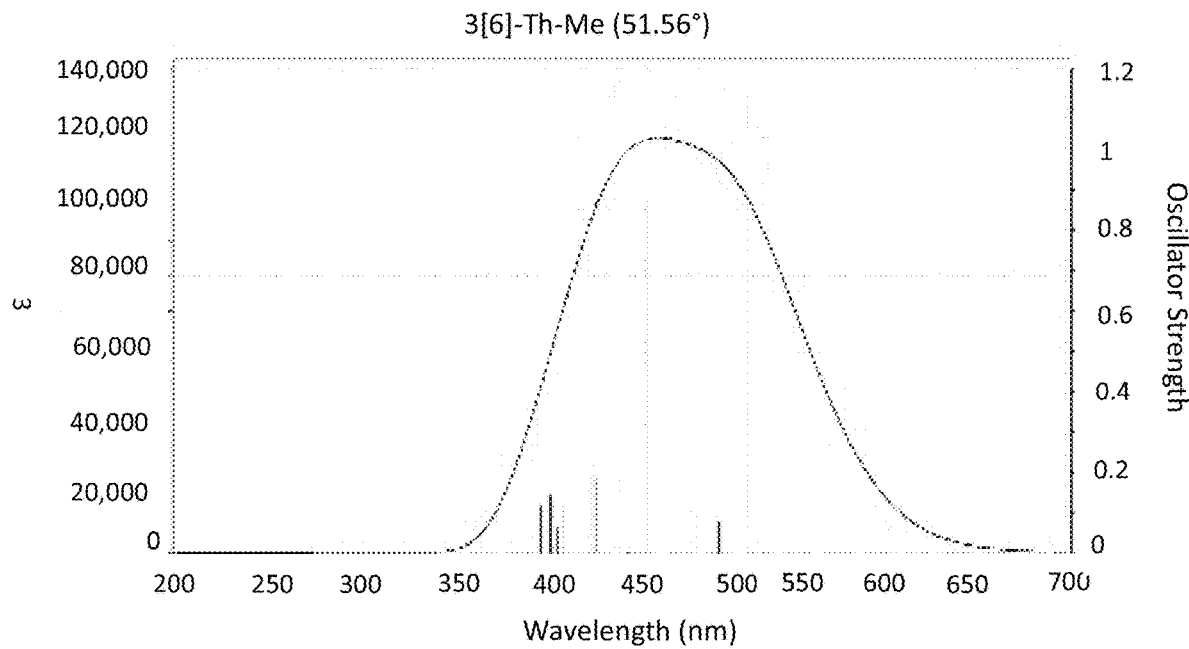
Figure 19E:
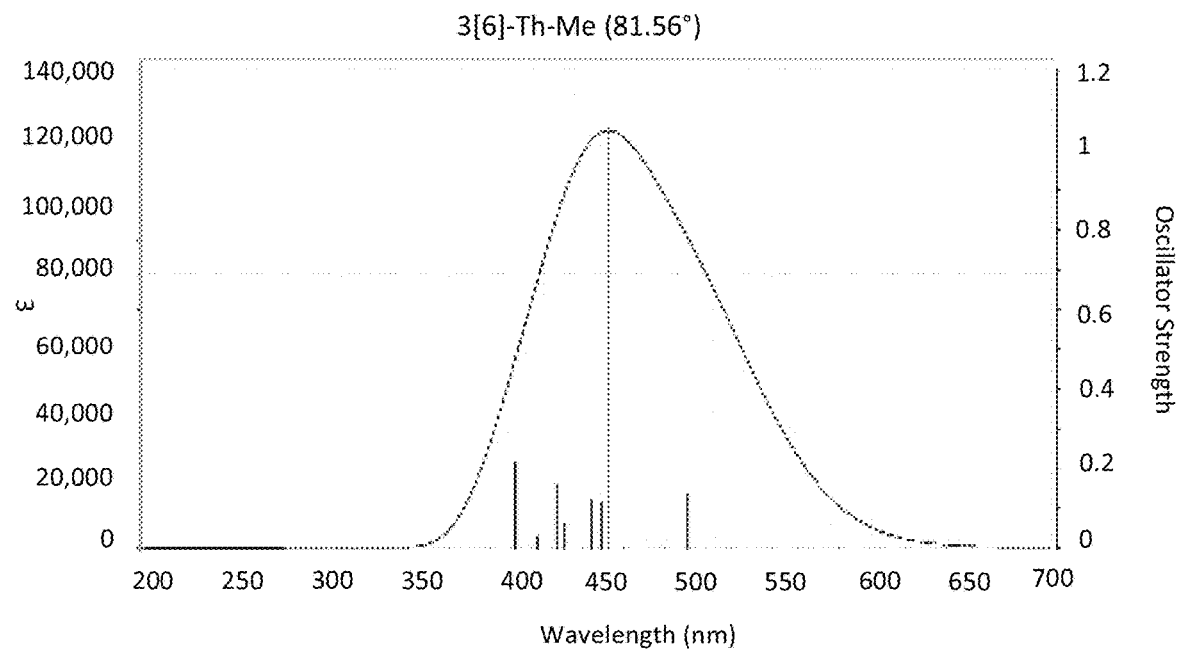
Figure 19F:
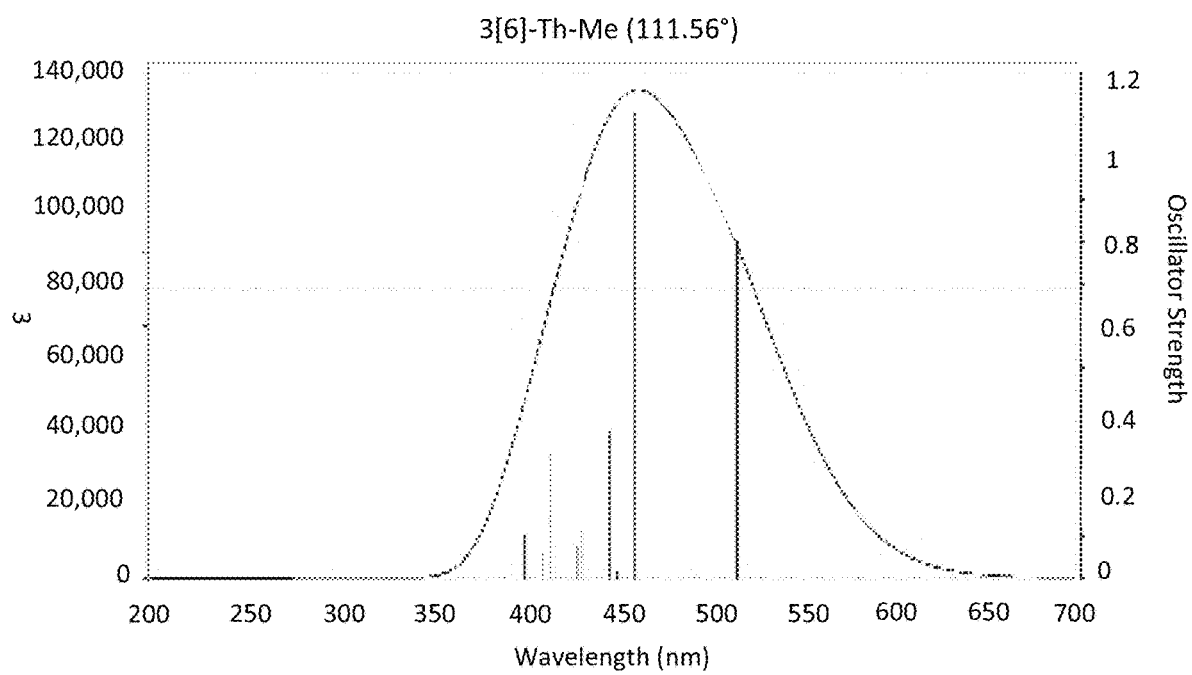
Figure 19G:
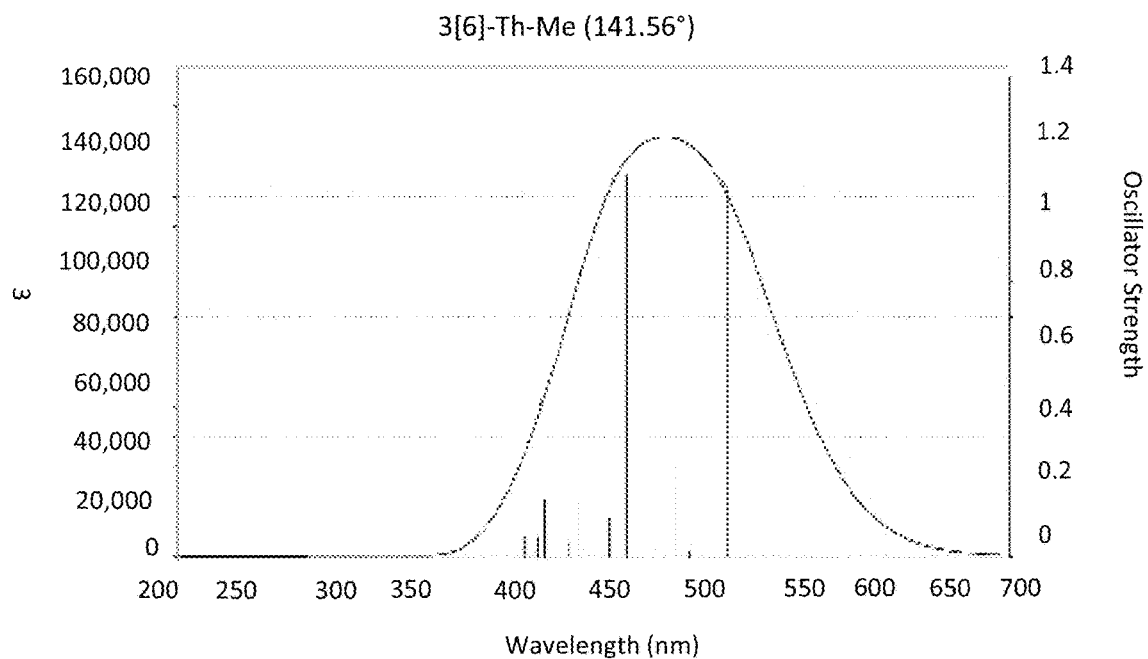
Figure 19H:
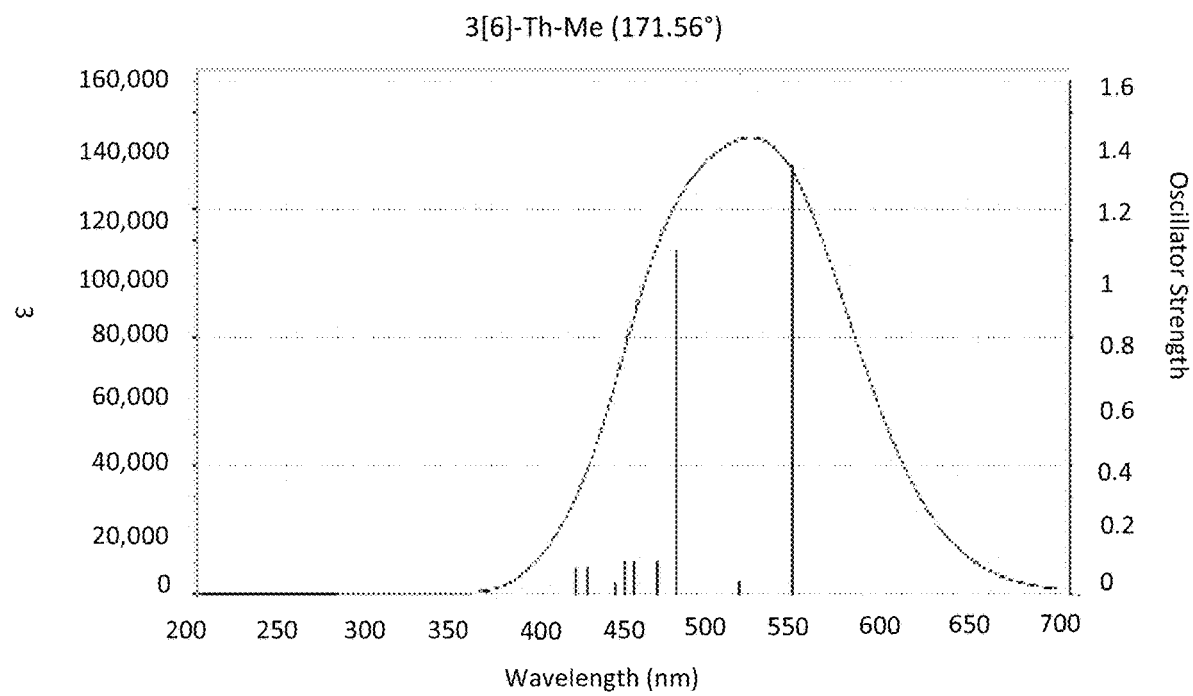
Figure 19I:
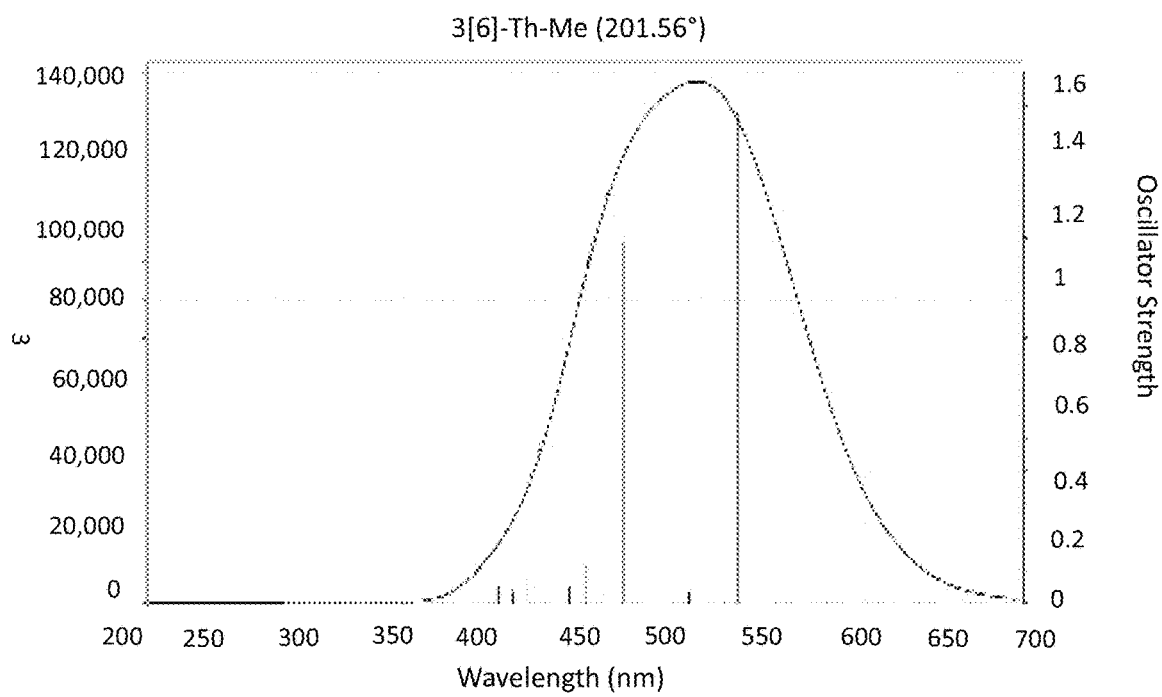
Figure 19J:
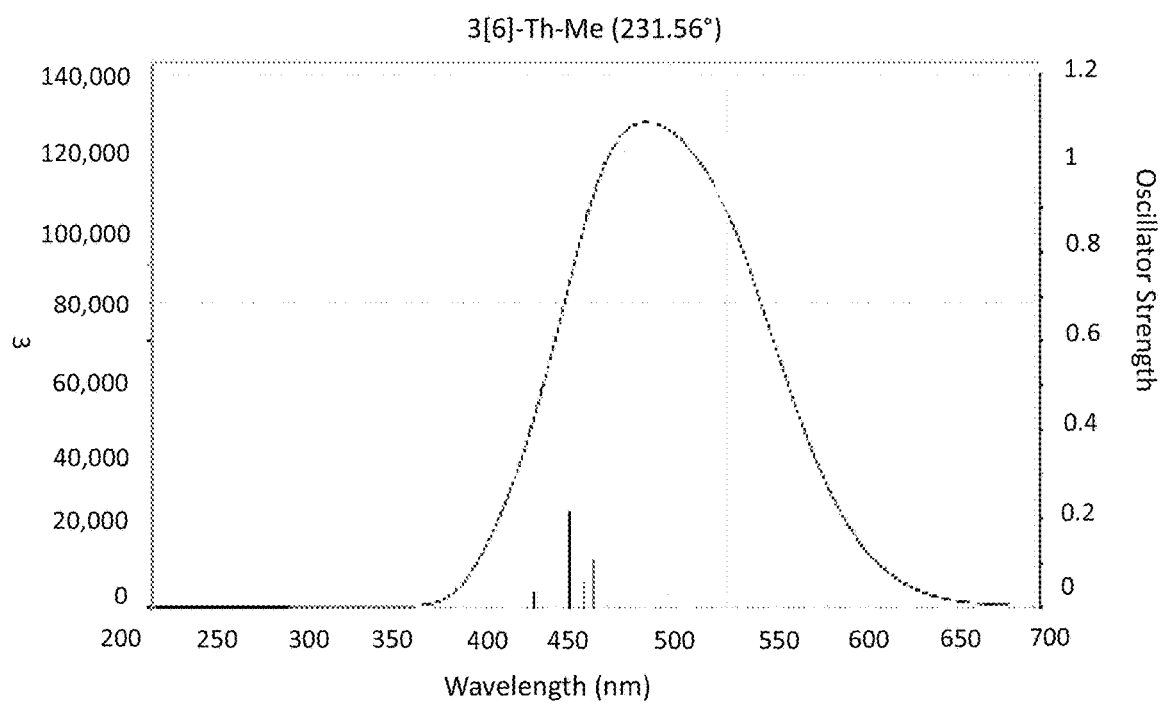
Figure 19K:
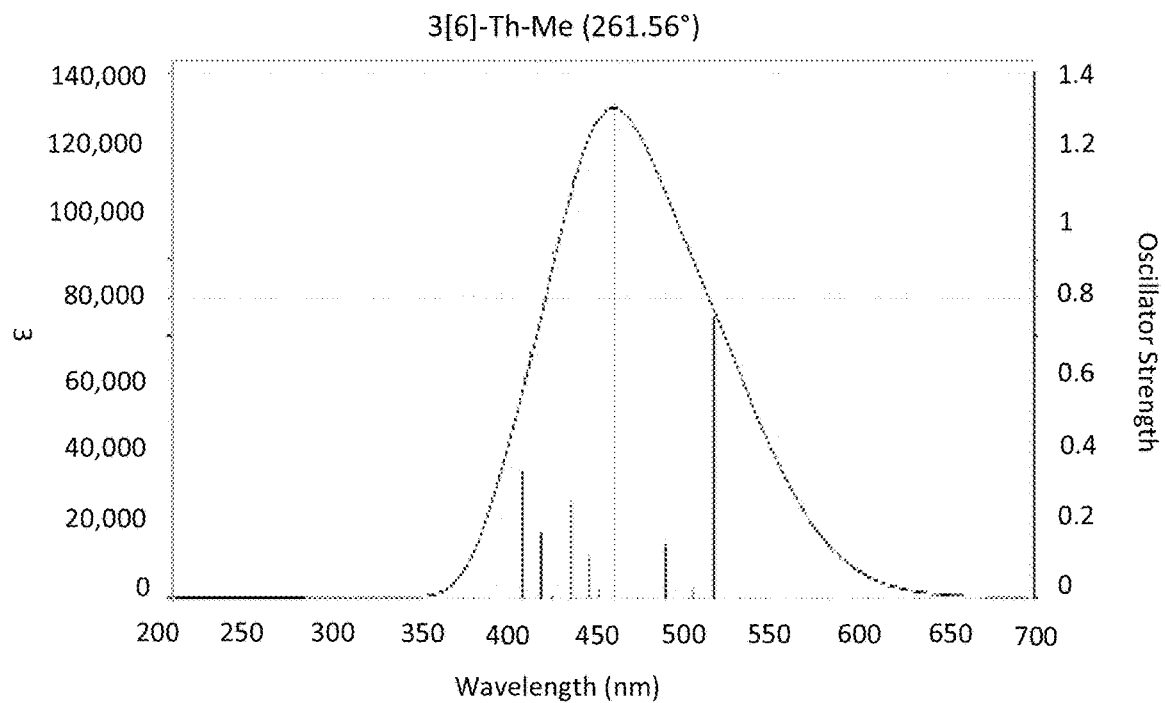
Figure 19L:
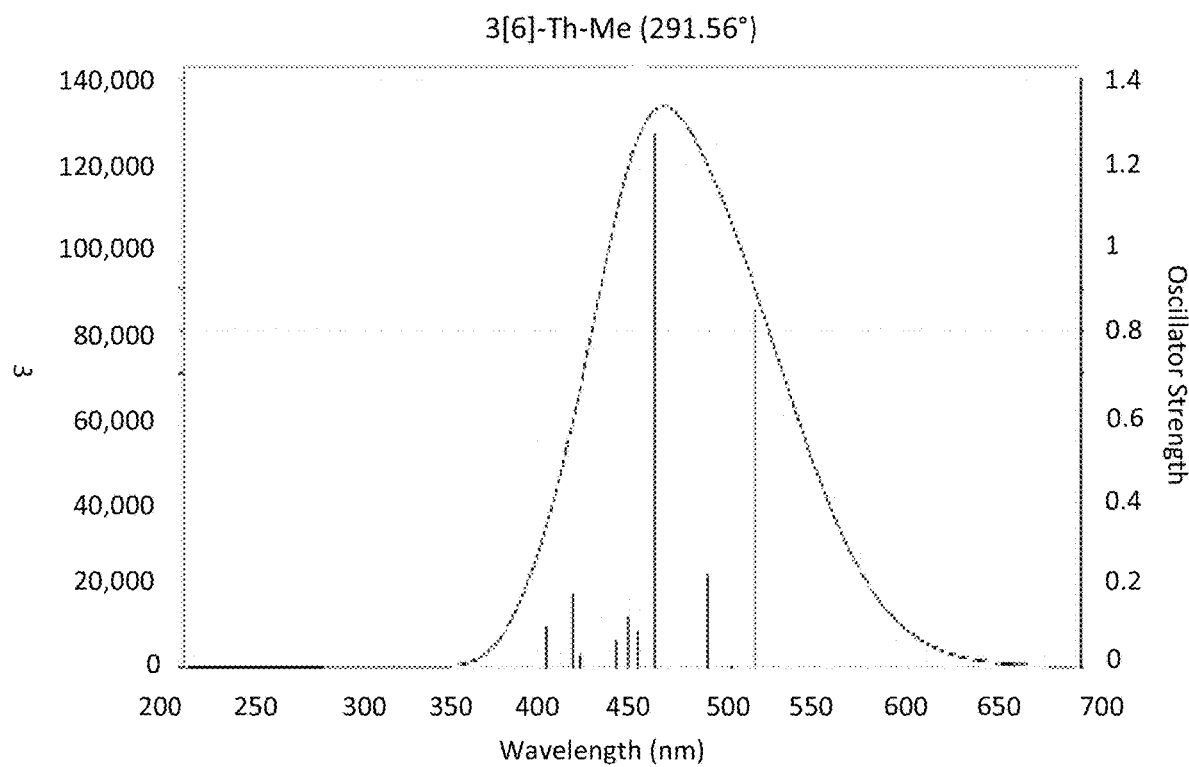
Figure 20A:
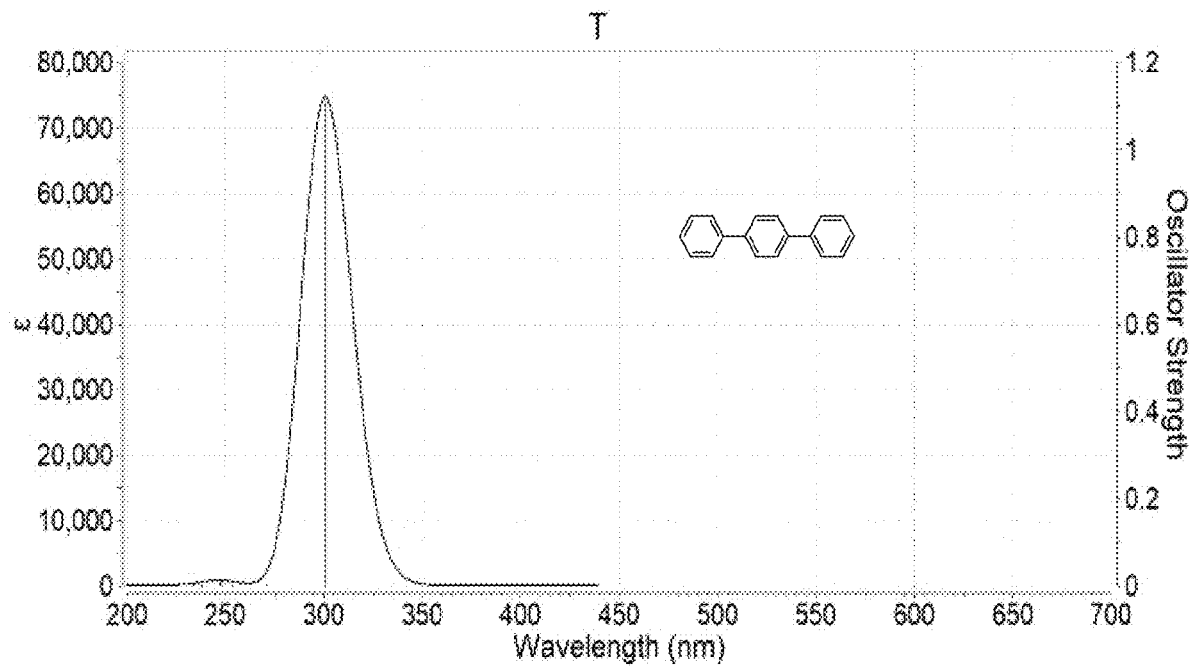
FIGS. 20A-20C are computed UV-Vis spectra of T (FIG. 20A), mT (FIG. 20B) and [8](FIG. 20C) with 6 excited states.
Figure 20B:
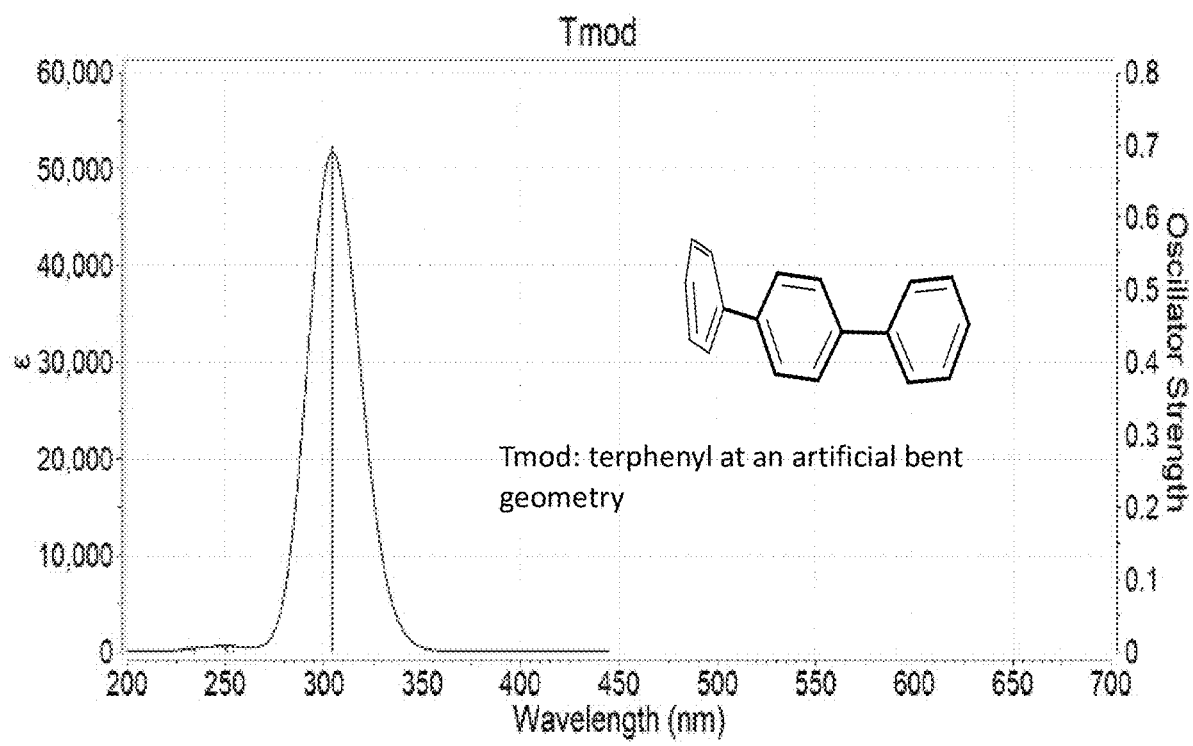
Figure 20C:
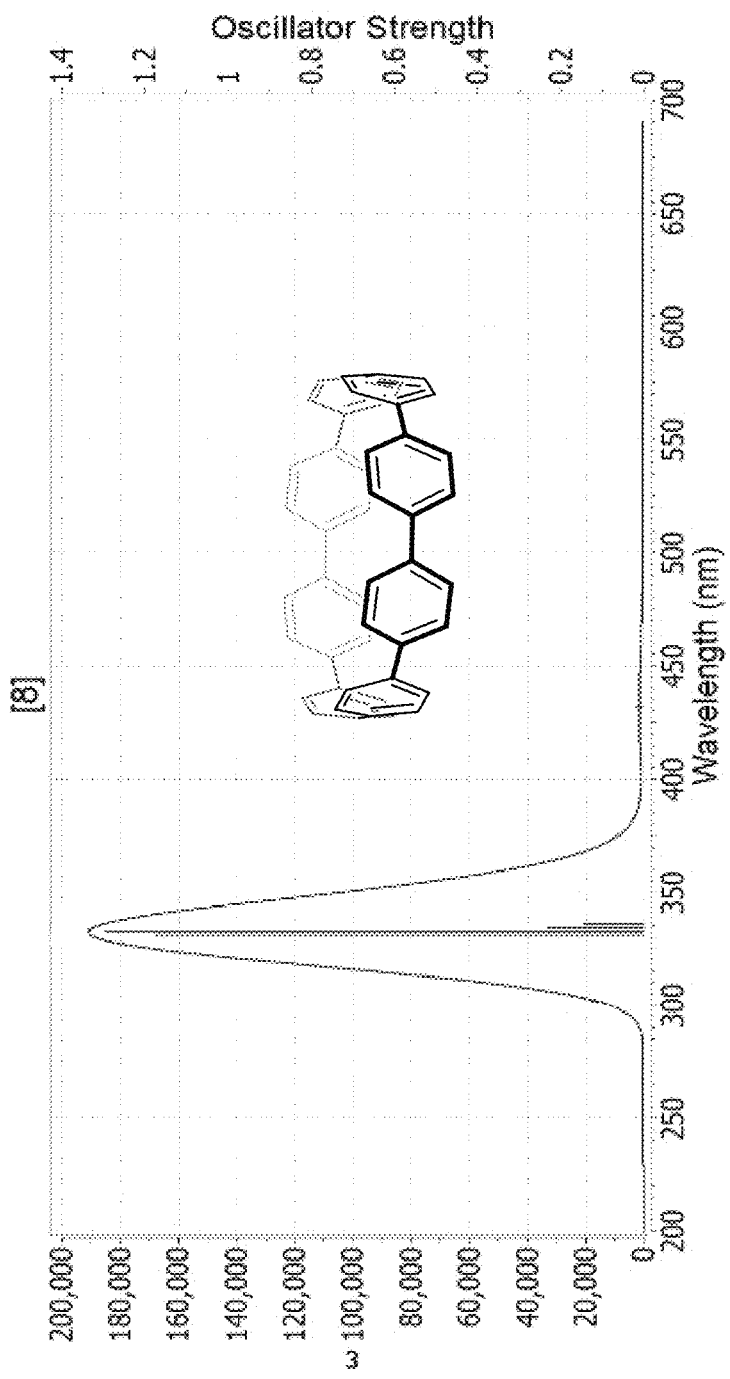
Figure 21A:
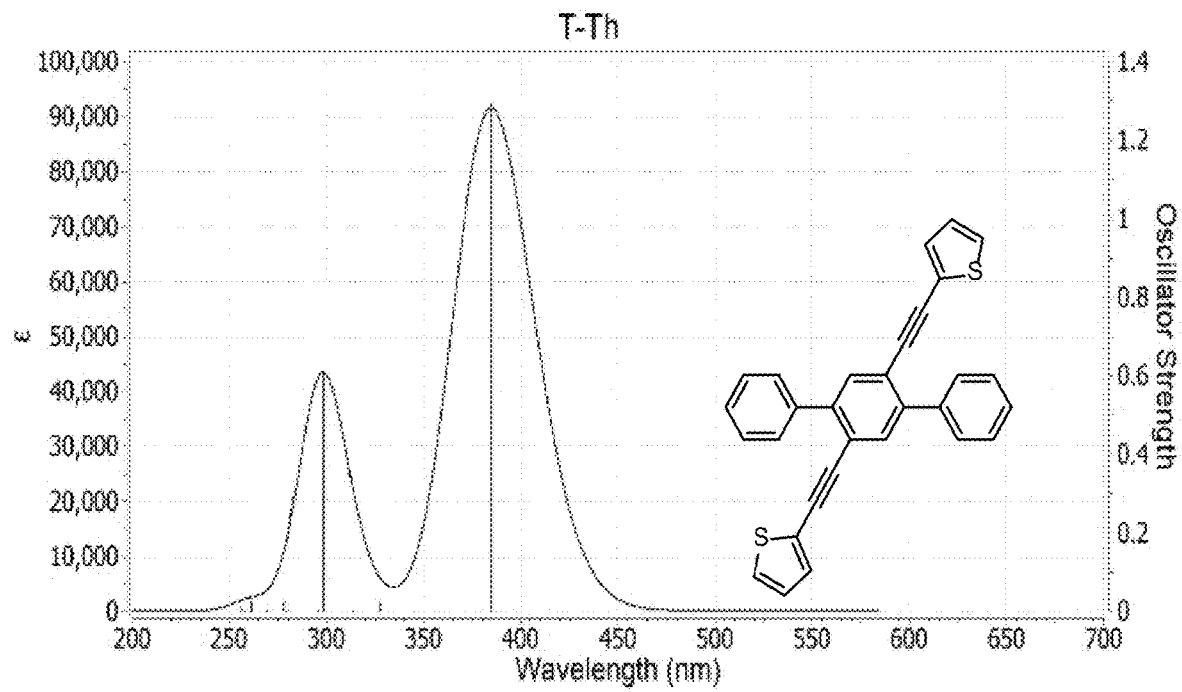
FIGS. 21A and 21B are computed UV-Vis spectra of T-Th and T-Ph, respectively, with 12 excited states.
Figure 21B:
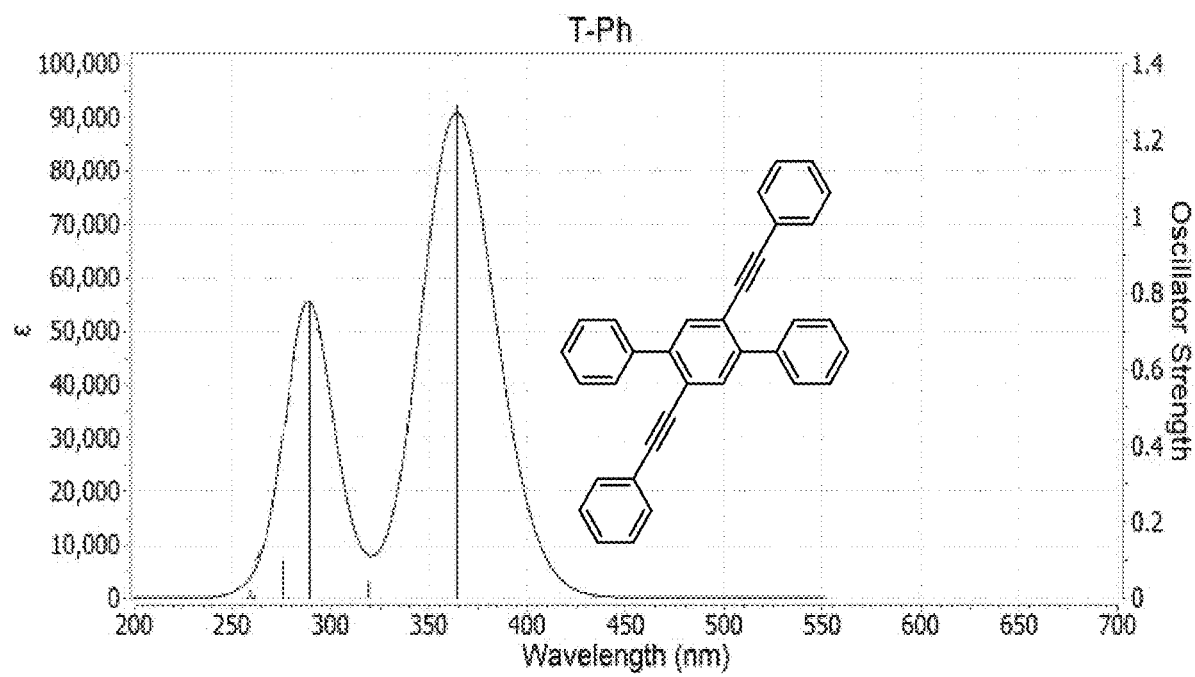
Figure 22A:
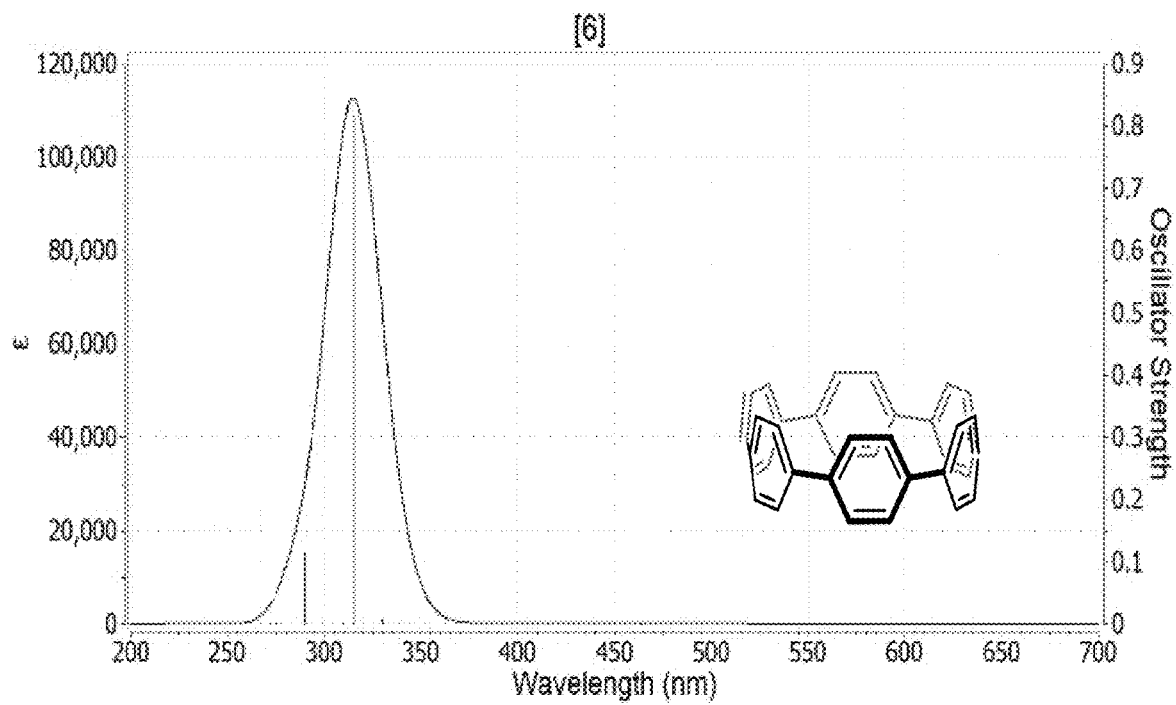
FIGS. 22A-22C are computed UV-Vis spectra of [6] (FIG. 22A), [6]-Th (FIG. 22B), [6]-Ph (FIG. 22C) with 12 excited states.
Figure 22B:
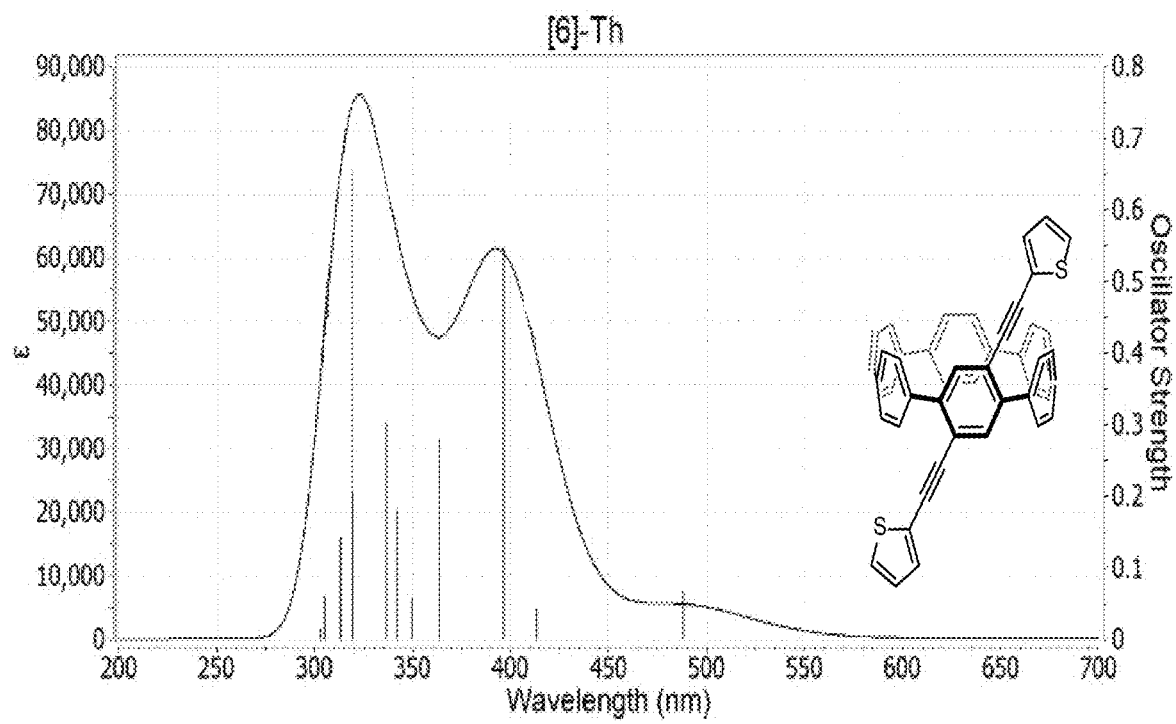
Figure 22C:
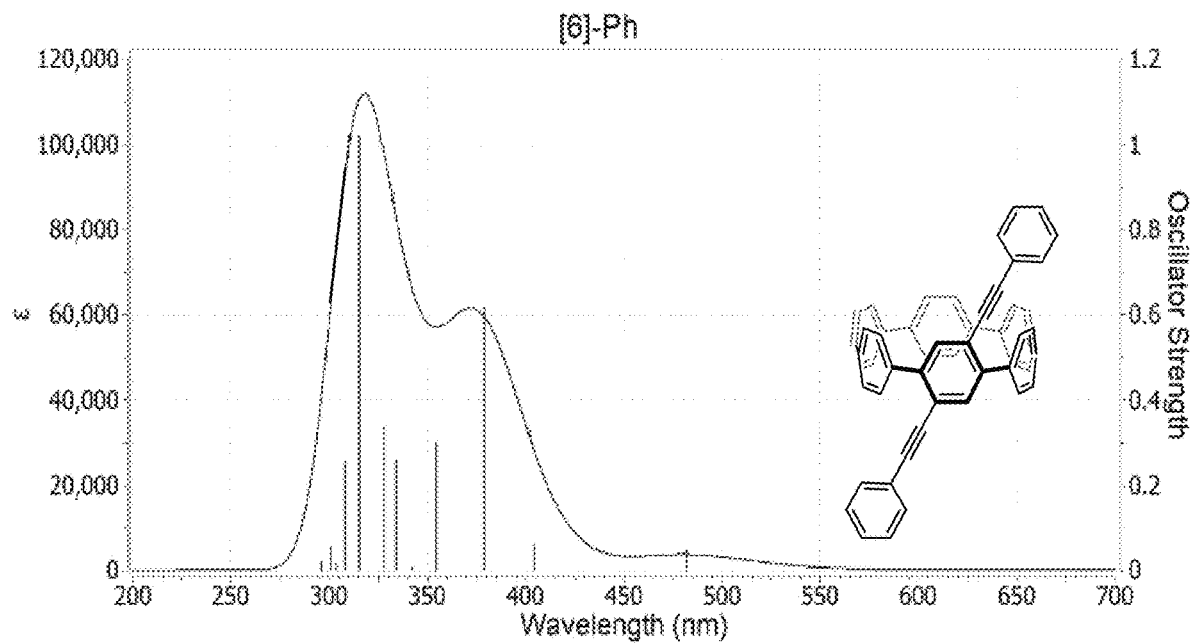
Figure 23A:
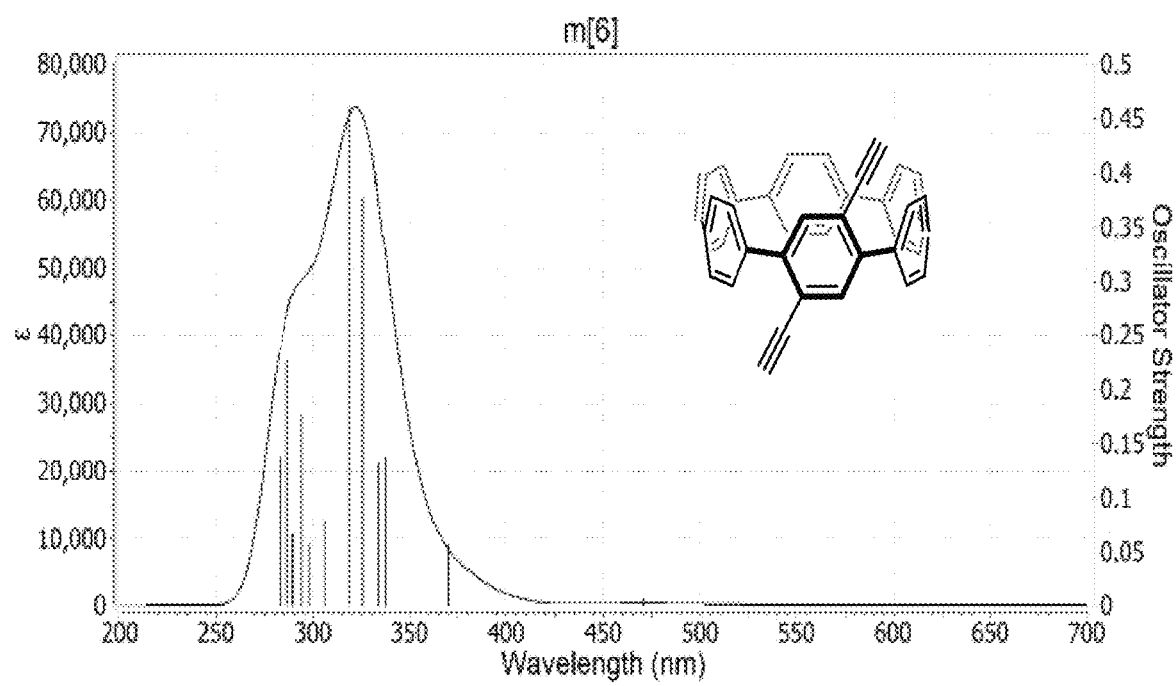
FIGS. 23A-23C are computed UV-Vis spectra of mT with 6 excited states (FIG. 23A) and monomer 5 (FIG. 23B) and monomer 8 (FIG. 23C) with 12 excited states.
Figure 23B:
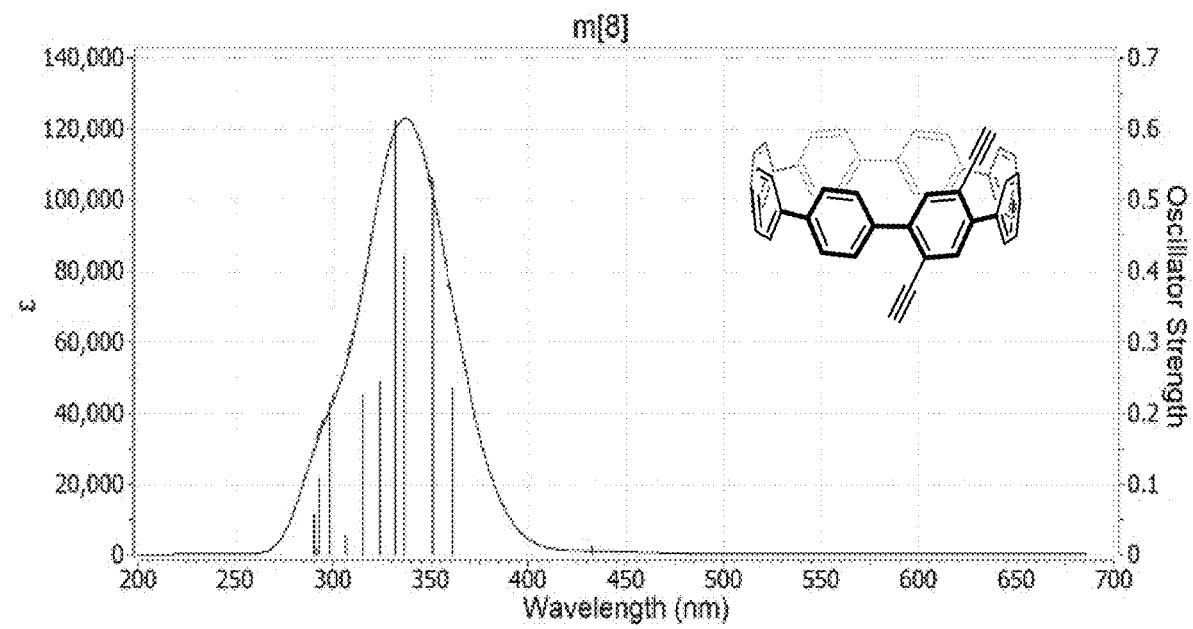
Figure 23C:
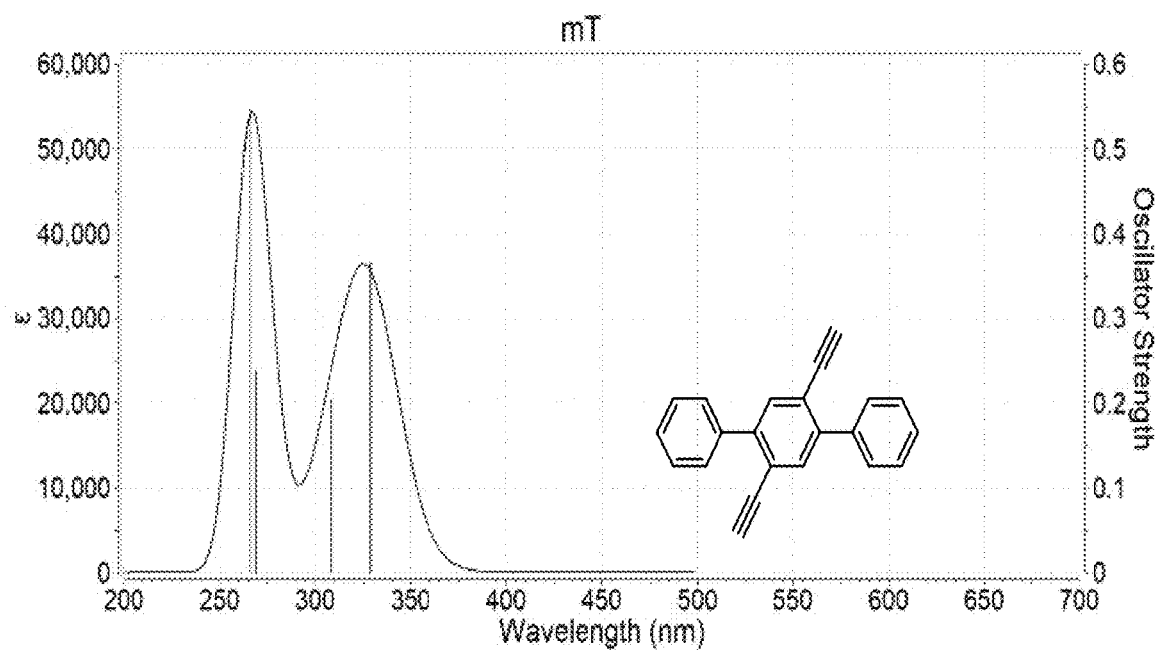
Figure 24A:
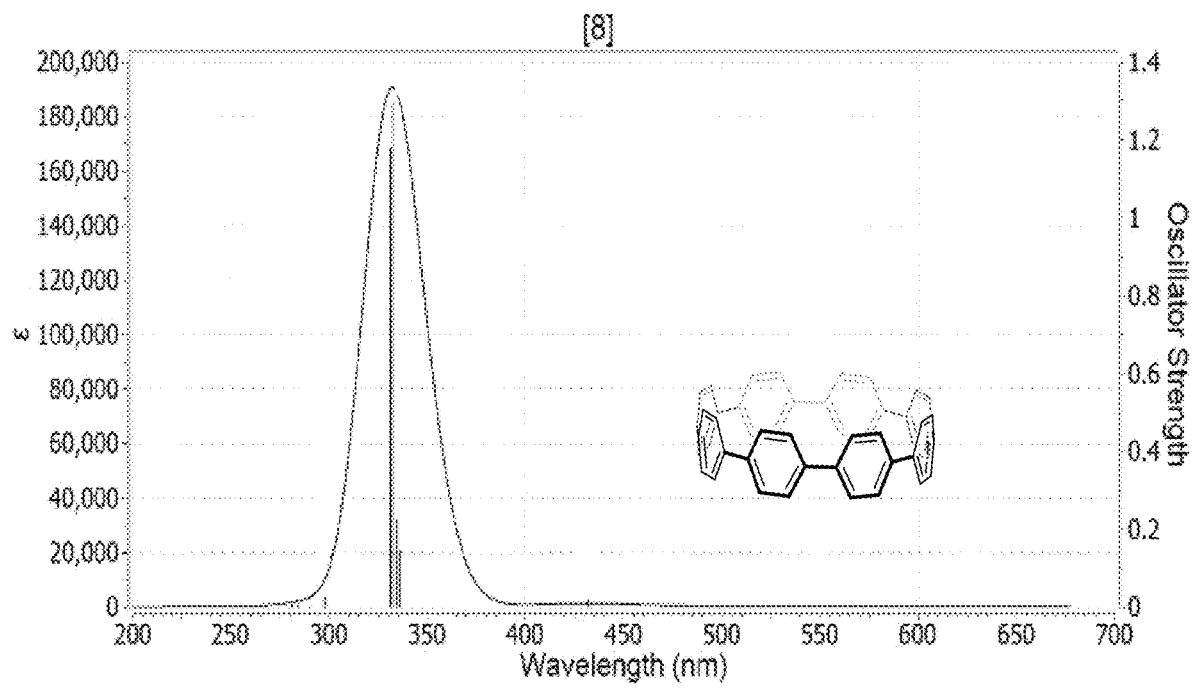
FIGS. 24A-24C are computed UV-Vis spectra of [8] (FIG. 24A), [8]-Th (FIG. 24B), [8]-Ph (FIG. 24C) with 12 excited states.
Figure 24B:
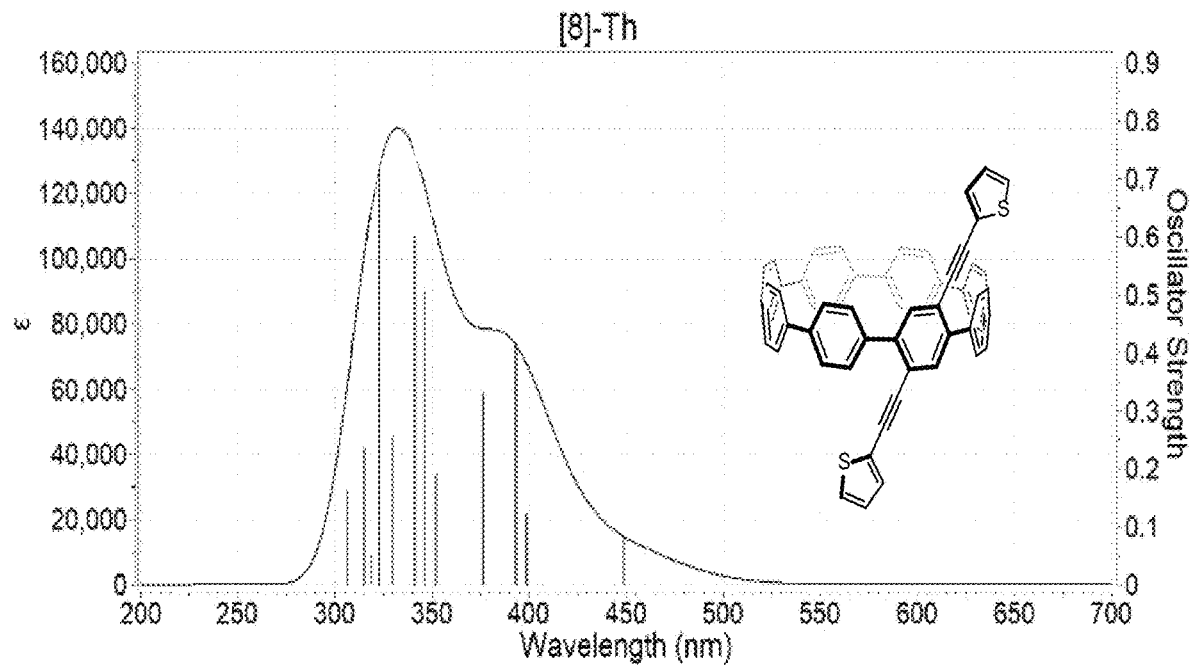
Figure 24C:
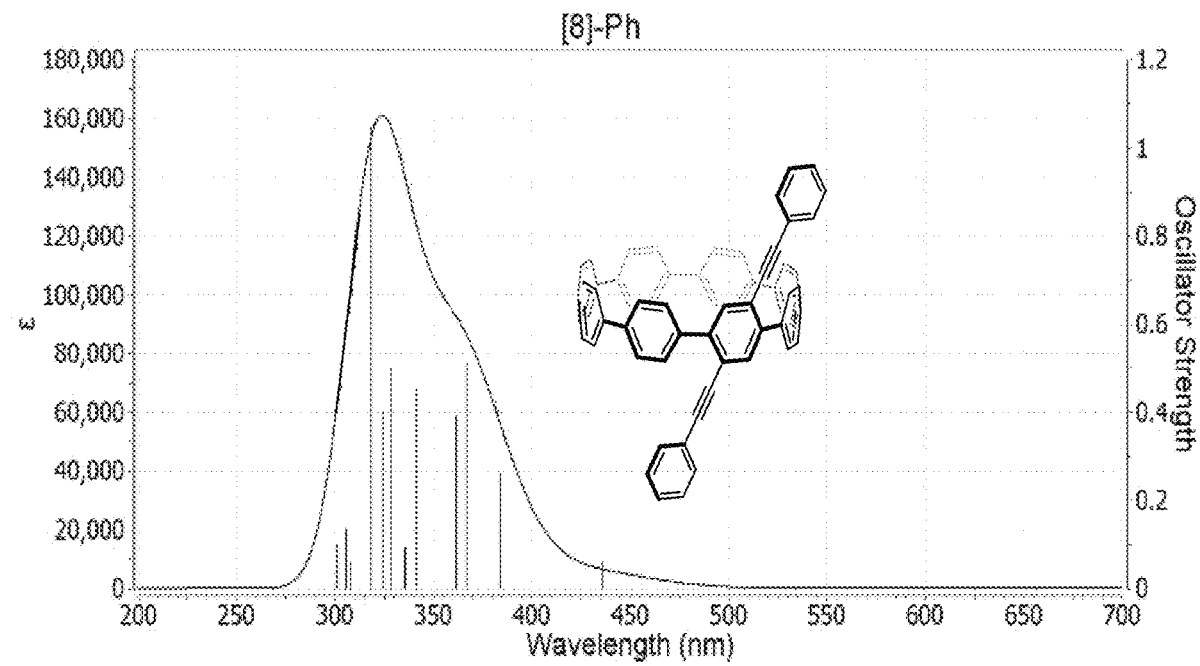
Figure 25A:
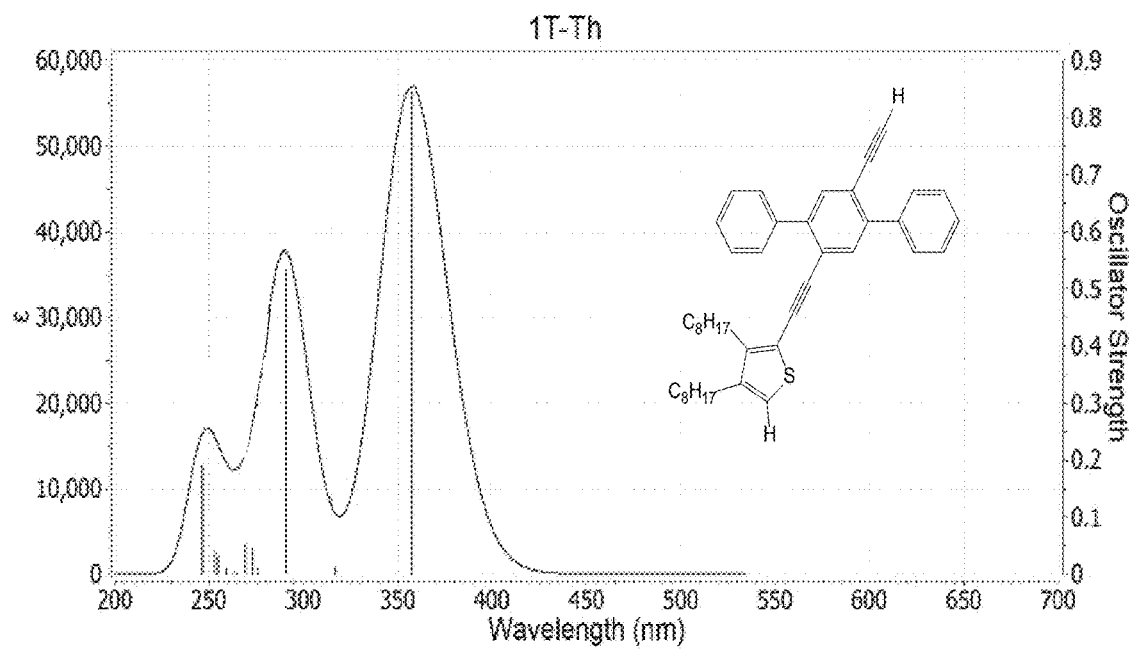
FIGS. 25A-25D are computed UV-Vis spectra of oligomers 1T-Th (FIG. 25A), 2T-Th (FIG. 25B), 3T-Th (FIG. 25C) and 4T-Th (FIG. 25D) corresponding to polymer PT-Th with 12 excited states.
Figure 25B:
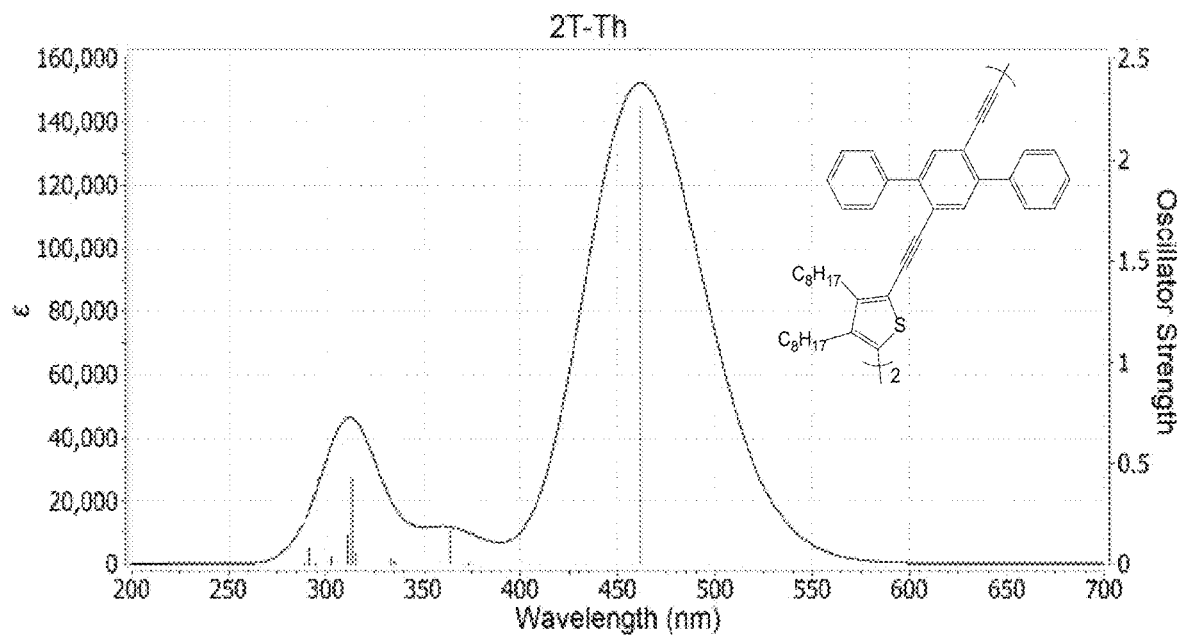
Figure 25C:
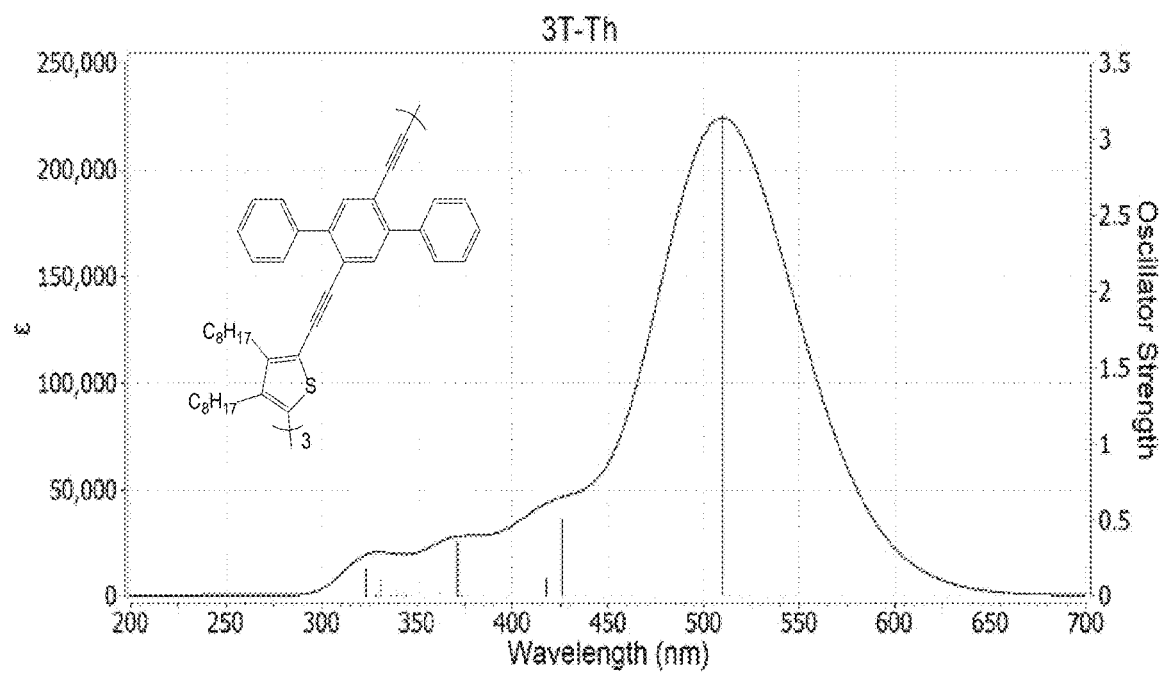
Figure 25D:
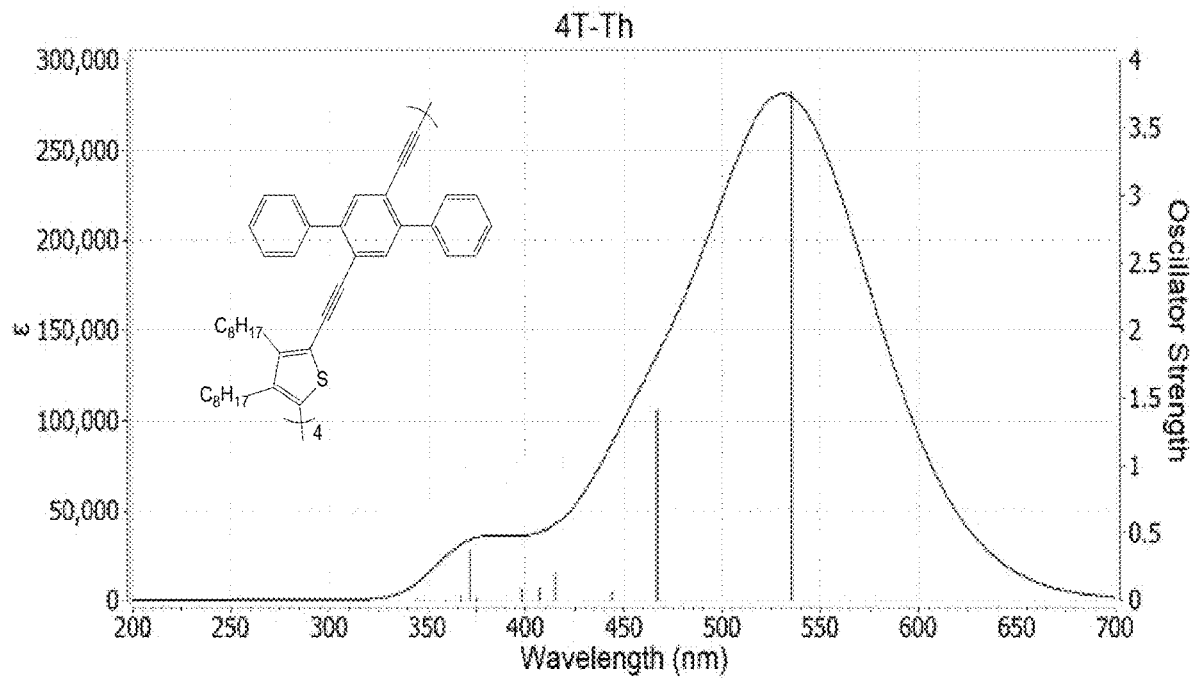
Figure 26A:
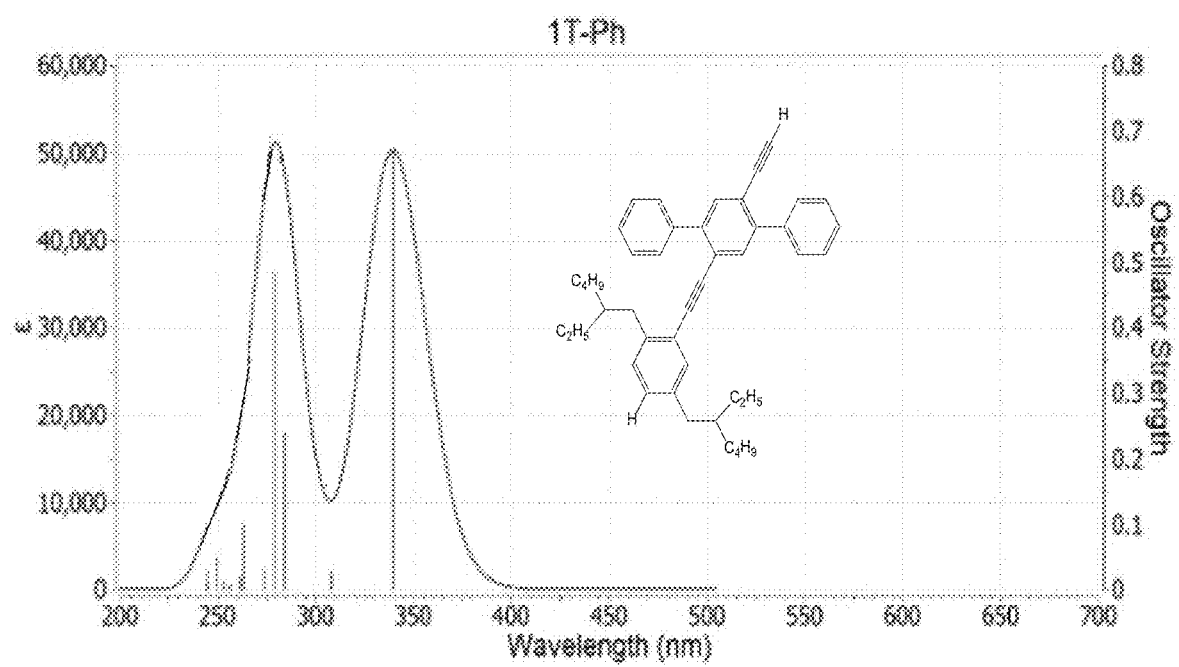
FIGS. 26A-26C are computed UV-Vis spectra of oligomers 1T-Ph (FIG. 26A), 2T-Ph (FIG. 26B), and 3T-Ph (FIG. 26C) corresponding to polymer PT-Ph with 12 excited states.
Figure 26B:
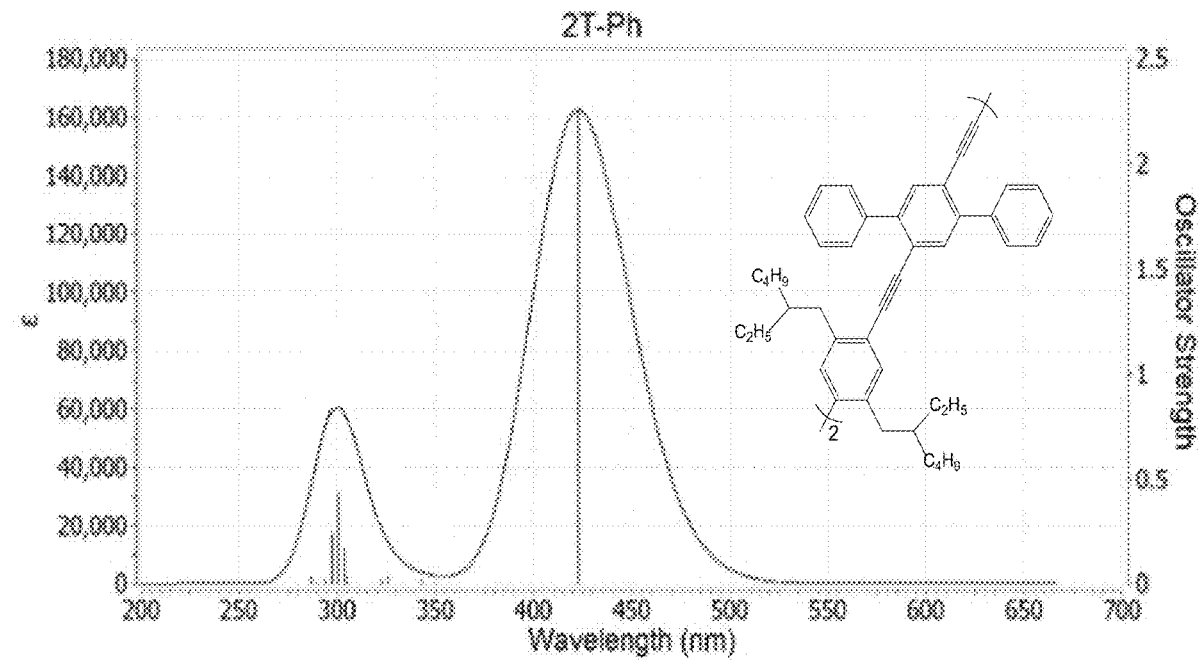
Figure 26C:
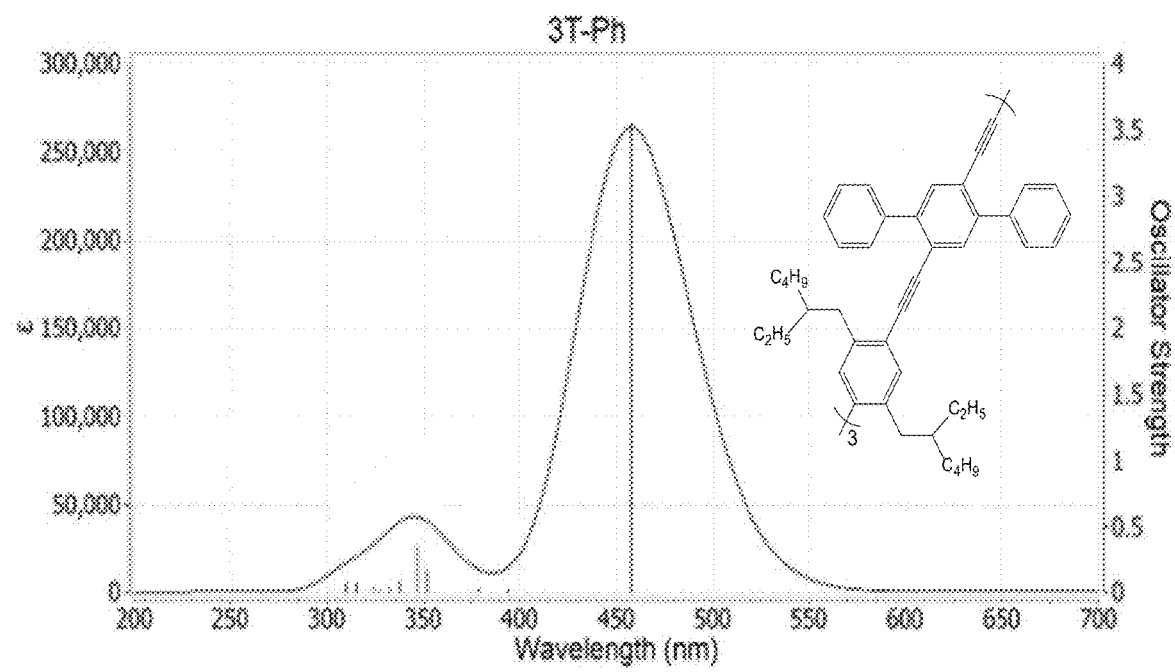
Figure 27A:
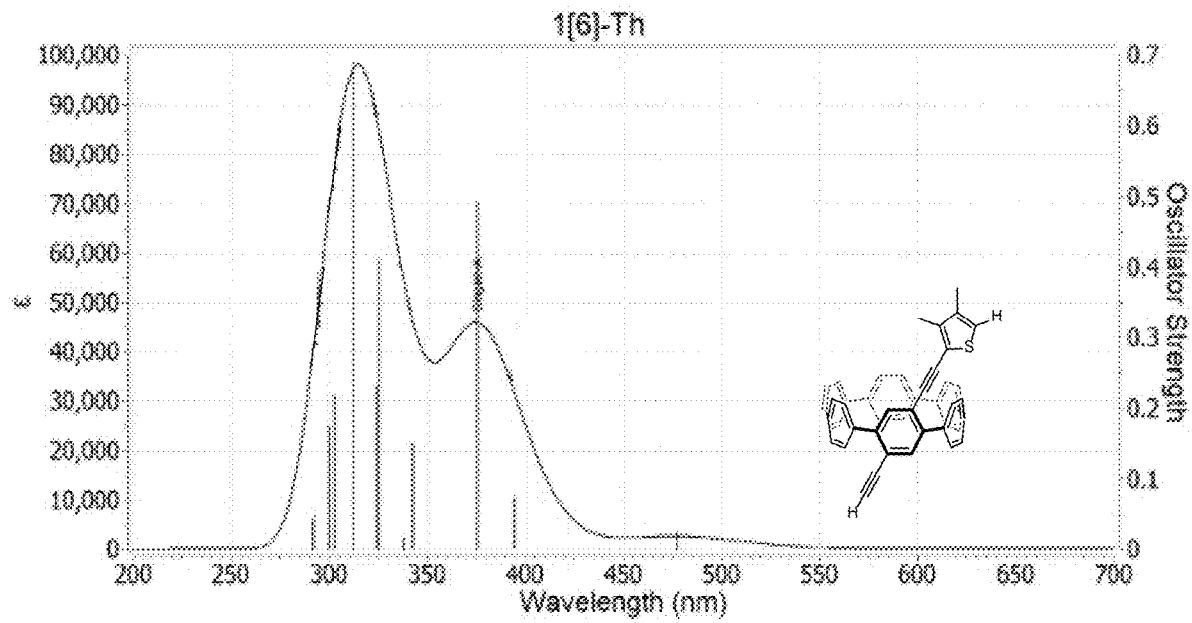
FIGS. 27A-27D are computed UV-Vis spectra of oligomers 1[6]-Th (FIG. 27A), 2[6]-Th (FIG. 27B), 3[6]-Th (FIG. 27C) and 4[6]-Th (FIG. 27D) corresponding to polymer P[6]-Th with 12 excited states.
Figure 27B:
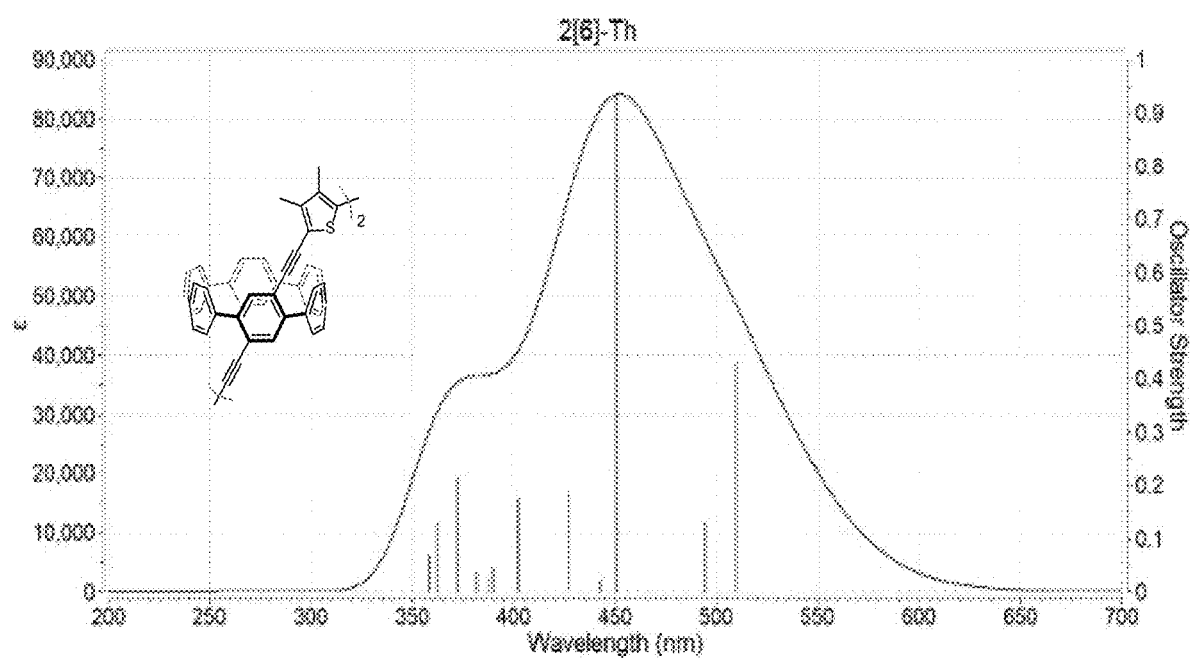
Figure 27C:
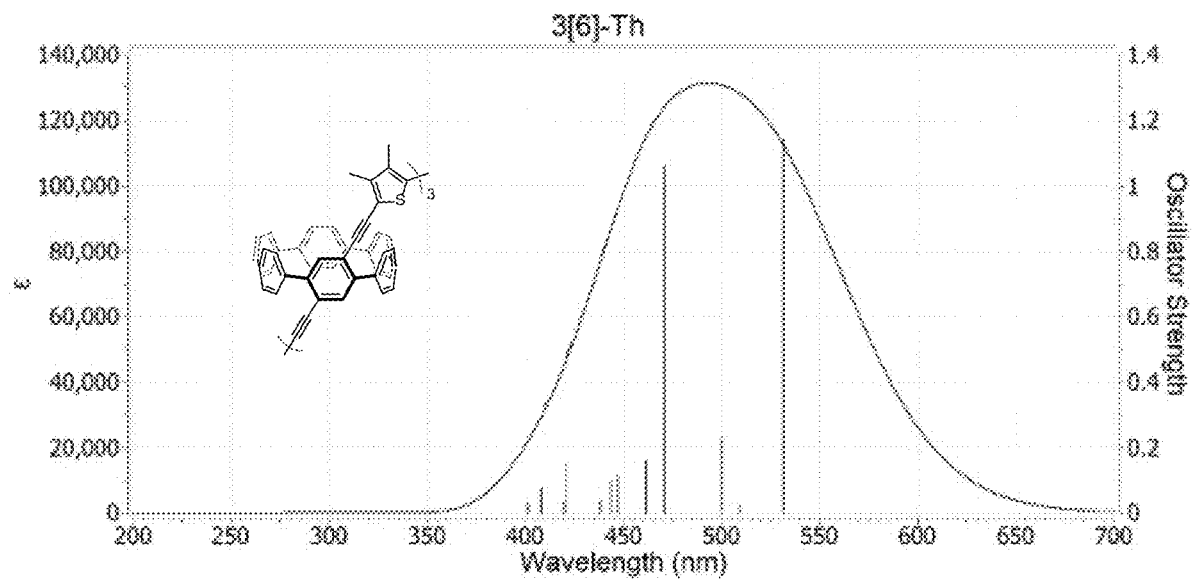
Figure 27D:
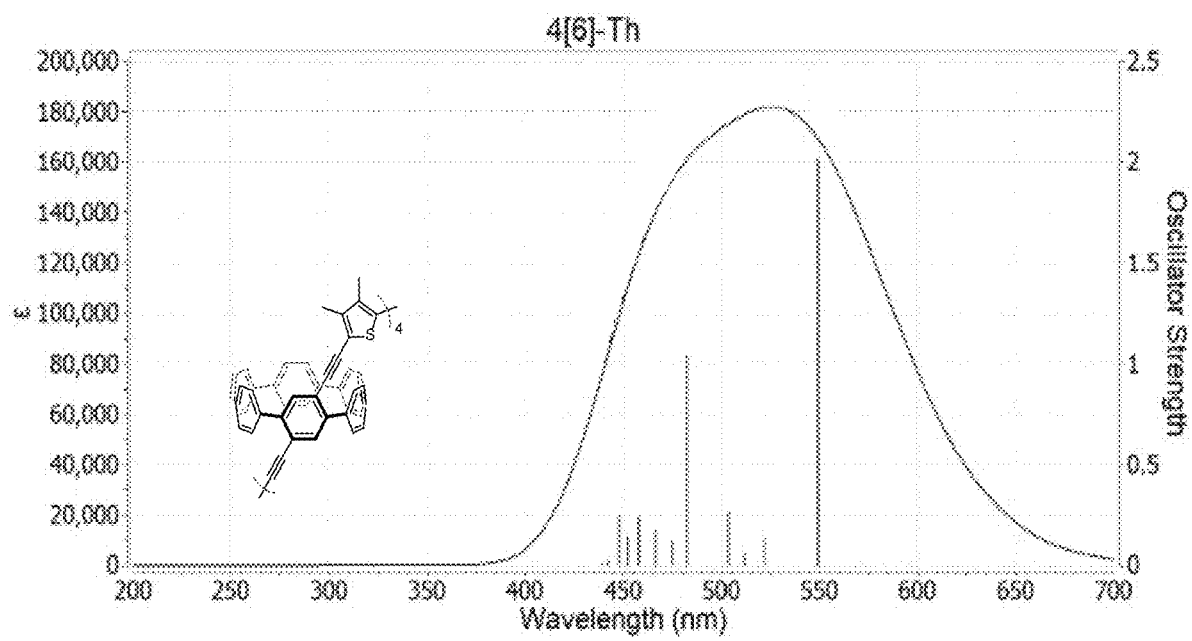
Figure 28A:
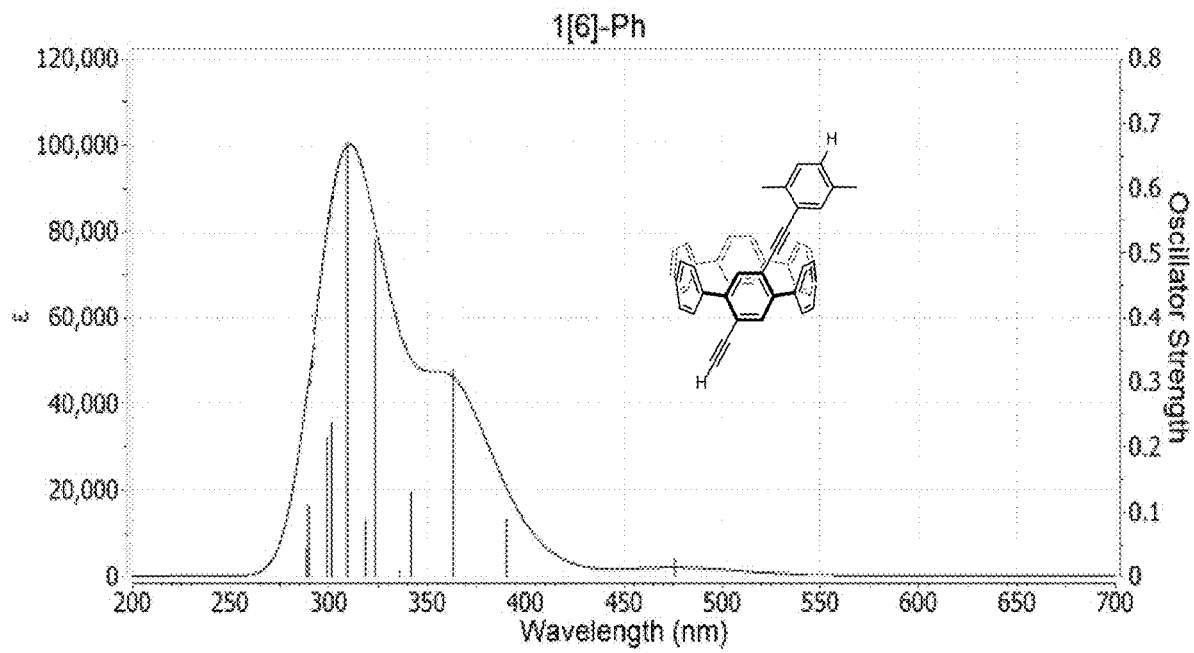
FIGS. 28A-28C are computed UV-Vis spectra of oligomers 1[6]-Ph (FIG. 28A), 2[6]-Ph (FIG. 28B), and 3[6]-Ph (FIG. 28C) corresponding to polymer P[6]-Ph with 12 excited states.
Figure 28B:
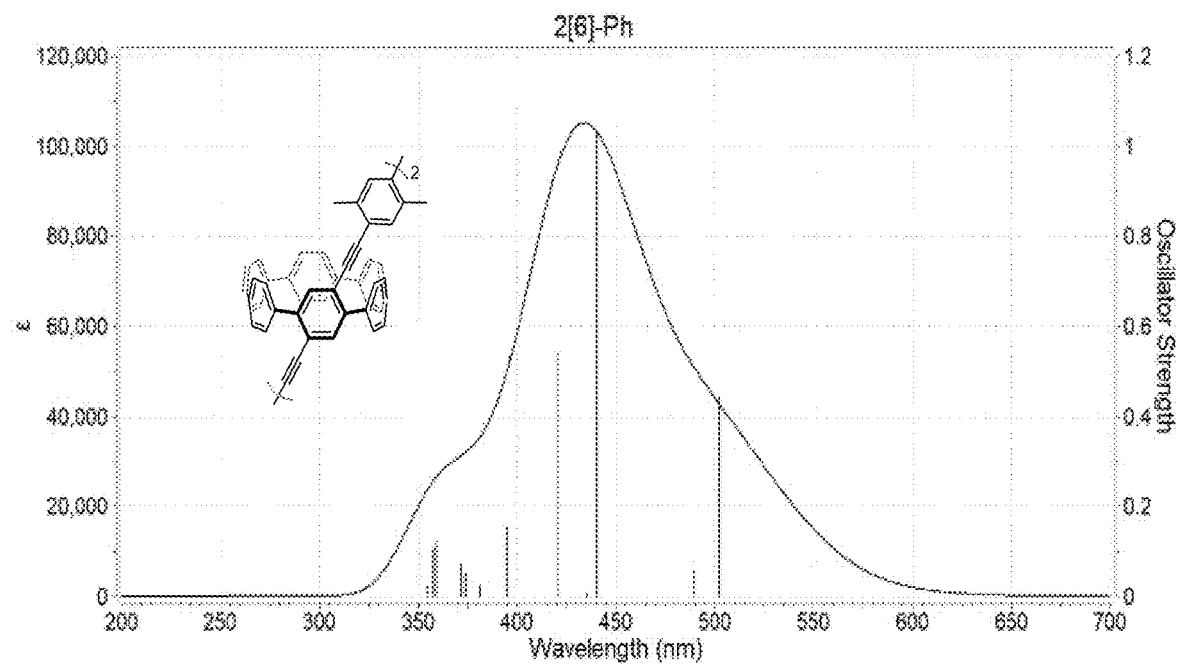
Figure 28C:
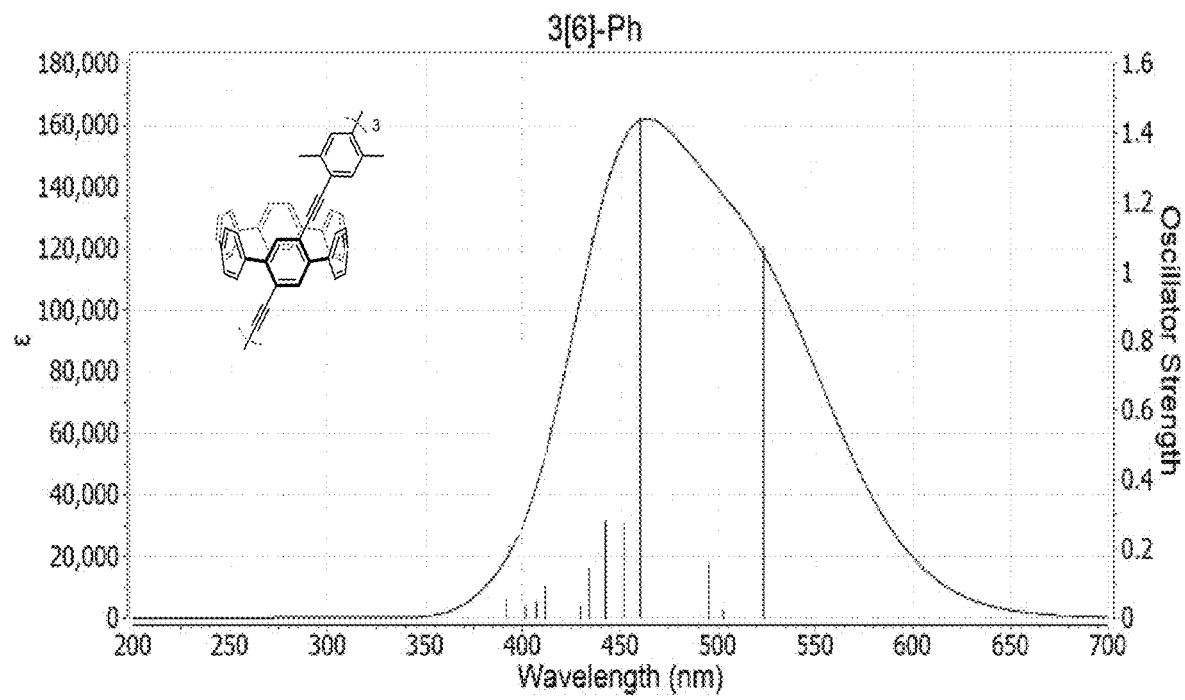
Figure 29A:
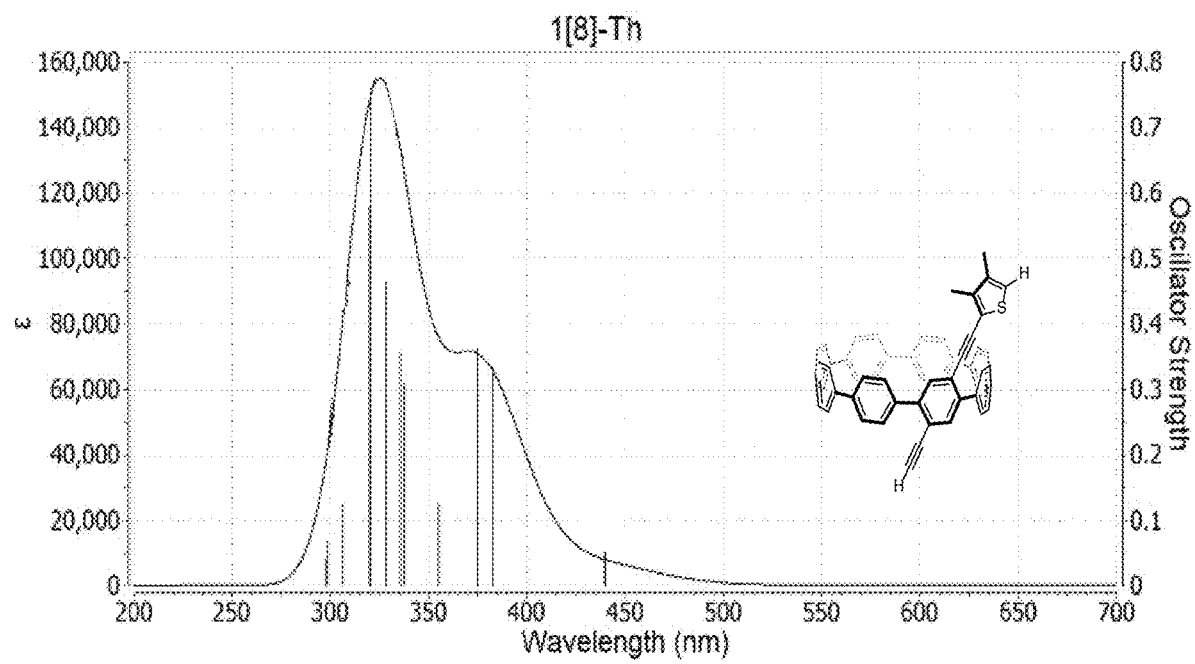
FIGS. 29A-29C are computed UV-Vis spectra of oligomers 1[8]-Th (FIG. 29A), 2[8]-Th (FIG. 29B), and 3[8]-Th (FIG. 29C) corresponding to polymer P[8]-Th with 12 excited states.
Figure 29B:
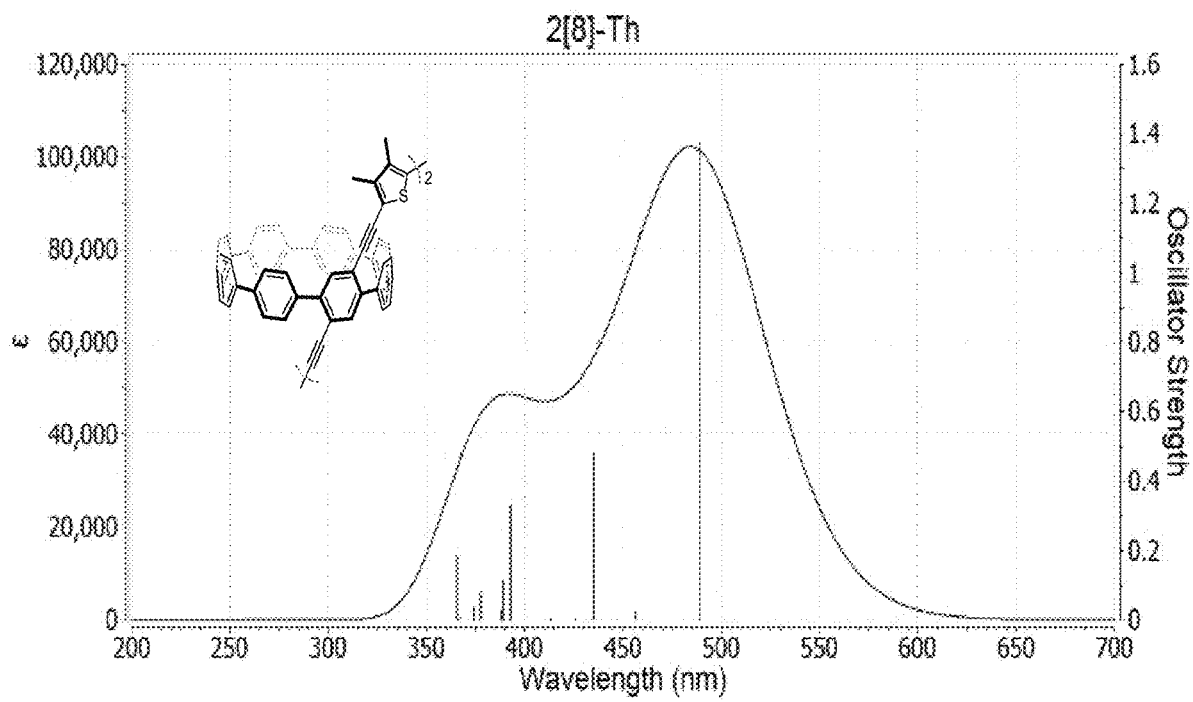
Figure 29C:
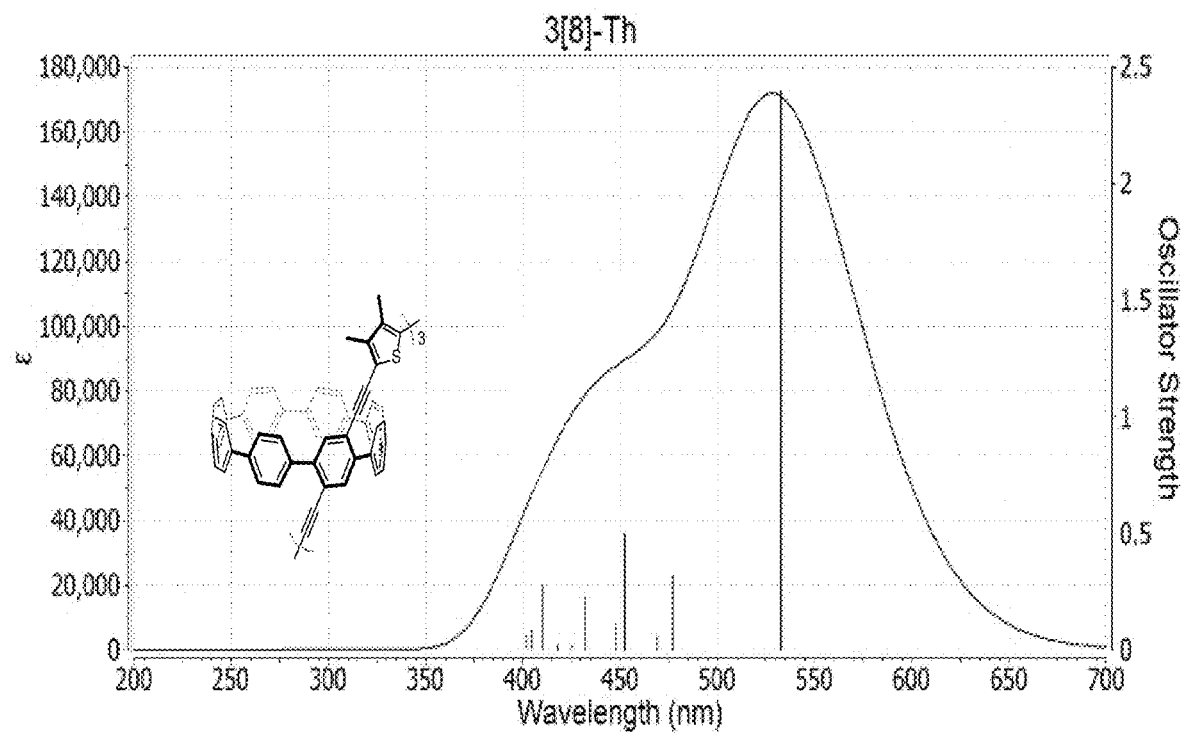
Figure 30A:
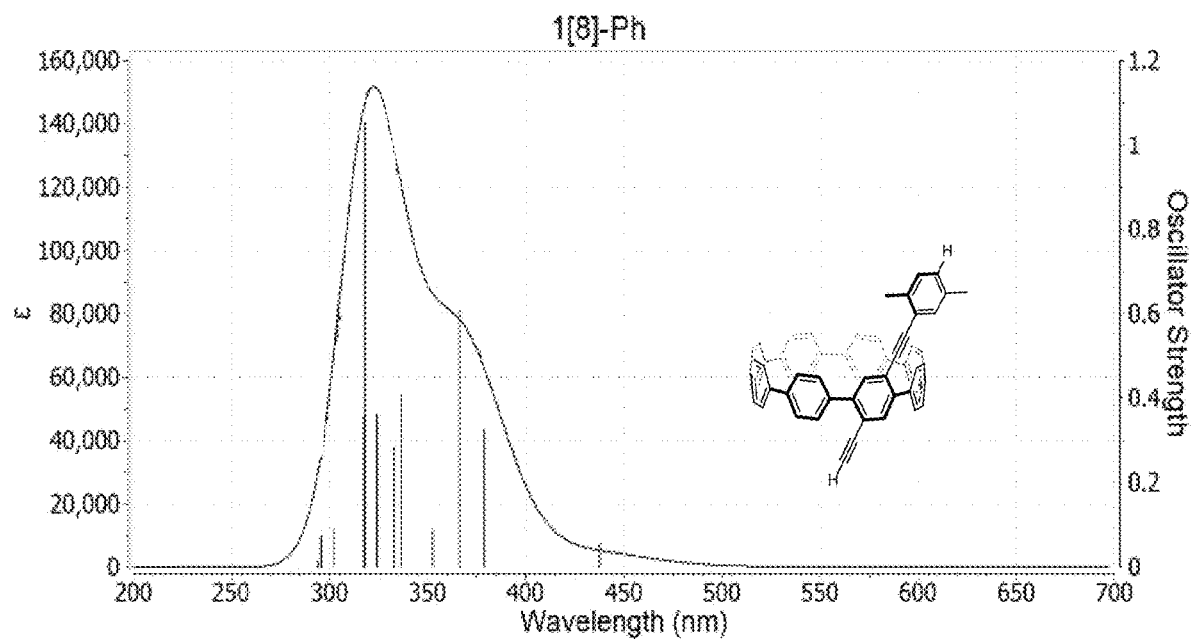
FIGS. 30A-30C are computed UV-Vis spectra of oligomers 1[8]-Ph (FIG. 30A), 2[8]-Ph (FIG. 30B), and 3[8]-Ph (FIG. 30C) corresponding to polymer P[8]-Ph with 12 excited states.
Figure 30B:
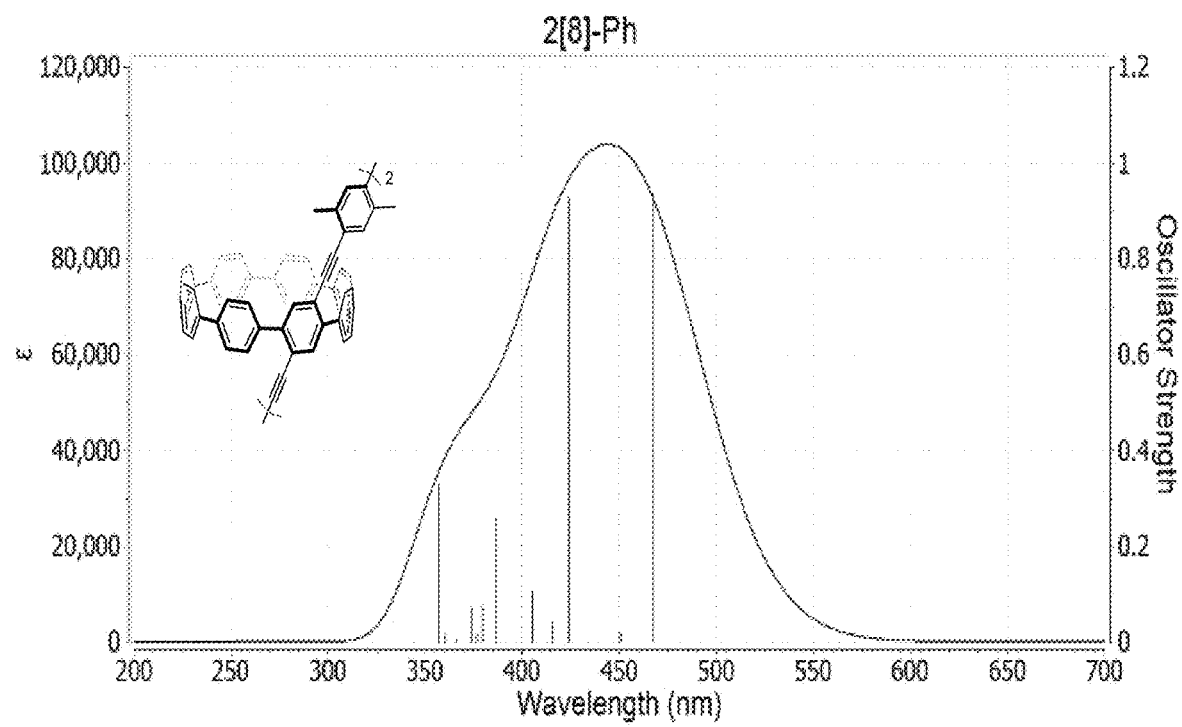
Figure 30C:
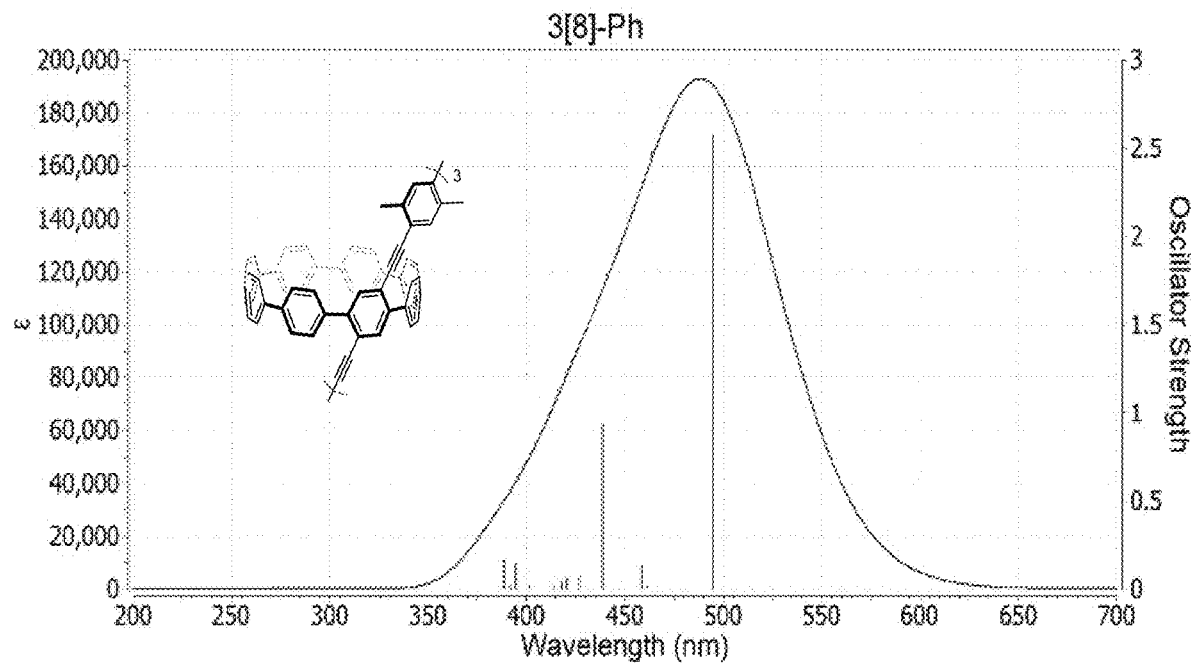
Figure 31A:
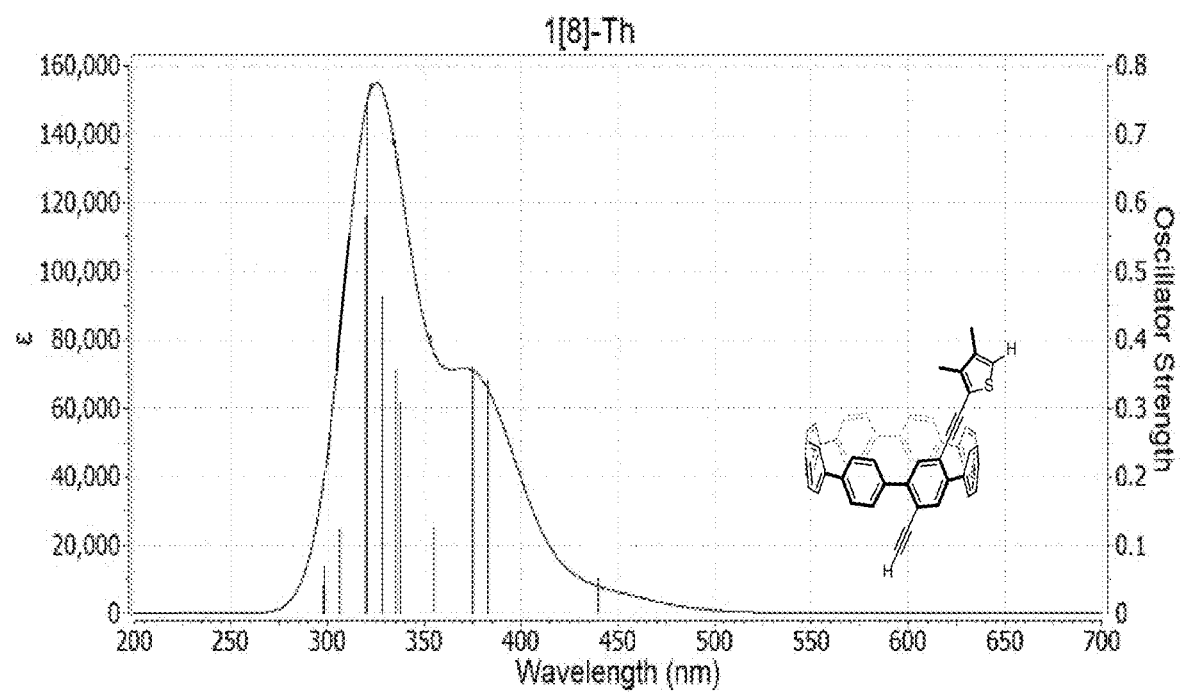
FIGS. 31A and 31B are computed UV-Vis spectra of oligomer 1[8]-Ph (FIG. 31A) and monomer [8]-Th (FIG. 31B) with 12 excited states.
Figure 31B:
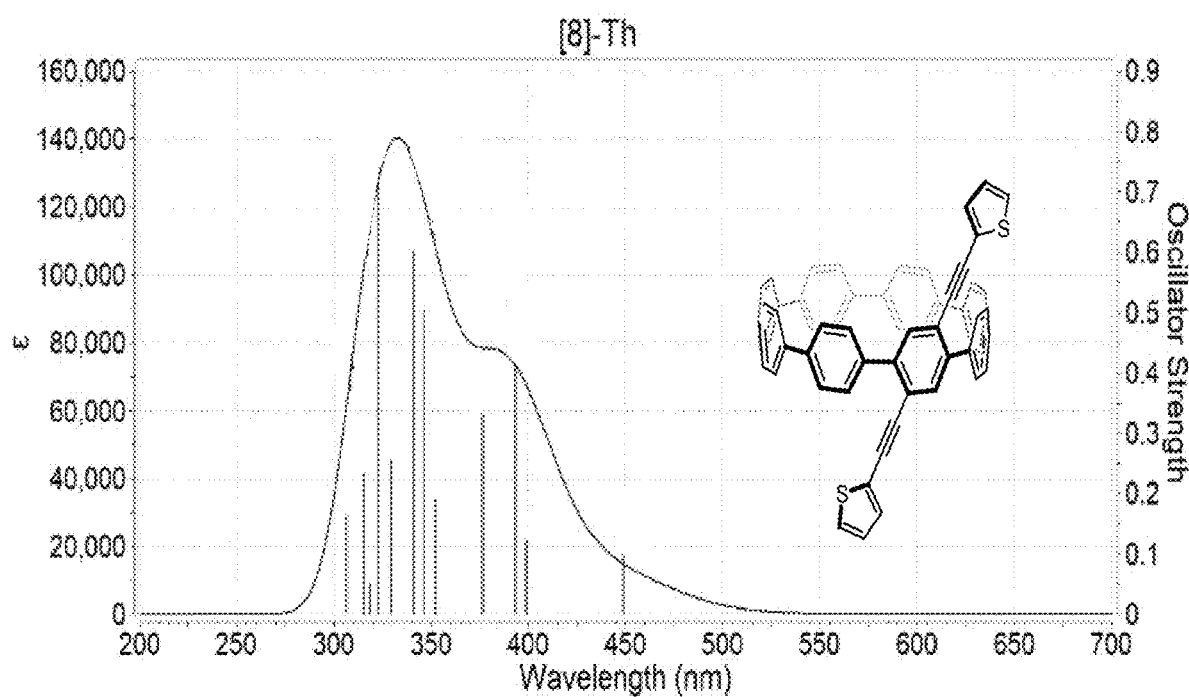
Figure 32A:
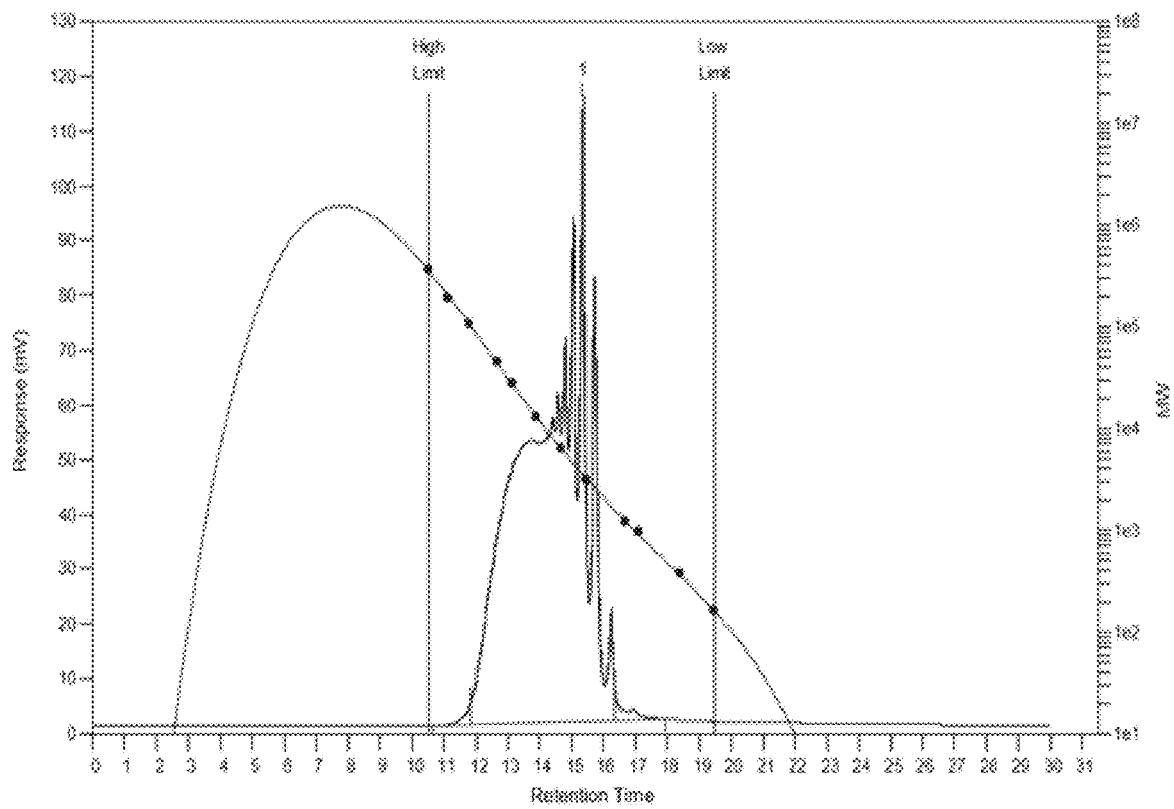
FIGS. 32A and 32B are GPC chromatographs for P[6]-Ph (FIG. 32A) and P[6]-Th (FIG. 32B) acquired in THF relative to polystyrene standards.
Figure 32B:
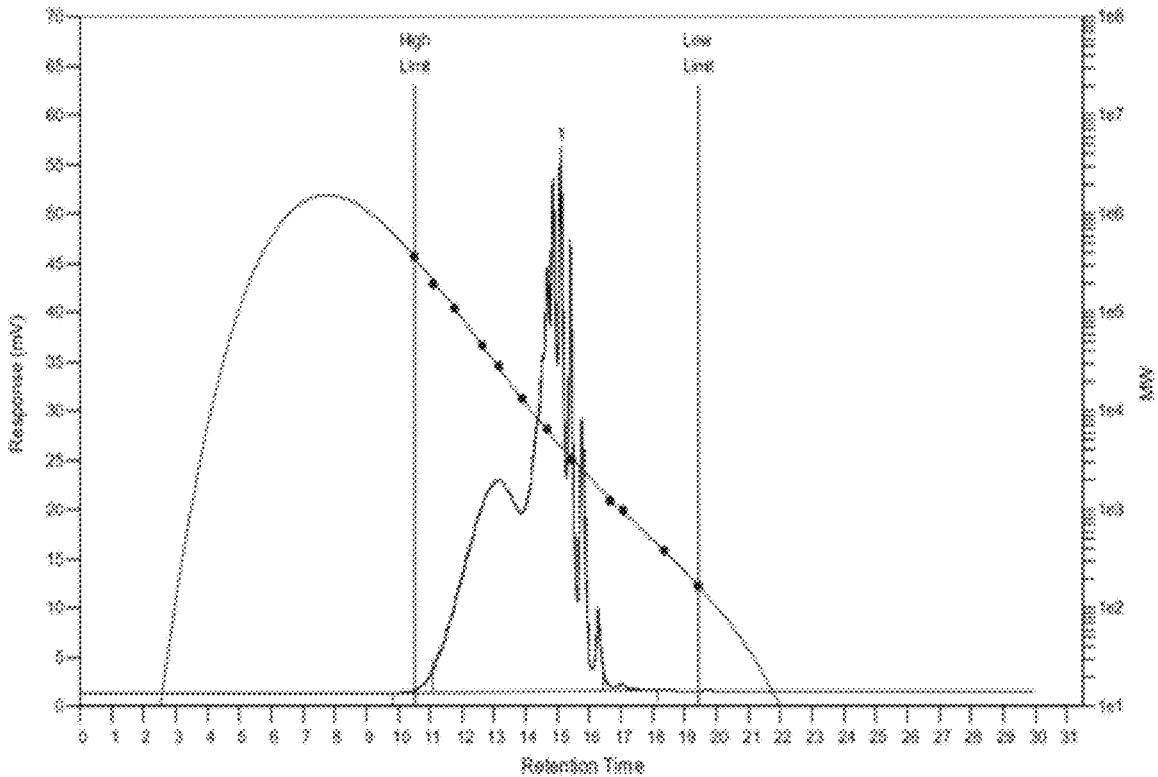
Figures 33A, 33B:
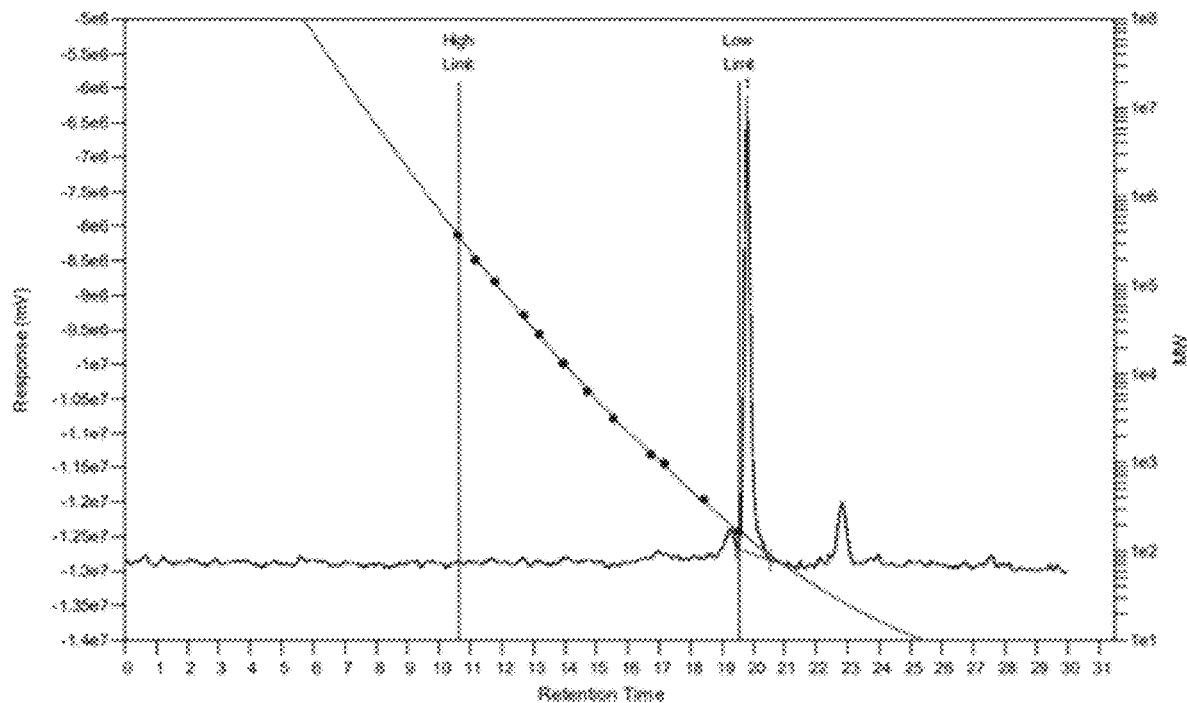
FIGS. 33A and 33B are GPC chromatographs for models [6]-Ph (FIG. 33A) and [6]-Th (FIG. 33B) acquired in THF relative to polystyrene standards.
Figure 34A:
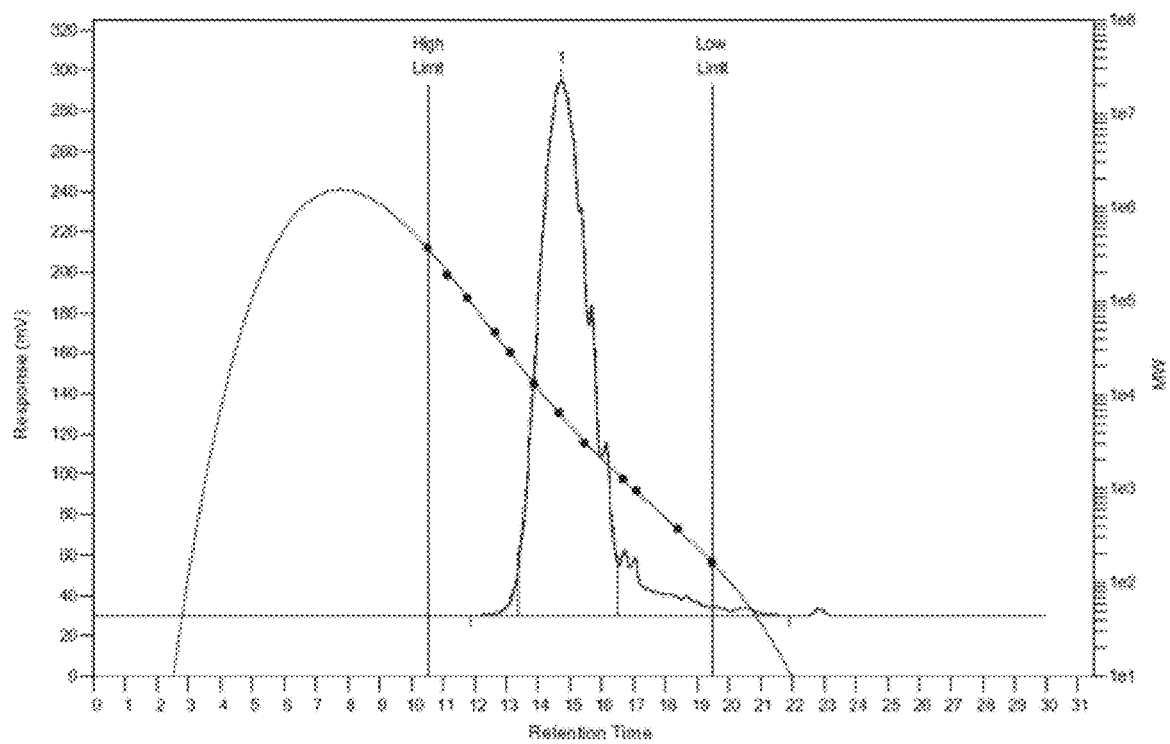
FIGS. 34A and 34B are GPC chromatographs for models P[8]-Ph (FIG. 34A) and P[8]-Th (FIG. 34B) acquired in THF relative to polystyrene standards.
Figure 34B:
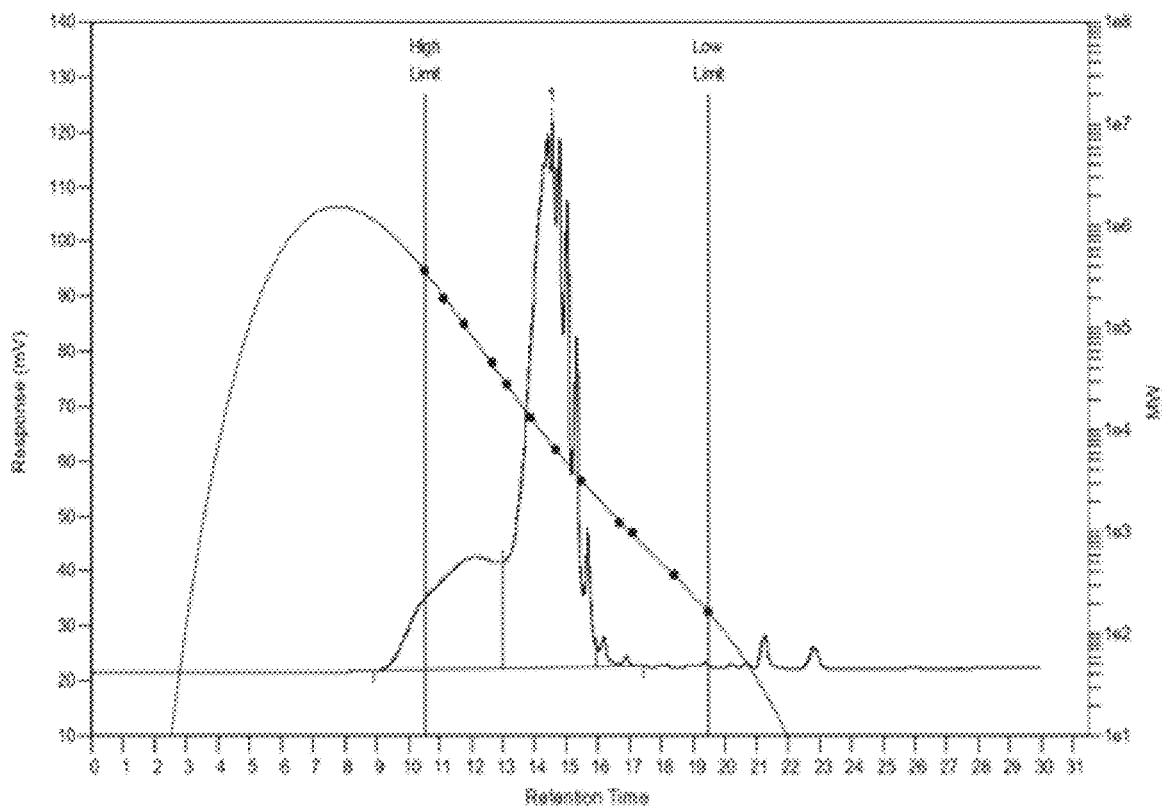
Figure 35A:
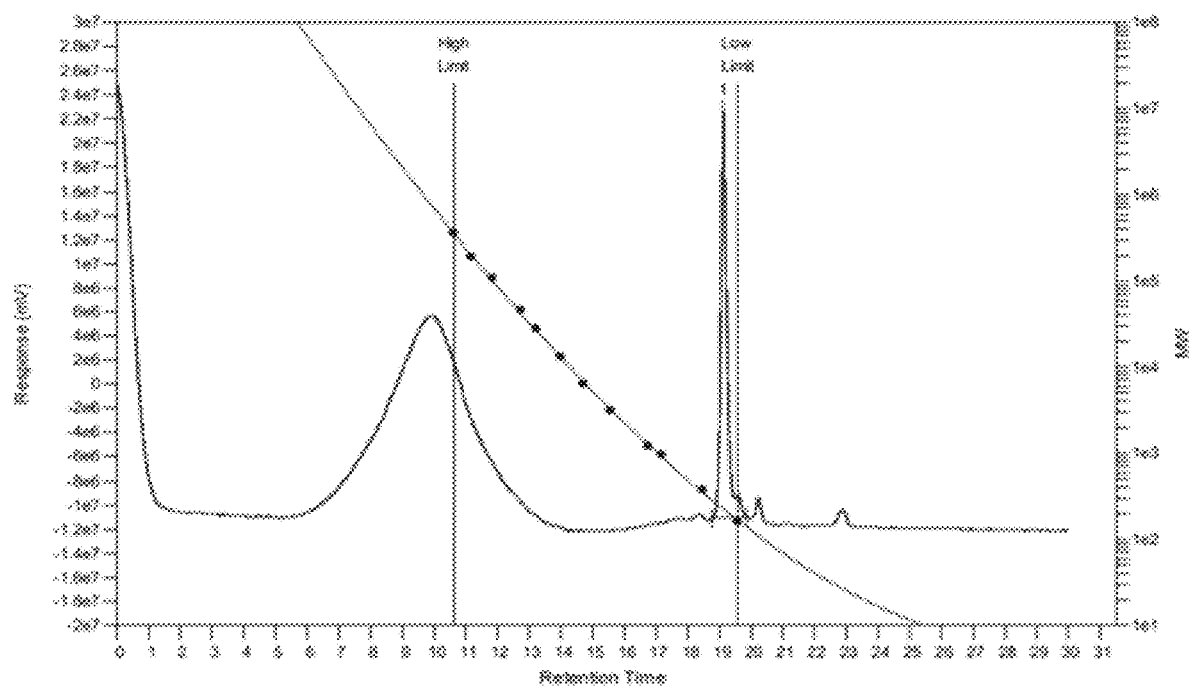
FIGS. 35A and 35B are GPC chromatographs for models [8]-Ph (FIG. 35A) and [8]-Th (FIG. 35B) acquired in THF relative to polystyrene standards.
Figure 35B:
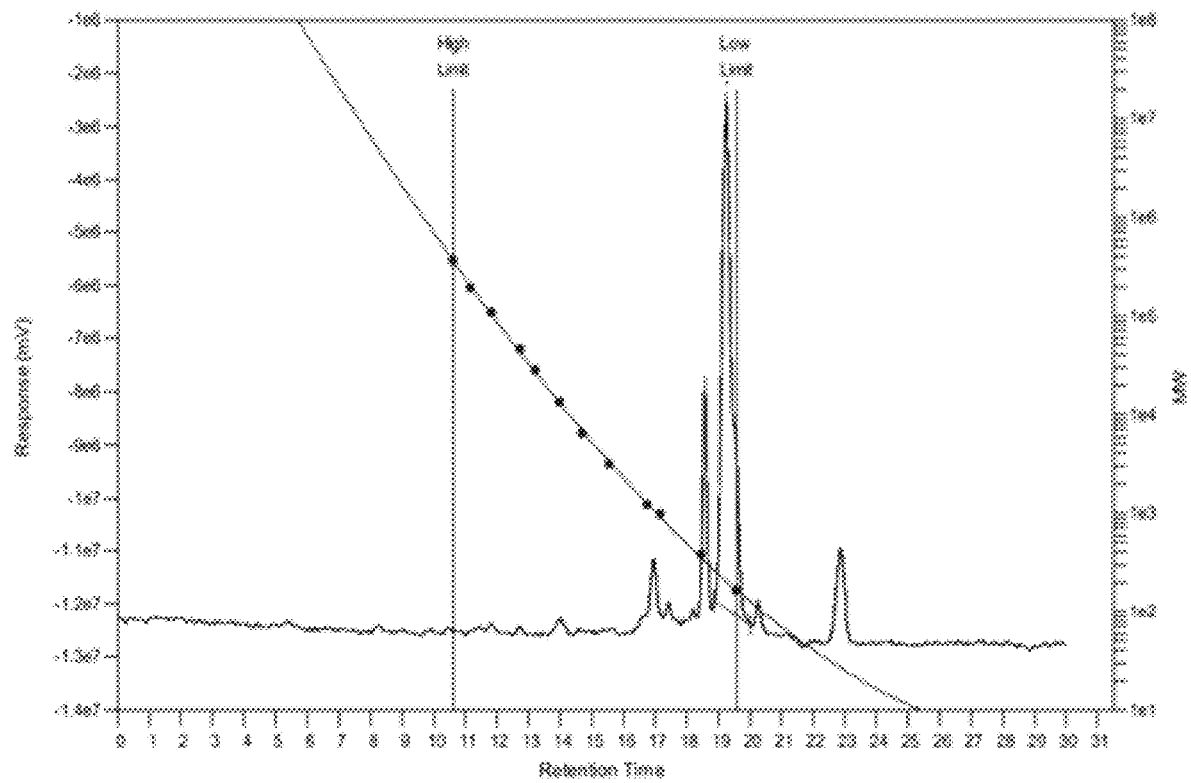

Deprotected macrocycle 9 (20 mg, 0.033 mmol, 1.00 equiv.) was added to a flame-dried flask and dissolved in THF (0.2 mL, 20 mM). Then a 0.05 M (in THF) solution of H$_2$SnCl$_4$ (1.5 mL, 0.073 mmol, 2.20 equiv.) was added dropwise. The reaction was stirred at room temperature for 30 min, then quenched with saturated sodium bicarbonate solution. The material was filtered through celite using water and DCM. The filtrate was extracted with DCM (3×), and the combined organic layers were washed with water (2×) and brine (1×) before being dried over sodium sulfate. Solvent was removed under reduced pressure. The material was purified by pipet column chromatography in 20% DCM in hexanes, yielding a red solid (12 mg, 71%). IR (neat): 3283, 3023, 2932, 2825, 1584, 1482, 1462, 1352, 1252, 1173, 1056, 947, 832, 819, 766, 728, 705 cm$^{-1}$. $^1$H NMR (500 MHz, CDCl$_3$, −10° C.) δ 8.52 (s, 2H), 7.72 (s, 2H), 7.68-7.48 (overlap, 18H), 3.64 (s, 2H). $^{13}$C NMR (126 MHz, CDCl$_3$, −10° C.) δ 137.49, 137.33, 135.58, 135.35, 135.13, 134.48, 133.35, 128.44, 128.03, 127.89, 127.53, 127.41, 127.39, 127.28, 127.21, 127.07, 118.59, 84.88, 83.40. See spectra section for $^1$H and $^{13}$C NMR spectra at −10° C. and 25° C. with assignments (FIGS. 16A and 16B). HRMS (TOF MS EI+) (m/z): [M]+ calculated for $C_{40}H_{24}$, 504.1878; found, 504.1878. See FIG. 15E and FIG. 15F for proton and carbon NMR spectra.

Example 5

DiTMSA[8]Macrocycle tetraOTES diOMe 7

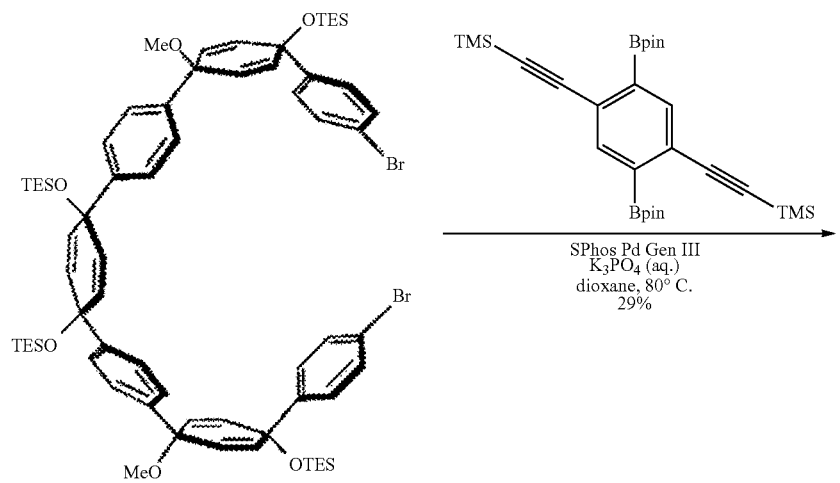

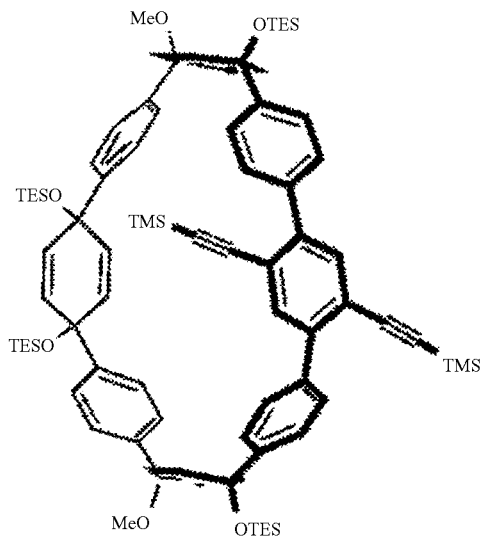

Figure 15G:
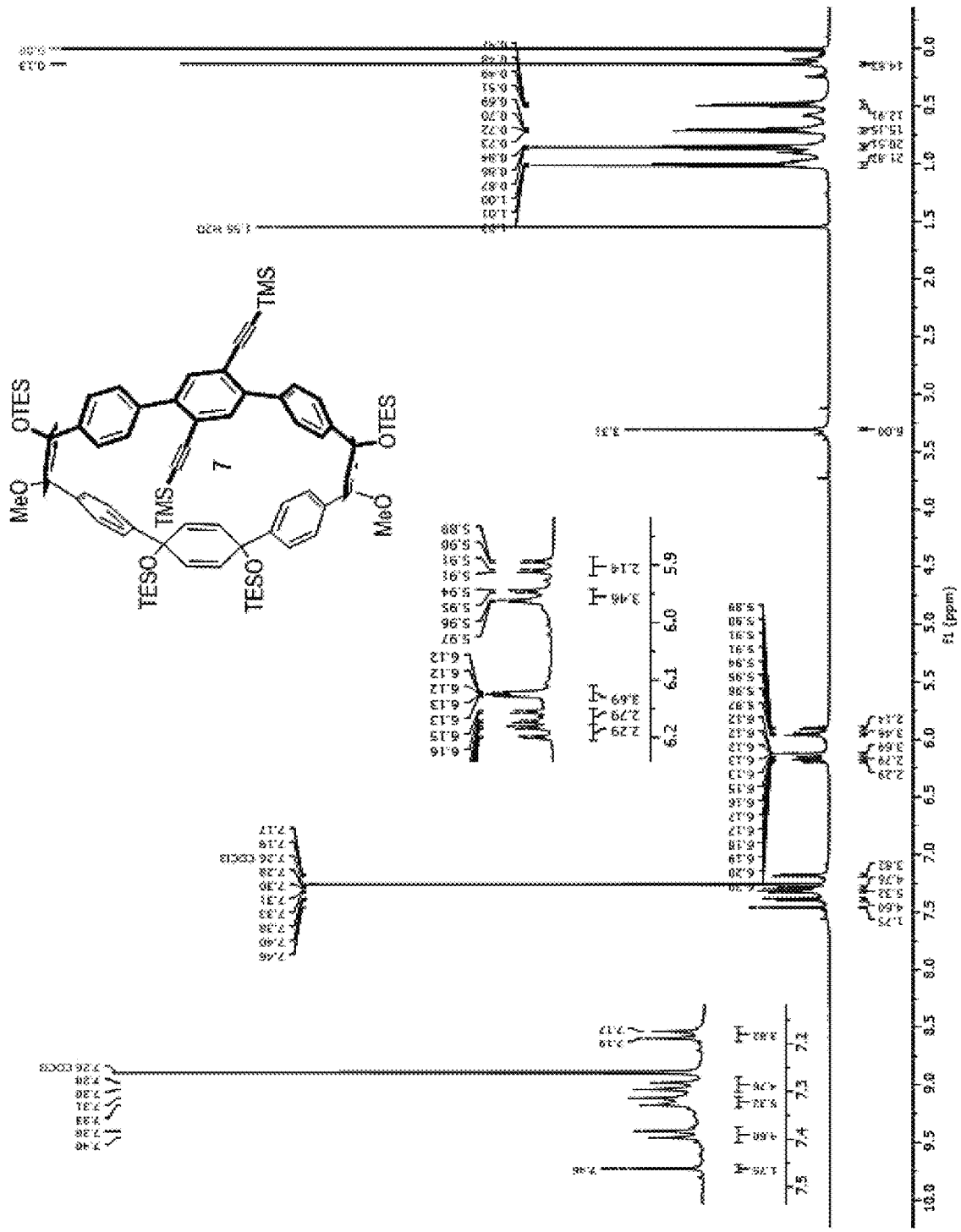
Figure 15H:
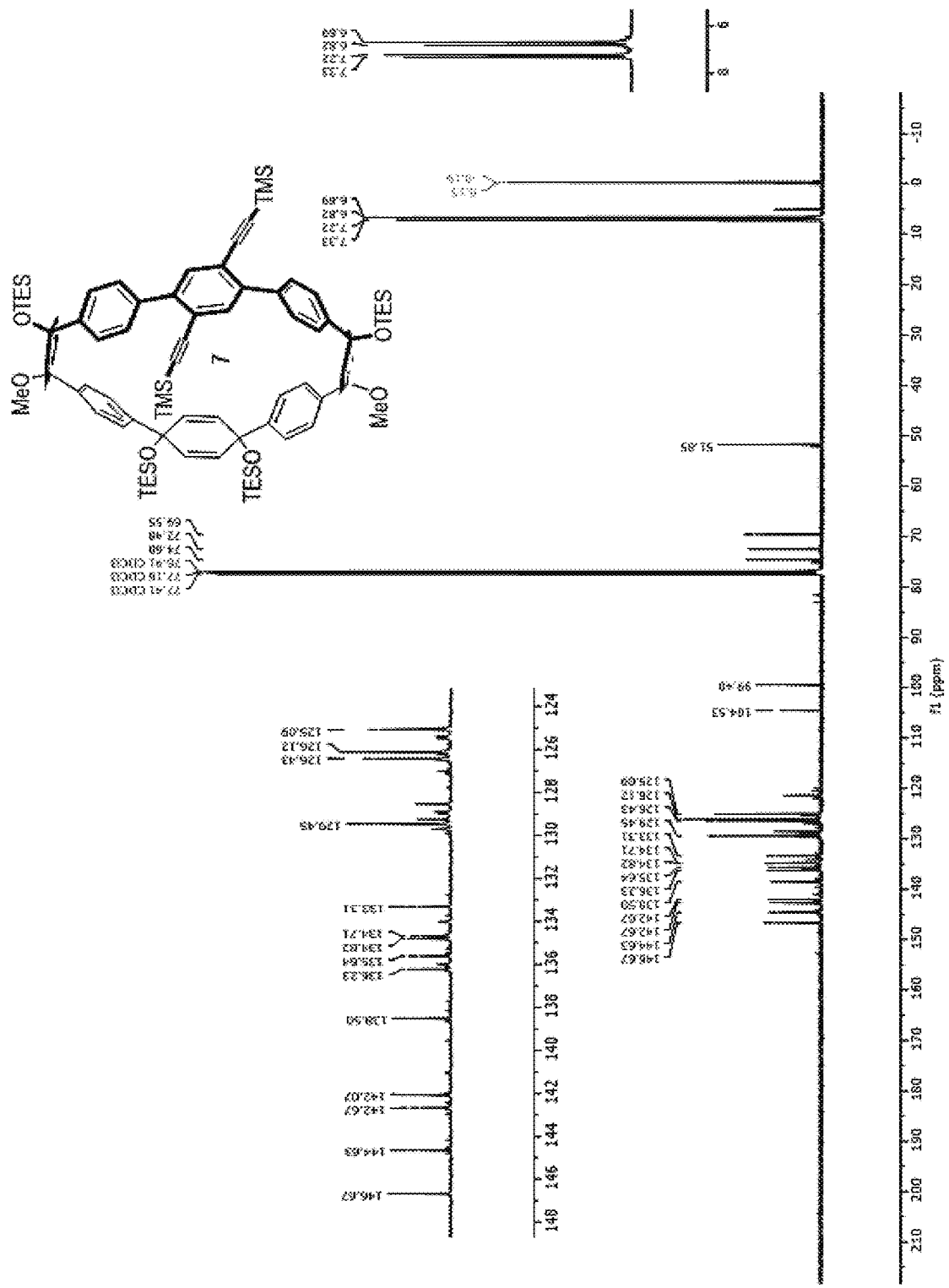

Dibromide 6 (1.8 g, 1.4 mmol, 1.00 eq), bisboronate 2 (882 mg, 1.7 mmol, 1.20 eq), and 3rd generation SPhos precatalyst (110 mg, 140 μmol, 0.1 eq) were dissolved in dioxane (280 mL, 5 mM) and purged with nitrogen while heating to 80° C. An aqueous solution of $K_3PO_4$ (28 mL) was added and the mixture was stirred for 18 h. The mixture was then filtered through celite and dried over anhydrous sodium sulfate. Solvent was removed under reduced pressure to yield a brown solid. The solid was purified by column chromatography on silica (hexanes to DCM) to yield 7 as an orange solid (558 mg, 29%). $^1$H NMR (600 MHz, $CDCl_3$) δ 7.46 (s, 2H), 7.39 (d, J=8.4 Hz, 4H), 7.32 (d, J=8.4 Hz, 4H), 7.29 (d, J=8.4 Hz, 4H), 7.18 (d, J=8.6 Hz, 4H), 6.19 (dd, J=10.1, 2.5 Hz, 2H), 6.16 (dd, J=10.1, 2.4 Hz, 2H), 6.12 (m, 4H), 5.95 (dd, J=10.2, 2.5 Hz, 2H), 5.90 (dd, J=10.1, 2.5 Hz, 2H), 3.31 (s, 6H), 1.01 (t, J=7.9 Hz, 18H), 0.86 (t, J=8.0 Hz, 18H), 0.71 (q, J=7.8 Hz, 12H), 0.49 (q, J=7.7 Hz, 12H), 0.13 (s, 12H). $^{13}$C NMR (126 MHz, $CDCl_3$) δ 146.67, 144.63, 142.67, 142.07, 138.50, 136.23, 135.64, 134.82, 134.71, 133.31, 129.45, 126.43, 126.12, 125.09, 104.53, 99.40, 74.60, 72.48, 69.55, 51.85, 7.33, 7.22, 6.82, 6.69. IR (neat): 2953, 2875, 2155, 1477, 1409, 1249 $cm^{-1}$. HRMS (ASAP) (m/z): $[M]^+$ calculated for $C_4H_{114}O_6Si_6$, 1386.7231; found, 1386.7169. See FIG. 15G and FIG. 15H for proton and carbon NMR spectra.

Example 6

Diethynyl[8]Macrocycle diOMe Tetraol 10

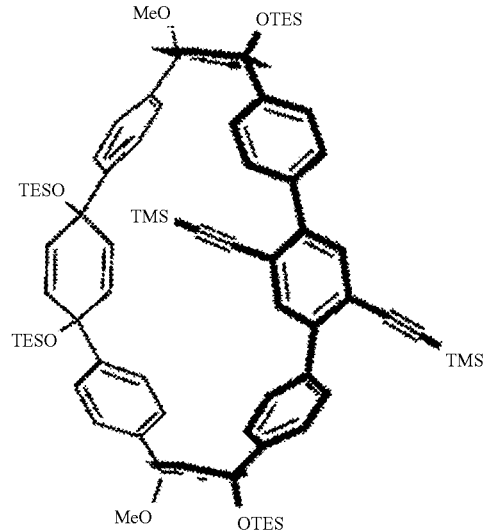

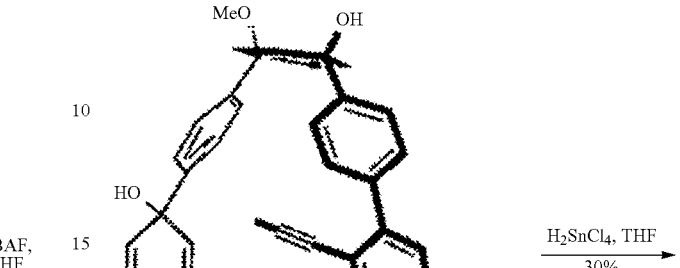

Example 7

Diethynyl[8]CPP 8

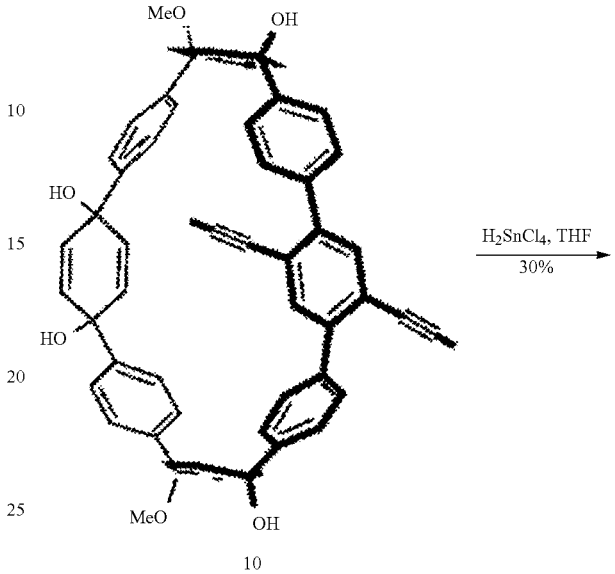

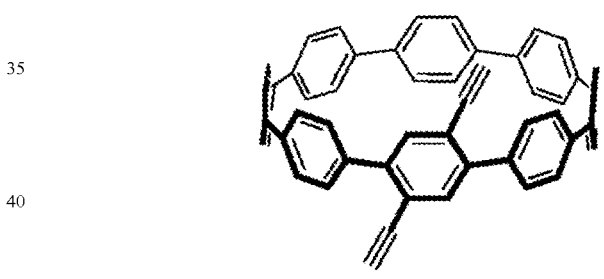

Figure 15I:
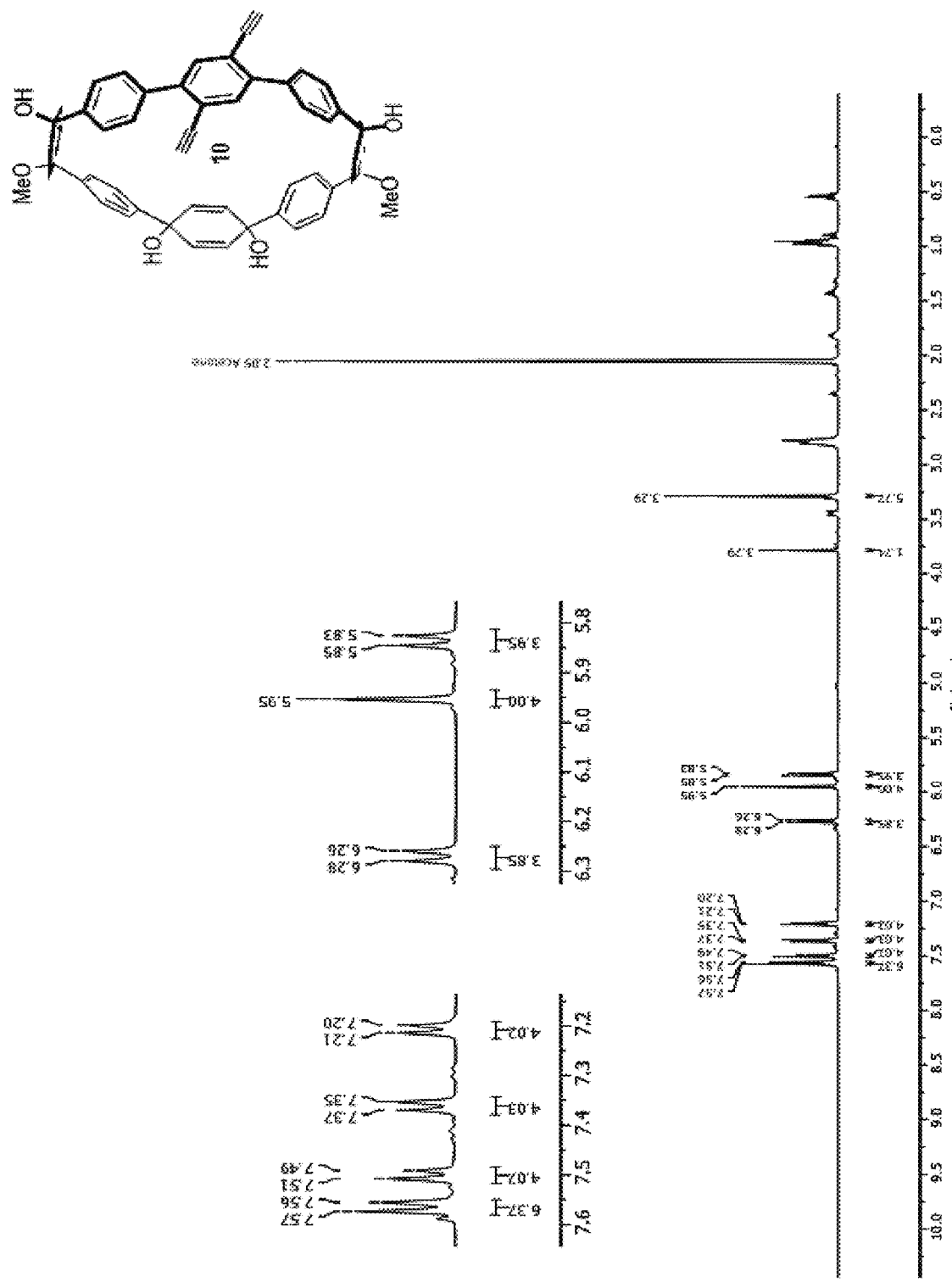
Figure 15J:
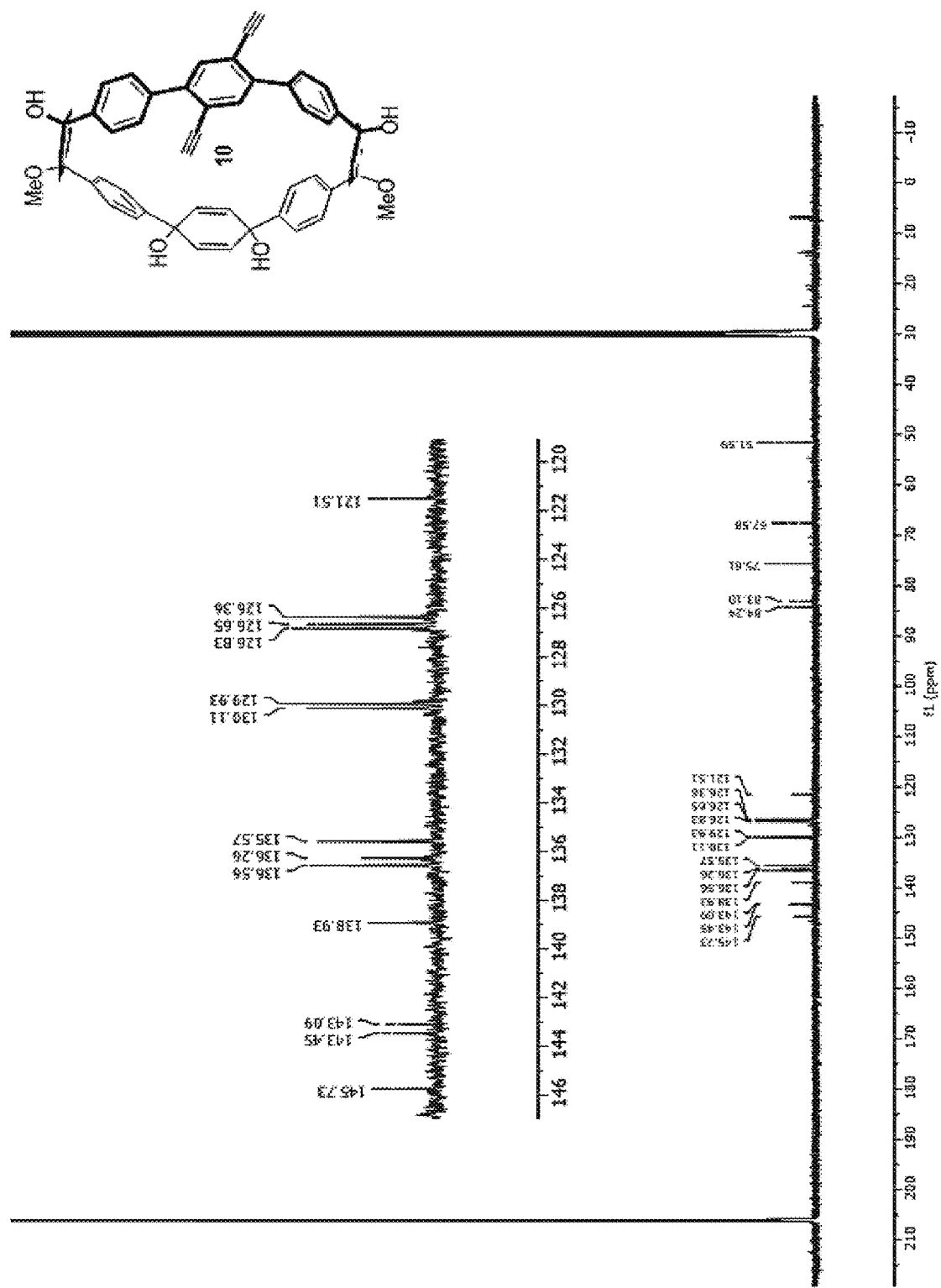

Macrocycle 7 (558 mg, 402 μmol, 1.00 eq) was dissolved in THF (2 mL, 200 mM) and a 1 M. solution of TBAF in THF (3.2 mL, 3.2 mmol, 8.00 eq) was added. The reaction was stirred for 1 h and quenched with water. THF was removed under reduced pressure to yield a suspension. The material was filtered and washed with water and DCM to yield an off-white solid (283 mg, 89%). $^1$H NMR (500 MHz, acetone-$d_6$) δ 7.57 (s, 2H), 7.56 (d, J=8.8 Hz, 4H), 7.50 (d, J=8.2 Hz, 4H), 7.36 (d, J=8.8 Hz, 4H), 7.21 (d, J=8.4 Hz, 4H), 6.27 (d, J=10.1 Hz, 4H), 5.95 (s, 4H), 5.84 (d, J=10.1 Hz, 4H), 3.79 (s, 2H), 3.29 (s, 6H). $^{13}$C NMR (126 MHz, acetone-$d_6$) δ 145.73, 143.45, 143.09, 138.93, 136.56, 136.26, 135.57, 130.11, 129.93, 126.83, 126.65, 126.36, 121.51, 84.24, 83.10, 75.61, 67.58, 51.59. IR (neat): 3293, 2958, 1477, 1409 cm$^{-1}$. See FIG. 15I and FIG. 15J for proton and carbon NMR spectra.

Figure 15K:
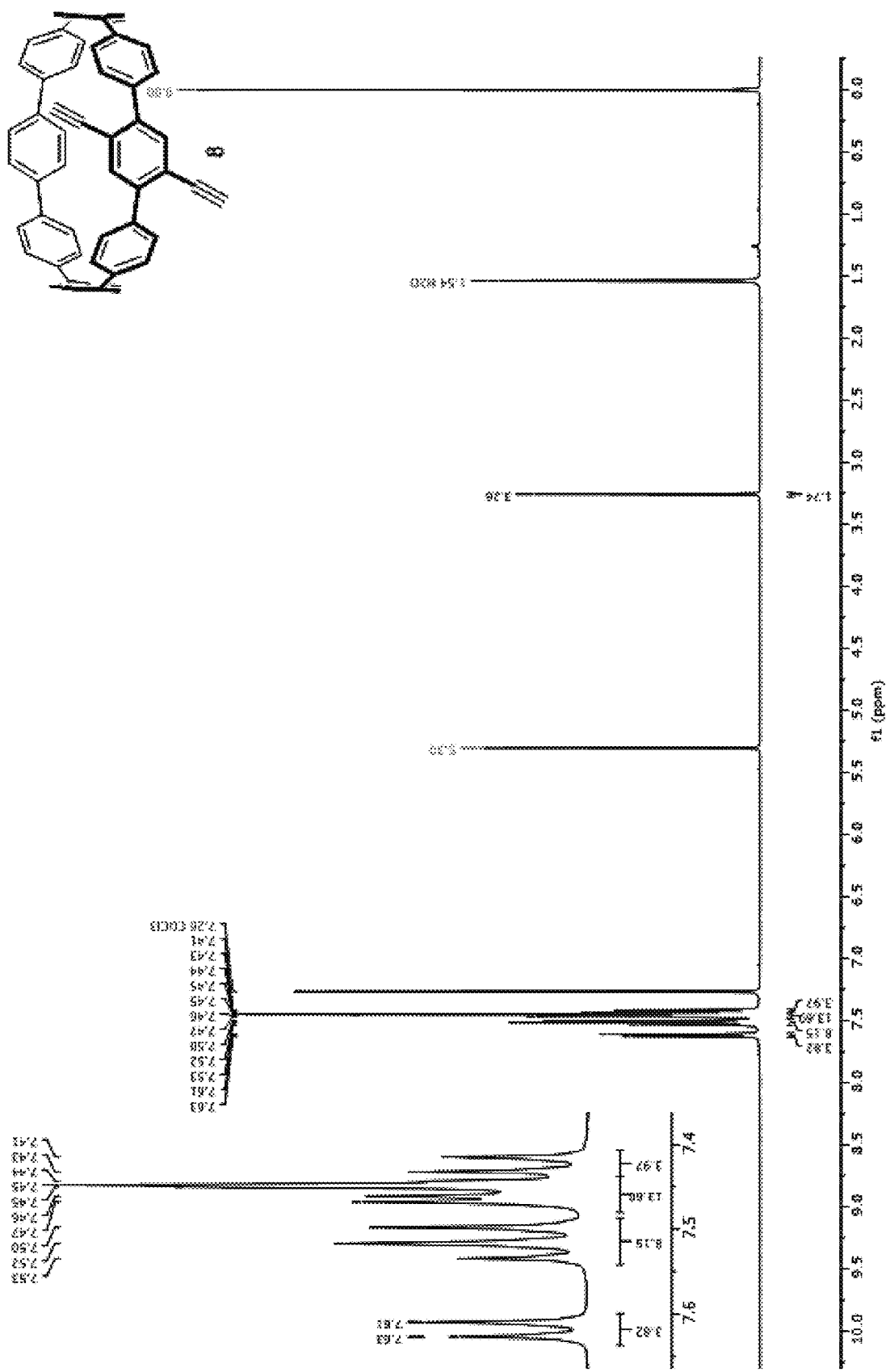
Figure 15L:
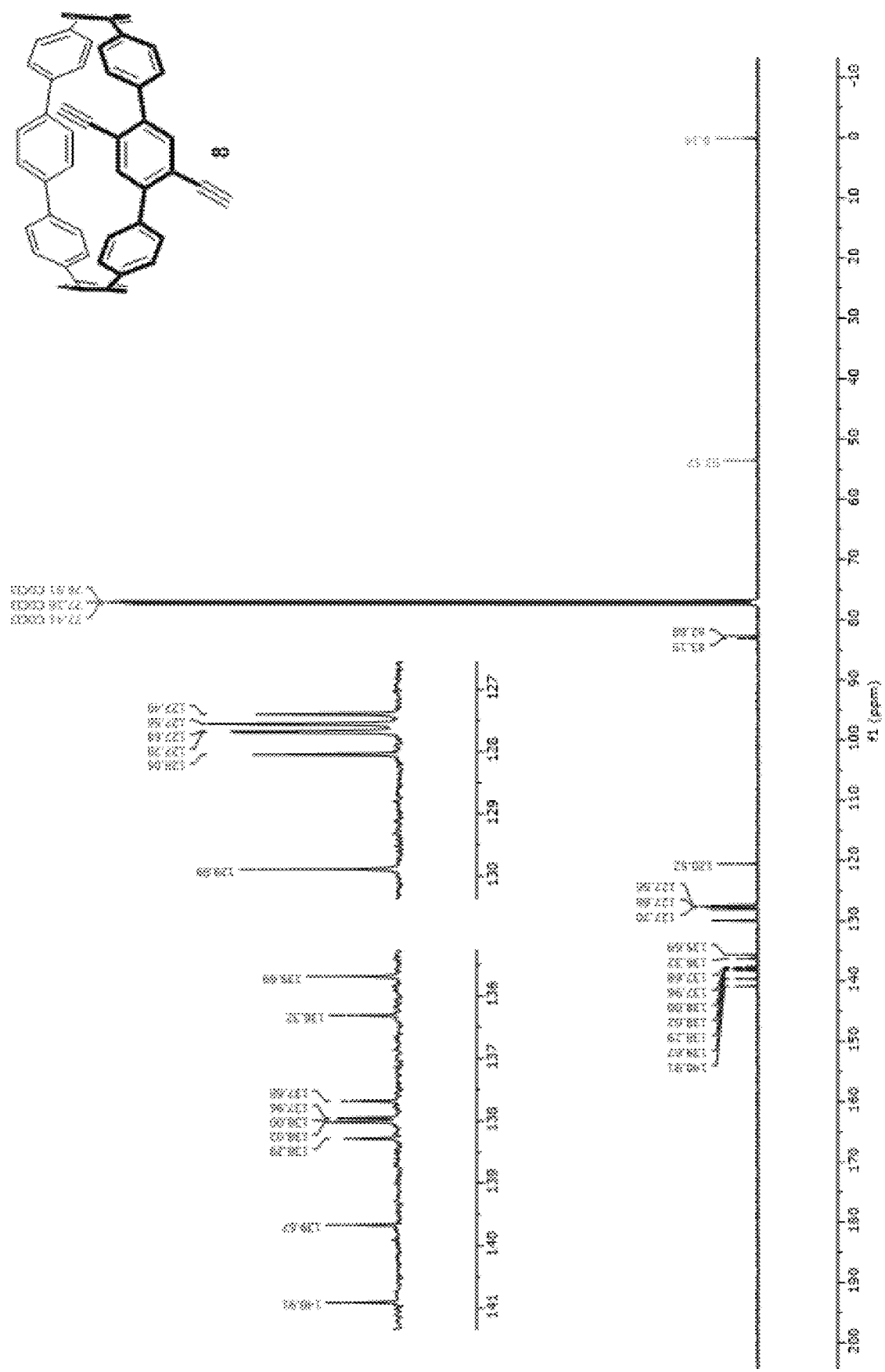

Deprotected macrocycle 10 (100 mg, 127 μmol, 1.00 eq) was dissolved in THF (3 mL, 40 mM). A solution of $SnCl_2 \cdot 2H_2O$ (95 mg, 420 μmol, 3.30 eq) and 12 M. HCl (67 μL, 800 μmol, 6.30 eq) in THF (3.2 mL) was added and the reaction was stirred for 1 h. The reaction was then quenched with a 1 M. aqueous solution of NaOH and extracted with DCM (3×5 mL). The combined extracts were dried over anhydrous sodium sulfate and solvent was removed under reduced pressure to yield a yellow solid. The material was purified by column chromatography in 40% to 100% DCM in hexanes to yield a yellow solid (25 mg, 30%). $^1$H NMR (500 MHz, CDCl$_3$) δ 7.62 (d, J=8.7 Hz, 4H), 7.54-7.49 (m, 8H), 7.48-7.44 (m, 14H), 7.42 (d, J=8.8 Hz, 4H), 3.26 (s, 2H). $^{13}$C NMR (126 MHz, CDCl$_3$) δ 140.78, 139.53, 138.15, 137.88, 137.87, 137.82, 137.54, 136.18, 135.56, 129.75, 127.91, 127.56, 127.54, 127.43, 127.27, 120.39, 83.02, 82.56. LRMS (MALDI) (m/z): [M]$^+$ calculated for $C_{52}H_{32}$, 656.250; found, 656.257. See FIG. 15K and FIG. 15L for proton and carbon NMR spectra.

Example 8

Comparative Compound 2',5'-bis(phenylethynyl)-1,1':4',1''-terphenyl (T-Ph)

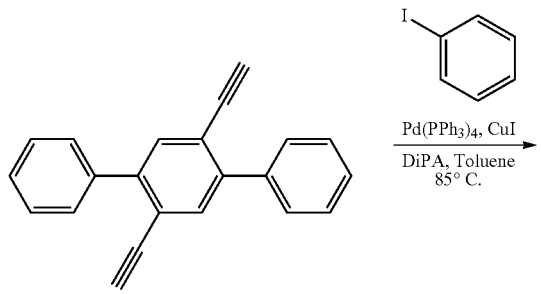

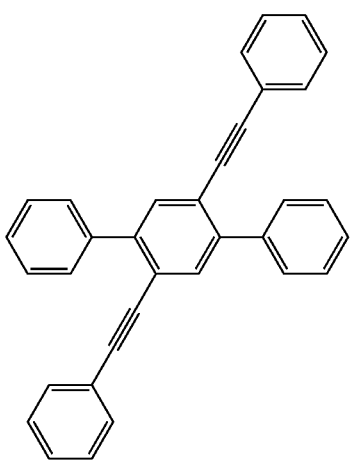

mT (25 mg, 90. μmol), Pd(PPh$_3$)$_4$ (5 mg, 4 μmol), and copper (1) iodide (2 mg, 9 μmol) were added to a Schlenk flask, which was then evacuated and backfilled with N$_2$ three times. Iodobenzene (38 mg, 0.19 mmol), dry and degassed diisopropylamine (2 mL) and toluene (2 mL) were added, and the reaction mixture was stirred at 85° C. for 8 h. The solution was then cooled to room temperature, diluted with diethyl ether (10 mL), washed twice with sat. NH$_4$Cl (10 mL), once with brine (10 mL) and dried over MgSO$_4$ before concentrating under reduced pressure. Purification by column chromatography (silica, 80:20 hexanes:DCM) afforded T-Ph (32 mg, 74 μmol, 83%) as a white solid. $^1$H NMR (400 MHz, CD$_2$Cl$_2$): δ 7.76 (dd, 4H, 7.2 Hz), 7.75 (s, 2H), 7.53 (t, 4H, 7.2 Hz), 7.46 (t, 2H, 7.4 Hz), 7.39-7.32 (m, 10H). $^{13}$C ($^1$H) NMR (100 MHz, CD$_2$Cl$_2$): δ 142.8, 139.8, 134.2, 131.7, 129.7, 128.9, 128.8, 128.5, 128.3, 123.4, 122.1, 94.1, 89.4. HRMS (EI): found m/z: 430.1723; calc. for C$_{34}$H$_{22}$: 430.1722.

Example 9

Comparative Compound 2',5'-bis(thiophen-2-ylethynyl)-1,1':4',1''-terphenyl (T-Th)

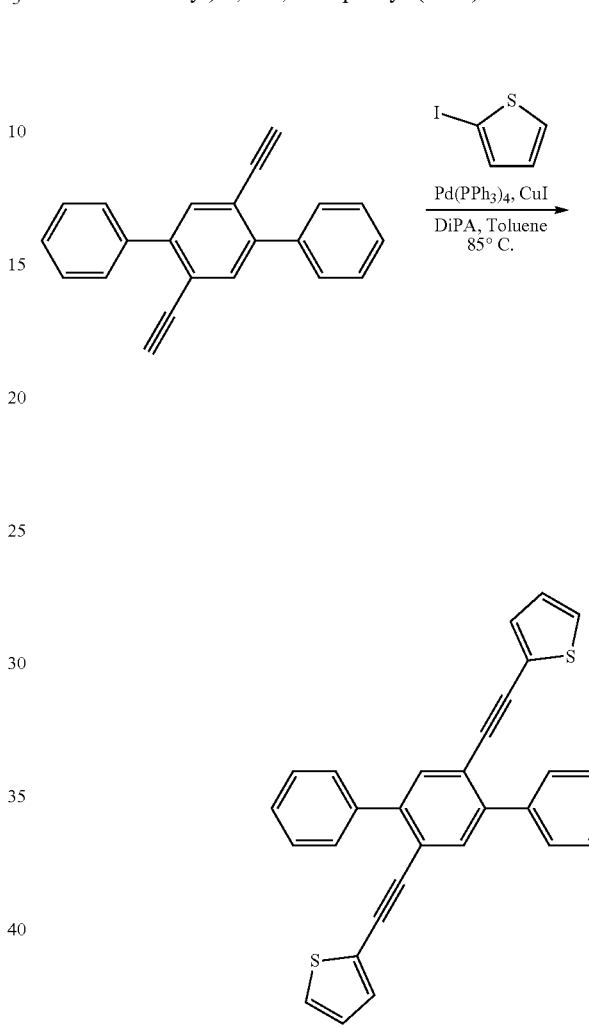

2',5'-diethynyl-1,1':4',1''-terphenyl (mT, 25 mg, 90. μmol), Pd(PPh$_3$)$_4$ (5 mg, 4 μmol), and copper (I) iodide (2 mg, 9 μmol) were added to a Schlenk flask, which was then evacuated and backfilled with N$_2$ three times. 2-iodothiophene (38 mg, 0.18 mmol), dry and degassed diisopropylamine (2 mL) and toluene (2 mL) were added, and the reaction mixture was stirred at 85° C. for 14 h. The solution was then cooled to room temperature, diluted with diethyl ether (10 mL), washed twice with sat. NH$_4$Cl (10 mL), once with brine (10 mL) and dried over MgSO$_4$ before concentrating under reduced pressure. Purification by column chromatography (silica, 80:20 hexanes:DCM) afforded T-Th (35 mg, 79 μmol, 88%) as a pearl-white solid. $^1$H NMR (400 MHz, CD$_2$Cl$_2$): δ 7.74-7.71 (m, 4H), 7.71 (s, 2H), 7.51 (t, 4H, 7.2 Hz), 7.44 (t, 2H, 7.2 Hz), 7.32 (dd, 2H, 5.2 Hz), 7.16 (dd, 2H, 3.6 Hz), 7.00 (dd, 2H, 5.2 Hz). $^{13}$C ($^1$H) NMR (100 MHz, CD$_2$Cl$_2$): δ 142.5, 139.5, 133.7, 132.4, 129.5, 128.5, 128.3, 128.2, 127.6, 123.3, 121.8, 93.1, 87.6. HRMS (EI): found m/z: 442.0851; calc. for C$_3$H$_{18}$S$_2$: 442.0850.

Example 10

Comparative Compound J61-Ph

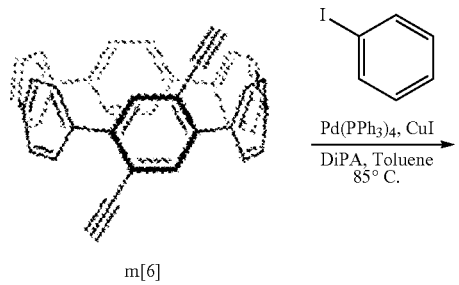

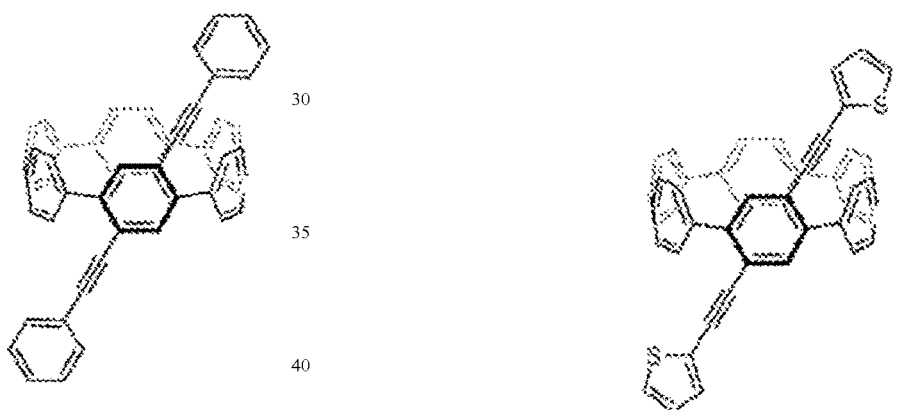

Monomer 5 (1 mL of an 8 mM solution in toluene, 9 μmol), iodobenzene (0.1 mL of a 0.2 M solution in toluene, 20 μmol), Pd(PPh$_3$)$_4$ (0.1 mL of a 4 mM solution in toluene, 0.4 μmol) and copper (1) iodide (0.1 mL of an 11 mM solution in toluene, 0.9 μmol) were added to a Schlenk flask under nitrogen atmosphere, followed by dry and degassed toluene (0.7 mL) and diisopropylamine (2 mL). The reaction mixture was stirred at 85° C. for 16 h. The solution was then cooled to room temperature, diluted with diethyl ether (10 mL), washed twice with sat. NH$_4$Cl (10 mL), once with brine (10 mL) and dried over MgSO$_4$ before concentrating under reduced pressure. Purification by column chromatography (silica, 90:10 hexanes:DCM) afforded [6]-Ph (5 mg, 8 μmol, 88%) as a red solid.

$^1$H NMR (400 MHz, CDCl$_3$): δ 7.79 (s, 2H), 7.67-7.50 (m, 22H), 7.48-7.42 (m, 6H). $^{13}$C ($^1$H) NMR (100 MHz, CDCl$_3$): δ 137.5, 137.1, 135.8, 135.6, 135.3, 134.1, 133.9, 131.6, 128.9, 128.7, 128.6, 128.1, 127.9, 127.6, 127.6, 127.4, 127.3, 127.3, 127.2, 123.3, 119.6, 96.6, 89.8. MALDI: found m/z: 657.178; calc. for [C$_{52}$H$_{32}$+H]$^+$: 657.2504.

Example 11

Comparative Compound [6]-Th

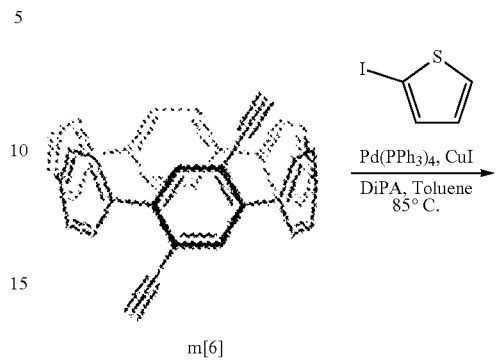

Monomer 5 (1 mL in an 8 mM solution in toluene, 9 μmol), 2-iodothiophene (0.1 mL of a 0.2 M solution in toluene, 20 μmol), Pd(PPh$_3$)$_4$ (0.1 mL of a 4 mM solution in toluene, 0.4 μmol) and copper (1) iodide (0.1 mL of a 9 mM solution in toluene, 0.9 μmol) were added to a Schlenk flask under nitrogen atmosphere, followed by dry and degassed toluene (0.7 mL) and diisopropylamine (2 mL). The reaction mixture was stirred at 85° C. for 18 h. The solution was then cooled to room temperature, diluted with diethyl ether (10 mL), washed twice with sat. NH$_4$Cl (10 mL), once with brine (10 mL) and dried over MgSO$_4$ before concentrating under reduced pressure. Purification by column chromatography (silica, 90:10 hexanes:DCM) afforded [6]-Th (4 mg, 6 μmol, 69%) as a red solid.

$^1$H NMR (400 MHz, CDCl$_3$): δ 7.73 (s, 2H), 7.66-7.49 (m, 18H), 7.41 (dd, 2H, 5.2 Hz), 7.39 (dd, 2H, 4.6 Hz), 7.11 (dd, 2H, 5.2 Hz). $^{13}$C ($^1$H) NMR (100 MHz, CDCl$_3$): δ 137.7, 137.2, 135.8, 135.7, 135.4, 134.1, 133.6, 132.3, 128.7, 128.2, 128.0, 127.9, 127.64, 127.59, 127.58, 127.5, 127.4, 127.3, 127.2, 123.3, 119.5, 93.6, 90.0. HRMS (EI): found m/z: 668.1639; calc. for C$_{48}$H$_{28}$S$_2$: 668.1632.

Example 12

Comparative Compound [8]-Ph

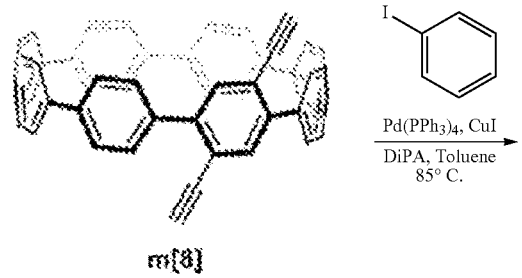

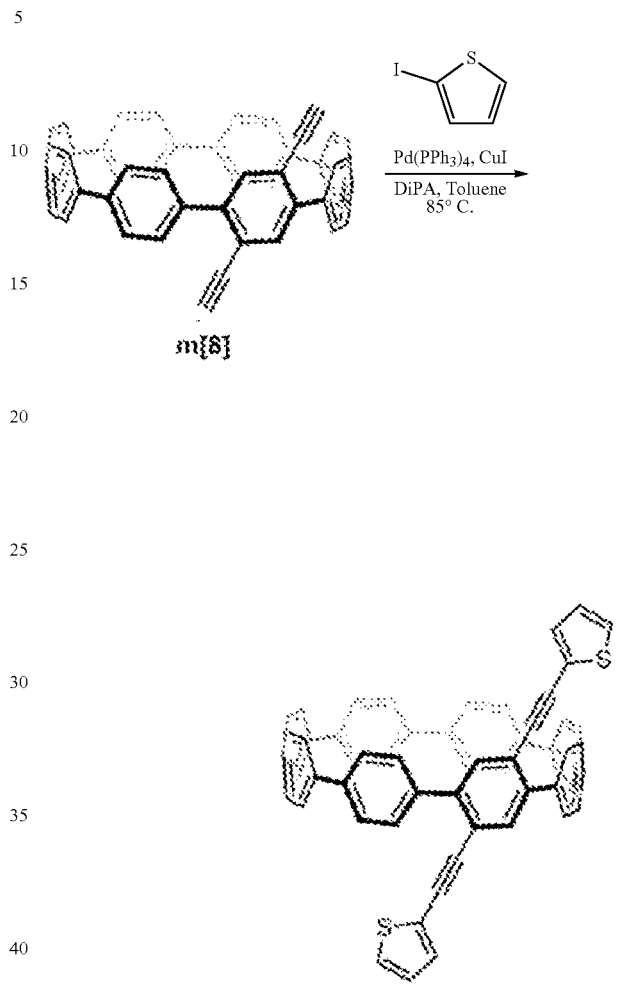

Monomer 8 (1 mL of a 9 mM solution in toluene, 9 µmol), iodobenzene (0.1 mL of a 0.2 M solution in toluene, 20 µmol), Pd(PPh$_3$)$_4$ (0.1 mL of a 4 mM solution in toluene, 0.4 µmol) and copper (I) iodide (0.1 mL of a 9 mM solution in toluene, 0.9 µmol) were added to a Schlenk flask under nitrogen atmosphere, followed by dry and degassed toluene (0.7 mL) and diisopropylamine (2 mL). The reaction mixture was stirred at 75° C. for 19 h. The solution was then cooled to room temperature, diluted with diethyl ether (10 mL), washed twice with sat. NH$_4$Cl (10 mL), once with brine (10 mL) and dried over MgSO$_4$ before concentrating under reduced pressure. Purification by column chromatography (silica, 90:10 hexanes:DCM) afforded [8]-Ph (5 mg, 6 µmol, 68%) as a red solid.

$^1$H NMR (400 MHz, CDCl$_3$): δ 7.70 (d, 4H, 8.6 Hz), 7.51-7.42 (m, 30H), 7.40-7.35 (m, 6H). $^{13}$C ($^1$H) NMR (100 MHz, CDCl$_3$): δ 140.6, 139.5, 138.3, 138.0, 137.9, 137.6, 137.0, 134.9, 131.5, 130.0, 128.6, 128.5, 128.0, 127.7, 127.6, 127.5, 127.3, 123.4, 121.3, 94.4, 89.6. MALDI: found m/z: 809.214; calc. for [C$_{64}$H$_{40}$+H]$^+$: 809.3130.

Example 13

Comparative Compound [8]-Th

Monomer 8 (1 mL of a 9 mM solution in toluene, 9 µmol), 2-iodothiophene (0.1 mL of a 0.2 M solution in toluene, 20 µmol), Pd(PPh$_3$)$_4$ (0.1 mL of a 5 mM solution in toluene, 0.4 µmol) and copper (1) iodide (0.1 mL of a 9 mM solution in toluene, 0.9 µmol) were added to a Schlenk flask under nitrogen atmosphere, followed by dry and degassed toluene (0.7 mL) and diisopropylamine (2 mL). The reaction mixture was stirred at 75° C. for 16 h. The solution was then cooled to room temperature, diluted with diethyl ether (10 mL), washed twice with sat. NH$_4$Cl (10 mL), once with brine (10 mL) and dried over MgSO$_4$ before concentrating under reduced pressure. Purification by column chromatography (silica, 90:10 hexanes:DCM) afforded [8]-Th (6 mg, 8 µmol, 80%) as a red solid.

$^1$H NMR (400 MHz, CD$_2$Cl$_2$): δ 7.68 (d, 4H, 8.5 Hz), 7.57-7.45 (m, 26H), 7.40 (dd, 2H, 5.2 Hz), 7.28 (dd, 2H, 3.6 Hz), 7.07 (dd, 2H, 5.2 Hz). $^{13}$C ($^1$H) NMR (100 MHz, CD$_2$Cl$_2$): δ 140.5, 139.7, 138.4, 138.1, 138.0, 137.9, 137.7, 136.9, 134.6, 132.1, 129.9, 128.1, 127.9, 127.72, 127.70, 127.6, 127.4, 123.5, 121.1, 93.4, 87.9. MALDI: found m/z: 821.004; calc. for [C$_{60}$H$_{36}$S$_2$+H]$^+$: 821.2258.

Example 14

PT-Ph

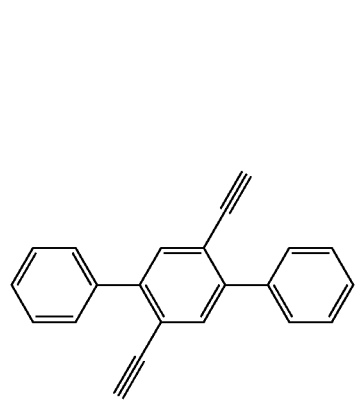
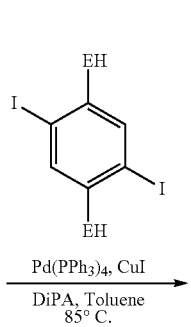

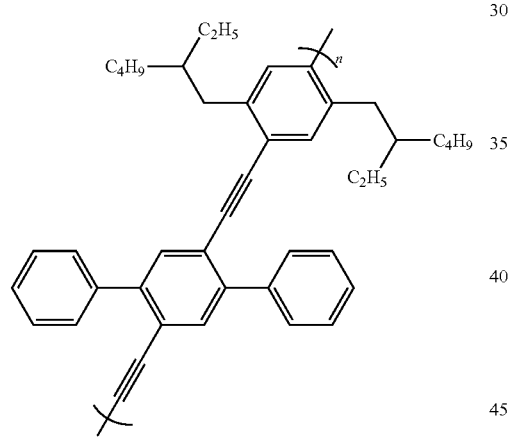

Figure 14A:
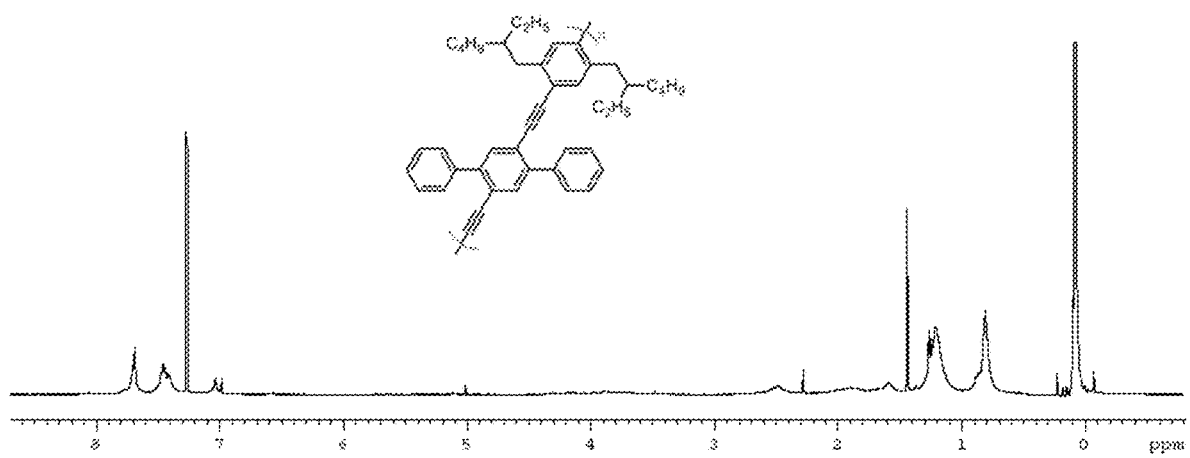
FIGS. 14A-14F show $^1$H-NMR spectra for different polymer embodiments disclosed herein.

2',5'-diethynyl-1,1':4',1"-terphenyl (mT, 25 mg, 90 µmol), 1,4-bis(2-ethylhexyl)-2,5-diiodobenzene (50. mg, 90 µmol), Pd(PPh$_3$)$_4$ (5 mg, 4 µmol), and copper (1) iodide (2 mg, 9 µmol) were added to a Schlenk flask, which was then evacuated and backfilled with N$_2$ three times. Dry and degassed diisopropylamine (4 mL) and toluene (4 mL) were added, and the reaction mixture was stirred at 80° C. for 72 h. The solution was then cooled to room temperature and concentrated to approximately 0.5 mL before being rapidly added to MeOH (50 mL). The precipitate was collected by filtration, and was purified by Soxhlet extraction: methanol (24 h), acetone (24 h), chloroform (2 h). The chloroform extract was concentrated and precipitated with 30 mL MeOH. Filtration yielded PT-Ph as a bright yellow solid. $^1$H NMR (400 MHz, CDCl$_3$): δ 7.81-7.68 (m), 7.55-7.35 (m), 7.09 (m), 2.62-0.45 (m). See FIG. 14A.

Example 15

Synthesis of PT-Th

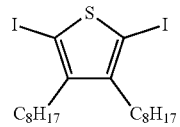
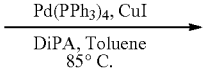

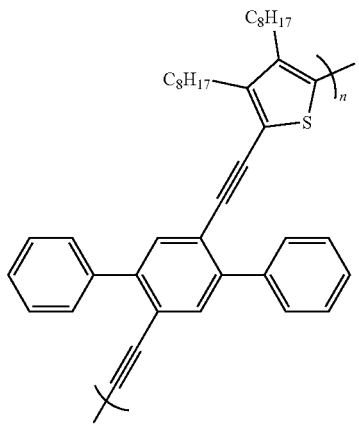

Figure 14B:
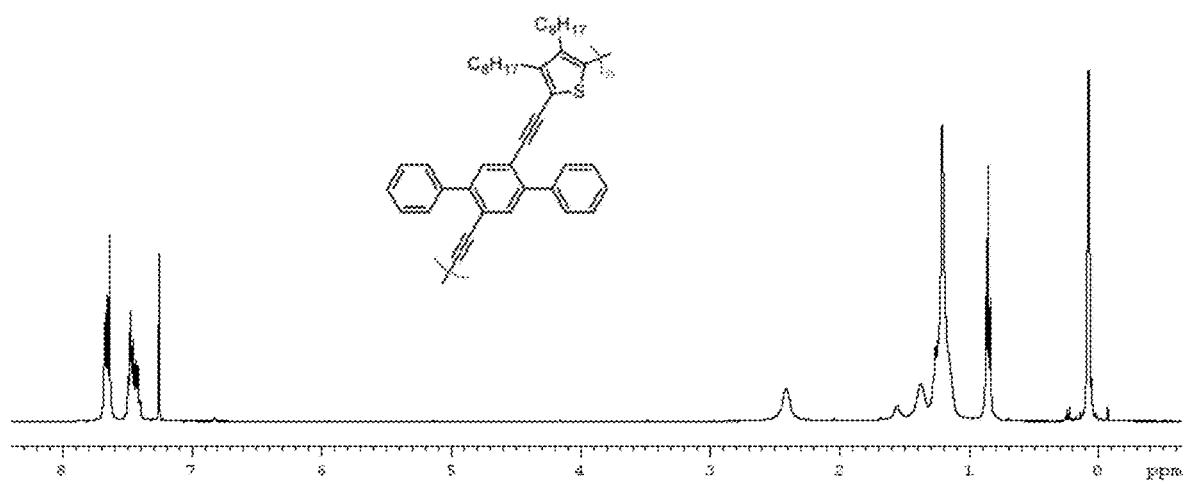

2',5'-diethynyl-1,1':4',1"-terphenyl (mT, 25 mg, 90 µmol), 2,5-diiodo-3,4-dioctylthiophene (50. mg, 90 µmol), Pd(PPh$_3$)$_4$ (5 mg, 4 µmol), and copper (1) iodide (2 mg, 9 µmol) were added to a Schlenk flask, which was then evacuated and backfilled with N$_2$ three times. Dry and degassed diisopropylamine (4 mL) and toluene (4 mL) were added, and the reaction mixture was stirred at 80° C. for 72 h. The solution was then cooled to room temperature and concentrated to approximately 0.5 mL before being rapidly added to MeOH (50 mL). The precipitate was collected by filtration, and was purified by Soxhlet extraction: methanol (24 h), acetone (24 h), chloroform (2 h). The chloroform extract was concentrated and precipitated with 30 mL MeOH. Filtration yielded PT-Th as an orange solid. $^1$H NMR (400 MHz, CDCl$_3$): δ 7.71-7.60 (m), 7.52-7.39 (m), 1.31-1.09 (m). See FIG. 14B.

Example 16

Synthesis of P[6]-Ph

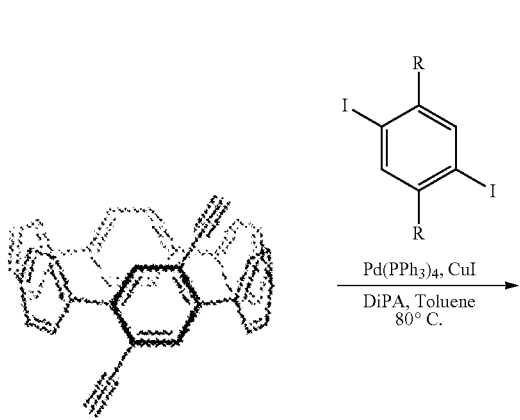

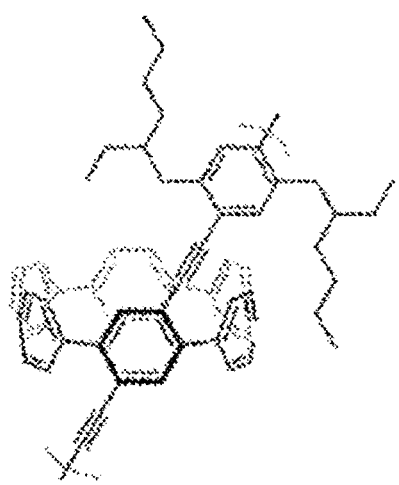

Figure 14C:
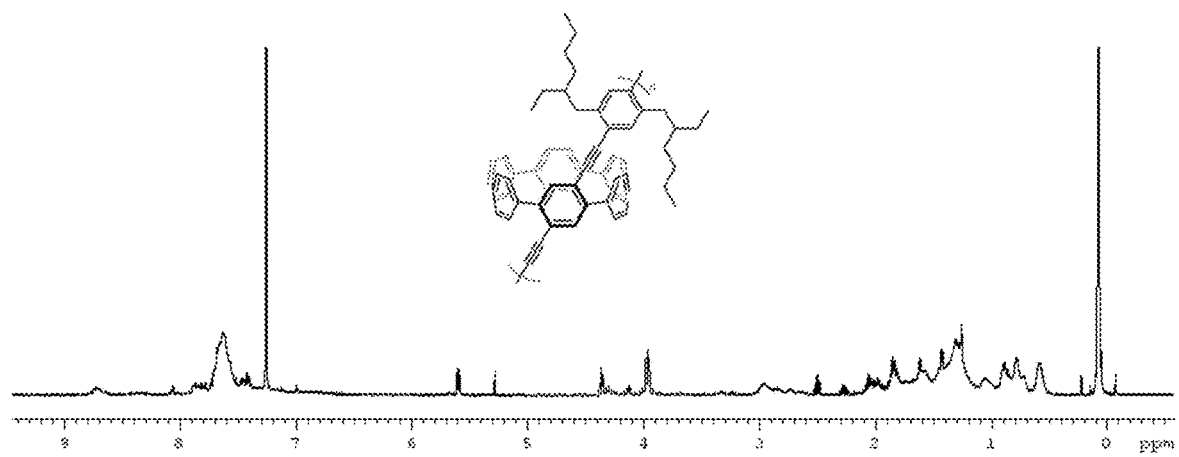

Monomer 5 (12 mg, 20. µmol), 1,4-Bis(2-ethylhexyl)-2,5-diiodobenzene (13 mg, 20. µmol), Pd(PPh$_3$)$_4$ (1 mg, 1 µmol), and copper (1) iodide (0.5 mg, 2 µmol) were added to a Schlenk tube, which was then evacuated and backfilled with N$_2$ three times. Dry and degassed diisopropylamine (2 mL) and toluene (2 mL) were added, and the reaction mixture was stirred at 80° C. for 72 h. The solution was then cooled to room temperature and concentrated to approximately 0.5 mL before being rapidly added to MeOH (50 mL). The precipitate was collected by filtration, and was purified by Soxhlet extraction: methanol (24 h), acetone (24 h), chloroform (2 h). The chloroform extract was concentrated and precipitated with 30 mL MeOH. Filtration yielded P[6]-Ph as a red solid. $^1$H NMR (400 MHz, CDCl$_3$): δ 7.84-7.60 (m), 1.38-1.02 (m), 0.93-0.61 (m). See FIG. 14C.

Example 17

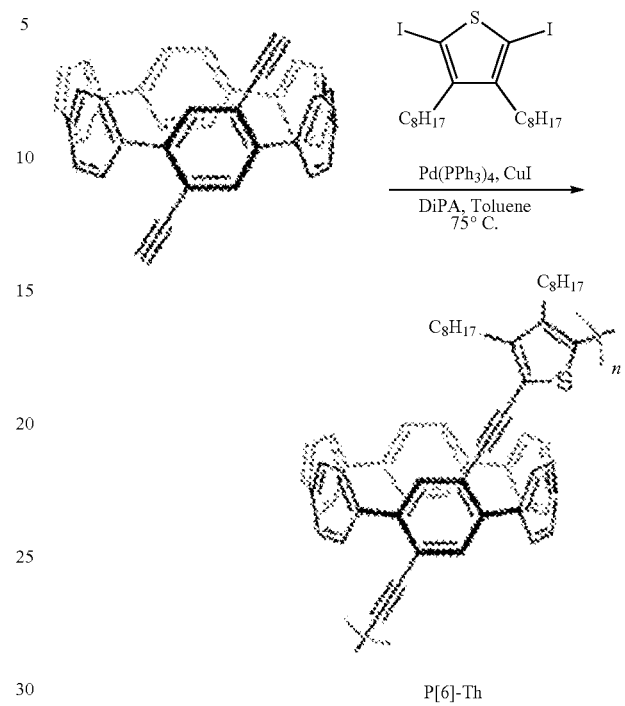

P[6]-Th

Figure 14D:
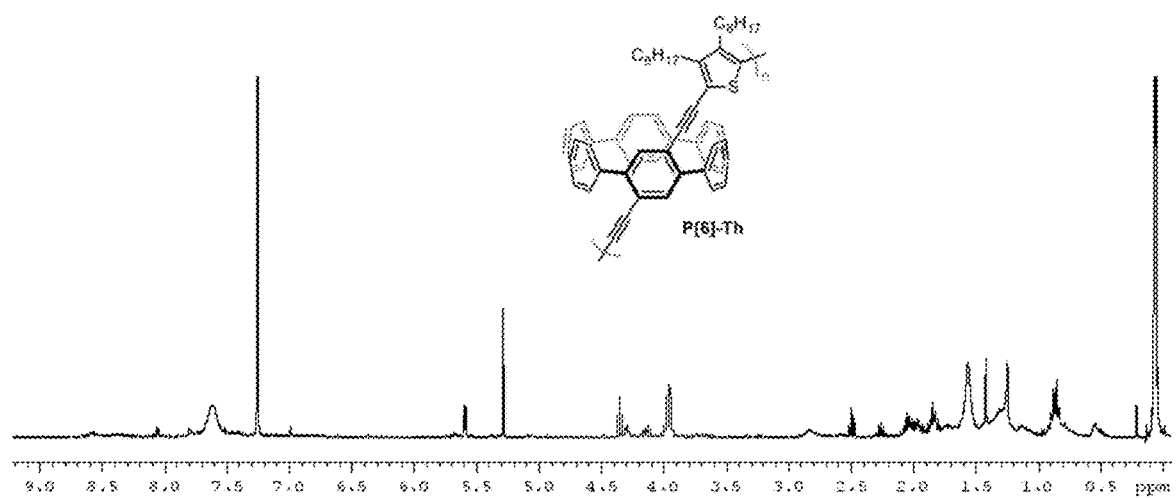

Monomer 5 (12 mg, 20. µmol), 2,5-diiodo-3,4-dioctylthiophene (13 mg, 20. µmol), Pd(PPh$_3$)$_4$ (1 mg, 1 µmol), and copper (1) iodide (0.5 mg, 2 µmol) were added to a Schlenk tube, which was then evacuated and backfilled with N$_2$ three times. Dry and degassed diisopropylamine (2 mL) and toluene (2 mL) were added, and the reaction mixture was stirred at 80° C. for 72 h. The solution was then cooled to room temperature and concentrated to approximately 0.5 mL before being rapidly added to MeOH (50 mL). The precipitate was collected by filtration, and was purified by Soxhlet extraction: methanol (24 h), acetone (24 h), chloroform (2 h). The chloroform extract was concentrated and precipitated with 30 mL MeOH. Filtration yielded P[6]-Th as a red solid. $^1$H NMR (400 MHz, CDCl$_3$): δ 7.91-7.34 (m), 2.10-0.51 (m), 0.86 (t). See FIG. 14D.

Example 18

Synthesis of P[8]-Ph

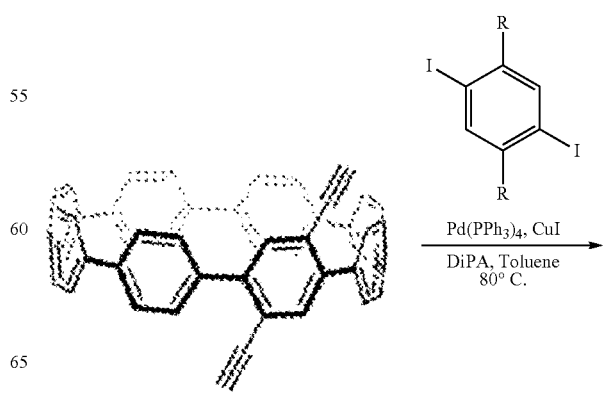

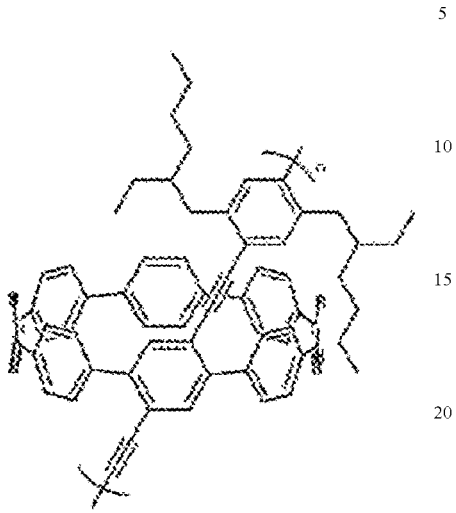

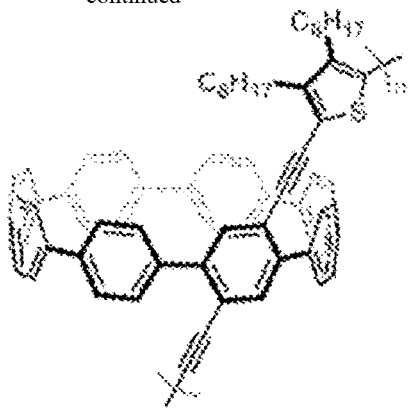

Figure 14E:
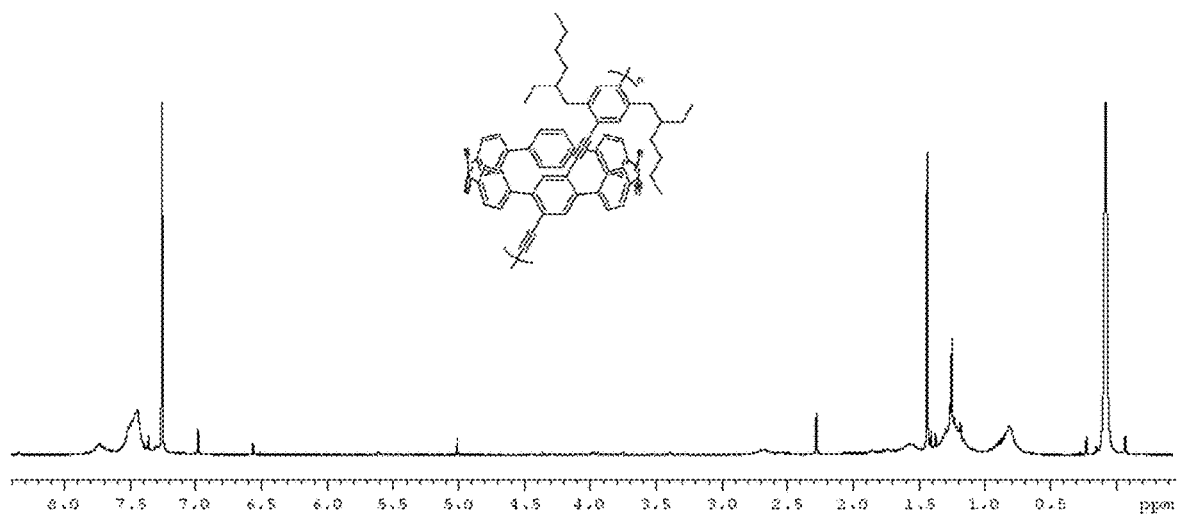

Monomer 8 (13 mg, 20. μmol), 1,4-Bis(2-ethylhexyl)-2,5-diiodobenzene (11 mg, 20. μmol), Pd(PPh$_3$)$_4$ (1 mg, 1 μmol), and copper (I) iodide (0.4 mg, 2 μmol) were added to a Schlenk tube, which was then evacuated and backfilled with N$_2$ three times. Dry and degassed diisopropylamine (2 mL) and toluene (2 mL) were added, and the reaction mixture was stirred at 80° C. for 72 h. The solution was then cooled to room temperature and concentrated to approximately 0.5 mL before being rapidly added to MeOH (50 mL). The precipitate was collected by filtration, and was purified by Soxhlet extraction: methanol (24 h), acetone (24 h), chloroform (2 h). The chloroform extract was concentrated and precipitated with 30 mL MeOH. Filtration yielded P[8]-Ph as a bright yellow solid. $^1$H NMR (400 MHz, CDCl$_3$): δ 7.89-7.28 (m), 1.89-1.07 (m), 1.01-0.56 (m). See FIG. 14E.

Example 19

Synthesis of P[8]-Th

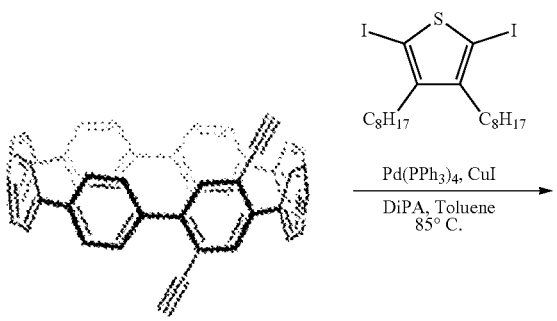

Figure 14F:
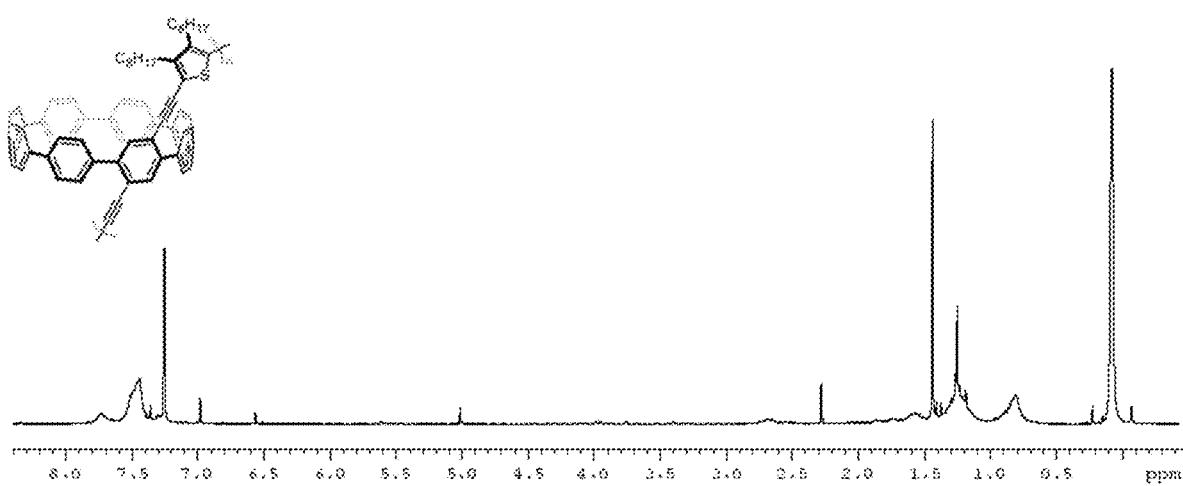

Monomer 8 (12 mg, 20. μmol), 2,5-diiodo-3,4-dioctylthiophene (12 mg, 20. μmol), Pd(PPh$_3$)$_4$ (1 mg, 1 μmol), and copper (I) iodide (0.4 mg, 2 μmol) were added to a Schlenk tube, which was then evacuated and backfilled with N$_2$ three times. Dry and degassed diisopropylamine (2 mL) and toluene (2 mL) were added, and the reaction mixture was stirred at 80° C. for 72 h. The solution was then cooled to room temperature and concentrated to approximately 0.5 mL before being rapidly added to MeOH (50 mL). The precipitate was collected by filtration, and was purified by Soxhlet extraction: methanol (24 h), acetone (24 h), chloroform (2 h). The chloroform extract was concentrated and precipitated with 30 mL MeOH. Filtration yielded P[8]-Th as an orange solid. $^1$H NMR (400 MHz, CDCl$_3$): δ 7.80-7.33 (m), 2.42-0.78 (m). See FIG. 14F.

Example 20

In this example, a linear pi-extension was explored using [6]- and [8]CPP nanohoop monomers. These macrocycles were functionalized with alkynes positioned para to each other on one phenylene unit thus establishing nascent linear conjugation pathways. The pi-extending alkyne moieties were positioned ortho-substituted to the macrocycle ring connections. Th monomers comprise cyclic/radial conjugation around the curved macrocycle, and linear conjugation through the conjugated alkyne substitutions (see FIG. 1). Electron delocalization can be distributed over both the linear π system of the conjugated backbone and that of the orthogonal curved CPP unit. Thus, intermolecular interactions can be facilitated not only by the planar, rod like π surfaces of the main chain, but also by the convex and concave surfaces of the off-chain CPPs. In this example, the polymer embodiments were analyzed and spectroscopic and computational comparisons were made with small molecule model systems.

Figure 2:
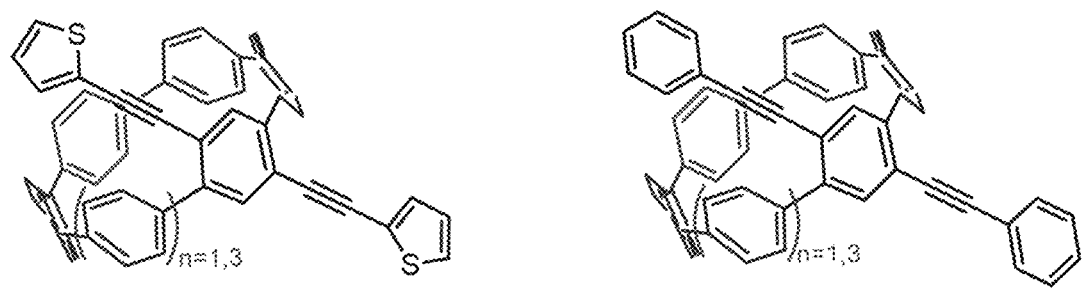
FIG. 2 illustrates a representation of combined linear and curved delocalization pathways with examples shown in small molecule embodiments.

A diarylation step was used to introduce phenylene or thiophene rings producing small molecules [n]-Ph and [n]-Th (see FIG. 2). A model system based on terphenyl, in which the central benzene is analogous to the tetrasubstituted ring featured in these CPPs, was also synthesized to allow for comparisons between curved orthogonal pi-systems and those that are linear. The phenylene units within the macrocycle embodiments have a small amount of conformational freedom to avoid steric hindrance from subsequent functionalizations, but are relatively rigid in comparison to the phenylenes present in terphenyl. These small model systems were then extrapolated to the analogous polymer systems (P[n]-Ph and P[n]-Th, FIG. 3), which feature a further-extended linear conjugated backbone but also have isomeric variance.

A para-substituted diyne was added on the nanohoop prior to final reductive aromatization to generate polymerizable monomers 5 and 8, respectively. In order to prepare these monomers, a modular building block approach using cyclohexadiene moieties as masked aromatic benzene rings was used (see, for example, Scheme 1). The tetrasubstituted benzene ring linchpin 1 was prepared on multigram scale from dibromo diiodo benzene via successive Sonogashira couplings (to install TME acetylene) and Suzuki-Miyaura borylation (to install pinacolborane). Advanced CPP intermediates 2 and 3 were prepared using lithiation-addition steps with high control of diastereoselectivity, followed by protection of the resultant alcohols as methyl or triethylsilyl ethers. In this manner, curved intermediates with varying numbers of phenyl rings or cyclohexadienes as masked phenylenes were assembled rapidly, allowing formation of macrocycles in the next step. Macrocyclizations of either 2 or 3 with bisboronate 1 were then carried out under dilute Suzuki cross-coupling conditions to yield 4 and 5 in 22% and 29% yield, respectively. Finally, global deprotection of the silyl groups and reductive aromatization using mild tin chloride conditions yielded the final dialkyne CPP monomers 5 and 8 in modest yields. A dialkynylated terphenyl model system mT (2',5'-diethynyl-p-terphenyl) was also made using a similar method to that used to make 1. In particular, 1,4-dibromo-2,5-diiodobenzene was subjected to double Suzuki cross coupling to chemoselectively assemble the terphenyl core while Sonogashira coupling of TMS acetylene and subsequent silyl deprotection afforded mT.

Example 21

In this example, the three monomers 5, 8, and comparison monomer mT from Example 1 were modified to provide further linear backbone π-extension using Sonogashira cross coupling reactions leading to well-defined small molecule oligomers (Chart 1, top) as well as polymers (Chart 1, bottom). The oligomers ([6]-Ph, [6]-Th, [8]-Ph and [8]-Th) comprised [6]- and [8]CPP with central phenylacetylene and thienylacetylene attachments. The polymers (P[6]-Ph, P[6]-Th, P[8]-Ph and P[8]-Th) were prepared by copolymerization using the respective dialkyne monomers 5 and 8 and the corresponding alkylated arylene dihalides. Terphenyl molecular (T-Ph and T-Th) and polymer (PT-Ph and PT-Th) models were derived from similar couplings with mT. In some embodiments, Soxhlet extractions with methanol and acetone were used to remove lower molecular weight impurities and the chloroform extracts that were used for photophysical analyses in some examples disclosed herein. The GPC molecular weight data for all polymers are presented in Table 1. Although the data for certain embodiments of the CPP-containing polymers reflect small oligomers, in some embodiments, substantial insolubilities in the concentrated THF solutions needed to introduce the polymers into the mobile phase were observed, so certain data of Table 1 only reflect the smaller THF soluble oligomers. Without being limited to a single theory of operation, it currently is believed that any insoluble material observed in this example may represent higher molecular weight material that either was simply insoluble or may have been supramolecularly crosslinked during polymerization by way of rotaxanation.

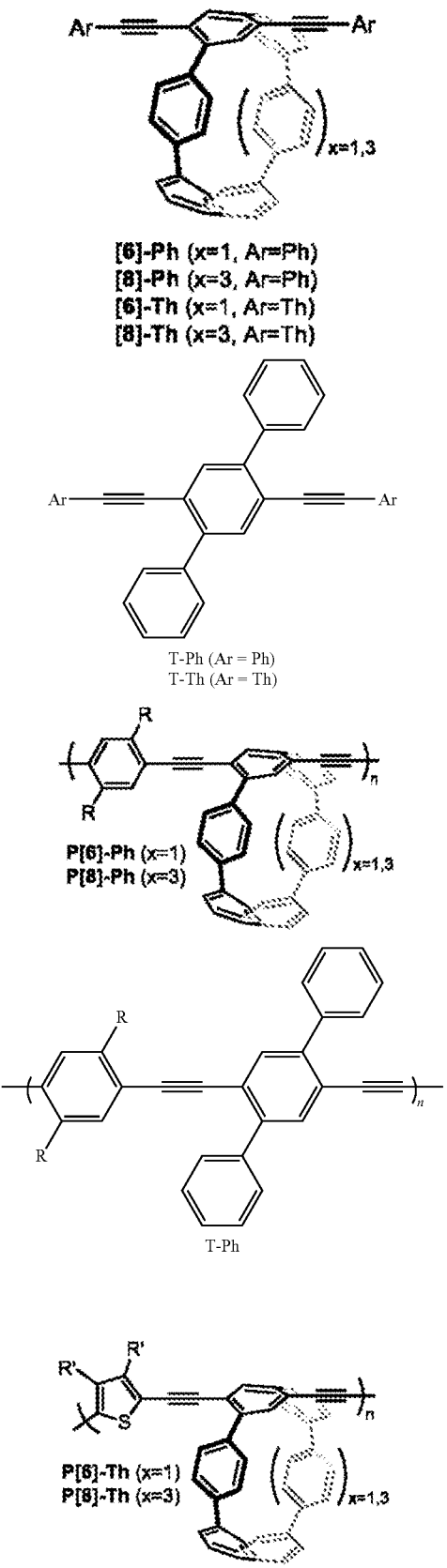

-continued

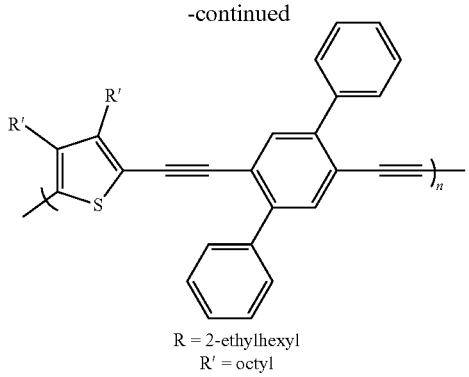

R = 2-ethylhexyl
R' = octyl

TABLE 1

Distribution of weight average and number average molecular weight and poly dispersity index for the polymer systems as determined in THF along with the approximate numbers of repeat units.

|     | PT-Ph | PT-Th | P[6]-Ph | P[6]-Th | P[8]-Ph | P[8]-Th |
|-----|-------|-------|---------|---------|---------|---------|
| Mw  | 6877  | 175548 | 14765  | 21599   | 6333    | 9061    |
|     | (~12 repeats) | (~292 repeats) | (~18 repeats) | (~27 repeats) | (~7 repeats) | (~9 repeats) |
| Mn  | 4771  | 50419 | 6053   | 3435    | 4482    | 6668    |
|     | (~8 repeats) | (~84 repeats) | (~8 repeats) | (~4 repeats) | (~5 repeats) | (~7 repeats) |
| PDI | 1.44  | 3.48  | 2.44   | 6.29    | 1.41    | 1.36    |

Example 22

Figure 4A:
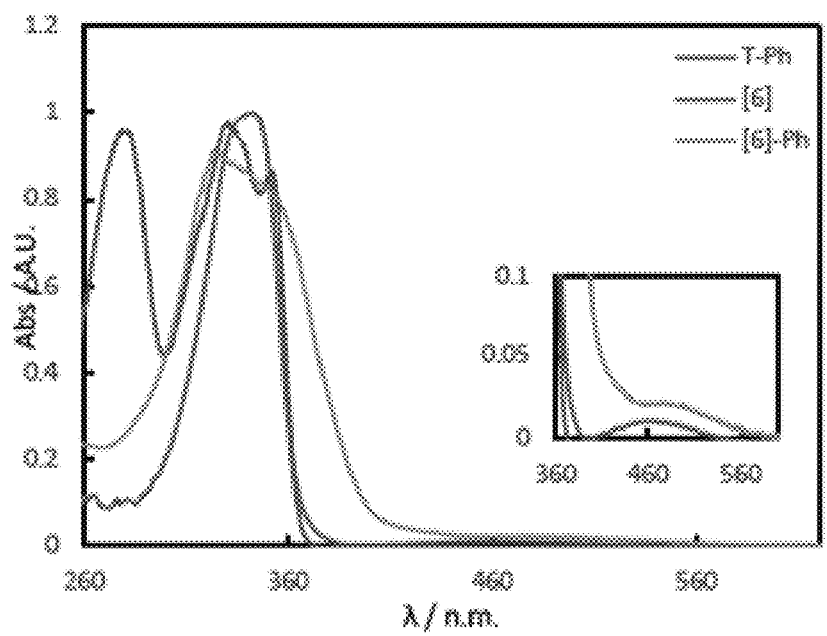
FIGS. 4A and 4B show UV-Vis spectra for oligomeric [6]-Ph (FIG. 4A) and [8]-Th (FIG. 4B) in comparison with the respective [6]- and [8]CPPs and the planar terphenyl models.
Figure 4B:
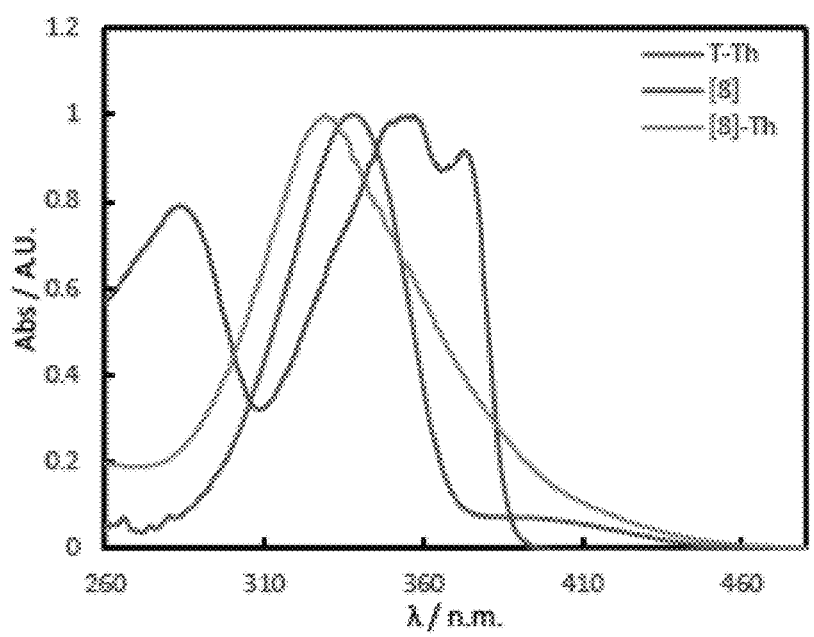

Extension of conjugation in monomers 5 and 8 along the alkyne-containing pathway ended up being more than a mere amalgamation of the two orthogonal π-systems (see FIGS. 4A and 4B). Generally, [n]CPPs can exhibit a characteristic absorbance at roughly the same energy ($\lambda_{abs}$=340 nm) regardless of size. In some embodiments, this corresponds to HOMO-1 and HOMO-2 to LUMO, or HOMO to LUMO+1 or LUMO+2 transitions, as the HOMO-LUMO transition is for the most part forbidden. Smaller CPPs, such as [6]CPP, also feature a very broad low energy absorption spanning ca. 400-525 nm (see FIG. 4A, inset), which may be the result of a minor contribution from the forbidden HOMO-LUMO transition. Both [6]-Ph and [6]-Th also have this feature (FIG. 4A), though it is bathochromically shifted and with increased molar absorptivity. The low-energy shoulder seen in [8]CPP (ca. 405 nm) is likely buried in the broad low-energy tails of [8]-Ph and [8]-Th. Diarylated monomers [6]-Ph and [6]-Th possessed broadened absorptions that encompass the main CPP absorption, though [6]-Ph has a more pronounced blue-shift of the (λmax at 322 nm vs the λmax of 338 nm for [6]-Th). [8]-Ph and [8]-Th similarly demonstrated pronounced blue-shifts and broadened spectral footprints compared to parent [8]CPP ($\lambda_{max}$=321 nm and $\lambda_{max}$=329 nm vs $\lambda_{max}$=338, respectively, FIG. 4B). The broadness of these absorptions may be attributed to the superimposition of the alkyne-containing linear system with that of the curved CPP macrocycle. The diphenylated CPPs [6]-Ph and [8]-Ph appear to have stronger contributions from the linear segment compared to thienylated species [6]-Th and [8]-Th, where CPP is clearly the major contributor.

The spectral properties of the arylene ethynylene/CPP hybrids were compared to a truncated model whereby the arylene ethynylene is attached to the central ring of a linear p-terphenyl chromophore yielding T-Ph and T-Th (Chart 1). These models both have a high-energy signature associated with the p-terphenyl core along with structured low-energy absorptions arising from the arylene ethynylene segment at ca. 330 nm and 350 nm (for T-Ph) or at ca. 360 nm and 375 nm (for T-Th). These structured low-energy features coincide with those from the CPP itself as well as from the respective [6]-Ph/Th and [8]-Ph/Th small molecule systems but the lack of fine structure coupled with the spectral broadening in the latter molecules clearly show that the electronic properties of CPP and the orthogonal arylene ethynylenes are not simply additive but rather that new electronic states are emerging even at this small molecule level.

Figure 5A:
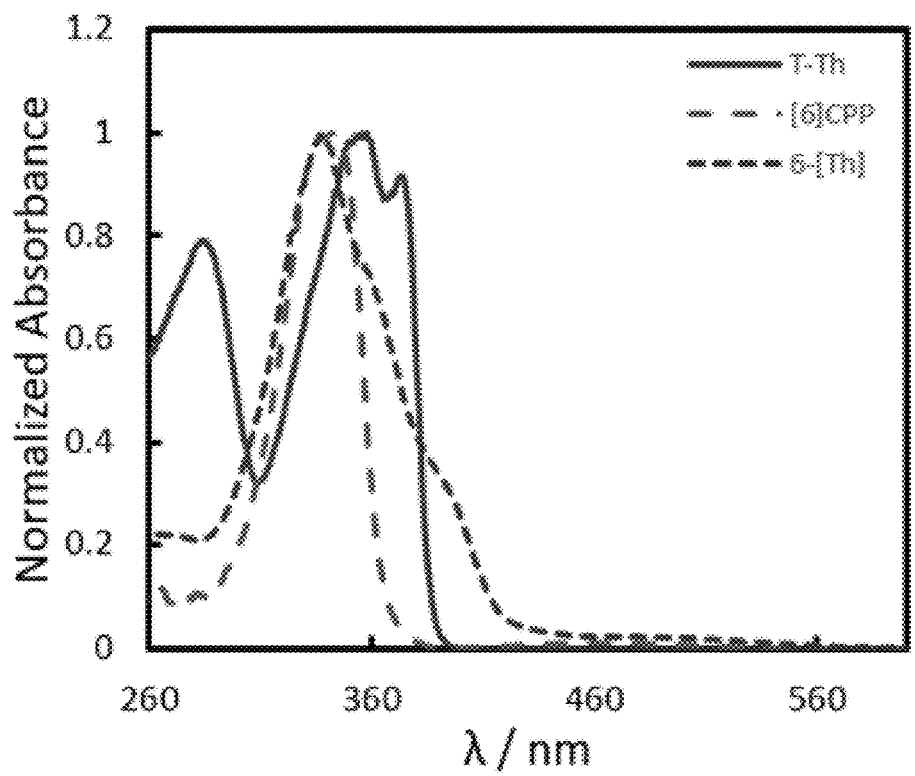
FIGS. 5A and 5B show UV-Vis spectra for oligomeric [6]-Th (FIG. 5A) and [8]-Ph (FIG. 5B) in comparison with the respective [6]- and [8]CPPs and the planar terphenyl models.
Figure 5B:
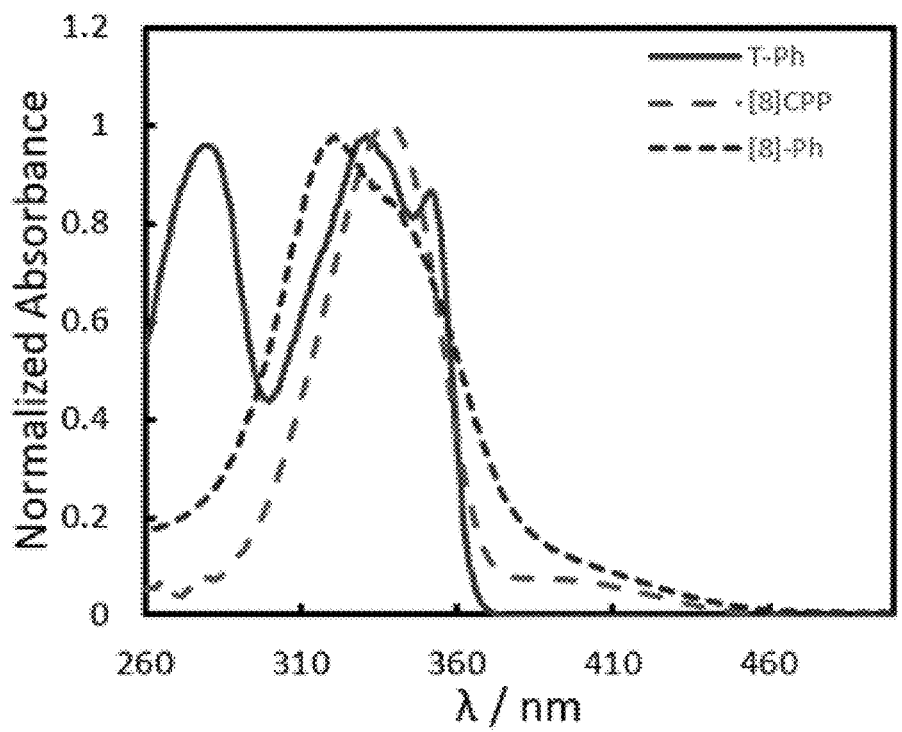
Figure 6A:
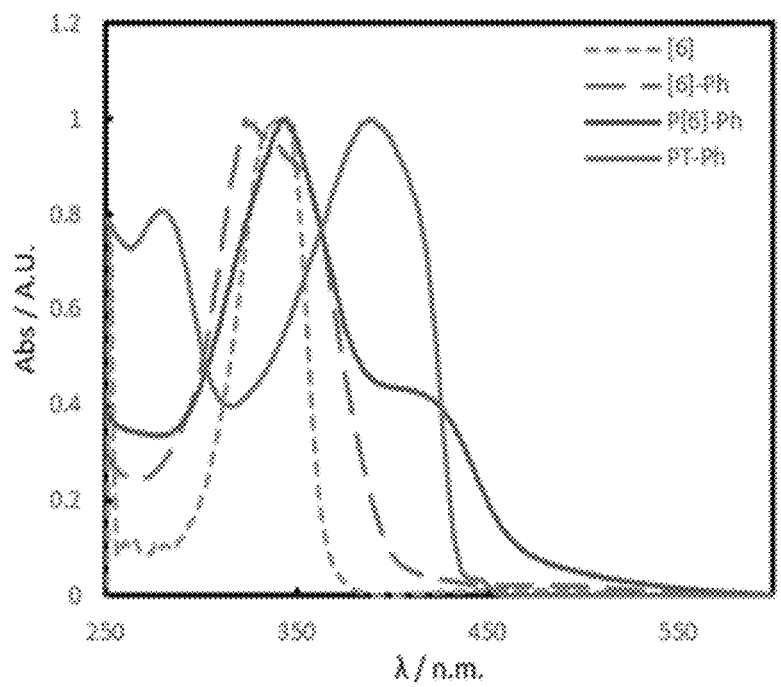
FIGS. 6A and 6B shows absorption spectra of [6]CPP polymers with phenylene ethynylene (P[6]-Ph, FIG. 6A) and thienylene ethynylene (P[8]-Th, FIG. 6B) linear conjugation linkages, illustrating the impact of gradually extending the orthogonal conjugated system relative to the small molecule models and the polymerized terphenyl analogues.
Figure 6B:
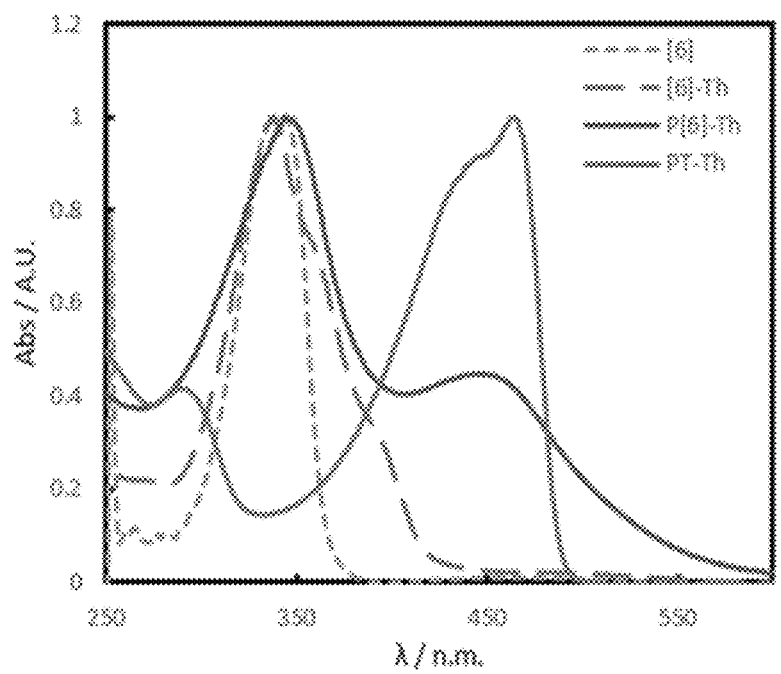

Short π-extensions through addition of benzene or thiophene on the dialkynylated core impacted the resulting photophysics, and these effects were strongly magnified in the corresponding conjugated polymers. Monomer 5, monomer 8 and the linear terphenyl model mT were polymerized with either a dialkylated phenyl or thienyl co-monomer. As a benchmark, the terphenyl-based polymer with the phenylene-ethynylene backbone PT-Ph presented a low energy absorption at 389 nm (with a pronounced shoulder at ca. 415 nm) associated with the linearly conjugated backbone, along with higher-energy absorption around 285 nm associated with the terphenyl moiety. P[6]-Ph possessed one major absorption at 348 nm which correlates with the pendant CPP macrocycle along the polymer backbone (FIGS. 6A and 6B), along with a lower energy broad feature at 338 nm that was assigned to the conjugated polymer backbone and the shallow absorption out to 550 nm also found for the parent [6]CPP and [6]-Ph (FIG. 4A, inset). Because the shoulder is further red-shifted and broader compared to that of the model polymer's sharp onset of absorption, this is not simply an artifact of any inherent molecular weight differences but suggests new electronic states that are not additive from the [6]CPP and the associated phenylene ethynylene backbone. The analogous thienylene ethynylene P[6]-Th demonstrated similar photophysical responses, showing a broad low energy ethynylene-based band at 450 nm along with a higher-energy CPP-based band at 350 nm. Here, the low-energy band corresponding to the alkyne-containing conjugated pathway is more coincident with that of the model species PT-Th ($\lambda_{abs}$ at 440 and 465 nm) and of the shallow tail of the CPP core extending to 550 nm. Additional photophysical data is provided by FIGS. 5A and 5B, which show UV-Vis spectra for oligomeric [6]-Th (FIG. 5A) and [8]-Ph (FIG. 5B) in comparison with the respective CPP and terphenyl model compounds.

Figure 7A:
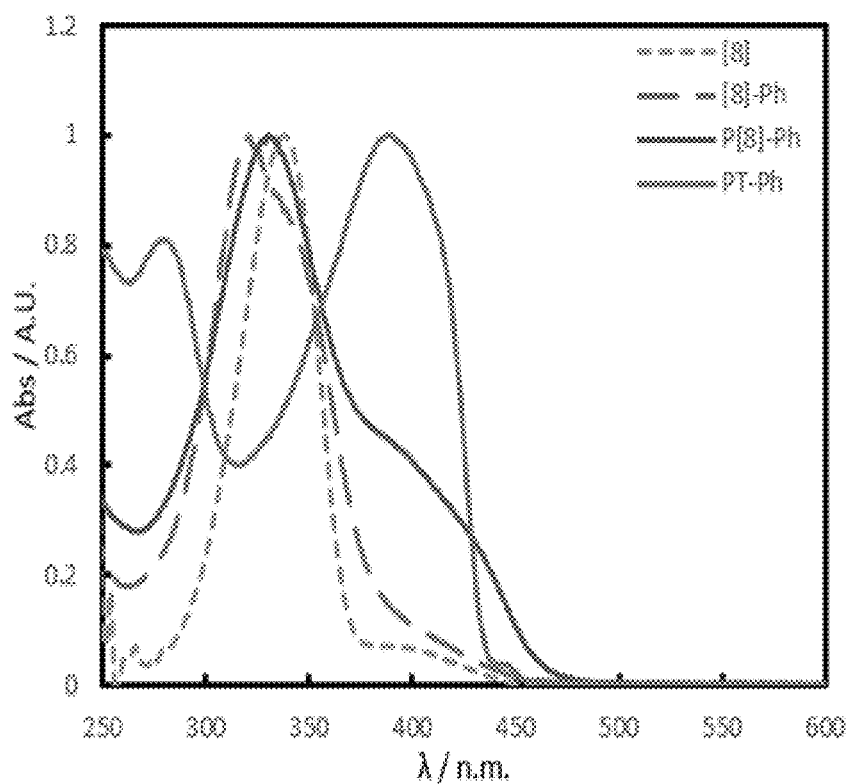
FIGS. 7A and 7B shows absorption spectra of [8]CPP polymers with phenylene ethynylene (P[8]-Ph, FIG. 7A) and thienylene ethynylene (P[8]-Th, FIG. 7B) linear conjugation linkages, illustrating the impact of gradually extending the orthogonal conjugated system relative to the small molecule models and the polymerized terphenyl analogues.
Figure 7B:
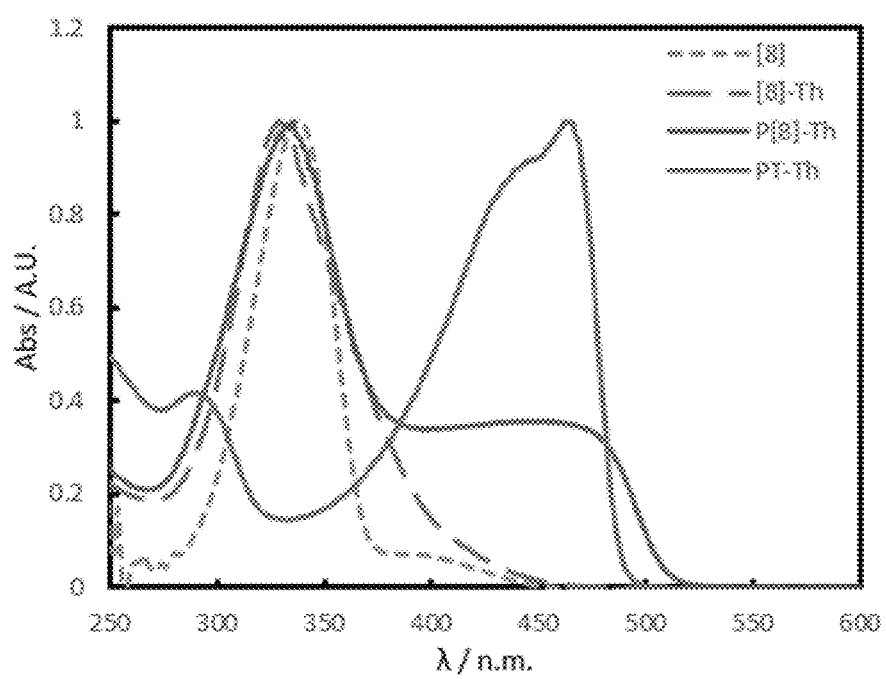

As with [6]CPP containing polymers P[6]-Ph and P[6]-Th, there is little change in the energy of the major [8]CPP-based transition at 335-340 nm upon polymerization of monomer 8 (FIGS. 7A and 7B). Both P[8]-Ph and P[8]-Th contain this characteristic signature along with the absorption arising from the conjugated polymer backbone, with variances due to the extent of polymerization. Since the low energy shoulder (ca. 400-450 nm) associated with [8]CPP molecules extends to a lesser degree into the visible region than [6]CPP, it is more effectively masked by the polymer absorption. However, in some embodiments, the stronger intensities for the low energy absorptions of the P[8]-Ph and -Th polymers suggests these may not be arising solely from CPP-based transitions but rather reflect the dual nature of the cyclic and linear conjugation. This is most pronounced in P[8]-Th where the broad emission shoulder extending from ca. 400-500 nm is quite distinct form the vibronic features present in the PT-Th model polymer at 440 nm and 465 nm.

Figure 8:
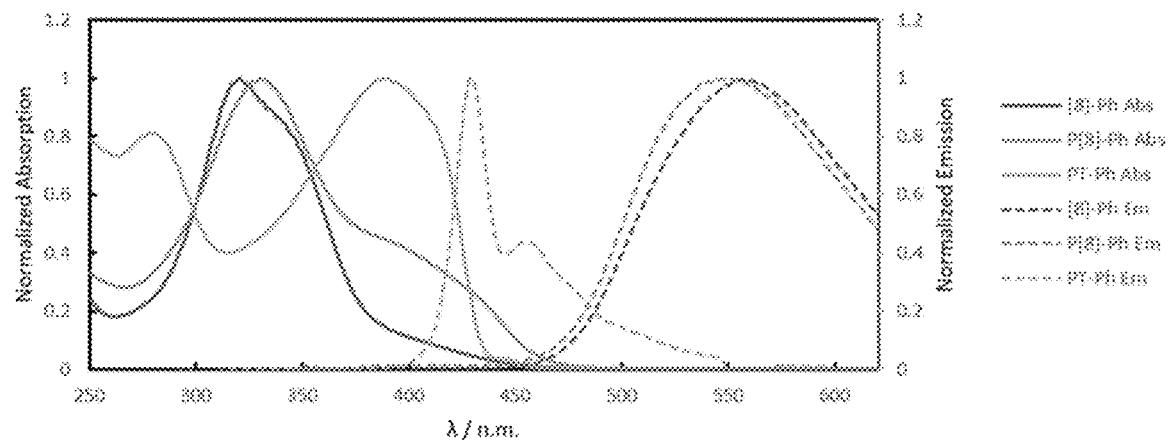
FIG. 8 shows UV-Vis absorption and emission spectra for phenylated [8]CPPs compared to that of the linear analogue.
Figure 9:
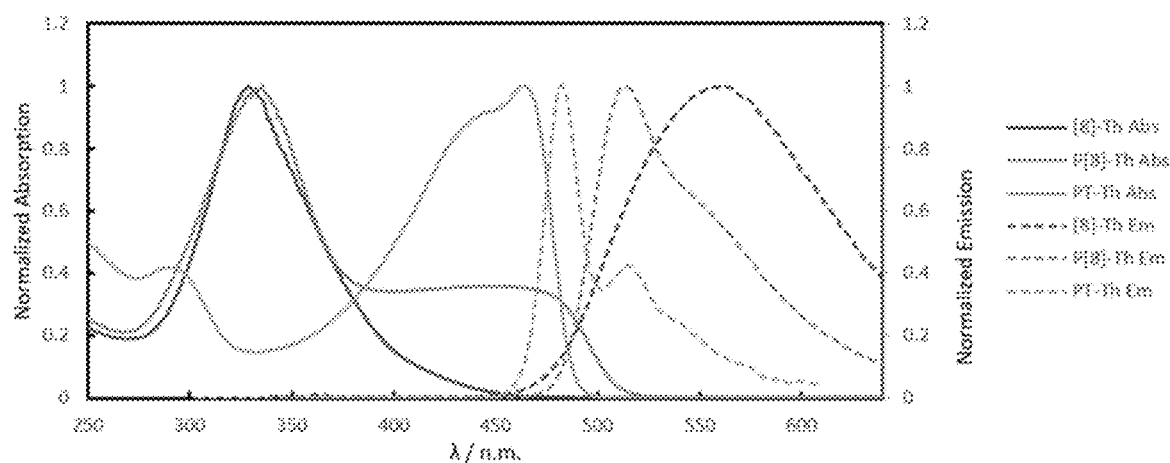
FIG. 9 shows UV-Vis absorption and emission spectra for thienylated [8]CPPs compared to that of the linear analogue.

To further probe the electronic processes operative within the hybrid radial-linear pi-electron materials, photoluminescence spectra were recorded (FIG. 8 and FIG. 9). [6]CPP by itself is negligibly photoluminescent, and this carried over into [6]-Ph/Th and the corresponding polymers P[6]-Ph/Th. [8]CPP shows a peak luminescence at 535 nm, and the hybrid materials also show different extents of photoluminescence. The emission profile for the oligomeric and polymeric phenylated [8]CPPs are very similar to this parent CPP emission although slightly redshifted (ca 10-25 nm). Notably, the luminescence from the phenylene ethynylene backbone of PT-Ph falls at a much higher energy (430 nm peak emission with a 460 nm vibronic shoulder), which suggest that the CPP moiety may be dominating the excited state processes for these structures albeit with some energetic influence from the attached linearly conjugated chains. In phenylated CPP embodiments, the substantial Stokes' shifts indicate pronounced excited state planarization/reorganization. In contrast, the emission profile for the thienylated [8]CPP analogues demonstrated some differences. [8]-Th fluorescence almost mirrors that of [8]-Ph falling at 560 nm, again redshifted by 25 nm from the [8]-CPP core. The corresponding CPP-based thienylene ethynylene polymer P[8]-Th is more drastically blue-shifted and vibronically structured (peaks at 515 nm and 560 nm) than is P[6]-Ph but is more blue shifted than is the corresponding terphenyl model PT-Th (with peaks at 485 nm and 520 nm). Clearly the excited state electronic structure of P[8]-Th is much more than an additive response from the thienylene ethynylene linear backbone and the CPP radial pendant components.

Example 23

Before modeling the UV-vis spectra of the polymers, a computational approach was validated by using the well-defined molecular structures listed in Chart 1. Accordingly, the average predicted UV-vis peak positions are 8 nm shifted to the longer wavelengths compared to the respective experiments. The range of this prediction error is between −29 and 24 nm, the maximum error is 8%. The high reliability of the computations can facilitate evaluating the polymer predictions. To further support these predictions, additional computations were performed that indicated negligible computational influence from 1) replacing alkyl groups with computationally more tractable methyl groups, 2) the chemical nature of the end-group substitution, and 3) the number of states involved in the relevant low energy regions (only singlets were considered). Details are provided by Table 2 below and FIGS. 17A-17D and 18A-18D. Results on oligomeric repeat units of the corresponding polymers are reported in this example and these are named in this example as n[6/8]-Th/Ph-x where n refers to the length of the oligomeric repeat unit and x refers to the chemical composition of the end group. For example, the trimeric structure of P[6]-Ph terminated with methyl groups is named 3[6]-Ph-Me.

TABLE 2

Predicted vs. experimental UV-vis peaks.

| Molecule | No. of states | Experimental [nm] | Calculated [nm] | Difference [nm] | Type |
|---|---|---|---|---|---|
| T | 6 | 280 | 301 | 21 | H-L |
| [8] | 6 | 340 | 334 | −6 | not H-L |
|  |  | 410 | 432 | 22 | H-L |
| mT | 6 | 298 | 322 | 24 | HL+ |
|  |  | 268 | 268 | 0 | not H-L |
| T-Th | 12 | (360) | 385 | 10 | H-L |
|  |  | 375 |  |  |  |
|  |  | 287 | 299 | 12 | not H-L |
| T-Ph | 12 | 353 | 364 | 11 | H-L |
|  |  | 285 | 285 | 0 | not H-L |
| [6] ($\lambda_2$) | 12 | 315 | 338 | 23 | not H-L |
| [6]-Th* | 12 | 488 | 487 | −1 | H-L |
| [6]-Ph* | 12 | 488 | 486 | −2 | H-L |
| Monomer 5 | 12 | 350 | 321 | −29 | not H-L |
|  |  | 295 | 290 | −5 | not H-L |
| [8]-Th | 12 | 375** | 390 | 15 | not H-L |
|  |  | 327 | 340 | 13 | not H-L |
| [8]-Ph | 12 | 412** | 436 | 24 | H-L |
|  |  | 346 | 365 | 19 | not H-L |
|  |  | 319 | 330 | 11 | not H-L |
| Monomer 8 | 12 | 340 | 337 | −3 | not H-L |
|  |  | 295 | 295 | 0 | not H-L |

*Broad peak not included.
**Refers to broad low intensity peaks

Figure 10:
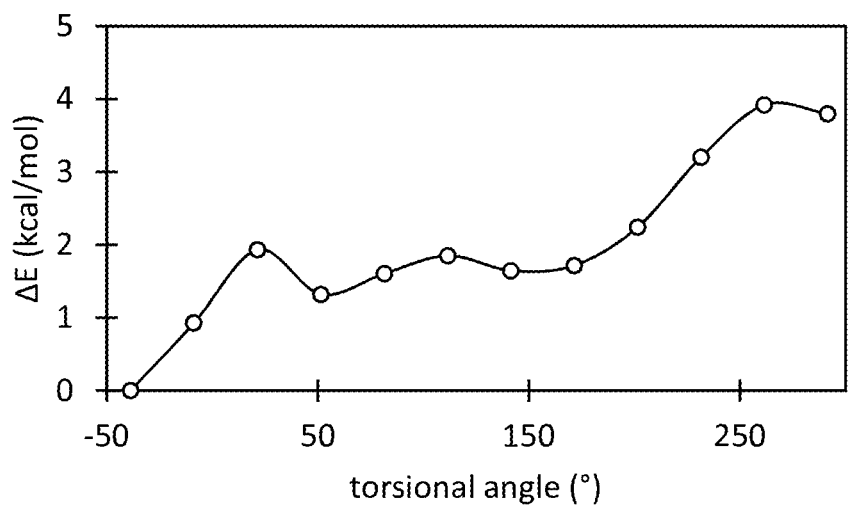
FIG. 10 is a rigid energy scan of 3[6]-Th-Me with a torsional angle varied from −38.66° to 291.56 with a step size of 30 between the middle [6]-CPP and the thiophene in the backbone. Torsion is defined as in FIG. 11.
Figure 11:
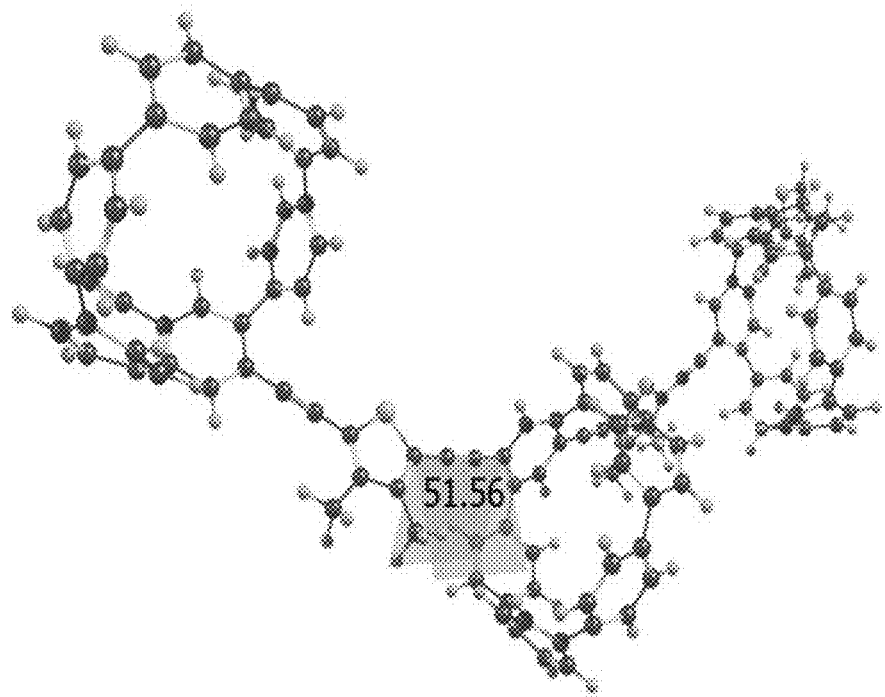
FIG. 11 shows the geometry of 3[6]-Th-Me with a torsional angle of 51.56 between the middle [6]-CPP and the thiophene in the backbone.
Figure 12:
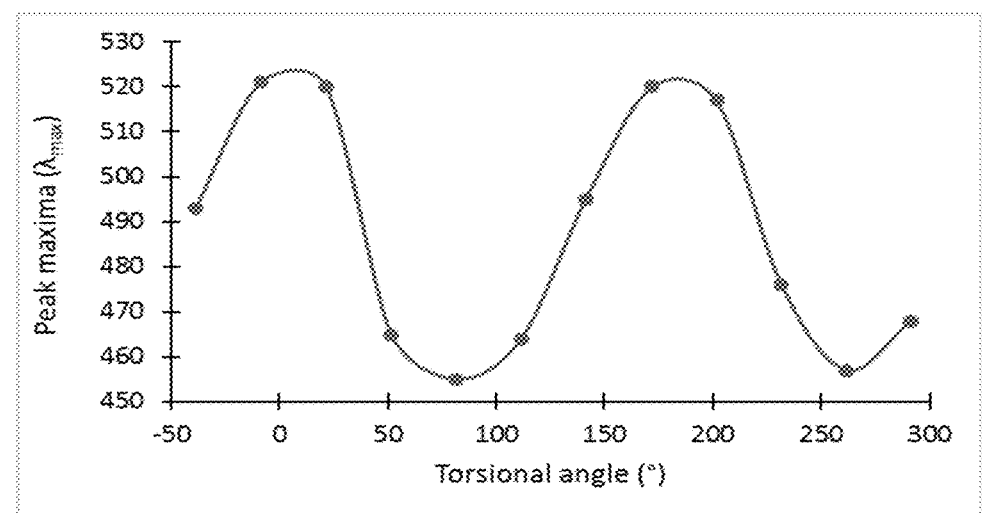
FIG. 12 is a graph showing variation of the computed Amax for 3[6]-Th-Me as a function of a torsion between the middle [6]CPP and the thiophene in the backbone, illustrated in FIG. 11.

To understand this effect conformational degrees of freedom on the UV-vis spectra, a single torsional angle around the linear $C_2$ alkyne group in 3[6]-Th-Me was changed (see FIGS. 10 and 11 and FIGS. 19A-19L). This change uses a relatively small energy change with a barrier of 4 kcal/mol. The shift of the UV-vis spectra was very significant, as expected with a variation by about 100 nm for the main peak at ~450 nm. The energy scan shows a rather small barrier (FIG. 10). Thus, it is possible that in solution for this trimer various conformers would coexist such that in some molecules the extended conjugation is disrupted. If that is the case, the peaks at higher wavelength would be suppressed. This effect is expected to be present not only for trimers but for any large oligomer. FIG. 12 indicates the variation of the long wavelength peak of this trimer as a function of the torsional defect illustrated in FIG. 10. The large shifts in FIG. 12 appear as a consequence of even relatively limited changes in torsion.

Additional results are provided by FIGS. 20A-20, 21A, 21B, 22A-22C, 23A-23C, 24A-24C, 25A-25D, 26A-26C, 27A-27D, 28A-28C, 29A-29C, 30A-30C, 31A, and 31B.

The polymer UV-vis spectra for all 6 polymer systems in Table 1 were modeled by a succession of different size oligomers with n=2, 3, and in some cases 4, with details provided herein. The extrapolation to polymers of infinite length was based on a linear fit of the lowest energy transition as a function of 1/n. Accordingly, the predicted long wavelength polymer peak is very substantially red shifted, as shown in Table 3. For example, for PT-Th, the predicted maximum is at 635 nm, while the experimental low energy peak value is around 465 nm. This difference is much larger than expected based on the validation described above. The corresponding predicted wavelengths for other polymers are still significantly larger (red shifted) as well compared to the experiment. A linear regression between 1/λ and 1/n was obtained. Using this linear fit, and substituting the experimental peak value for the polymer, approximate conjugation lengths that are shown in Table 3 were obtained. The observed peak wavelength of 465 nm of PT-Th corresponds to a chain length of only 2.04 units. The fact that the polymer absorption bands are broader than the bands of the monomers then can be attributed to a distribution of different chain lengths and different conformational defects limiting the range of delocalization to about two units on average.

TABLE 3

Summary of the low energy UV-vis computed peak positions for six polymers and their oligomers compared with the experimental data.

| | Polymer type | Experimental λ (nm) for polymer | Predicted for infinite polymer λ (nm) | Predicted conjugation Length of polymer (number of units) | Experimental peak used for length determination λ (nm) | oligomer type | Predicted λ(nm) |
|---|---|---|---|---|---|---|---|
| 1 | PT-Th | 340-500 | 635 | 2.04 | 465 | 1T-Th | 356 |
| | | | | | | 2T-Th | 462 |
| | | | | | | 3T-Th | 510 |
| | | | | | | 4T-Th | 534 |
| 2 | PT-Ph | 320-440 | 549 | 1.56 | 393 | 1T-Ph | 340 |
| | | | | | | 2T-Ph | 423 |
| | | | | | | 3T-Ph | 458 |
| 3 | P[6]-Th | 405-525 | 593 | 1.19 | 455 | 1[6]-Th | 376 |
| | | | | | | 2[6]-Th | 509 |
| | | | | | | 3[6]-Th | 532 |
| | | | | | | 4[6]-Th | 549 |
| 4 | P[6]-Ph | 395-475 | 574 | 0.99 | 435 | 1[6]-Ph | 363 |
| | | | | | | 2[6]-Ph | 502 |
| | | | | | | 3[6]-Ph | 524 |
| 5 | P[8]-Th | 385-525 | 650 | 1.87 | 480 | 1[8]-Th | 383 |
| | | | | | | 2[8]-Th | 489 |
| | | | | | | 3[8]-Th | 533 |
| 6 | P[8]-Ph | 380-485 | 560 | 1.49 | 440 | 1[8]-Ph | 379 |
| | | | | | | 2[8]-Ph | 468 |
| | | | | | | 3[8]-Ph | 495 |

Additional calculations were performed on some of the monomers with THE solvent and compared it with the calculations performed in gas phase. We observed a small red shift in UV-Vis peaks of monomers resulting from this solvent effect, ranging from 1-3 nm with the maximum of 10 nm, (see Table S3 shown below). The predicted red shifts even without solvent effect remain large, of the order of 130-200 nm, with respect to the experiments for the polymers. The key argument presented in our work remains valid concerning the lack of a major experimentally observed red shift for polymers against the predicted large red shift from monomers to polymers leading us to conclude that the pi-states become localized over rather limited regions in the polymers.

TABLE 4

The effect of solvent on the predicted UV-vis peaks using TD-DFT.

| Compound | No. of states | Experimental [nm] | Calculated without THF [nm] | Difference from experimental [nm] | Calculated with THF [nm] | Difference from experimental [nm] | Type |
|---|---|---|---|---|---|---|---|
| T-Th | 12 | (360) 375 | 385 | 10 | 397 | 20 | H-L |
| | | 287 | 299 | 12 | 302 | 15 | not H-L |
| [6]-Ph | 12 | 488 | 486 | -2 | 487 | -1 | H-L |
| [6]-Th | 12 | 488 | 487 | -1 | 487 | -1 | H-L |
| | | 398 | 393 | -5 | 405 | 7 | not H-L |
| | | 339 | 337 | -2 | 338 | -1 | not H-L |

The experimental molecular weight data indicate diverse ranges of average chain lengths for different polymers ranging from approx. 4 to 292 units. On the other hand, the computed UV-vis spectra data indicate that the effective conjugation length is limited to about 0.99 to 2.04 units for these polymers (Table 3). For this reason, conformational defects may be present that reduce the effective conjugation length and limit it to only a few repeat units. As such, the experimentally observed peaks are close to the predicted peaks for the systems such as 2T-Th, 2T-Ph, 2[8]-Th, and 3[6]-Th and not the predicted extrapolated polymer values (Table 3).

Figure 13A:
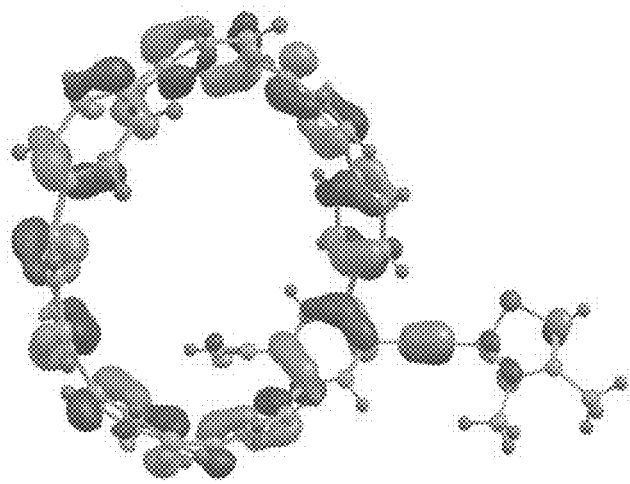
FIGS. 13A-13H show HOMO and LUMO orbitals for certain polymerizable nanohoop monomer compounds and polymer embodiments disclosed herein, which further illustrates conjugation in certain geometries; wherein (i)
Figure 13B:
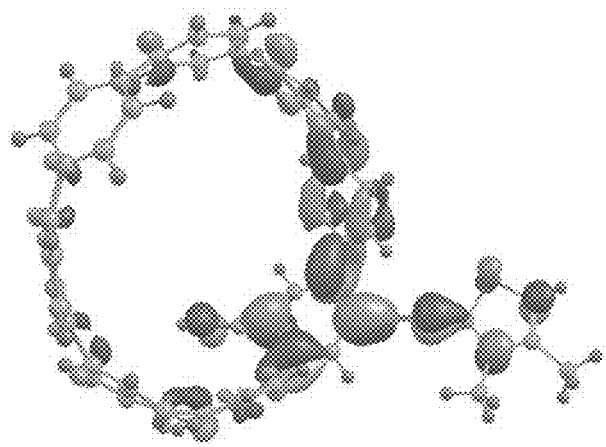
Figure 13C:
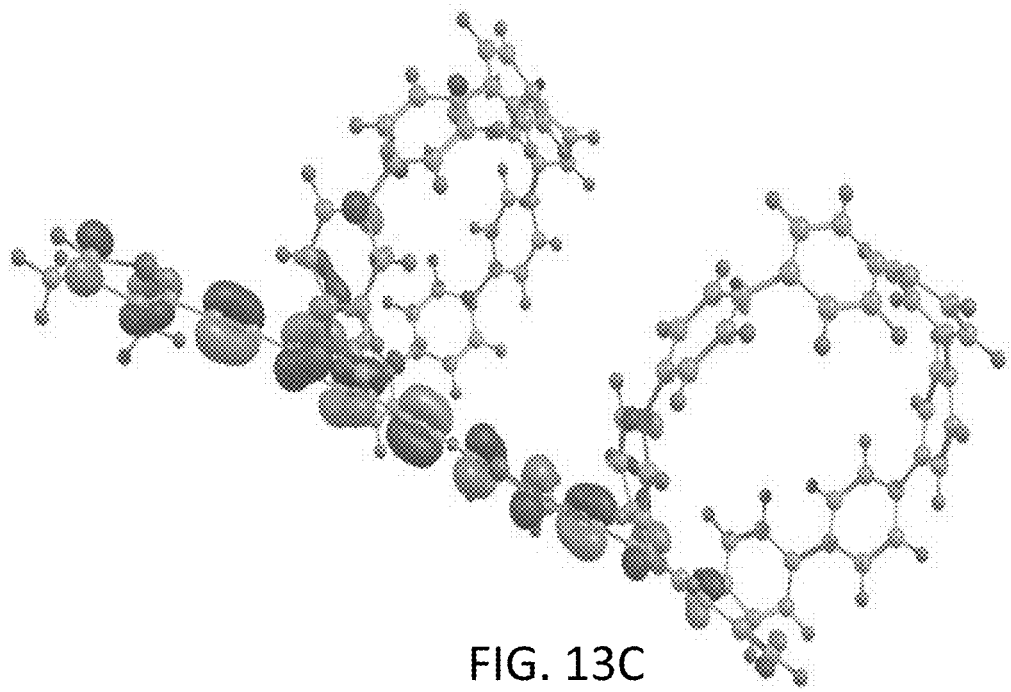
Figure 13D:
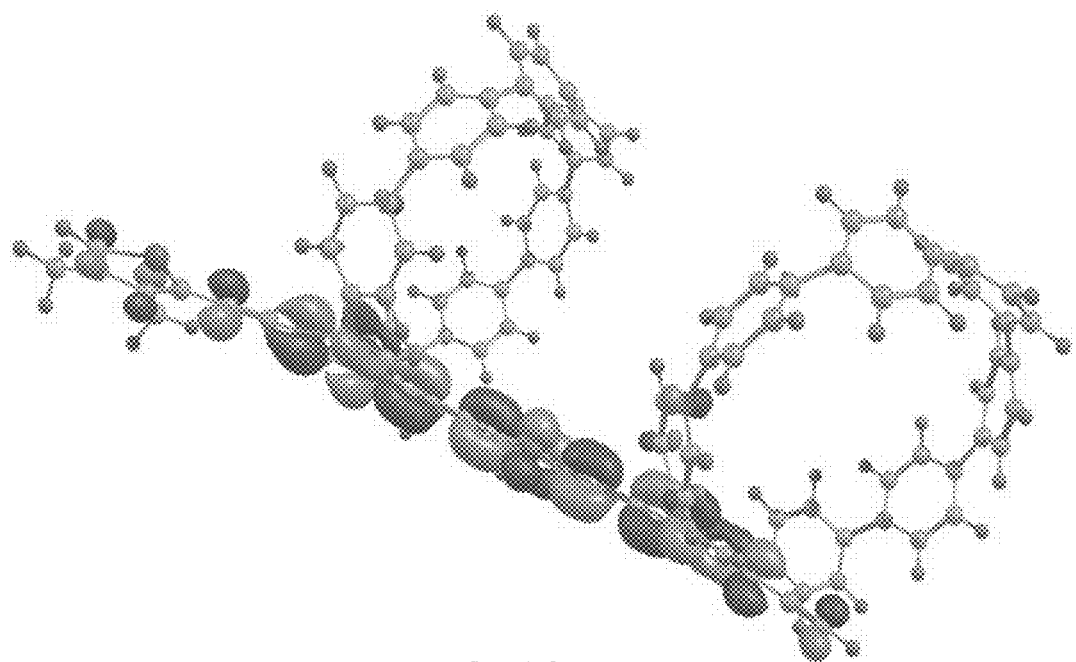
Figure 13E:
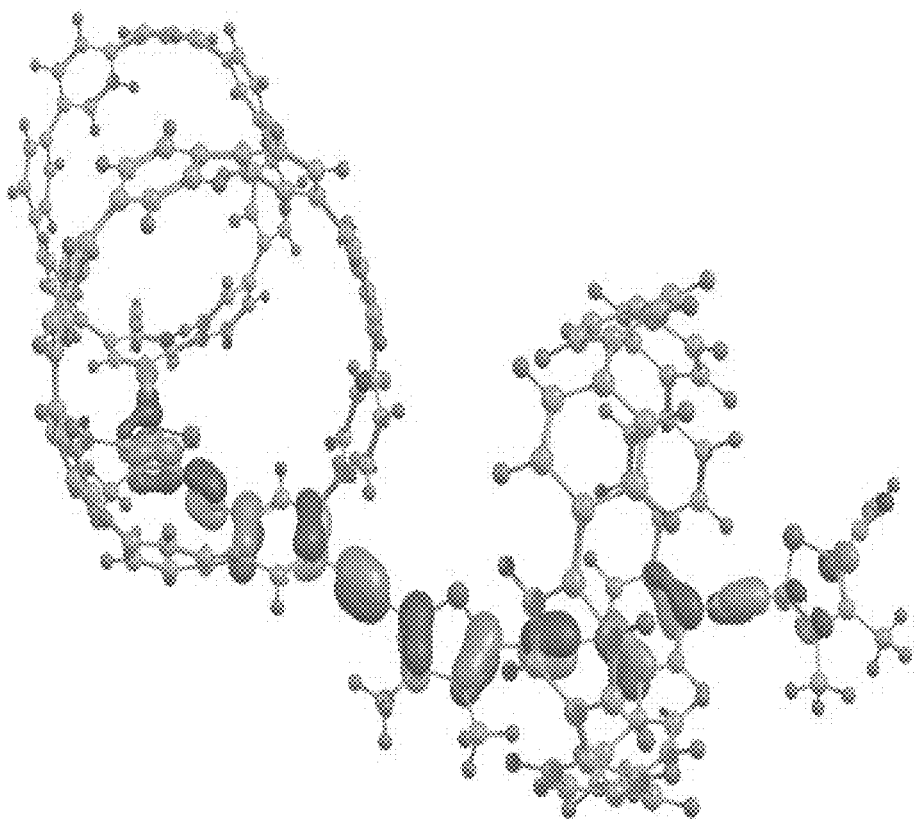
Figure 13F:
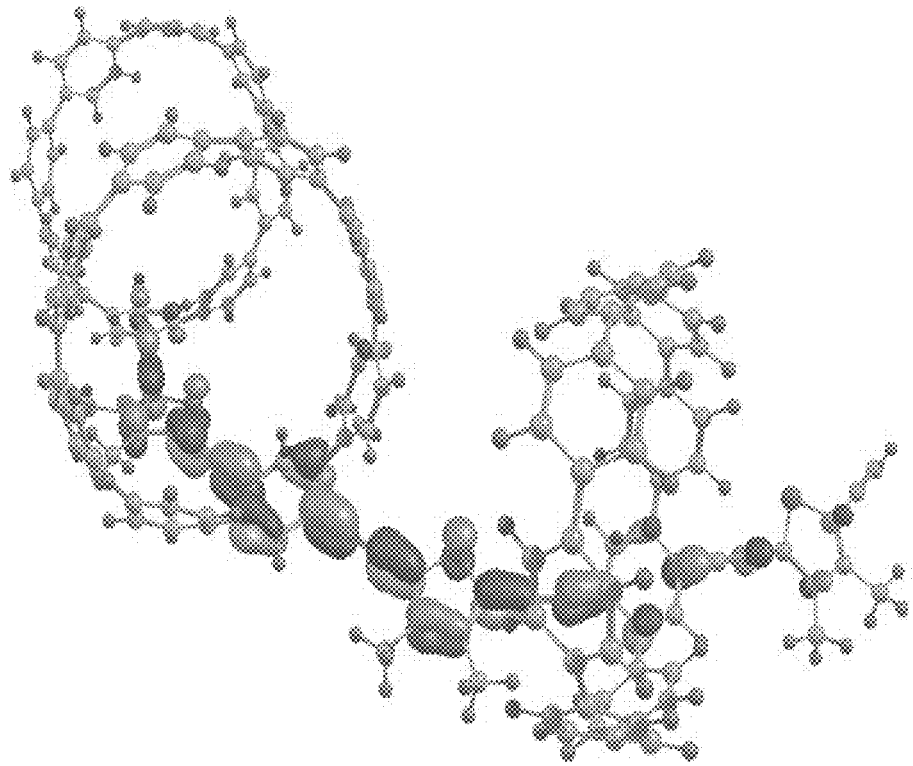
Figure 13G:
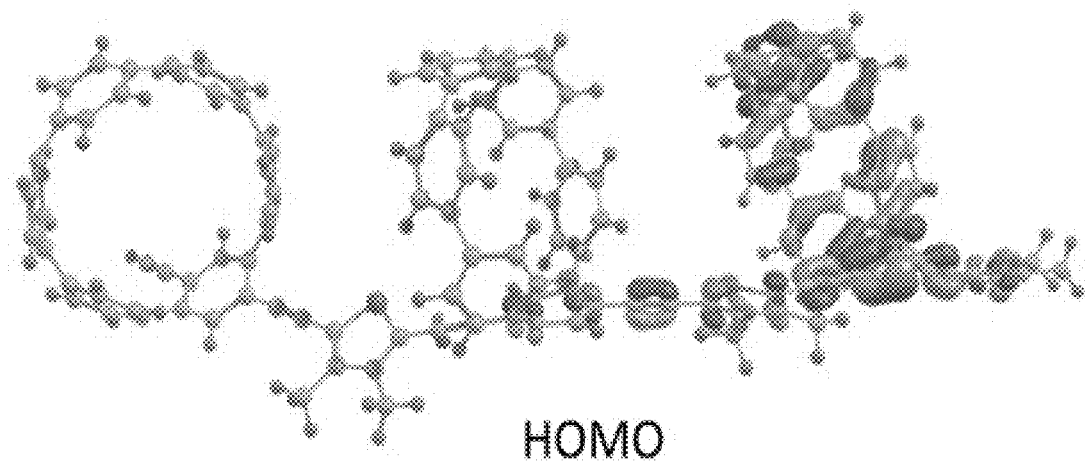
Figure 13H:
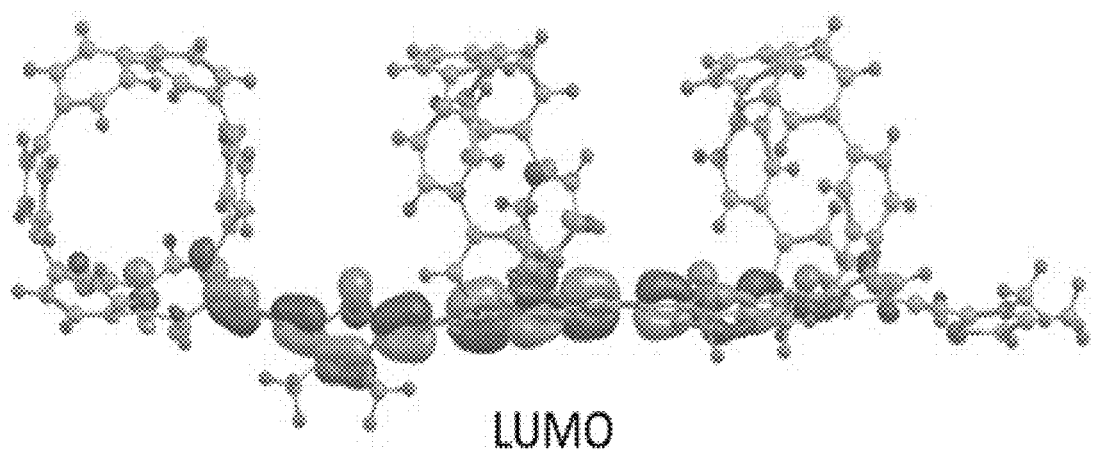

The unusual line shapes for the lowest energy peaks observed for the P[n] polymers in the UV-Vis experiment, especially for P[8]-Th, may be indicative of a broad distribution of conjugation lengths. It is interesting that the respective UV-Vis experimentally observed bands for the model systems without CPP units, PT-Th and PT-Ph are also very broad but appear at a larger relative intensity compared to the higher energy peaks. In some embodiments, the HOMO-LUMO transitions in [n]CPPs are forbidden in the ideal $D_{nh}$ symmetry or nearly forbidden in the real systems that have a lower symmetry. The respective lowest energy peaks show up as weak absorption peaks that are increasing in relative intensity as the CPPs are substituted by linearly conjugated side groups. This linear-radial conjugation effect is completely absent in the terphenyl derivatives, where this long wavelength tail is missing in the absorption spectrum. The enhanced long tail seen in the experimental spectra for the polymers, especially most clearly for P[8]-Th, is not simply an enhanced HOMO-LUMO transition of the [8]CPP part of the polymer. Computed spectra of 2[8]-Th-Me and 3[8]-Th-Me are shown in FIGS. 13C to 13F and spectra for monomer 1[8]-Th are shown in FIGS. 13A and 13B. The dominant long wavelength (low energy) peaks in the trimers of the [8]CPP containing polymers in the predictions belong to the HOMO→LUMO transition of the linear part of the oligomer, with very little contributions from the circular conjugated components. These strongly allowed transitions overwhelm the weakly allowed HOMO→LUMO transitions of the CPPs. The polymers containing [6]CPP are different: here the CPP and the linear conjugated parts display significant mixing in the HOMO, while the LUMO is localized mostly on the linear part, as shown in FIGS. 13G and 13H. On the other hand, the 2-3 of the higher energy transitions for all four systems display various signs of unique behavior not seen in isolated CPPs or in linear conjugated polymers. While, in some embodiments, each individual case is different, the following types of such new transitions are seen in the oligomer computations: transitions involving orbitals localized mostly on the CPP part to orbitals localized mostly on the linear part or vice versa. Then some transitions are comprised of orbitals containing genuine mixing between the linear and circular conjugated components for either one or both orbitals involved in the transition.

The situation for the model systems with terphenyl in place of the CPP components is somewhat different. For both 3T-Th and 3T-Ph, the lowest energy transition is mostly HOMO→LUMO, and includes primarily the main chain. However, this transition does not overlap with the low energy transition of the terphenyl component, since that is not forbidden as opposed to the CPP case. The higher energy transitions involve orbitals for 3T-Ph that are mostly confined to the main chain. However, in the case of 3T-Th the higher energy transitions are similar to that of the CPP based polymers in that there is mixing with one type or another orbital between the main chain and the adjacent phenyls representing the terphenyl component.

In view of the many possible embodiments to which the principles of the present disclosure may be applied, it should be recognized that the illustrated embodiments are only preferred examples and should not be taken as limiting in scope. Rather, the scope of the present disclosure is defined by the following claims. We therefore claim as our invention all that comes within the scope and spirit of these claims.

We claim:

1. A polymer having a structure according to Formula I

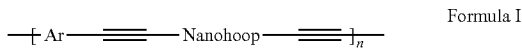

Formula I wherein the nanohoop comprises six or more aromatic ring systems and wherein each aromatic ring system is directly bound to at least two other aromatic ring systems of the nanohoop by two separate single covalent bonds positioned para, ortho, or meta relative to one another, wherein one of the two separate single covalent bonds is directly bound to one of the at least two other aromatic ring systems and the other of the separate single covalent bonds is directly bound to the other of the at least two other aromatic ring systems; Ar is an aromatic ring system; and n is an integer selected from 2 or greater.

2. The polymer of claim 1, wherein each nanohoop is bound to each of the two adjacent alkyne groups of Formula I by two different carbon atoms of a single aromatic ring system of the nanohoop.

3. The polymer of claim 2, wherein the two different carbon atoms of the single aromatic ring system of the nanohoop are positioned para relative to one another.

4. The polymer of claim 1, wherein each nanohoop is bound to each of the two adjacent alkyne groups of Formula I by two different carbon atoms of two different aromatic ring systems of the nanohoop, wherein one of the two different carbon atoms is part of one of the two different aromatic ring systems and the other of the two different carbon atoms is part of the other of the two different aromatic ring systems.

5. The polymer of claim 1, wherein the Ar group is an aryl ring or a heteroaryl ring.

6. The polymer of claim 1, wherein the Ar group is selected from phenyl, naphthyl, pyridinyl, thiophenyl, furanyl, or imidazoyl.

7. The polymer of claim 1, wherein n is an integer ranging from 2 to 10,000.

8. The polymer of claim 1, having a structure according to Formulas IIA or IIB

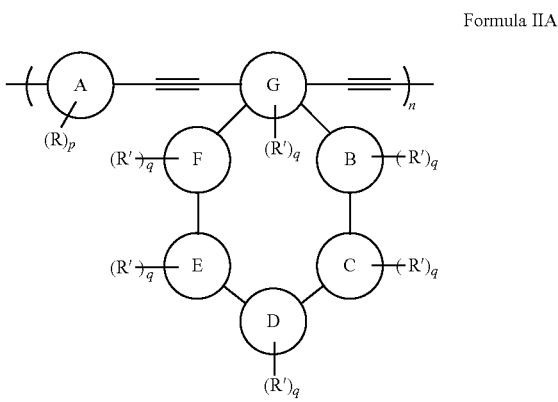

Formula IIA

Formula IIB

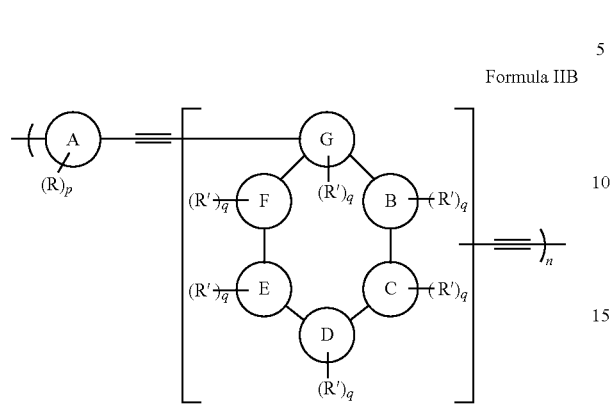

wherein each A ring independently is an aromatic ring system; each R independently is selected from aliphatic, heteroaliphatic, haloaliphatic, haloheteroaliphatic, aromatic, or an organic functional group; each of rings B, C, D, E, F, and G independently is an aromatic ring system; each R' independently is aliphatic, heteroaliphatic, haloaliphatic, aromatic, or an organic functional group; each m independently is an integer selected from 1 to 95; each p independently is an integer selected from 0 to 10; n is an integer selected from 2 or greater; and each q independently is an integer selected from 0 to 10.

9. The polymer of claim 8, wherein each of rings A, B, C, D, E, F, and G independently is aryl or heteroaryl.

10. The polymer of claim 8, wherein each A ring is a phenyl ring, furan, thiophene, or pyrrole, and wherein each of rings B, C, D, E, F, and G independently is phenyl.

11. The polymer of claim 8, wherein p is 2 and each R independently is selected from aliphatic.

12. The polymer of claim 1, having a structure according to Formulas IIIA, IIIB, IVA', or IVB'

Formula IIIA

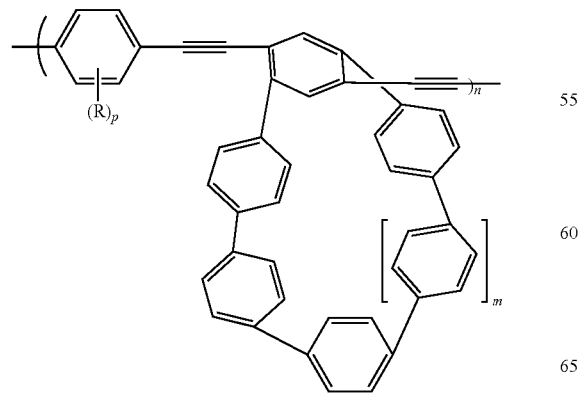

Formula IIIB

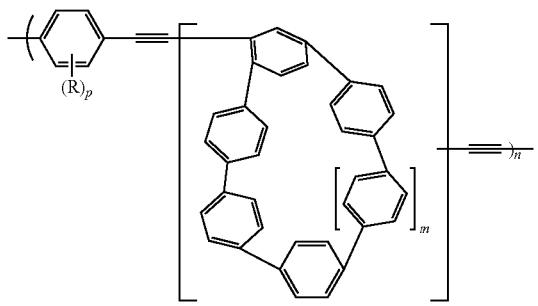

Formula IVA'

Formula IVB'

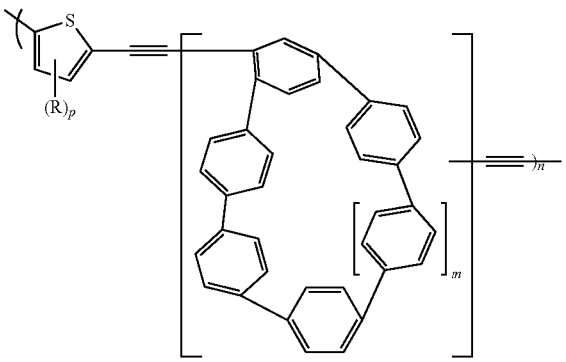

wherein each R independently is selected from aliphatic, heteroaliphatic, haloaliphatic, haloheteroaliphatic, aromatic, or an organic functional group; each m independently is an integer selected from 1 to 95; and each p independently is an integer selected from 0 to 10.

13. The polymer of claim 1, wherein the polymer is selected from
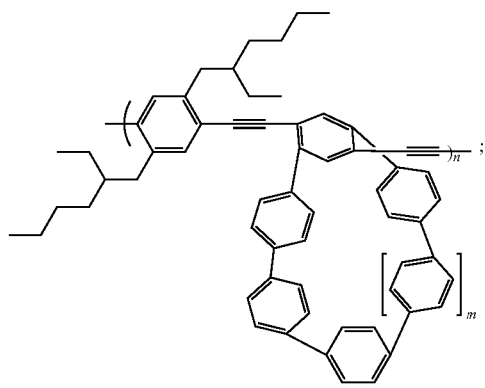
m = 1 or 3
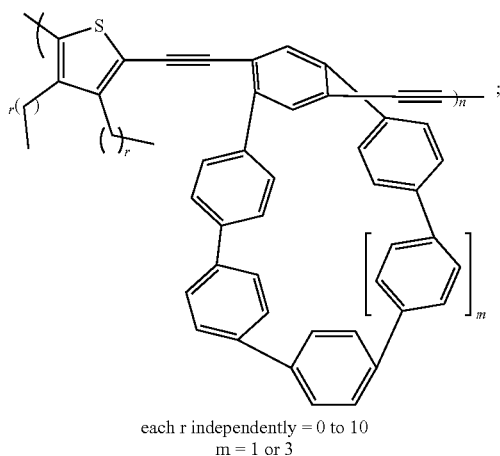
each r independently = 0 to 10
m = 1 or 3
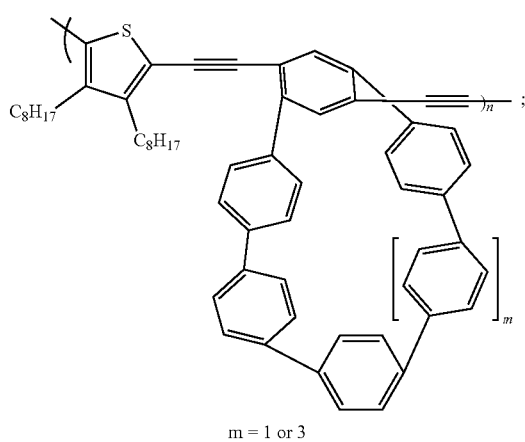
m = 1 or 3
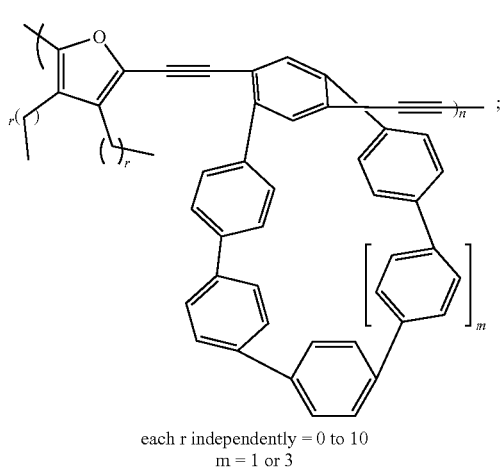
each r independently = 0 to 10
m = 1 or 3
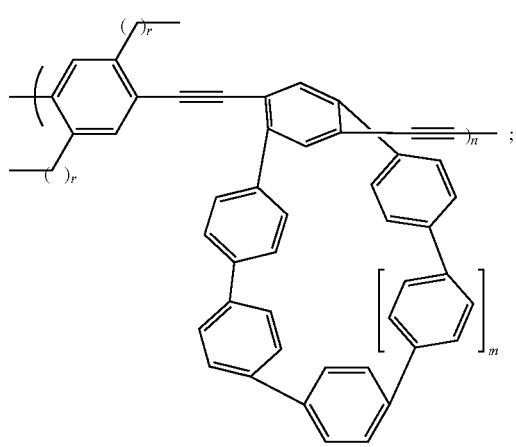
each r independently = 0 to 10
m = 1 or 3
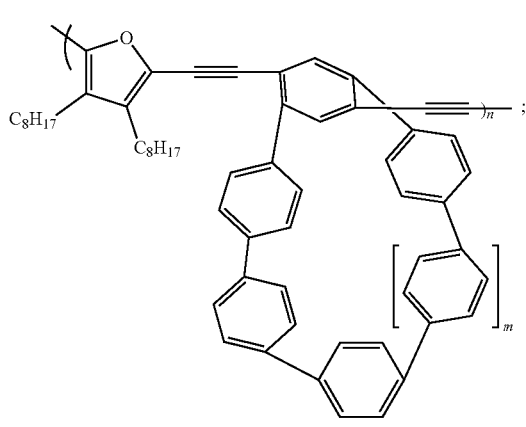
m = 1 or 3

73
-continued
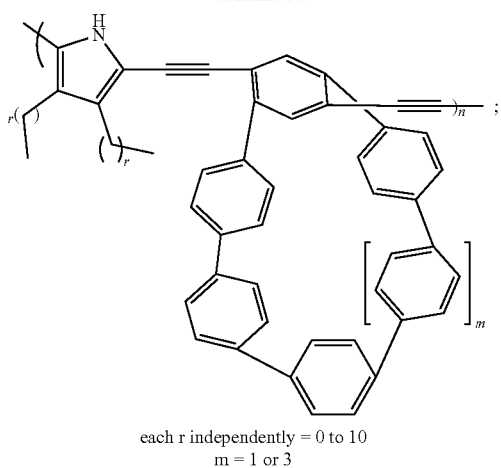
each r independently = 0 to 10
m = 1 or 3
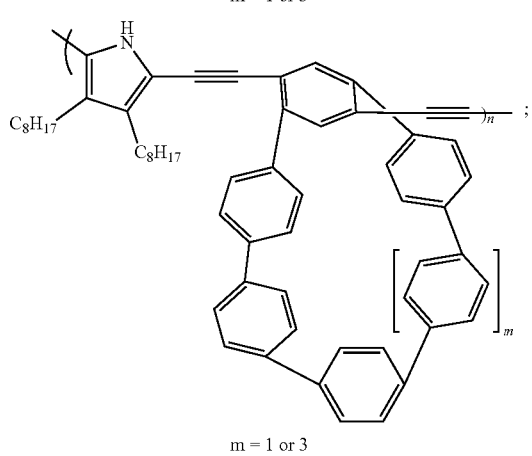
m = 1 or 3
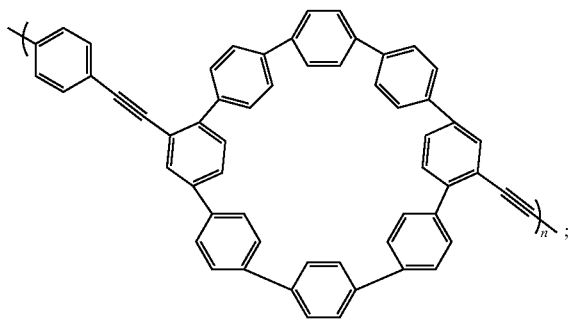
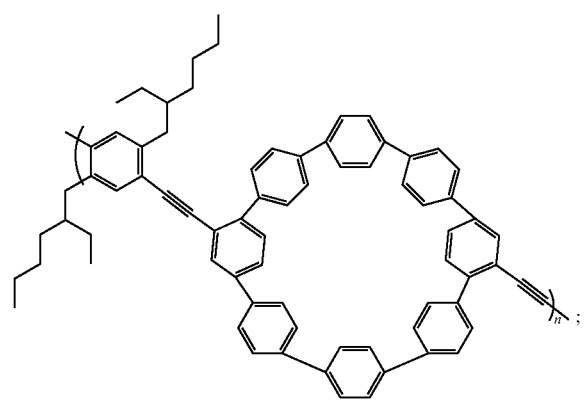
74
-continued
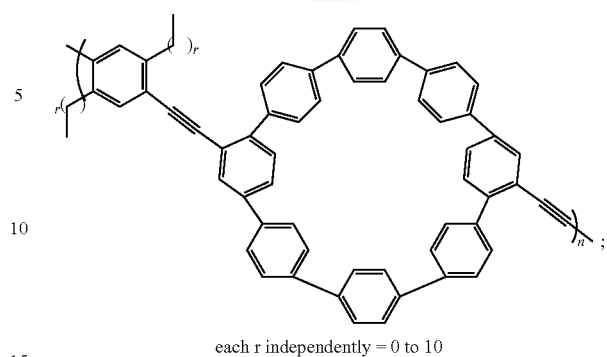
each r independently = 0 to 10
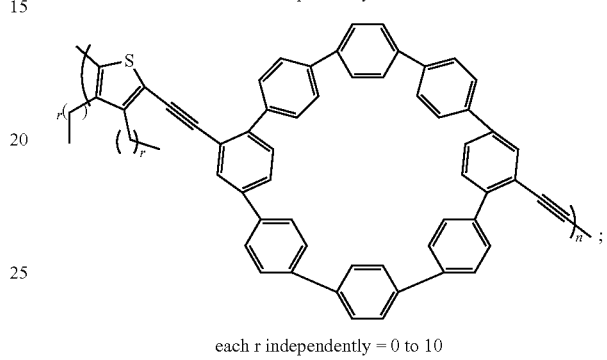
each r independently = 0 to 10
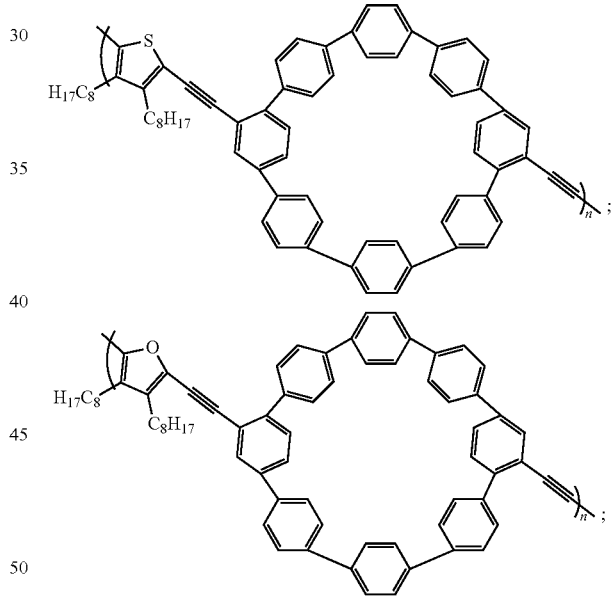
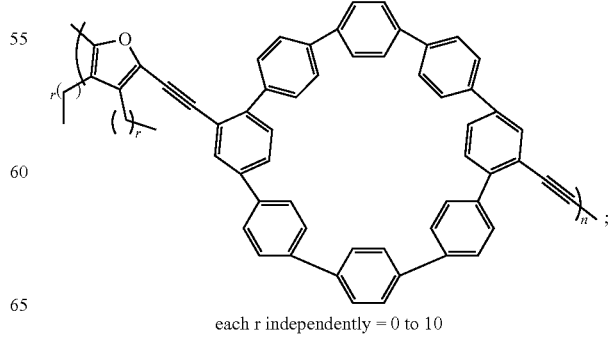
each r independently = 0 to 10

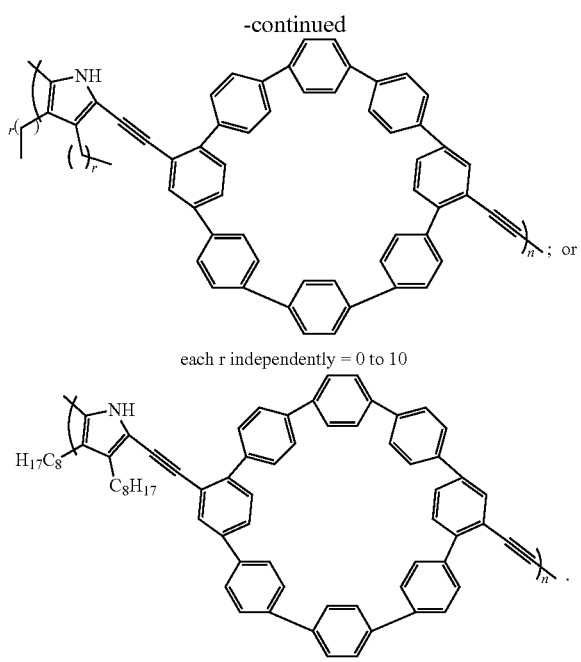

each r independently = 0 to 10

14. The polymer of claim 1, wherein the polymer is

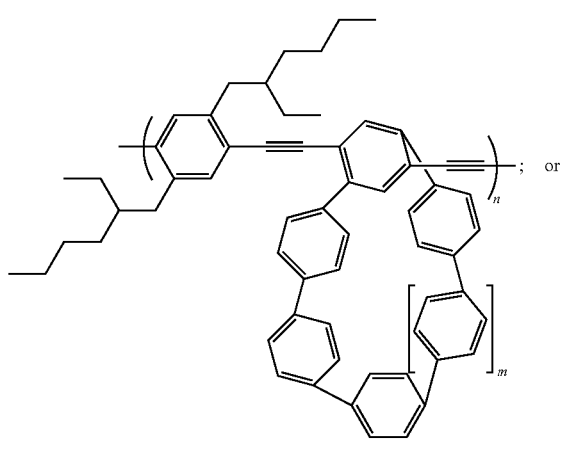

m = 1 or 3

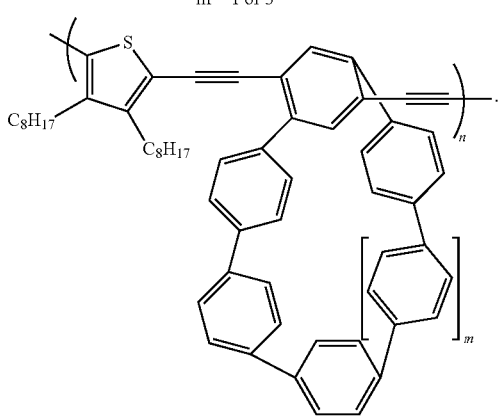

15. A method, comprising exposing a polymerizable nanohoop monomer to a transition metal catalyst, a copper-containing reagent, a base, and an aromatic coupling partner functionalized with a halogen atom to provide the polymer according to claim 1; wherein the polymerizable nanohoop monomer has a structure according to Formula V

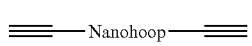

Formula V wherein the nanohoop of Formula V comprises six or more aromatic ring systems and wherein each aromatic ring system is directly bound to at least two other aromatic ring systems of the nanohoop by two separate single covalent bonds positioned para, ortho, or meta relative to one another, wherein one of the two separate single covalent bonds is directly bound to one of the at least two other aromatic ring systems and the other of the separate single covalent bonds is directly bound to the other of the at least two other aromatic ring systems.

16. The method of claim 15, wherein the transition metal catalyst is a palladium catalyst, the copper-containing reagent is CuI, the base is an amine base, $Cs_2CO_3$, $K_2CO_3$, or $K_3PO_4$, and the aromatic coupling partner comprises an aryl or heteroaryl ring functionalized with the halogen atom.

17. A compound having a structure according to Formula V or Formula VI for use in making the polymer of claim 1,

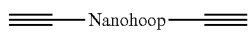

Formula V

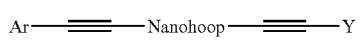

Formula VI wherein the nanohoop comprises six or more aromatic ring systems and wherein each aromatic ring system is directly bound to at least two other aromatic ring systems of the nanohoop by two separate single covalent bonds positioned para, ortho, or meta relative to one another, wherein one of the two separate single covalent bonds is directly bound to one of the at least two other aromatic ring systems and the other of the separate single covalent bonds is directly bound to the other of the at least two other aromatic ring systems; Ar is an aromatic ring system; and Y is hydrogen, copper, a palladium complex, or an aromatic ring system; and wherein the compound having a structure according to Formula V or Formula VI reacts to become part of the polymer.

18. The compound of claim 17, wherein the compound has a structure according to Formula VIIA, VIIB, VIIIA, or VIIIB

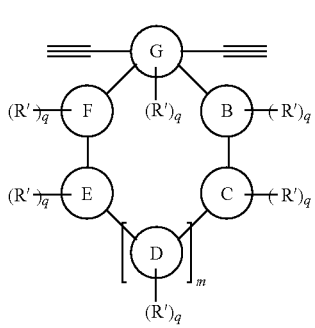

Formula VIIA

Formula VIIB

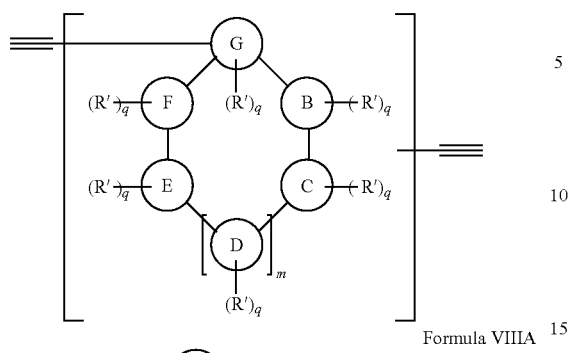

Formula VIIIA

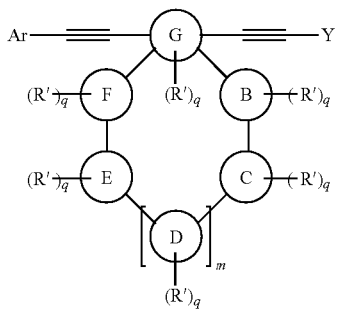

Formula VIIIB

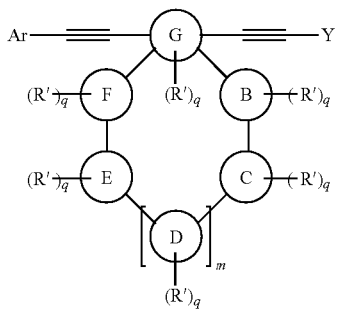

wherein each of rings B, C, D, E, F, and G independently is an aromatic ring system; each R' independently is aliphatic, heteroaliphatic, haloaliphatic, aromatic, or an organic functional group; each m independently is an integer selected from 1 to 95; and each q independently is an integer selected from 0 to 10.

19. The compound of claim 17, wherein the compound has a structure according to Formula IXA, IXB, XA, or XB.

Formula IXA

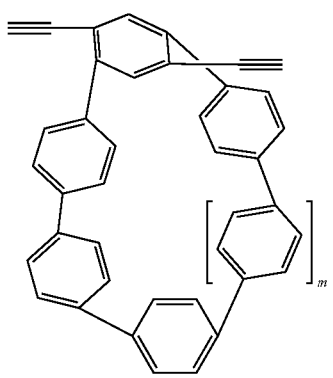

Formula IXB

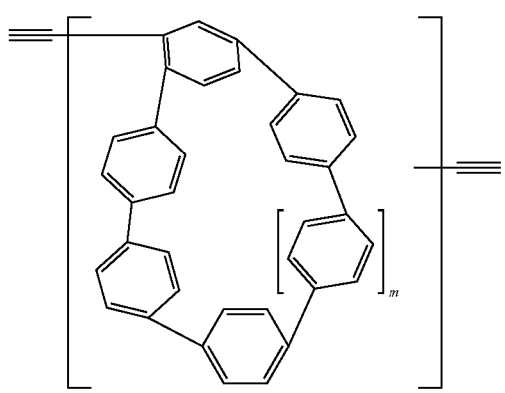

Formula XA

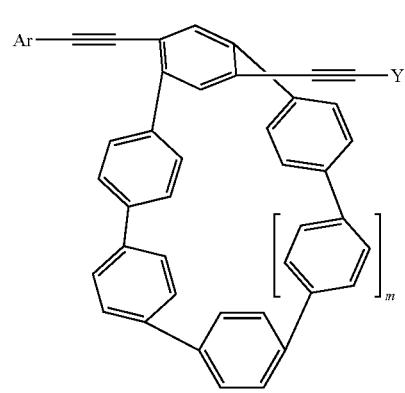

Formula XB

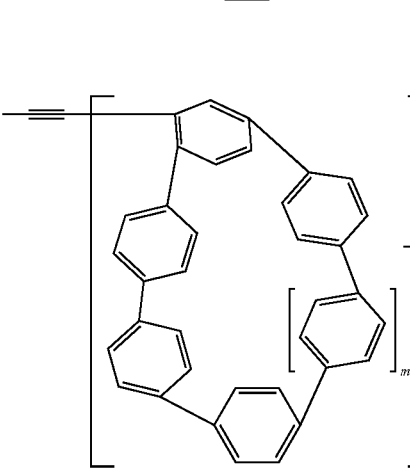

wherein m is 1 or 3.

20. A method, comprising:
coupling a nanohoop intermediate with an aromatic monomer functionalized with an alkyne moiety to provide a non-aromatized nanohoop intermediate; and
exposing the non-aromatized nanohoop intermediate to a reductive aromatization to provide the compound according to claim 17, wherein the compound has a structure according to Formula V.

21. The method of claim 20, wherein the aromatic monomer is functionalized with two alkyne moieties.

* * * * *